(12) United States Patent
Boyd-Kirkup et al.

(10) Patent No.: US 11,685,789 B2
(45) Date of Patent: *Jun. 27, 2023

(54) CD47 ANTIGEN-BINDING MOLECULES

(71) Applicant: Hummingbird Bioscience Pte. Ltd., Singapore (SG)

(72) Inventors: Jerome Boyd-Kirkup, Singapore (SG); Dipti Thakkar, Singapore (SG); Piers Ingram, Singapore (SG); Zhihao Wu, Singapore (SG); Konrad Paszkiewicz, Singapore (SG); Peter Brauer, Singapore (SG); Siyu Guan, Singapore (SG)

(73) Assignee: Hummingbird Bioscience Pte. Ltd., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 17/847,020

(22) Filed: Jun. 22, 2022

(65) Prior Publication Data

US 2022/0356250 A1 Nov. 10, 2022

Related U.S. Application Data

(63) Continuation of application No. 16/760,899, filed as application No. PCT/EP2018/079931 on Nov. 1, 2018.

(30) Foreign Application Priority Data

| Nov. 1, 2017 | (GB) | 1718101 |
| Dec. 7, 2017 | (GB) | 1720425 |
| Dec. 7, 2017 | (GB) | 1720426 |

(51) Int. Cl.
| C07K 16/28 | (2006.01) |
| A61K 39/395 | (2006.01) |
| A61P 35/00 | (2006.01) |
| C12N 15/09 | (2006.01) |
| C12N 15/62 | (2006.01) |
| C07H 21/00 | (2006.01) |
| A61K 39/00 | (2006.01) |
| C12N 15/11 | (2006.01) |

(52) U.S. Cl.
CPC .... *C07K 16/2896* (2013.01); *A61K 39/39558* (2013.01); *A61P 35/00* (2018.01); *C07H 21/00* (2013.01); *C07K 16/2803* (2013.01); *C12N 15/09* (2013.01); *C12N 15/62* (2013.01); *A61K 2039/505* (2013.01); *C07K 2317/24* (2013.01); *C07K 2317/31* (2013.01); *C07K 2317/55* (2013.01); *C07K 2317/565* (2013.01); *C07K 2317/622* (2013.01); *C07K 2317/76* (2013.01); *C07K 2317/92* (2013.01); *C12N 15/11* (2013.01)

(58) Field of Classification Search
CPC ............ C07K 16/2803; C07K 2317/24; C07K 2317/31; C07K 2317/565; C07K 2317/76; C07K 2317/92; A61K 39/39558; A61P 35/00

See application file for complete search history.

(56) References Cited

U.S. PATENT DOCUMENTS

2022/0298254 A1 9/2022 Boyd-Kirkup et al.

FOREIGN PATENT DOCUMENTS

| CN | 105950561 A | 9/2016 |
| WO | WO 2011/034969 A1 | 3/2011 |
| WO | WO 2012/163805 A1 | 12/2012 |
| WO | WO 2013/119714 A1 | 8/2013 |
| WO | WO 2014/087248 A2 | 6/2014 |
| WO | WO 2014/093678 A2 | 6/2014 |
| WO | WO 2014/121093 A1 | 8/2014 |
| WO | WO 2015/128653 A2 | 9/2015 |
| WO | WO 2016/188449 A1 | 12/2016 |
| WO | WO 2017/049251 A2 | 3/2017 |
| WO | WO 2017/081101 A1 | 5/2017 |
| WO | WO 2017/121771 A1 | 7/2017 |
| WO | WO 2017/196793 A1 | 11/2017 |
| WO | WO 2018/075857 A1 | 4/2018 |
| WO | WO 2018/201051 A1 | 11/2018 |

OTHER PUBLICATIONS

Paul, Fundamental Immunology, 3rd Edition, 1993, pp. 292-295.*
Rudikoff et al., Proc. Natl. Acad. Sci. USA, 79(6):1979-1983, 1982.*
Murphy et al., Journal of Immunological Methods, vol. 463, p. 127-133, 2018.*
International Search Report and Written Opinion for International Application No. PCT/EP2018/079931, dated Feb. 25, 2019.
International Preliminary Report on Patentability for International Application No. PCT/EP2018/079931, dated May 14, 2020.
Carpenter et al., B-cell maturation antigen is a promising target for adoptive T-cell therapy of multiple myeloma. Clin Cancer Res. Apr. 15, 2013;19(8):2048-60. doi: 10.1158/1078-0432.CCR-12-2422. Epub Jan. 23, 2013.

(Continued)

*Primary Examiner* — Hong Sang

(74) *Attorney, Agent, or Firm* — Wolf, Greenfield & Sacks, P.C.

(57) ABSTRACT

CD47 antigen-binding molecules are disclosed. Also disclosed are nucleic acids and expression vectors encoding, compositions comprising, and methods using, the CD47 antigen-binding molecules.

11 Claims, 16 Drawing Sheets

Specification includes a Sequence Listing.

(56) References Cited

OTHER PUBLICATIONS

Dheilly et al., Selective Blockade of the Ubiquitous Checkpoint Receptor CD47 Is Enabled by Dual-Targeting Bispecific Antibodies. Mol Ther. Feb. 1, 2017;25(2):523-533. doi: 10.1016/j.ymthe. 2016.11.006.
Hipp et al., A novel BCMA/CD3 bispecific T-cell engager for the treatment of multiple myeloma induces selective lysis in vitro and in vivo. Leukemia. Aug. 2017;31(8):1743-1751. doi: 10.1038/leu. 2016.388. Epub Dec. 27, 2016.
Lee et al., Designing APRIL-Based Therapeutics for Targeting BCMA in Multiple Myeloma. Cancer-Targeted Gene and Cell Therapy I. May 1, 2014;22(Suppl 1):S104. Doi: doi.org/10.1016/ S1525-0016(16)35285-6. 1 page.
Piccione et al., A bispecific antibody targeting CD47 and CD20 selectively binds and eliminates dual antigen expressing lymphoma cells. MAbs. 2015;7(5):946-56. doi: 10.1080/19420862.2015. 1062192.
Pietsch et al., Anti-leukemic activity and tolerability of anti-human CD47 monoclonal antibodies. Blood Cancer Journal. 2017;7:e536. Doi: 10.1038/bcj.2017.7.
Schuepbach-Mallepell et al., Stoichiometry of Heteromeric BAFF and APRIL Cytokines Dictates Their Receptor Binding and Signaling Properties. J Biol Chem. Jun. 26, 2015;290(26):16330-42. doi: 10.1074/jbc.M115.661405. Epub May 7, 2015.

\* cited by examiner

| Legend | Population | Live cell % | % FITC positive |
|---|---|---|---|
| | Negative Control (PBS) | 71.54 | 27 |
| | B6H12 Control | 73.39 | 59 |
| | 1-1-A1 mAb | 77.51 | 74.63 |

SEQUENCE LISTING

<160> NUMBER OF SEQ ID NOS: 179

<210> SEQ ID NO 1
<211> LENGTH: 323
<212> TYPE: PRT
<213> ORGANISM: Homo sapiens
<220> FEATURE:
<223> OTHER INFORMATION: CD47 isoform OA3-323

<400> SEQUENCE: 1

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Lys
    290                 295                 300

Ala Val Glu Glu Pro Leu Asn Ala Phe Lys Glu Ser Lys Gly Met Met
305                 310                 315                 320

Asn Asp Glu

<210> SEQ ID NO 2
<211> LENGTH: 292
<212> TYPE: PRT
<213> ORGANISM: Homo sapiens

```
<220> FEATURE:
<223> OTHER INFORMATION: CD47 isoform OA3-293

<400> SEQUENCE: 2

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val
    290

<210> SEQ ID NO 3
<211> LENGTH: 305
<212> TYPE: PRT
<213> ORGANISM: Homo sapiens
<220> FEATURE:
<223> OTHER INFORMATION: CD47 isoform OA3-305

<400> SEQUENCE: 3

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
```

```
            35                  40                  45
Gln Asn Thr Thr Glu Val Tyr Val Lys Trp Lys Phe Lys Gly Arg Asp
     50                  55                  60
Ile Tyr Thr Phe Asp Gly Ala Leu Asn Lys Ser Thr Val Pro Thr Asp
 65                  70                  75                  80
Phe Ser Ser Ala Lys Ile Glu Val Ser Gln Leu Leu Lys Gly Asp Ala
                 85                  90                  95
Ser Leu Lys Met Asp Lys Ser Asp Ala Val Ser His Thr Gly Asn Tyr
            100                 105                 110
Thr Cys Glu Val Thr Glu Leu Thr Arg Glu Gly Glu Thr Ile Ile Glu
            115                 120                 125
Leu Lys Tyr Arg Val Val Ser Trp Phe Ser Pro Asn Glu Asn Ile Leu
        130                 135                 140
Ile Val Ile Phe Pro Ile Phe Ala Ile Leu Leu Phe Trp Gly Gln Phe
145                 150                 155                 160
Gly Ile Lys Thr Leu Lys Tyr Arg Ser Gly Gly Met Asp Glu Lys Thr
                165                 170                 175
Ile Ala Leu Leu Val Ala Gly Leu Val Ile Thr Val Ile Val Ile Val
            180                 185                 190
Gly Ala Ile Leu Phe Val Pro Gly Glu Tyr Ser Leu Lys Asn Ala Thr
        195                 200                 205
Gly Leu Gly Leu Ile Val Thr Ser Thr Gly Ile Leu Ile Leu Leu His
    210                 215                 220
Tyr Tyr Val Phe Ser Thr Ala Ile Gly Leu Thr Ser Phe Val Ile Ala
225                 230                 235                 240
Ile Leu Val Ile Gln Val Ile Ala Tyr Ile Leu Ala Val Val Gly Leu
                245                 250                 255
Ser Leu Cys Ile Ala Ala Cys Ile Pro Met His Gly Pro Leu Leu Ile
            260                 265                 270
Ser Gly Leu Ser Ile Leu Ala Leu Ala Gln Leu Leu Gly Leu Val Tyr
        275                 280                 285
Met Lys Phe Val Ala Ser Asn Gln Lys Thr Ile Gln Pro Pro Arg Asn
    290                 295                 300
Asn
305

<210> SEQ ID NO 4
<211> LENGTH: 311
<212> TYPE: PRT
<213> ORGANISM: Homo sapiens
<220> FEATURE:
<223> OTHER INFORMATION: CD47 isoform OA3-312

<400> SEQUENCE: 4

Met Trp Pro Leu Val Ala Ala Leu Leu Leu Gly Ser Ala Cys Cys Gly
 1               5                  10                  15
Ser Ala Gln Leu Leu Phe Asn Lys Thr Lys Ser Val Glu Phe Thr Phe
                20                  25                  30
Cys Asn Asp Thr Val Val Ile Pro Cys Phe Val Thr Asn Met Glu Ala
            35                  40                  45
Gln Asn Thr Thr Glu Val Tyr Val Lys Trp Lys Phe Lys Gly Arg Asp
     50                  55                  60
Ile Tyr Thr Phe Asp Gly Ala Leu Asn Lys Ser Thr Val Pro Thr Asp
 65                  70                  75                  80
Phe Ser Ser Ala Lys Ile Glu Val Ser Gln Leu Leu Lys Gly Asp Ala
```

```
                85                  90                  95
Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
            115                 120                 125

Leu Lys Tyr Arg Val Val Ser Trp Phe Ser Pro Asn Glu Asn Ile Leu
            130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
            195                 200                 205

Gly Leu Gly Leu Ile Val Thr Ser Thr Gly Ile Leu Ile Leu Leu His
            210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
            275                 280                 285

Met Lys Phe Val Ala Ser Asn Gln Lys Thr Ile Gln Pro Pro Arg Lys
            290                 295                 300

Ala Val Glu Glu Pro Leu Asn
305                 310

<210> SEQ ID NO 5
<211> LENGTH: 305
<212> TYPE: PRT
<213> ORGANISM: Homo sapiens
<220> FEATURE:
<223> OTHER INFORMATION: mature CD47 isoform OA3-323

<400> SEQUENCE: 5

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
            35                  40                  45

Thr Phe Asp Gly Ala Leu Asn Lys Ser Thr Val Pro Thr Asp Phe Ser
        50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Phe Ser Pro Asn Glu Asn Ile Leu Ile Val
            115                 120                 125

Ile Phe Pro Ile Phe Ala Ile Leu Leu Phe Trp Gly Gln Phe Gly Ile
```

```
            130                 135                 140
Lys Thr Leu Lys Tyr Arg Ser Gly Gly Met Asp Glu Lys Thr Ile Ala
145                 150                 155                 160

Leu Leu Val Ala Gly Leu Val Ile Thr Val Ile Val Ile Val Gly Ala
                165                 170                 175

Ile Leu Phe Val Pro Gly Glu Tyr Ser Leu Lys Asn Ala Thr Gly Leu
                180                 185                 190

Gly Leu Ile Val Thr Ser Thr Gly Ile Leu Ile Leu Leu His Tyr Tyr
                195                 200                 205

Val Phe Ser Thr Ala Ile Gly Leu Thr Ser Phe Val Ile Ala Ile Leu
210                 215                 220

Val Ile Gln Val Ile Ala Tyr Ile Leu Ala Val Val Gly Leu Ser Leu
225                 230                 235                 240

Cys Ile Ala Ala Cys Ile Pro Met His Gly Pro Leu Leu Ile Ser Gly
                245                 250                 255

Leu Ser Ile Leu Ala Leu Ala Gln Leu Leu Gly Leu Val Tyr Met Lys
                260                 265                 270

Phe Val Ala Ser Asn Gln Lys Thr Ile Gln Pro Pro Arg Lys Ala Val
                275                 280                 285

Glu Glu Pro Leu Asn Ala Phe Lys Glu Ser Lys Gly Met Met Asn Asp
        290                 295                 300

Glu
305

<210> SEQ ID NO 6
<211> LENGTH: 274
<212> TYPE: PRT
<213> ORGANISM: Homo sapiens
<220> FEATURE:
<223> OTHER INFORMATION: mature CD47 isoform OA3-293

<400> SEQUENCE: 6

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
                20                  25                  30

Thr Thr Glu Val Tyr Val Lys Trp Lys Phe Lys Gly Arg Asp Ile Tyr
                35                  40                  45

Thr Phe Asp Gly Ala Leu Asn Lys Ser Thr Val Pro Thr Asp Phe Ser
        50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
                100                 105                 110

Tyr Arg Val Val Ser Trp Phe Ser Pro Asn Glu Asn Ile Leu Ile Val
            115                 120                 125

Ile Phe Pro Ile Phe Ala Ile Leu Leu Phe Trp Gly Gln Phe Gly Ile
        130                 135                 140

Lys Thr Leu Lys Tyr Arg Ser Gly Gly Met Asp Glu Lys Thr Ile Ala
145                 150                 155                 160

Leu Leu Val Ala Gly Leu Val Ile Thr Val Ile Val Ile Val Gly Ala
                165                 170                 175

Ile Leu Phe Val Pro Gly Glu Tyr Ser Leu Lys Asn Ala Thr Gly Leu
```

```
                180                 185                 190

Gly Leu Ile Val Thr Ser Thr Gly Ile Leu Ile Leu Leu His Tyr Tyr
            195                 200                 205

Val Phe Ser Thr Ala Ile Gly Leu Thr Ser Phe Val Ile Ala Ile Leu
        210                 215                 220

Val Ile Gln Val Ile Ala Tyr Ile Leu Ala Val Val Gly Leu Ser Leu
225                 230                 235                 240

Cys Ile Ala Ala Cys Ile Pro Met His Gly Pro Leu Leu Ile Ser Gly
                245                 250                 255

Leu Ser Ile Leu Ala Leu Ala Gln Leu Leu Gly Leu Val Tyr Met Lys
            260                 265                 270

Phe Val

<210> SEQ ID NO 7
<211> LENGTH: 287
<212> TYPE: PRT
<213> ORGANISM: Homo sapiens
<220> FEATURE:
<223> OTHER INFORMATION: mature CD47 isoform OA3-305

<400> SEQUENCE: 7

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Phe Ser Pro Asn Glu Asn Ile Leu Ile Val
        115                 120                 125

Ile Phe Pro Ile Phe Ala Ile Leu Leu Phe Trp Gly Gln Phe Gly Ile
    130                 135                 140

Lys Thr Leu Lys Tyr Arg Ser Gly Gly Met Asp Glu Lys Thr Ile Ala
145                 150                 155                 160

Leu Leu Val Ala Gly Leu Val Ile Thr Val Ile Val Ile Val Gly Ala
                165                 170                 175

Ile Leu Phe Val Pro Gly Glu Tyr Ser Leu Lys Asn Ala Thr Gly Leu
            180                 185                 190

Gly Leu Ile Val Thr Ser Thr Gly Ile Leu Ile Leu Leu His Tyr Tyr
        195                 200                 205

Val Phe Ser Thr Ala Ile Gly Leu Thr Ser Phe Val Ile Ala Ile Leu
    210                 215                 220

Val Ile Gln Val Ile Ala Tyr Ile Leu Ala Val Val Gly Leu Ser Leu
225                 230                 235                 240

Cys Ile Ala Ala Cys Ile Pro Met His Gly Pro Leu Leu Ile Ser Gly
                245                 250                 255

Leu Ser Ile Leu Ala Leu Ala Gln Leu Leu Gly Leu Val Tyr Met Lys
            260                 265                 270
```

```
Phe Val Ala Ser Asn Gln Lys Thr Ile Gln Pro Pro Arg Asn Asn
            275                 280                 285

<210> SEQ ID NO 8
<211> LENGTH: 293
<212> TYPE: PRT
<213> ORGANISM: Homo sapiens
<220> FEATURE:
<223> OTHER INFORMATION: mature CD47 isoform OA3-312

<400> SEQUENCE: 8

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Phe Ser Pro Asn Glu Asn Ile Leu Ile Val
        115                 120                 125

Ile Phe Pro Ile Phe Ala Ile Leu Leu Phe Trp Gly Gln Phe Gly Ile
    130                 135                 140

Lys Thr Leu Lys Tyr Arg Ser Gly Gly Met Asp Glu Lys Thr Ile Ala
145                 150                 155                 160

Leu Leu Val Ala Gly Leu Val Ile Thr Val Ile Val Ile Val Gly Ala
                165                 170                 175

Ile Leu Phe Val Pro Gly Glu Tyr Ser Leu Lys Asn Ala Thr Gly Leu
            180                 185                 190

Gly Leu Ile Val Thr Ser Thr Gly Ile Leu Ile Leu Leu His Tyr Tyr
        195                 200                 205

Val Phe Ser Thr Ala Ile Gly Leu Thr Ser Phe Val Ile Ala Ile Leu
    210                 215                 220

Val Ile Gln Val Ile Ala Tyr Ile Leu Ala Val Val Gly Leu Ser Leu
225                 230                 235                 240

Cys Ile Ala Ala Cys Ile Pro Met His Gly Pro Leu Leu Ile Ser Gly
                245                 250                 255

Leu Ser Ile Leu Ala Leu Ala Gln Leu Leu Gly Leu Val Tyr Met Lys
            260                 265                 270

Phe Val Ala Ser Asn Gln Lys Thr Ile Gln Pro Pro Arg Lys Ala Val
        275                 280                 285

Glu Glu Pro Leu Asn
    290

<210> SEQ ID NO 9
<211> LENGTH: 109
<212> TYPE: PRT
<213> ORGANISM: Artificial Sequence
<220> FEATURE:
<223> OTHER INFORMATION: Synthetic-V-type Ig-like domain
```

```
<400> SEQUENCE: 9

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile
            100                 105

<210> SEQ ID NO 10
<211> LENGTH: 123
<212> TYPE: PRT
<213> ORGANISM: Homo sapiens
<220> FEATURE:
<223> OTHER INFORMATION: CD47 extracellular region 1

<400> SEQUENCE: 10

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Phe Ser Pro Asn Glu
        115                 120

<210> SEQ ID NO 11
<211> LENGTH: 21
<212> TYPE: PRT
<213> ORGANISM: Homo sapiens
<220> FEATURE:
<223> OTHER INFORMATION: CD47 transmembrane region 1

<400> SEQUENCE: 11

Asn Ile Leu Ile Val Ile Phe Pro Ile Phe Ala Ile Leu Leu Phe Trp
1               5                   10                  15

Gly Gln Phe Gly Ile
            20

<210> SEQ ID NO 12
<211> LENGTH: 14
<212> TYPE: PRT
<213> ORGANISM: Homo sapiens
<220> FEATURE:
```

<223> OTHER INFORMATION: CD47 cytoplasmic region 1

<400> SEQUENCE: 12

Lys Thr Leu Lys Tyr Arg Ser Gly Gly Met Asp Glu Lys Thr
1               5                   10

<210> SEQ ID NO 13
<211> LENGTH: 21
<212> TYPE: PRT
<213> ORGANISM: Homo sapiens
<220> FEATURE:
<223> OTHER INFORMATION: CD47 transmembrane region 2

<400> SEQUENCE: 13

Ile Ala Leu Leu Val Ala Gly Leu Val Ile Thr Val Ile Val
1               5                   10                  15

Gly Ala Ile Leu Phe
            20

<210> SEQ ID NO 14
<211> LENGTH: 10
<212> TYPE: PRT
<213> ORGANISM: Homo sapiens
<220> FEATURE:
<223> OTHER INFORMATION: CD47 extracellular region 2

<400> SEQUENCE: 14

Val Pro Gly Glu Tyr Ser Leu Lys Asn Ala
1               5                   10

<210> SEQ ID NO 15
<211> LENGTH: 21
<212> TYPE: PRT
<213> ORGANISM: Homo sapiens
<220> FEATURE:
<223> OTHER INFORMATION: CD47 transmembrane region 3

<400> SEQUENCE: 15

Thr Gly Leu Gly Leu Ile Val Thr Ser Thr Gly Ile Leu Ile Leu Leu
1               5                   10                  15

His Tyr Tyr Val Phe
            20

<210> SEQ ID NO 16
<211> LENGTH: 7
<212> TYPE: PRT
<213> ORGANISM: Homo sapiens
<220> FEATURE:
<223> OTHER INFORMATION: CD47 cytoplasmic region 2

<400> SEQUENCE: 16

Ser Thr Ala Ile Gly Leu Thr
1               5

<210> SEQ ID NO 17
<211> LENGTH: 21
<212> TYPE: PRT
<213> ORGANISM: Homo sapiens
<220> FEATURE:
<223> OTHER INFORMATION: CD47 transmembrane region 4

<400> SEQUENCE: 17

Ser Phe Val Ile Ala Ile Leu Val Ile Gln Val Ile Ala Tyr Ile Leu
1               5                   10                  15

Ala Val Val Gly Leu

20

<210> SEQ ID NO 18
<211> LENGTH: 12
<212> TYPE: PRT
<213> ORGANISM: Homo sapiens
<220> FEATURE:
<223> OTHER INFORMATION: CD47 extracellular region 3

<400> SEQUENCE: 18

Ser Leu Cys Ile Ala Ala Cys Ile Pro Met His Gly
1               5                   10

<210> SEQ ID NO 19
<211> LENGTH: 21
<212> TYPE: PRT
<213> ORGANISM: Homo sapiens
<220> FEATURE:
<223> OTHER INFORMATION: CD47 transmembrane region 5

<400> SEQUENCE: 19

Pro Leu Leu Ile Ser Gly Leu Ser Ile Leu Ala Leu Ala Gln Leu Leu
1               5                   10                  15

Gly Leu Val Tyr Met
            20

<210> SEQ ID NO 20
<211> LENGTH: 34
<212> TYPE: PRT
<213> ORGANISM: Homo sapiens
<220> FEATURE:
<223> OTHER INFORMATION: CD47 cytoplasmic region 3

<400> SEQUENCE: 20

Lys Phe Val Ala Ser Asn Gln Lys Thr Ile Gln Pro Pro Arg Lys Ala
1               5                   10                  15

Val Glu Glu Pro Leu Asn Ala Phe Lys Glu Ser Lys Gly Met Met Asn
            20                  25                  30

Asp Glu

<210> SEQ ID NO 21
<211> LENGTH: 10
<212> TYPE: PRT
<213> ORGANISM: Homo sapiens
<220> FEATURE:
<223> OTHER INFORMATION: CD47 region targeted by 1-1-A1 and 1-1-A1_BM

<400> SEQUENCE: 21

Val Lys Trp Lys Phe Lys Gly Arg Asp Ile
1               5                   10

<210> SEQ ID NO 22
<211> LENGTH: 11
<212> TYPE: PRT
<213> ORGANISM: Homo sapiens
<220> FEATURE:
<223> OTHER INFORMATION: CD47 region targeted by 5-48-A6 and 5-48-D2

<400> SEQUENCE: 22

Lys Thr Lys Ser Val Glu Phe Thr Phe Cys Asn
1               5                   10

<210> SEQ ID NO 23
<211> LENGTH: 117
<212> TYPE: PRT

<213> ORGANISM: Artificial Sequence
<220> FEATURE:
<223> OTHER INFORMATION: Synthetic-1-1-A1_BM heavy chain variable region

<400> SEQUENCE: 23

Gln Val Gln Leu Gln Gln Ser Gly Pro Asp Leu Lys Lys Pro Gly Ala
1               5                   10                  15

Ser Val Lys Val Ser Cys Lys Val Ser Gly Tyr Thr Phe Thr Asn Tyr
                20                  25                  30

Val Ile His Trp Val Arg Gln Lys Pro Gly Gln Gly Leu Glu Trp Met
            35                  40                  45

Gly Tyr Ile Asn Pro Tyr Asn Asp Gly Thr Lys Ser Asn Glu Lys Phe
        50                  55                  60

Lys Gly Lys Ala Thr Leu Thr Ser Asp Lys Ser Ser Thr Ser Ala Tyr
65                  70                  75                  80

Met Glu Leu Ser Ser Leu Thr Ser Glu Asp Thr Ala Val Tyr Tyr Cys
                85                  90                  95

Ala Ser Gly Gly Tyr Tyr Thr Met Asp Tyr Trp Gly Gln Gly Thr Ser
            100                 105                 110

Val Thr Val Ser Ser
        115

<210> SEQ ID NO 24
<211> LENGTH: 8
<212> TYPE: PRT
<213> ORGANISM: Artificial Sequence
<220> FEATURE:
<223> OTHER INFORMATION: Synthetic-1-1-A1_BM, Synthetic-1-1-A1,
      Synthetic-11A1H1, Synthetic-11A1H2, Synthetic-11A1H3, Synthetic-
      11A1H4, Synthetic-11A1H6, Synthetic-11A1H8 heavy chain CDR1

<400> SEQUENCE: 24

Gly Tyr Thr Phe Thr Asn Tyr Val
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic-1-1-A1_BM, Synthetic-1-1-A1,
      Synthetic-11A1H1, Synthetic-11A1H2, Synthetic-11A1H3, Synthetic-
      11A1H4, Synthetic-11A1H6, Synthetic-11A1H8 heavy chain CDR2

<400> SEQUENCE: 25

Ile Asn Pro Tyr Asn Asp Gly Thr
1               5

<210> SEQ ID NO 26
<211> LENGTH: 10
<212> TYPE: PRT
<213> ORGANISM: Artificial Sequence
<220> FEATURE:
<223> OTHER INFORMATION: Synthetic-1-1-A1_BM, Synthetic-1-1-A1,
      Synthetic-11A1H1, Synthetic-11A1H2, Synthetic-11A1H3, Synthetic-
      11A1H4, Synthetic-11A1H6, Synthetic-11A1H8, Synthetic-11A1H5,
      Synthetic-11A1H7, Synthetic-11A1H9, Synthetic-11A1H10, Synthetic-
      11A1H11 heavy chain CDR3

<400> SEQUENCE: 26

Ala Ser Gly Gly Tyr Tyr Thr Met Asp Tyr
1               5                   10

<210> SEQ ID NO 27

```
<211> LENGTH: 25
<212> TYPE: PRT
<213> ORGANISM: Artificial Sequence
<220> FEATURE:
<223> OTHER INFORMATION: Synthetic-1-1-A1_BM heavy chain FR1

<400> SEQUENCE: 27

Gln Val Gln Leu Gln Gln Ser Gly Pro Asp Leu Lys Lys Pro Gly Ala
1               5                   10                  15

Ser Val Lys Val Ser Cys Lys Val Ser
            20                  25

<210> SEQ ID NO 28
<211> LENGTH: 17
<212> TYPE: PRT
<213> ORGANISM: Artificial Sequence
<220> FEATURE:
<223> OTHER INFORMATION: Synthetic-1-1-A1_BM heavy chain FR2

<400> SEQUENCE: 28

Ile His Trp Val Arg Gln Lys Pro Gly Gln Gly Leu Glu Trp Met Gly
1               5                   10                  15

Tyr

<210> SEQ ID NO 29
<211> LENGTH: 38
<212> TYPE: PRT
<213> ORGANISM: Artificial Sequence
<220> FEATURE:
<223> OTHER INFORMATION: Synthetic-1-1-A1_BM heavy chain FR3

<400> SEQUENCE: 29

Lys Ser Asn Glu Lys Phe Lys Gly Lys Ala Thr Leu Thr Ser Asp Lys
1               5                   10                  15

Ser Ser Thr Ser Ala Tyr Met Glu Leu Ser Ser Leu Thr Ser Glu Asp
            20                  25                  30

Thr Ala Val Tyr Tyr Cys
            35

<210> SEQ ID NO 30
<211> LENGTH: 11
<212> TYPE: PRT
<213> ORGANISM: Artificial Sequence
<220> FEATURE:
<223> OTHER INFORMATION: Synthetic-1-1-A1_BM heavy chain FR4

<400> SEQUENCE: 30

Trp Gly Gln Gly Thr Ser Val Thr Val Ser Ser
1               5                   10

<210> SEQ ID NO 31
<211> LENGTH: 112
<212> TYPE: PRT
<213> ORGANISM: Artificial Sequence
<220> FEATURE:
<223> OTHER INFORMATION: Synthetic-1-1-A1_BM light chain variable region

<400> SEQUENCE: 31

Asp Val Val Met Thr Gln Thr Pro Leu Ser Leu Pro Val Thr Leu Gly
1               5                   10                  15

Asp Gln Ala Ser Ile Ser Cys Arg Ser Ser Gln His Leu Glu Tyr Ser
            20                  25                  30

Asn Gly Tyr Ser Tyr Leu His Trp Tyr Gln Gln Arg Pro Gly Gln Ser
        35                  40                  45
```

```
Pro Gln Leu Leu Ile Tyr Lys Ile Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Ser Gln Ser
                85                  90                  95

Thr His Val Pro Tyr Thr Phe Gly Gly Gly Thr Lys Leu Glu Ile Lys
            100                 105                 110
```

<210> SEQ ID NO 32
<211> LENGTH: 11
<212> TYPE: PRT
<213> ORGANISM: Artificial Sequence
<220> FEATURE:
<223> OTHER INFORMATION: Synthetic-1-1-A1_BM, Synthetic-1-1-A1,
      Synthetic-11A1H1, Synthetic-11A1H2, Synthetic-11A1H3, Synthetic-
      11A1H4, Synthetic-11A1H5, Synthetic-11A1H10, Synthetic-11A1H11
      light chain CDR1

<400> SEQUENCE: 32

```
Gln His Leu Glu Tyr Ser Asn Gly Tyr Ser Tyr
1               5                   10
```

<210> SEQ ID NO 33
<211> LENGTH: 3
<212> TYPE: PRT
<213> ORGANISM: Artificial Sequence
<220> FEATURE:
<223> OTHER INFORMATION: Synthetic-1-1-A1_BM, Synthetic-1-1-A1,
      Synthetic-11A1H1, Synthetic-11A1H2, Synthetic-11A1H3, Synthetic-
      11A1H4, Synthetic-11A1H5, Synthetic-11A1H11 light chain CDR2

<400> SEQUENCE: 33

```
Lys Ile Ser
1
```

<210> SEQ ID NO 34
<211> LENGTH: 9
<212> TYPE: PRT
<213> ORGANISM: Artificial Sequence
<220> FEATURE:
<223> OTHER INFORMATION: Synthetic-1-1-A1_BM, Synthetic-1-1-A1,
      Synthetic-11A1H1, Synthetic-11A1H2, Synthetic-11A1H3, Synthetic-
      11A1H4, Synthetic-11A1H5, Synthetic-11A1H6, Synthetic-11A1H7
      11A1H8, Synthetic-11A1H9 11A1H10 light chain CDR3

<400> SEQUENCE: 34

```
Ser Gln Ser Thr His Val Pro Tyr Thr
1               5
```

<210> SEQ ID NO 35
<211> LENGTH: 26
<212> TYPE: PRT
<213> ORGANISM: Artificial Sequence
<220> FEATURE:
<223> OTHER INFORMATION: Synthetic-1-1-A1_BM light chain FR1

<400> SEQUENCE: 35

```
Asp Val Val Met Thr Gln Thr Pro Leu Ser Leu Pro Val Thr Leu Gly
1               5                   10                  15

Asp Gln Ala Ser Ile Ser Cys Arg Ser
            20                  25
```

<210> SEQ ID NO 36
<211> LENGTH: 17

```
<212> TYPE: PRT
<213> ORGANISM: Artificial Sequence
<220> FEATURE:
<223> OTHER INFORMATION: Synthetic-1-1-A1_BM light chain FR2

<400> SEQUENCE: 36

Leu His Trp Tyr Gln Gln Arg Pro Gly Gln Ser Pro Gln Leu Leu Ile
1               5                   10                  15

Tyr

<210> SEQ ID NO 37
<211> LENGTH: 36
<212> TYPE: PRT
<213> ORGANISM: Artificial Sequence
<220> FEATURE:
<223> OTHER INFORMATION: Synthetic-1-1-A1_BM light chain FR3

<400> SEQUENCE: 37

Asn Arg Phe Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Leu Gly
            20                  25                  30

Val Tyr Tyr Cys
        35

<210> SEQ ID NO 38
<211> LENGTH: 10
<212> TYPE: PRT
<213> ORGANISM: Artificial Sequence
<220> FEATURE:
<223> OTHER INFORMATION: Synthetic-1-1-A1_BM light chain FR4

<400> SEQUENCE: 38

Phe Gly Gly Gly Thr Lys Leu Glu Ile Lys
1               5                   10

<210> SEQ ID NO 39
<211> LENGTH: 117
<212> TYPE: PRT
<213> ORGANISM: Artificial Sequence
<220> FEATURE:
<223> OTHER INFORMATION: Synthetic-1-1-A1 heavy chain variable region

<400> SEQUENCE: 39

Glu Val Gln Leu Gln Gln Ser Gly Pro Asp Leu Val Lys Pro Gly Ala
1               5                   10                  15

Ser Val Lys Met Ser Cys Lys Ala Ser Gly Tyr Thr Phe Thr Asn Tyr
            20                  25                  30

Val Ile His Trp Val Lys Gln Lys Pro Gly Gln Gly Leu Glu Trp Ile
        35                  40                  45

Gly Tyr Ile Asn Pro Tyr Asn Asp Gly Thr Lys Ser Asn Glu Lys Phe
    50                  55                  60

Lys Gly Lys Ala Thr Leu Thr Ser Asp Lys Ser Ser Thr Ser Ala Tyr
65                  70                  75                  80

Met Glu Leu Ser Ser Leu Thr Ser Glu Asp Ser Ala Val Tyr Tyr Cys
                85                  90                  95

Ala Ser Gly Gly Tyr Tyr Thr Met Asp Tyr Trp Gly Gln Gly Thr Ser
            100                 105                 110

Val Thr Val Ser Ser
        115
```

-continued

```
<210> SEQ ID NO 40
<211> LENGTH: 25
<212> TYPE: PRT
<213> ORGANISM: Artificial Sequence
<220> FEATURE:
<223> OTHER INFORMATION: Synthetic-1-1-A1 heavy chain FR1

<400> SEQUENCE: 40

Glu Val Gln Leu Gln Gln Ser Gly Pro Asp Leu Val Lys Pro Gly Ala
1               5                   10                  15

Ser Val Lys Met Ser Cys Lys Ala Ser
            20                  25

<210> SEQ ID NO 41
<211> LENGTH: 17
<212> TYPE: PRT
<213> ORGANISM: Artificial Sequence
<220> FEATURE:
<223> OTHER INFORMATION: Synthetic-1-1-A1 heavy chain FR2

<400> SEQUENCE: 41

Ile His Trp Val Lys Gln Lys Pro Gly Gln Gly Leu Glu Trp Ile Gly
1               5                   10                  15

Tyr

<210> SEQ ID NO 42
<211> LENGTH: 38
<212> TYPE: PRT
<213> ORGANISM: Artificial Sequence
<220> FEATURE:
<223> OTHER INFORMATION: Synthetic-1-1-A1 heavy chain FR3

<400> SEQUENCE: 42

Lys Ser Asn Glu Lys Phe Lys Gly Lys Ala Thr Leu Thr Ser Asp Lys
1               5                   10                  15

Ser Ser Thr Ser Ala Tyr Met Glu Leu Ser Ser Leu Thr Ser Glu Asp
            20                  25                  30

Ser Ala Val Tyr Tyr Cys
        35

<210> SEQ ID NO 43
<211> LENGTH: 11
<212> TYPE: PRT
<213> ORGANISM: Artificial Sequence
<220> FEATURE:
<223> OTHER INFORMATION: Synthetic-1-1-A1 heavy chain FR4

<400> SEQUENCE: 43

Trp Gly Gln Gly Thr Ser Val Thr Val Ser Ser
1               5                   10

<210> SEQ ID NO 44
<211> LENGTH: 112
<212> TYPE: PRT
<213> ORGANISM: Artificial Sequence
<220> FEATURE:
<223> OTHER INFORMATION: Synthetic-1-1-A1 light chain variable region

<400> SEQUENCE: 44

Asp Val Val Met Thr Gln Thr Pro Leu Ser Leu Pro Val Ser Leu Gly
1               5                   10                  15

Asp Gln Ala Ser Ile Ser Cys Arg Ser Ser Gln His Leu Glu Tyr Ser
            20                  25                  30

Asn Gly Tyr Ser Tyr Leu His Trp Tyr Leu Gln Lys Pro Gly Gln Ser
```

```
                35                  40                  45
Pro Gln Leu Leu Ile Tyr Lys Ile Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Tyr Thr Phe Gly Gly Gly Thr Lys Leu Glu Ile Lys
            100                 105                 110
```

<210> SEQ ID NO 45
<211> LENGTH: 26
<212> TYPE: PRT
<213> ORGANISM: Artificial Sequence
<220> FEATURE:
<223> OTHER INFORMATION: Synthetic-1-1-A1 light chain FR1

<400> SEQUENCE: 45

```
Asp Val Val Met Thr Gln Thr Pro Leu Ser Leu Pro Val Ser Leu Gly
 1               5                  10                  15

Asp Gln Ala Ser Ile Ser Cys Arg Ser Ser
             20                  25
```

<210> SEQ ID NO 46
<211> LENGTH: 17
<212> TYPE: PRT
<213> ORGANISM: Artificial Sequence
<220> FEATURE:
<223> OTHER INFORMATION: Synthetic-1-1-A1 light chain FR2

<400> SEQUENCE: 46

```
Leu His Trp Tyr Leu Gln Lys Pro Gly Gln Ser Pro Gln Leu Leu Ile
 1               5                  10                  15

Tyr
```

<210> SEQ ID NO 47
<211> LENGTH: 36
<212> TYPE: PRT
<213> ORGANISM: Artificial Sequence
<220> FEATURE:
<223> OTHER INFORMATION: Synthetic-1-1-A1 light chain FR3

<400> SEQUENCE: 47

```
Asn Arg Phe Ser Gly Val Pro Asp Arg Phe Ser Gly Ser Gly Ser Gly
 1               5                  10                  15

Thr Asp Phe Thr Leu Lys Ile Ser Arg Val Glu Ala Glu Asp Leu Gly
             20                  25                  30

Val Tyr Phe Cys
         35
```

<210> SEQ ID NO 48
<211> LENGTH: 10
<212> TYPE: PRT
<213> ORGANISM: Artificial Sequence
<220> FEATURE:
<223> OTHER INFORMATION: Synthetic-1-1-A1 light chain FR4

<400> SEQUENCE: 48

```
Phe Gly Gly Gly Thr Lys Leu Glu Ile Lys
 1               5                  10
```

<210> SEQ ID NO 49

```
<211> LENGTH: 123
<212> TYPE: PRT
<213> ORGANISM: Artificial Sequence
<220> FEATURE:
<223> OTHER INFORMATION: Synthetic-5-48-A6 heavy chain variable region

<400> SEQUENCE: 49

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Val Pro Thr Gly Arg Ile Lys Ser Tyr Phe Tyr Ala Met Asp Tyr
            100                 105                 110

Trp Gly Gln Gly Thr Ser Val Thr Val Ser Ser
        115                 120

<210> SEQ ID NO 50
<211> LENGTH: 8
<212> TYPE: PRT
<213> ORGANISM: Artificial Sequence
<220> FEATURE:
<223> OTHER INFORMATION: Synthetic-5-48-A6 heavy chain CDR1

<400> SEQUENCE: 50

Gly Phe Ser Leu Thr Ser Tyr Gly
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic-5-48-A6 heavy chain CDR2

<400> SEQUENCE: 51

Ile Trp Ala Gly Gly Ser Thr
1               5

<210> SEQ ID NO 52
<211> LENGTH: 17
<212> TYPE: PRT
<213> ORGANISM: Artificial Sequence
<220> FEATURE:
<223> OTHER INFORMATION: Synthetic-5-48-A6 heavy chain CDR3

<400> SEQUENCE: 52

Ala Arg Val Pro Thr Gly Arg Ile Lys Ser Tyr Phe Tyr Ala Met Asp
1               5                   10                  15

Tyr

<210> SEQ ID NO 53
<211> LENGTH: 25
<212> TYPE: PRT
<213> ORGANISM: Artificial Sequence
<220> FEATURE:
```

```
<223> OTHER INFORMATION: Synthetic-5-48-A6 heavy chain FR1

<400> SEQUENCE: 53

Gln Val Gln Leu Lys Glu Ser Gly Pro Gly Leu Val Ala Pro Ser Gln
1               5                   10                  15

Ser Leu Ser Ile Thr Cys Thr Val Ser
            20                  25

<210> SEQ ID NO 54
<211> LENGTH: 17
<212> TYPE: PRT
<213> ORGANISM: Artificial Sequence
<220> FEATURE:
<223> OTHER INFORMATION: Synthetic-5-48-A6 heavy chain FR2

<400> SEQUENCE: 54

Val His Trp Val Arg Gln Pro Pro Gly Lys Gly Leu Glu Trp Leu Gly
1               5                   10                  15

Val

<210> SEQ ID NO 55
<211> LENGTH: 38
<212> TYPE: PRT
<213> ORGANISM: Artificial Sequence
<220> FEATURE:
<223> OTHER INFORMATION: Synthetic-5-48-A6 heavy chain FR3

<400> SEQUENCE: 55

Asn Tyr Asn Ser Ala Leu Met Ser Arg Leu Ser Ile Ser Lys Asp Asn
1               5                   10                  15

Ser Lys Ser Gln Val Phe Leu Lys Met Asn Ser Leu Gln Thr Asp Asp
            20                  25                  30

Thr Ala Met Tyr Tyr Cys
        35

<210> SEQ ID NO 56
<211> LENGTH: 11
<212> TYPE: PRT
<213> ORGANISM: Artificial Sequence
<220> FEATURE:
<223> OTHER INFORMATION: Synthetic-5-48-A6 heavy chain FR4

<400> SEQUENCE: 56

Trp Gly Gln Gly Thr Ser Val Thr Val Ser Ser
1               5                   10

<210> SEQ ID NO 57
<211> LENGTH: 107
<212> TYPE: PRT
<213> ORGANISM: Artificial Sequence
<220> FEATURE:
<223> OTHER INFORMATION: Synthetic-5-48-A6 light chain variable region

<400> SEQUENCE: 57

Asp Ile Lys Met Thr Gln Ser Pro Ser Ser Met Tyr Ser Ser Leu Gly
1               5                   10                  15

Glu Arg Val Thr Ile Thr Cys Lys Ala Ser Gln Asp Ile Ser Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60
```

```
Ser Gly Ser Gly Gln Asp Tyr Ser Leu Thr Ile Ser Ser Leu Glu Tyr
 65                  70                  75                  80

Glu Asp Met Gly Ile Tyr Tyr Cys Leu Gln Tyr Asp Glu Phe Pro Tyr
                 85                  90                  95

Thr Phe Gly Gly Gly Thr Lys Leu Glu Ile Lys
            100                 105

<210> SEQ ID NO 58
<211> LENGTH: 6
<212> TYPE: PRT
<213> ORGANISM: Artificial Sequence
<220> FEATURE:
<223> OTHER INFORMATION: Synthetic-5-48-A6 light chain CDR1

<400> SEQUENCE: 58

Gln Asp Ile Ser Ser Tyr
1               5

<210> SEQ ID NO 59
<211> LENGTH: 3
<212> TYPE: PRT
<213> ORGANISM: Artificial Sequence
<220> FEATURE:
<223> OTHER INFORMATION: Synthetic-5-48-A6 light chain CDR2

<400> SEQUENCE: 59

Arg Ala Asn
1

<210> SEQ ID NO 60
<211> LENGTH: 9
<212> TYPE: PRT
<213> ORGANISM: Artificial Sequence
<220> FEATURE:
<223> OTHER INFORMATION: Synthetic-5-48-A6 light chain CDR3

<400> SEQUENCE: 60

Leu Gln Tyr Asp Glu Phe Pro Tyr Thr
1               5

<210> SEQ ID NO 61
<211> LENGTH: 26
<212> TYPE: PRT
<213> ORGANISM: Artificial Sequence
<220> FEATURE:
<223> OTHER INFORMATION: Synthetic-5-48-A6 light chain FR1

<400> SEQUENCE: 61

Asp Ile Lys Met Thr Gln Ser Pro Ser Ser Met Tyr Ser Ser Leu Gly
1               5                   10                  15

Glu Arg Val Thr Ile Thr Cys Lys Ala Ser
            20                  25

<210> SEQ ID NO 62
<211> LENGTH: 17
<212> TYPE: PRT
<213> ORGANISM: Artificial Sequence
<220> FEATURE:
<223> OTHER INFORMATION: Synthetic-5-48-A6 light chain FR2

<400> SEQUENCE: 62

Leu Ser Trp Phe Gln Gln Lys Pro Gly Lys Ser Pro Lys Thr Leu Ile
1               5                   10                  15

Tyr
```

<210> SEQ ID NO 63
<211> LENGTH: 36
<212> TYPE: PRT
<213> ORGANISM: Artificial Sequence
<220> FEATURE:
<223> OTHER INFORMATION: Synthetic-5-48-A6 light chain FR3

<400> SEQUENCE: 63

```
Arg Leu Val Asp Gly Val Pro Ser Arg Phe Ser Gly Ser Gly Ser Gly
1               5                   10                  15

Gln Asp Tyr Ser Leu Thr Ile Ser Ser Leu Glu Tyr Glu Asp Met Gly
            20                  25                  30

Ile Tyr Tyr Cys
            35
```

<210> SEQ ID NO 64
<211> LENGTH: 10
<212> TYPE: PRT
<213> ORGANISM: Artificial Sequence
<220> FEATURE:
<223> OTHER INFORMATION: Synthetic-5-48-A6 light chain FR4

<400> SEQUENCE: 64

```
Phe Gly Gly Gly Thr Lys Leu Glu Ile Lys
1               5                   10
```

<210> SEQ ID NO 65
<211> LENGTH: 115
<212> TYPE: PRT
<213> ORGANISM: Artificial Sequence
<220> FEATURE:
<223> OTHER INFORMATION: Synthetic-5-48-D2 heavy chain variable region

<400> SEQUENCE: 65

```
Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Thr Gly Thr Gly Phe Ala Tyr Trp Gly Gln Gly Thr Leu Val Thr
            100                 105                 110

Val Ser Ala
        115
```

<210> SEQ ID NO 66
<211> LENGTH: 8
<212> TYPE: PRT
<213> ORGANISM: Artificial Sequence
<220> FEATURE:
<223> OTHER INFORMATION: Synthetic-5-48-D2 heavy chain CDR1

<400> SEQUENCE: 66

```
Gly Phe Asp Phe Ser Arg Tyr Trp
1               5
```

-continued

<210> SEQ ID NO 67
<211> LENGTH: 8
<212> TYPE: PRT
<213> ORGANISM: Artificial Sequence
<220> FEATURE:
<223> OTHER INFORMATION: Synthetic-5-48-D2 heavy chain CDR2

<400> SEQUENCE: 67

Ile Asn Pro Asp Ser Ser Thr Ile
1               5

<210> SEQ ID NO 68
<211> LENGTH: 8
<212> TYPE: PRT
<213> ORGANISM: Artificial Sequence
<220> FEATURE:
<223> OTHER INFORMATION: Synthetic-5-48-D2 heavy chain CDR3

<400> SEQUENCE: 68

Ala Thr Gly Thr Gly Phe Ala Tyr
1               5

<210> SEQ ID NO 69
<211> LENGTH: 25
<212> TYPE: PRT
<213> ORGANISM: Artificial Sequence
<220> FEATURE:
<223> OTHER INFORMATION: Synthetic-5-48-D2 heavy chain FR1

<400> SEQUENCE: 69

Glu Val Lys Leu Leu Glu Ser Gly Gly Gly Leu Val Gln Pro Gly Gly
1               5                   10                  15

Ser Leu Lys Leu Ser Cys Ala Ala Ser
            20                  25

<210> SEQ ID NO 70
<211> LENGTH: 17
<212> TYPE: PRT
<213> ORGANISM: Artificial Sequence
<220> FEATURE:
<223> OTHER INFORMATION: Synthetic-5-48-D2 heavy chain FR2

<400> SEQUENCE: 70

Met Ser Trp Val Arg Gln Ala Pro Gly Lys Gly Leu Glu Trp Ile Gly
1               5                   10                  15

Glu

<210> SEQ ID NO 71
<211> LENGTH: 38
<212> TYPE: PRT
<213> ORGANISM: Artificial Sequence
<220> FEATURE:
<223> OTHER INFORMATION: Synthetic-5-48-D2 heavy chain FR3

<400> SEQUENCE: 71

Asn Tyr Thr Pro Ser Leu Lys Asp Lys Phe Ile Ile Ser Arg Asp Asn
1               5                   10                  15

Ala Lys Asn Thr Leu Tyr Leu Gln Met Ser Lys Val Arg Ser Glu Asp
            20                  25                  30

Thr Ala Leu Tyr Tyr Cys
            35

<210> SEQ ID NO 72
<211> LENGTH: 11

```
<212> TYPE: PRT
<213> ORGANISM: Artificial Sequence
<220> FEATURE:
<223> OTHER INFORMATION: Synthetic-5-48-D2 heavy chain FR4

<400> SEQUENCE: 72

Trp Gly Gln Gly Thr Leu Val Thr Val Ser Ala
1               5                   10

<210> SEQ ID NO 73
<211> LENGTH: 107
<212> TYPE: PRT
<213> ORGANISM: Artificial Sequence
<220> FEATURE:
<223> OTHER INFORMATION: Synthetic-5-48-D2 light chain variable region

<400> SEQUENCE: 73

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Val Thr Pro Trp
                85                  90                  95

Thr Phe Gly Gly Val Thr Lys Leu Glu Ile Lys
            100                 105

<210> SEQ ID NO 74
<211> LENGTH: 6
<212> TYPE: PRT
<213> ORGANISM: Artificial Sequence
<220> FEATURE:
<223> OTHER INFORMATION: Synthetic-5-48-D2 light chain CDR1

<400> SEQUENCE: 74

Glu Asn Ile Tyr Ser Tyr
1               5

<210> SEQ ID NO 75
<211> LENGTH: 3
<212> TYPE: PRT
<213> ORGANISM: Artificial Sequence
<220> FEATURE:
<223> OTHER INFORMATION: Synthetic-5-48-D2 light chain CDR2

<400> SEQUENCE: 75

Asn Ala Lys
1

<210> SEQ ID NO 76
<211> LENGTH: 9
<212> TYPE: PRT
<213> ORGANISM: Artificial Sequence
<220> FEATURE:
<223> OTHER INFORMATION: Synthetic-5-48-D2 light chain CDR3

<400> SEQUENCE: 76

Gln His His Tyr Val Thr Pro Trp Thr
1               5
```

<210> SEQ ID NO 77
<211> LENGTH: 26
<212> TYPE: PRT
<213> ORGANISM: Artificial Sequence
<220> FEATURE:
<223> OTHER INFORMATION: Synthetic-5-48-D2 light chain FR1

<400> SEQUENCE: 77

Asp Ile Gln Met Thr Gln Ser Pro Ala Ser Leu Ser Ala Ser Val Gly
1               5                   10                  15

Glu Thr Val Thr Ile Thr Cys Arg Ala Ser
            20                  25

<210> SEQ ID NO 78
<211> LENGTH: 17
<212> TYPE: PRT
<213> ORGANISM: Artificial Sequence
<220> FEATURE:
<223> OTHER INFORMATION: Synthetic-5-48-D2 light chain FR2

<400> SEQUENCE: 78

Leu Ala Trp Tyr Gln Gln Lys Gln Gly Lys Ser Pro Gln Leu Leu Val
1               5                   10                  15

Tyr

<210> SEQ ID NO 79
<211> LENGTH: 36
<212> TYPE: PRT
<213> ORGANISM: Artificial Sequence
<220> FEATURE:
<223> OTHER INFORMATION: Synthetic-5-48-D2 light chain FR3

<400> SEQUENCE: 79

Thr Leu Ala Glu Gly Val Pro Ser Arg Phe Ser Gly Ser Gly Ser Gly
1               5                   10                  15

Thr Gln Phe Ser Leu Lys Ile Asn Ser Leu Gln Pro Glu Asp Phe Gly
            20                  25                  30

Ser Tyr Tyr Cys
        35

<210> SEQ ID NO 80
<211> LENGTH: 10
<212> TYPE: PRT
<213> ORGANISM: Artificial Sequence
<220> FEATURE:
<223> OTHER INFORMATION: Synthetic-5-48-D2 light chain FR4

<400> SEQUENCE: 80

Phe Gly Gly Val Thr Lys Leu Glu Ile Lys
1               5                   10

<210> SEQ ID NO 81
<211> LENGTH: 19
<212> TYPE: PRT
<213> ORGANISM: Artificial Sequence
<220> FEATURE:
<223> OTHER INFORMATION: Synthetic-1-1-A1 heavy chain SignalP

<400> SEQUENCE: 81

Met Glu Trp Ser Trp Ile Phe Leu Phe Leu Leu Ser Gly Thr Ala Gly
1               5                   10                  15

Val His Ser

-continued

<210> SEQ ID NO 82
<211> LENGTH: 19
<212> TYPE: PRT
<213> ORGANISM: Artificial Sequence
<220> FEATURE:
<223> OTHER INFORMATION: Synthetic-1-1-A1 light chain SignalP

<400> SEQUENCE: 82

Met Lys Leu Pro Val Arg Leu Leu Val Leu Met Phe Trp Ile Pro Ala
1               5                   10                  15

Ser Ser Ser

<210> SEQ ID NO 83
<211> LENGTH: 19
<212> TYPE: PRT
<213> ORGANISM: Artificial Sequence
<220> FEATURE:
<223> OTHER INFORMATION: Synthetic-5-48-A6 heavy chain SignalP

<400> SEQUENCE: 83

Met Ala Val Leu Val Leu Phe Leu Cys Leu Val Ala Phe Pro Ser Cys
1               5                   10                  15

Val Leu Ser

<210> SEQ ID NO 84
<211> LENGTH: 20
<212> TYPE: PRT
<213> ORGANISM: Artificial Sequence
<220> FEATURE:
<223> OTHER INFORMATION: Synthetic-5-48-A6 light chain SignalP

<400> SEQUENCE: 84

Met Arg Thr Pro Ala Gln Phe Leu Gly Ile Leu Leu Leu Trp Phe Pro
1               5                   10                  15

Gly Ile Lys Cys
            20

<210> SEQ ID NO 85
<211> LENGTH: 18
<212> TYPE: PRT
<213> ORGANISM: Artificial Sequence
<220> FEATURE:
<223> OTHER INFORMATION: Synthetic-5-48-D2 heavy chain SignalP

<400> SEQUENCE: 85

Met Asp Phe Gly Leu Ile Phe Phe Ile Val Ala Leu Leu Lys Gly Val
1               5                   10                  15

Gln Cys

<210> SEQ ID NO 86
<211> LENGTH: 20
<212> TYPE: PRT
<213> ORGANISM: Artificial Sequence
<220> FEATURE:
<223> OTHER INFORMATION: Synthetic-5-48-D2 light chain SignalP

<400> SEQUENCE: 86

Met Ser Val Pro Thr Gln Val Leu Gly Leu Leu Leu Leu Trp Leu Thr
1               5                   10                  15

Gly Ala Arg Cys
            20

<210> SEQ ID NO 87

```
<211> LENGTH: 351
<212> TYPE: DNA
<213> ORGANISM: Artificial Sequence
<220> FEATURE:
<223> OTHER INFORMATION: Synthetic-1-1-A1_BM heavy chain DNA

<400> SEQUENCE: 87
caggtgcagc tgcagcagtc tggaccagac ctgaagaagc tggagccag cgtgaaggtg      60 tcctgtaagg tgtccggcta caccttcaca aactatgtga tccactgggt gaggcagaag    120
ccaggacagg gcctggagtg gatgggctac atcaacccct ataatgacgg caccaagtct    180
aatgagaagt ttaagggcaa ggccacccctg acatctgata agagcagcac cagcgcctac   240
atggagctgt ctagcctgac cagcgaggac acagccgtgt actattgcgc ttccggcggc    300
tactatacaa tggattattg gggccagggc accagcgtga cagtgtcctc t             351

<210> SEQ ID NO 88
<211> LENGTH: 336
<212> TYPE: DNA
<213> ORGANISM: Artificial Sequence
<220> FEATURE:
<223> OTHER INFORMATION: Synthetic-1-1-A1_BM light chain DNA

<400> SEQUENCE: 88
gacgtggtca tgacccagac accactgtcc ctgcctgtga ccctgggcga tcaggcctct     60
atcagctgta gaagctccca gcacctggag tacagcaacg gctactccta tctgcactgg   120
tatcagcagc gcccaggaca gtctccacag ctgctgatct acaagatctc taatcggttc   180
agcggcgtgc ctgacaggtt ttccggctct ggcagcggca ccgatttcac actgaagatc   240
agcagagtgg aggctgagga cctgggcgtg tactattgct cccagtctac ccacgtgccc   300
tatacatttg gcggcggcac caagctggag atcaag                             336

<210> SEQ ID NO 89
<211> LENGTH: 351
<212> TYPE: DNA
<213> ORGANISM: Artificial Sequence
<220> FEATURE:
<223> OTHER INFORMATION: Synthetic-1-1-A1 heavy chain DNA

<400> SEQUENCE: 89
gaggtccagc tgcagcagtc tggacctgac ctagtaaagc ctgggggcttc agtgaagatg    60 tcctgcaagg cttctggata cacattcact aattatgtta cactgggt gaagcagaag     120 cctgggcagg gccttgagtg gattggatat attaatcctt acaatgatgg tactaagtcc   180
aatgagaagt tcaaaggcaa ggccacactg acttcagaca atcctccac ctcagcctac    240 atggagctca gcagcctgac ctctgaggac tctgcggtct attactgtgc aagcggaggg   300
tactatacta tggactattg gggtcaagga acctcagtca ccgtctcctc g             351

<210> SEQ ID NO 90
<211> LENGTH: 336
<212> TYPE: DNA
<213> ORGANISM: Artificial Sequence
<220> FEATURE:
<223> OTHER INFORMATION: Synthetic-1-1-A1 light chain DNA

<400> SEQUENCE: 90
gatgttgtga tgacccaaac tccactctcc ctgcctgtca gtcttggaga tcaagcctcc     60
atctcttgca gatctagtca acaccttgaa tacagtaatg gatactccta tttgcattgg   120
tacctgcaga agccaggcca gtctccacag ctcctgatct acaaaatttc caaccgattt   180
```

```
tctggggtcc cagacaggtt cagtggcagt ggatcaggga cagatttcac actcaagatc    240
agcagagtgg aggctgagga tctgggggtt tatttctgct ctcaaagtac acatgttccg    300
tacacattcg agggggggac caagctggaa ataaaa                              336
```

```
<210> SEQ ID NO 91
<211> LENGTH: 369
<212> TYPE: DNA
<213> ORGANISM: Artificial Sequence
<220> FEATURE:
<223> OTHER INFORMATION: Synthetic-5-48-A6 heavy chain DNA

<400> SEQUENCE: 91
caggtgcagc tgaaggagtc aggacctggc ctggtggcgc cctcacagag cctgtccatc     60
acttgcactg tctctgggtt ttcattaacc agttatggtg tacactgggt tcgccagcct    120
ccaggaaagg gtctggagtg gctgggagta atatgggctg gtggaagcac aaattataat    180
tcggctctca tgtccagact gagcatcagc aaagacaact ccaagagcca agttttctta    240
aaaatgaaca gtctgcaaac tgatgacaca gccatgtact actgtgccag agttccgaca    300
ggtcggatta aatcttattt ctatgctatg gactactggg gtcaaggaac ctcagtcacc    360
gtctcctcg                                                           369
```

```
<210> SEQ ID NO 92
<211> LENGTH: 321
<212> TYPE: DNA
<213> ORGANISM: Artificial Sequence
<220> FEATURE:
<223> OTHER INFORMATION: Synthetic-5-48-A6 light chain DNA

<400> SEQUENCE: 92
gacatcaaga tgacccagtc tccatcttcc atgtattcat ctcttggaga gagagtcact     60
atcacttgca aggcgagtca ggacattagt agctatttaa gctggttcca gcagaaacca    120
gggaagtctc ctaagaccct gatctatcgt gcaaacagat tggtggatgg ggtcccatca    180
aggttcagtg gcagtggatc tgggcaagat tattctctca ccatcagcag cctggagtat    240
gaagatatgg gaatttatta ttgtctacag tatgatgagt ttccgtacac gttcggaggg    300
gggaccaagc tggaaataaa a                                             321
```

```
<210> SEQ ID NO 93
<211> LENGTH: 345
<212> TYPE: DNA
<213> ORGANISM: Artificial Sequence
<220> FEATURE:
<223> OTHER INFORMATION: Synthetic-5-48-D2 heavy chain DNA

<400> SEQUENCE: 93
gaggtgaagc ttctcgagtc tggaggtggc ctggtgcagc ctggaggatc cctgaaactc     60
tcctgtgcag cctcaggatt cgattttagt agatactgga tgagttgggt ccggcaggct    120
ccagggaaag ggctagaatg gattggagaa attaatccag atagcagtac gataaactat    180
acgccatctc taaaggataa attcatcatc tccagagaca cgccaaaaa tacgctgtac    240 ctgcaaatga gcaaagtgag atctgaggac acagcccttt attactgtgc aactgggacg    300
gggtttgctt actggggcca aggactctg gtcactgtct ctgcg                    345
```

```
<210> SEQ ID NO 94
<211> LENGTH: 321
<212> TYPE: DNA
```

<213> ORGANISM: Artificial Sequence
<220> FEATURE:
<223> OTHER INFORMATION: Synthetic-5-48-D2 light chain DNA

<400> SEQUENCE: 94

```
gacatccaga tgactcagtc tccagcttcc ctatctgcat ctgtgggaga aactgtcacc      60
atcacatgtc gagcaagtga aaatatttac agttatttag catggtatca gcagaaacag    120
ggaaaatctc ctcagctcct ggtctataat gcaaaaacct tagcagaagg tgtgccctca    180
aggttcagtg gcagtggatc aggcacacag ttttctctga agatcaacag cctgcagcct    240
gaagattttg ggagttatta ctgtcaacat cattatgtta ctccgtggac gttcggtgga    300
gtcaccaagc tggaaatcaa a                                              321
```

<210> SEQ ID NO 95
<211> LENGTH: 504
<212> TYPE: PRT
<213> ORGANISM: Homo sapiens

<400> SEQUENCE: 95

```
Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
                20                  25                  30

Glu Leu Gln Val Ile Gln Pro Asp Lys Ser Val Leu Val Ala Ala Gly
            35                  40                  45

Glu Thr Ala Thr Leu Arg Cys Thr Ala Thr Ser Leu Ile Pro Val Gly
        50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285
```

```
Glu Asn Gly Asn Val Ser Arg Thr Glu Thr Ala Ser Thr Val Thr Glu
    290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
        355                 360                 365

Glu Arg Asn Ile Tyr Ile Val Val Gly Val Val Cys Thr Leu Leu Val
    370                 375                 380

Ala Leu Leu Met Ala Ala Leu Tyr Leu Val Arg Ile Arg Gln Lys Lys
385                 390                 395                 400

Ala Gln Gly Ser Thr Ser Ser Thr Arg Leu His Glu Pro Glu Lys Asn
                405                 410                 415

Ala Arg Glu Ile Thr Gln Asp Thr Asn Asp Ile Thr Tyr Ala Asp Leu
            420                 425                 430

Asn Leu Pro Lys Gly Lys Lys Pro Ala Pro Gln Ala Ala Glu Pro Asn
        435                 440                 445

Asn His Thr Glu Tyr Ala Ser Ile Gln Thr Ser Pro Gln Pro Ala Ser
    450                 455                 460

Glu Asp Thr Leu Thr Tyr Ala Asp Leu Asp Met Val His Leu Asn Arg
465                 470                 475                 480

Thr Pro Lys Gln Pro Ala Pro Lys Pro Glu Pro Ser Phe Ser Glu Tyr
                485                 490                 495

Ala Ser Val Gln Val Pro Arg Lys
            500

<210> SEQ ID NO 96
<211> LENGTH: 508
<212> TYPE: PRT
<213> ORGANISM: Homo sapiens

<400> SEQUENCE: 96

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65              70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
```

```
                145                 150                 155                 160
Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
                180                 185                 190

Asp Phe Gln Thr Asn Val Asp Pro Val Gly Glu Ser Val Ser Tyr Ser
                195                 200                 205

Ile His Ser Thr Ala Lys Val Val Leu Thr Arg Glu Asp Val His Ser
                210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
                260                 265                 270

Cys Gln Val Arg Lys Phe Tyr Pro Gln Arg Leu Gln Leu Thr Trp Leu
                275                 280                 285

Glu Asn Gly Asn Val Ser Arg Thr Glu Thr Ala Ser Thr Val Thr Glu
                290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
                340                 345                 350

Pro Lys Glu Gln Gly Ser Asn Thr Ala Ala Glu Asn Thr Gly Ser Asn
                355                 360                 365

Glu Arg Asn Ile Tyr Ile Val Val Gly Val Val Cys Thr Leu Leu Val
                370                 375                 380

Ala Leu Leu Met Ala Ala Leu Tyr Leu Val Arg Ile Arg Gln Lys Lys
385                 390                 395                 400

Ala Gln Gly Ser Thr Ser Ser Thr Arg Leu His Glu Pro Glu Lys Asn
                405                 410                 415

Ala Arg Glu Ile Thr Gln Val Gln Ser Leu Asp Thr Asn Asp Ile Thr
                420                 425                 430

Tyr Ala Asp Leu Asn Leu Pro Lys Gly Lys Lys Pro Ala Pro Gln Ala
                435                 440                 445

Ala Glu Pro Asn Asn His Thr Glu Tyr Ala Ser Ile Gln Thr Ser Pro
450                 455                 460

Gln Pro Ala Ser Glu Asp Thr Leu Thr Tyr Ala Asp Leu Asp Met Val
465                 470                 475                 480

His Leu Asn Arg Thr Pro Lys Gln Pro Ala Pro Lys Pro Glu Pro Ser
                485                 490                 495

Phe Ser Glu Tyr Ala Ser Val Gln Val Pro Arg Lys
                500                 505

<210> SEQ ID NO 97
<211> LENGTH: 503
<212> TYPE: PRT
<213> ORGANISM: Homo sapiens

<400> SEQUENCE: 97

Met Glu Pro Ala Gly Pro Ala Pro Gly Arg Leu Gly Pro Leu Leu Cys
1               5                   10                  15
```

```
Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Val Glu Phe Lys Ser Gly Ala Gly Thr Glu Leu Ser Val Arg
    130                 135                 140

Ala Lys Pro Ser Ala Pro Val Val Ser Gly Pro Ala Ala Arg Ala Thr
145                 150                 155                 160

Pro Gln His Thr Val Ser Phe Thr Cys Glu Ser His Gly Phe Ser Pro
                165                 170                 175

Arg Asp Ile Thr Leu Lys Trp Phe Lys Asn Gly Asn Glu Leu Ser Asp
            180                 185                 190

Phe Gln Thr Asn Val Asp Pro Val Gly Glu Ser Val Ser Tyr Ser Ile
        195                 200                 205

His Ser Thr Ala Lys Val Val Leu Thr Arg Glu Asp Val His Ser Gln
    210                 215                 220

Val Ile Cys Glu Val Ala His Val Thr Leu Gln Gly Asp Pro Leu Arg
225                 230                 235                 240

Gly Thr Ala Asn Leu Ser Glu Thr Ile Arg Val Pro Pro Thr Leu Glu
                245                 250                 255

Val Thr Gln Gln Pro Val Arg Ala Glu Asn Gln Val Asn Val Thr Cys
            260                 265                 270

Gln Val Arg Lys Phe Tyr Pro Gln Arg Leu Gln Leu Thr Trp Leu Glu
        275                 280                 285

Asn Gly Asn Val Ser Arg Thr Glu Thr Ala Ser Thr Val Thr Glu Asn
    290                 295                 300

Lys Asp Gly Thr Tyr Asn Trp Met Ser Trp Leu Leu Val Asn Val Ser
305                 310                 315                 320

Ala His Arg Asp Asp Val Lys Leu Thr Cys Gln Val Glu His Asp Gly
                325                 330                 335

Gln Pro Ala Val Ser Lys Ser His Asp Leu Lys Val Ser Ala His Pro
            340                 345                 350

Lys Glu Gln Gly Ser Asn Thr Ala Ala Glu Asn Thr Gly Ser Asn Glu
        355                 360                 365

Arg Asn Ile Tyr Ile Val Val Gly Val Val Cys Thr Leu Leu Val Ala
    370                 375                 380

Leu Leu Met Ala Ala Leu Tyr Leu Val Arg Ile Arg Gln Lys Lys Ala
385                 390                 395                 400

Gln Gly Ser Thr Ser Ser Thr Arg Leu His Glu Pro Glu Lys Asn Ala
                405                 410                 415

Arg Glu Ile Thr Gln Asp Thr Asn Asp Ile Thr Tyr Ala Asp Leu Asn
            420                 425                 430

Leu Pro Lys Gly Lys Lys Pro Ala Pro Gln Ala Ala Glu Pro Asn Asn
```

```
              435                 440                 445
His Thr Glu Tyr Ala Ser Ile Gln Thr Ser Pro Gln Pro Ala Ser Glu
    450                 455                 460

Asp Thr Leu Thr Tyr Ala Asp Leu Asp Met Val His Leu Asn Arg Thr
465                 470                 475                 480

Pro Lys Gln Pro Ala Pro Lys Pro Glu Pro Ser Phe Ser Glu Tyr Ala
                485                 490                 495

Ser Val Gln Val Pro Arg Lys
            500

<210> SEQ ID NO 98
<211> LENGTH: 474
<212> TYPE: PRT
<213> ORGANISM: Homo sapiens

<400> SEQUENCE: 98

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Ala Pro Val Val Ser Gly Pro Ala Ala
        115                 120                 125

Arg Ala Thr Pro Gln His Thr Val Ser Phe Thr Cys Glu Ser His Gly
130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
            180                 185                 190

His Ser Gln Val Ile Cys Glu Val Ala His Val Thr Leu Gln Gly Asp
        195                 200                 205

Pro Leu Arg Gly Thr Ala Asn Leu Ser Glu Thr Ile Arg Val Pro Pro
    210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
            260                 265                 270

Thr Glu Asn Lys Asp Gly Thr Tyr Asn Trp Met Ser Trp Leu Leu Val
        275                 280                 285

Asn Val Ser Ala His Arg Asp Asp Val Lys Leu Thr Cys Gln Val Glu
    290                 295                 300
```

His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
            325                 330                 335

Ser Asn Glu Arg Asn Ile Tyr Ile Val Val Gly Val Val Cys Thr Leu
            340                 345                 350

Leu Val Ala Leu Leu Met Ala Ala Leu Tyr Leu Val Arg Ile Arg Gln
        355                 360                 365

Lys Lys Ala Gln Gly Ser Thr Ser Ser Thr Arg Leu His Glu Pro Glu
    370                 375                 380

Lys Asn Ala Arg Glu Ile Thr Gln Asp Thr Asn Asp Ile Thr Tyr Ala
385                 390                 395                 400

Asp Leu Asn Leu Pro Lys Gly Lys Lys Pro Ala Pro Gln Ala Ala Glu
            405                 410                 415

Pro Asn Asn His Thr Glu Tyr Ala Ser Ile Gln Thr Ser Pro Gln Pro
            420                 425                 430

Ala Ser Glu Asp Thr Leu Thr Tyr Ala Asp Leu Asp Met Val His Leu
        435                 440                 445

Asn Arg Thr Pro Lys Gln Pro Ala Pro Lys Pro Glu Pro Ser Phe Ser
    450                 455                 460

Glu Tyr Ala Ser Val Gln Val Pro Arg Lys
465                 470

<210> SEQ ID NO 99
<211> LENGTH: 478
<212> TYPE: PRT
<213> ORGANISM: Homo sapiens

<400> SEQUENCE: 99

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Ala Pro Val Val Ser Gly Pro Ala Ala
        115                 120                 125

Arg Ala Thr Pro Gln His Thr Val Ser Phe Thr Cys Glu Ser His Gly
    130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
            180                 185                 190

His Ser Gln Val Ile Cys Glu Val Ala His Val Thr Leu Gln Gly Asp
        195                 200                 205

Pro Leu Arg Gly Thr Ala Asn Leu Ser Glu Thr Ile Arg Val Pro Pro
    210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
            260                 265                 270

Thr Glu Asn Lys Asp Gly Thr Tyr Asn Trp Met Ser Trp Leu Leu Val
        275                 280                 285

Asn Val Ser Ala His Arg Asp Asp Val Lys Leu Thr Cys Gln Val Glu
290                 295                 300

His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
                325                 330                 335

Ser Asn Glu Arg Asn Ile Tyr Ile Val Val Gly Val Val Cys Thr Leu
            340                 345                 350

Leu Val Ala Leu Leu Met Ala Ala Leu Tyr Leu Val Arg Ile Arg Gln
        355                 360                 365

Lys Lys Ala Gln Gly Ser Thr Ser Ser Thr Arg Leu His Glu Pro Glu
370                 375                 380

Lys Asn Ala Arg Glu Ile Thr Gln Val Gln Ser Leu Asp Thr Asn Asp
385                 390                 395                 400

Ile Thr Tyr Ala Asp Leu Asn Leu Pro Lys Gly Lys Lys Pro Ala Pro
                405                 410                 415

Gln Ala Ala Glu Pro Asn Asn His Thr Glu Tyr Ala Ser Ile Gln Thr
            420                 425                 430

Ser Pro Gln Pro Ala Ser Glu Asp Thr Leu Thr Tyr Ala Asp Leu Asp
        435                 440                 445

Met Val His Leu Asn Arg Thr Pro Lys Gln Pro Ala Pro Lys Pro Glu
450                 455                 460

Pro Ser Phe Ser Glu Tyr Ala Ser Val Gln Val Pro Arg Lys
465                 470                 475

<210> SEQ ID NO 100
<211> LENGTH: 473
<212> TYPE: PRT
<213> ORGANISM: Homo sapiens

<400> SEQUENCE: 100

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Val Glu Phe Lys Ser Gly Ala Gly Thr Glu Leu Ser

```
                100             105             110
   Val Arg Ala Lys Pro Ser Ala Pro Val Val Ser Gly Pro Ala Ala Arg
                115                 120                 125
   Ala Thr Pro Gln His Thr Val Ser Phe Thr Cys Glu Ser His Gly Phe
                130                 135                 140
   Ser Pro Arg Asp Ile Thr Leu Lys Trp Phe Lys Asn Gly Asn Glu Leu
   145                 150                 155                 160
   Ser Asp Phe Gln Thr Asn Val Asp Pro Val Gly Glu Ser Val Ser Tyr
                       165                 170                 175
   Ser Ile His Ser Thr Ala Lys Val Val Leu Thr Arg Glu Asp Val His
                   180                 185                 190
   Ser Gln Val Ile Cys Glu Val Ala His Val Thr Leu Gln Gly Asp Pro
               195                 200                 205
   Leu Arg Gly Thr Ala Asn Leu Ser Glu Thr Ile Arg Val Pro Pro Thr
               210                 215                 220
   Leu Glu Val Thr Gln Gln Pro Val Arg Ala Glu Asn Gln Val Asn Val
   225                 230                 235                 240
   Thr Cys Gln Val Arg Lys Phe Tyr Pro Gln Arg Leu Gln Leu Thr Trp
                       245                 250                 255
   Leu Glu Asn Gly Asn Val Ser Arg Thr Glu Thr Ala Ser Thr Val Thr
                   260                 265                 270
   Glu Asn Lys Asp Gly Thr Tyr Asn Trp Met Ser Trp Leu Leu Val Asn
               275                 280                 285
   Val Ser Ala His Arg Asp Asp Val Lys Leu Thr Cys Gln Val Glu His
               290                 295                 300
   Asp Gly Gln Pro Ala Val Ser Lys Ser His Asp Leu Lys Val Ser Ala
   305                 310                 315                 320
   His Pro Lys Glu Gln Gly Ser Asn Thr Ala Ala Glu Asn Thr Gly Ser
                       325                 330                 335
   Asn Glu Arg Asn Ile Tyr Ile Val Val Gly Val Val Cys Thr Leu Leu
                   340                 345                 350
   Val Ala Leu Leu Met Ala Ala Leu Tyr Leu Val Arg Ile Arg Gln Lys
               355                 360                 365
   Lys Ala Gln Gly Ser Thr Ser Ser Thr Arg Leu His Glu Pro Glu Lys
               370                 375                 380
   Asn Ala Arg Glu Ile Thr Gln Asp Thr Asn Asp Ile Thr Tyr Ala Asp
   385                 390                 395                 400
   Leu Asn Leu Pro Lys Gly Lys Lys Pro Ala Pro Gln Ala Ala Glu Pro
                       405                 410                 415
   Asn Asn His Thr Glu Tyr Ala Ser Ile Gln Thr Ser Pro Gln Pro Ala
                   420                 425                 430
   Ser Glu Asp Thr Leu Thr Tyr Ala Asp Leu Asp Met Val His Leu Asn
               435                 440                 445
   Arg Thr Pro Lys Gln Pro Ala Pro Lys Pro Glu Pro Ser Phe Ser Glu
               450                 455                 460
   Tyr Ala Ser Val Gln Val Pro Arg Lys
   465                 470

<210> SEQ ID NO 101
<211> LENGTH: 343
<212> TYPE: PRT
<213> ORGANISM: Homo sapiens

<400> SEQUENCE: 101
```

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
                100                 105                 110

Ser Val Arg Ala Lys Pro Ser Ala Pro Val Val Ser Gly Pro Ala Ala
            115                 120                 125

Arg Ala Thr Pro Gln His Thr Val Ser Phe Thr Cys Glu Ser His Gly
    130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
                180                 185                 190

His Ser Gln Val Ile Cys Glu Val Ala His Val Thr Leu Gln Gly Asp
            195                 200                 205

Pro Leu Arg Gly Thr Ala Asn Leu Ser Glu Thr Ile Arg Val Pro Pro
    210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
                260                 265                 270

Thr Glu Asn Lys Asp Gly Thr Tyr Asn Trp Met Ser Trp Leu Leu Val
            275                 280                 285

Asn Val Ser Ala His Arg Asp Asp Val Lys Leu Thr Cys Gln Val Glu
            290                 295                 300

His Asp Gly Gln Pro Ala Val Ser Lys Ser His Asp Leu Lys Val Ser
305                 310                 315                 320

Ala His Pro Lys Glu Gln Gly Ser Asn Thr Ala Glu Asn Thr Gly
                325                 330                 335

Ser Asn Glu Arg Asn Ile Tyr
            340

<210> SEQ ID NO 102
<211> LENGTH: 21
<212> TYPE: PRT
<213> ORGANISM: Homo sapiens

<400> SEQUENCE: 102

Ile Val Val Gly Val Val Cys Thr Leu Leu Val Ala Leu Leu Met Ala
1               5                   10                  15

Ala Leu Tyr Leu Val
            20
```

<210> SEQ ID NO 103
<211> LENGTH: 110
<212> TYPE: PRT
<213> ORGANISM: Homo sapiens

<400> SEQUENCE: 103

```
Arg Ile Arg Gln Lys Lys Ala Gln Gly Ser Thr Ser Ser Thr Arg Leu
1               5                   10                  15

His Glu Pro Glu Lys Asn Ala Arg Glu Ile Thr Gln Asp Thr Asn Asp
            20                  25                  30

Ile Thr Tyr Ala Asp Leu Asn Leu Pro Lys Gly Lys Lys Pro Ala Pro
        35                  40                  45

Gln Ala Ala Glu Pro Asn Asn His Thr Glu Tyr Ala Ser Ile Gln Thr
    50                  55                  60

Ser Pro Gln Pro Ala Ser Glu Asp Thr Leu Thr Tyr Ala Asp Leu Asp
65                  70                  75                  80

Met Val His Leu Asn Arg Thr Pro Lys Gln Pro Ala Pro Lys Pro Glu
                85                  90                  95

Pro Ser Phe Ser Glu Tyr Ala Ser Val Gln Val Pro Arg Lys
            100                 105                 110
```

<210> SEQ ID NO 104
<211> LENGTH: 106
<212> TYPE: PRT
<213> ORGANISM: Homo sapiens

<400> SEQUENCE: 104

```
Glu Glu Leu Gln Val Ile Gln Pro Asp Lys Ser Val Leu Val Ala Ala
1               5                   10                  15

Gly Glu Thr Ala Thr Leu Arg Cys Thr Ala Thr Ser Leu Ile Pro Val
            20                  25                  30

Gly Pro Ile Gln Trp Phe Arg Gly Ala Gly Pro Gly Arg Glu Leu Ile
        35                  40                  45

Tyr Asn Gln Lys Glu Gly His Phe Pro Arg Val Thr Thr Val Ser Asp
    50                  55                  60

Leu Thr Lys Arg Asn Asn Met Asp Phe Ser Ile Arg Ile Gly Asn Ile
65                  70                  75                  80

Thr Pro Ala Asp Ala Gly Thr Tyr Tyr Cys Val Lys Phe Arg Lys Gly
                85                  90                  95

Ser Pro Asp Asp Val Glu Phe Lys Ser Gly
            100                 105
```

<210> SEQ ID NO 105
<211> LENGTH: 100
<212> TYPE: PRT
<213> ORGANISM: Homo sapiens

<400> SEQUENCE: 105

```
Pro Ser Ala Pro Val Val Ser Gly Pro Ala Ala Arg Ala Thr Pro Gln
1               5                   10                  15

His Thr Val Ser Phe Thr Cys Glu Ser His Gly Phe Ser Pro Arg Asp
            20                  25                  30

Ile Thr Leu Lys Trp Phe Lys Asn Gly Asn Glu Leu Ser Asp Phe Gln
        35                  40                  45

Thr Asn Val Asp Pro Val Gly Glu Ser Val Ser Tyr Ser Ile His Ser
    50                  55                  60
```

```
Thr Ala Lys Val Val Leu Thr Arg Glu Asp Val His Ser Gln Val Ile
 65                  70                  75                  80

Cys Glu Val Ala His Val Thr Leu Gln Gly Asp Pro Leu Arg Gly Thr
                 85                  90                  95

Ala Asn Leu Ser
            100

<210> SEQ ID NO 106
<211> LENGTH: 95
<212> TYPE: PRT
<213> ORGANISM: Homo sapiens

<400> SEQUENCE: 106

Pro Thr Leu Glu Val Thr Gln Gln Pro Val Arg Ala Glu Asn Gln Val
  1               5                  10                  15

Asn Val Thr Cys Gln Val Arg Lys Phe Tyr Pro Gln Arg Leu Gln Leu
                 20                  25                  30

Thr Trp Leu Glu Asn Gly Asn Val Ser Arg Thr Glu Thr Ala Ser Thr
             35                  40                  45

Val Thr Glu Asn Lys Asp Gly Thr Tyr Asn Trp Met Ser Trp Leu Leu
 50                  55                  60

Val Asn Val Ser Ala His Arg Asp Asp Val Lys Leu Thr Cys Gln Val
 65                  70                  75                  80

Glu His Asp Gly Gln Pro Ala Val Ser Lys Ser His Asp Leu Lys
                 85                  90                  95

<210> SEQ ID NO 107
<211> LENGTH: 447
<212> TYPE: PRT
<213> ORGANISM: Artificial Sequence
<220> FEATURE:
<223> OTHER INFORMATION: Synthetic-1-1-A1_BM VH-CH1-CH2-CH3

<400> SEQUENCE: 107

Gln Val Gln Leu Gln Gln Ser Gly Pro Asp Leu Lys Lys Pro Gly Ala
  1               5                  10                  15

Ser Val Lys Val Ser Cys Lys Val Ser Gly Tyr Thr Phe Thr Asn Tyr
                 20                  25                  30

Val Ile His Trp Val Arg Gln Lys Pro Gly Gln Gly Leu Glu Trp Met
             35                  40                  45

Gly Tyr Ile Asn Pro Tyr Asn Asp Gly Thr Lys Ser Asn Glu Lys Phe
 50                  55                  60

Lys Gly Lys Ala Thr Leu Thr Ser Asp Lys Ser Ser Thr Ser Ala Tyr
 65                  70                  75                  80

Met Glu Leu Ser Ser Leu Thr Ser Glu Asp Thr Ala Val Tyr Tyr Cys
                 85                  90                  95

Ala Ser Gly Gly Tyr Tyr Thr Met Asp Tyr Trp Gly Gln Gly Thr Ser
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
```

```
            180                 185                 190
Leu Gly Thr Gln Thr Tyr Ile Cys Asn Val Asn His Lys Pro Ser Asn
        195                 200                 205

Thr Lys Val Asp Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 108
<211> LENGTH: 219
<212> TYPE: PRT
<213> ORGANISM: Artificial Sequence
<220> FEATURE:
<223> OTHER INFORMATION: Synthetic-1-1-A1_BM VL-Ckappa

<400> SEQUENCE: 108

Asp Val Val Met Thr Gln Thr Pro Leu Ser Leu Pro Val Thr Leu Gly
1               5                   10                  15

Asp Gln Ala Ser Ile Ser Cys Arg Ser Ser Gln His Leu Glu Tyr Ser
            20                  25                  30

Asn Gly Tyr Ser Tyr Leu His Trp Tyr Gln Gln Arg Pro Gly Gln Ser
        35                  40                  45

Pro Gln Leu Leu Ile Tyr Lys Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Ser Gln Ser
                85                  90                  95

Thr His Val Pro Tyr Thr Phe Gly Gly Gly Thr Lys Leu Glu Ile Lys
```

```
                100                 105                 110
Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 109
<211> LENGTH: 447
<212> TYPE: PRT
<213> ORGANISM: Artificial Sequence
<220> FEATURE:
<223> OTHER INFORMATION: Synthetic-1-1-A1 VH-CH1-CH2-CH3

<400> SEQUENCE: 109

Glu Val Gln Leu Gln Gln Ser Gly Pro Asp Leu Val Lys Pro Gly Ala
1               5                   10                  15

Ser Val Lys Met Ser Cys Lys Ala Ser Gly Tyr Thr Phe Thr Asn Tyr
            20                  25                  30

Val Ile His Trp Val Lys Gln Lys Pro Gly Gln Gly Leu Glu Trp Ile
        35                  40                  45

Gly Tyr Ile Asn Pro Tyr Asn Asp Gly Thr Lys Ser Asn Glu Lys Phe
    50                  55                  60

Lys Gly Lys Ala Thr Leu Thr Ser Asp Lys Ser Ser Thr Ser Ala Tyr
65                  70                  75                  80

Met Glu Leu Ser Ser Leu Thr Ser Glu Asp Ser Ala Val Tyr Tyr Cys
                85                  90                  95

Ala Ser Gly Gly Tyr Tyr Thr Met Asp Tyr Trp Gly Gln Gly Thr Ser
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
```

```
                    245                 250                 255
Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 110
<211> LENGTH: 219
<212> TYPE: PRT
<213> ORGANISM: Artificial Sequence
<220> FEATURE:
<223> OTHER INFORMATION: Synthetic-1-1-A1 VL-Ckappa

<400> SEQUENCE: 110

Asp Val Val Met Thr Gln Thr Pro Leu Ser Leu Pro Val Ser Leu Gly
1               5                   10                  15

Asp Gln Ala Ser Ile Ser Cys Arg Ser Ser Gln His Leu Glu Tyr Ser
            20                  25                  30

Asn Gly Tyr Ser Tyr Leu His Trp Tyr Leu Gln Lys Pro Gly Gln Ser
        35                  40                  45

Pro Gln Leu Leu Ile Tyr Lys Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
```

```
              165                 170                 175
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 111
<211> LENGTH: 453
<212> TYPE: PRT
<213> ORGANISM: Artificial Sequence
<220> FEATURE:
<223> OTHER INFORMATION: Synthetic-5-48-A6 VH-CH1-CH2-CH3

<400> SEQUENCE: 111

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ala Gly Ser Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Val Pro Thr Gly Arg Ile Lys Ser Tyr Phe Tyr Ala Met Asp Tyr
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
```

```
            305                 310                 315                 320
Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
                355                 360                 365

Val Ser Leu Thr Cys Leu Val Lys Gly Phe Tyr Pro Ser Asp Ile Ala
                370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly Lys
                450

<210> SEQ ID NO 112
<211> LENGTH: 214
<212> TYPE: PRT
<213> ORGANISM: Artificial Sequence
<220> FEATURE:
<223> OTHER INFORMATION: Synthetic-5-48-A6 VL-Ckappa

<400> SEQUENCE: 112

Asp Ile Lys Met Thr Gln Ser Pro Ser Ser Met Tyr Ser Ser Leu Gly
1               5                   10                  15

Glu Arg Val Thr Ile Thr Cys Lys Ala Ser Gln Asp Ile Ser Ser Tyr
                20                  25                  30

Leu Ser Trp Phe Gln Gln Lys Pro Gly Lys Ser Pro Lys Thr Leu Ile
                35                  40                  45

Tyr Arg Ala Asn Arg Leu Val Asp Gly Val Pro Ser Arg Phe Ser Gly
50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
```

-continued

<210> SEQ ID NO 113
<211> LENGTH: 445
<212> TYPE: PRT
<213> ORGANISM: Artificial Sequence
<220> FEATURE:
<223> OTHER INFORMATION: Synthetic-5-48-D2 VH-CH1-CH2-CH3

<400> SEQUENCE: 113

```
Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Thr Gly Thr Gly Phe Ala Tyr Trp Gly Gln Gly Thr Leu Val Thr
            100                 105                 110

Val Ser Ala Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
```

```
                355                 360                 365
Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
                435                 440                 445

<210> SEQ ID NO 114
<211> LENGTH: 214
<212> TYPE: PRT
<213> ORGANISM: Artificial Sequence
<220> FEATURE:
<223> OTHER INFORMATION: Synthetic-5-48-D2 VL-Ckappa

<400> SEQUENCE: 114

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
                20                  25                  30

Leu Ala Trp Tyr Gln Gln Lys Gln Gly Lys Ser Pro Gln Leu Leu Val
                35                  40                  45

Tyr Asn Ala Lys Thr Leu Ala Glu Gly Val Pro Ser Arg Phe Ser Gly
50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Val Thr Pro Trp
                85                  90                  95

Thr Phe Gly Gly Val Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 115
<211> LENGTH: 446
<212> TYPE: PRT
<213> ORGANISM: Artificial Sequence
<220> FEATURE:
<223> OTHER INFORMATION: Synthetic-anti-CD33 VH-CH1-CH2-CH3

<400> SEQUENCE: 115
```

-continued

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Ile
            35                  40                  45

Gly Tyr Ile Tyr Pro Tyr Asn Gly Gly Thr Gly Tyr Asn Gln Lys Phe
        50                  55                  60

Lys Ser Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Pro Ala Met Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
```

```
                      420                 425                 430
Asn His Tyr Thr Gln Lys Ser Leu Ser Leu Ser Pro Gly Lys
        435                 440                 445

<210> SEQ ID NO 116
<211> LENGTH: 218
<212> TYPE: PRT
<213> ORGANISM: Artificial Sequence
<220> FEATURE:
<223> OTHER INFORMATION: Synthetic-anti-CD33 VL-Ckappa

<400> SEQUENCE: 116

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Tyr
            20                  25                  30

Gly Ile Ser Phe Met Asn Trp Phe Gln Gln Lys Pro Gly Lys Ala Pro
        35                  40                  45

Lys Leu Leu Ile Tyr Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Asp Asp Phe Ala Thr Tyr Tyr Cys Gln Gln Ser Lys
                85                  90                  95

Glu Val Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 117
<211> LENGTH: 318
<212> TYPE: PRT
<213> ORGANISM: Artificial Sequence
<220> FEATURE:
<223> OTHER INFORMATION: Synthetic-Rhesus macaque CD47 (UniProt:
      F7F5Y9-1, v2)

<400> SEQUENCE: 117

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60
```

-continued

```
Ile Tyr Thr Phe Asp Gly Ala Leu Asn Lys Ser Thr Ala Pro Ala Asn
 65                  70                  75                  80

Phe Ser Ser Ala Lys Ile Glu Val Ser Gln Leu Leu Lys Gly Asp Ala
                 85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Met Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Asn
    290                 295                 300

Asp Asn Phe Arg Leu Lys Asn Glu Glu Lys Phe Ile Leu Asn
305                 310                 315

<210> SEQ ID NO 118
<211> LENGTH: 330
<212> TYPE: PRT
<213> ORGANISM: Artificial Sequence
<220> FEATURE:
<223> OTHER INFORMATION: Synthetic-Human IgG1 constant region (IGHG1;
      UniProt:P01857-1, v1)

<400> SEQUENCE: 118

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
```

```
            100                 105                 110
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 119
<211> LENGTH: 98
<212> TYPE: PRT
<213> ORGANISM: Artificial Sequence
<220> FEATURE:
<223> OTHER INFORMATION: Synthetic-CH1 IgG1

<400> SEQUENCE: 119

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 120
<211> LENGTH: 12
<212> TYPE: PRT
<213> ORGANISM: Artificial Sequence
```

<220> FEATURE:
<223> OTHER INFORMATION: Synthetic-Hinge IgG1 (positions 99-110 of
      P01857-1, v1)

<400> SEQUENCE: 120

Glu Pro Lys Ser Cys Asp Lys Thr His Thr Cys Pro
1               5                   10

<210> SEQ ID NO 121
<211> LENGTH: 113
<212> TYPE: PRT
<213> ORGANISM: Artificial Sequence
<220> FEATURE:
<223> OTHER INFORMATION: Synthetic-CH2 IgG1 (positions 111-223 of
      P01857-1, v1)

<400> SEQUENCE: 121

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys

<210> SEQ ID NO 122
<211> LENGTH: 107
<212> TYPE: PRT
<213> ORGANISM: Artificial Sequence
<220> FEATURE:
<223> OTHER INFORMATION: Synthetic-CH3 IgG1 (positions 224-330 of
      P01857-1, v1)

<400> SEQUENCE: 122

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 123
<211> LENGTH: 107
<212> TYPE: PRT

<213> ORGANISM: Artificial Sequence
<220> FEATURE:
<223> OTHER INFORMATION: Synthetic-CH3 (D356E, L358M; positions numbered according to EU numbering)

<400> SEQUENCE: 123

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 124
<211> LENGTH: 107
<212> TYPE: PRT
<213> ORGANISM: Artificial Sequence
<220> FEATURE:
<223> OTHER INFORMATION: Synthetic-Ckappa CL (IGCK; UniProt: P01834-1, v2)

<400> SEQUENCE: 124

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 125
<211> LENGTH: 451
<212> TYPE: PRT
<213> ORGANISM: Artificial Sequence
<220> FEATURE:
<223> OTHER INFORMATION: Synthetic-J6M0 VH-CH1-CH2-CH3

<400> SEQUENCE: 125

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Trp Met His Trp Val Arg Gln Ala Pro Gly Gln Gly Leu Glu Trp Met
        35                  40                  45

```
Gly Ala Thr Tyr Arg Gly His Ser Asp Thr Tyr Tyr Asn Gln Lys Phe
    50                  55                  60
Lys Gly Arg Val Thr Ile Thr Ala Asp Lys Ser Thr Ser Thr Ala Tyr
 65              70                  75                  80
Met Glu Leu Ser Ser Leu Arg Ser Glu Asp Thr Ala Val Tyr Tyr Cys
                85                  90                  95
Ala Arg Gly Ala Ile Tyr Asp Gly Tyr Asp Val Leu Asp Asn Trp Gly
            100                 105                 110
Gln Gly Thr Leu Val Thr Val Ser Ala Ser Thr Lys Gly Pro Ser
                115                 120                 125
Val Phe Pro Leu Ala Pro Ser Ser Lys Ser Thr Ser Gly Gly Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
                195                 200                 205
Lys Pro Ser Asn Thr Lys Val Asp Lys Lys Val Glu Pro Lys Ser Cys
210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
                275                 280                 285
His Asn Ala Lys Thr Lys Pro Arg Glu Glu Gln Tyr Asn Ser Thr Tyr
                290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Arg Asp Glu Leu Thr Lys Asn Gln Val Ser
                355                 360                 365
Leu Thr Cys Leu Val Lys Gly Phe Tyr Pro Ser Asp Ile Ala Val Glu
                370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
                435                 440                 445
Pro Gly Lys
450
```

```
<210> SEQ ID NO 126
<211> LENGTH: 214
<212> TYPE: PRT
<213> ORGANISM: Artificial Sequence
<220> FEATURE:
<223> OTHER INFORMATION: Synthetic-J6M0 VL-Ckappa

<400> SEQUENCE: 126

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Asn Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Arg Lys Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 127
<211> LENGTH: 117
<212> TYPE: PRT
<213> ORGANISM: Artificial Sequence
<220> FEATURE:
<223> OTHER INFORMATION: Synthetic-11A1H1 VH

<400> SEQUENCE: 127

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Val Ile His Trp Val Arg Gln Ala Pro Gly Lys Gly Leu Glu Trp Met
        35                  40                  45

Gly Tyr Ile Asn Pro Tyr Asn Asp Gly Thr Lys Ser Asn Glu Lys Phe
50                  55                  60

Lys Gly Arg Val Thr Leu Thr Ser Asp Lys Ser Ser Thr Ser Ala Tyr
65                  70                  75                  80

Met Glu Leu Ser Ser Leu Arg Ser Glu Asp Thr Ala Val Tyr Tyr Cys
                85                  90                  95
```

```
Ala Ser Gly Gly Tyr Tyr Thr Met Asp Tyr Trp Gly Gln Gly Thr Leu
            100                 105                 110

Val Thr Val Ser Ser
        115

<210> SEQ ID NO 128
<211> LENGTH: 112
<212> TYPE: PRT
<213> ORGANISM: Artificial Sequence
<220> FEATURE:
<223> OTHER INFORMATION: Synthetic-11A1H1, Synthetic-11A1H2, Synthetic-
      11A1H3, Synthetic-11A1H4, Synthetic-11A1H5  VL

<400> SEQUENCE: 128

Asp Val Val Met Thr Gln Ser Pro Leu Ser Leu Pro Val Thr Leu Gly
1               5                   10                  15

Gln Pro Ala Ser Ile Ser Cys Arg Ser Ser Gln His Leu Glu Tyr Ser
            20                  25                  30

Asn Gly Tyr Ser Tyr Leu His Trp Tyr Gln Gln Arg Pro Gly Gln Ser
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Val Glu Ile Lys
            100                 105                 110

<210> SEQ ID NO 129
<211> LENGTH: 117
<212> TYPE: PRT
<213> ORGANISM: Artificial Sequence
<220> FEATURE:
<223> OTHER INFORMATION: Synthetic-11A1H2 VH

<400> SEQUENCE: 129

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Val Ile His Trp Val Arg Gln Ala Pro Gly Lys Gly Leu Glu Trp Met
        35                  40                  45

Gly Tyr Ile Asn Pro Tyr Asn Asp Gly Thr Lys Ser Asn Glu Lys Phe
    50                  55                  60

Lys Gly Arg Val Thr Leu Thr Ser Asp Thr Ser Thr Thr Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Gly Tyr Tyr Thr Met Asp Tyr Trp Gly Gln Gly Thr Leu
            100                 105                 110

Val Thr Val Ser Ser
        115

<210> SEQ ID NO 130
<211> LENGTH: 113
<212> TYPE: PRT
<213> ORGANISM: Artificial Sequence
<220> FEATURE:
<223> OTHER INFORMATION: Synthetic-11A1H3 VH
```

<400> SEQUENCE: 130

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Asp Gly Thr Lys Ser Asn Glu Lys Phe
    50                  55                  60

Gln Gly Arg Val Thr Leu Thr Ser Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Gly Tyr Tyr Thr Met Asp Tyr Trp Gly Gln Gly Thr Leu
            100                 105                 110

Val

<210> SEQ ID NO 131
<211> LENGTH: 113
<212> TYPE: PRT
<213> ORGANISM: Artificial Sequence
<220> FEATURE:
<223> OTHER INFORMATION: Synthetic-11A1H4, Synthetic-11A1H6, Synthetic-
      11A1H8 VH

<400> SEQUENCE: 131

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Val Ile His Trp Val Arg Gln Ala Pro Gly Gln Gly Leu Glu Trp Met
        35                  40                  45

Gly Tyr Ile Asn Pro Tyr Asn Asp Gly Thr Lys Tyr Asn Gln Lys Phe
    50                  55                  60

Lys Gly Arg Val Thr Leu Thr Ser Asp Thr Ser Thr Thr Thr Ala Tyr
65                  70                  75                  80

Met Glu Leu Ser Arg Leu Arg Ser Asp Asp Thr Ala Val Tyr Tyr Cys
                85                  90                  95

Ala Ser Gly Gly Tyr Tyr Thr Met Asp Tyr Trp Gly Gln Gly Thr Leu
            100                 105                 110

Val

<210> SEQ ID NO 132
<211> LENGTH: 117
<212> TYPE: PRT
<213> ORGANISM: Artificial Sequence
<220> FEATURE:
<223> OTHER INFORMATION: Synthetic-11A1H5, Synthetic-11A1H7, Synthetic-
      11A1H9, Synthetic-11A1H10, Synthetic-11A1H11 VH

<400> SEQUENCE: 132

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Val Ile His Trp Val Arg Gln Ala Pro Gly Gln Gly Leu Glu Trp Met
        35                  40                  45

Gly Tyr Ile Asn Pro Tyr Asn Gly Gly Thr Asn Tyr Ala Gln Lys Phe
            50                  55                  60

Lys Gly Arg Val Thr Leu Thr Ser Asp Thr Ser Thr Thr Thr Ala Tyr
 65                  70                  75                  80

Met Glu Leu Ser Arg Leu Arg Ser Glu Asp Thr Ala Val Tyr Tyr Cys
                85                  90                  95

Ala Ser Gly Gly Tyr Tyr Thr Met Asp Tyr Trp Gly Gln Gly Thr Leu
            100                 105                 110

Val Thr Val Ser Ser
            115

<210> SEQ ID NO 133
<211> LENGTH: 112
<212> TYPE: PRT
<213> ORGANISM: Artificial Sequence
<220> FEATURE:
<223> OTHER INFORMATION: Synthetic-11A1H6, Synthetic-11A1H7 VL

<400> SEQUENCE: 133

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln His Leu Glu Tyr Ser
            20                  25                  30

Gln Gly Tyr Ser Tyr Leu His Trp Tyr Gln Gln Arg Pro Gly Gln Ser
            35                  40                  45

Pro Arg Leu Leu Ile Tyr Lys Val Ser Asn Arg Asp Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Val Glu Ile Lys
            100                 105                 110

<210> SEQ ID NO 134
<211> LENGTH: 112
<212> TYPE: PRT
<213> ORGANISM: Artificial Sequence
<220> FEATURE:
<223> OTHER INFORMATION: Synthetic-11A1H8, Synthetic-11A1H9 VL

<400> SEQUENCE: 134

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln His Leu Glu Tyr Ser
            20                  25                  30

Thr Gly Tyr Ser Tyr Leu His Trp Tyr Gln Gln Arg Pro Gly Gln Ser
            35                  40                  45

Pro Arg Leu Leu Ile Tyr Lys Val Ser Asn Arg Asp Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Val Glu Ile Lys
            100                 105                 110

```
<210> SEQ ID NO 135
<211> LENGTH: 112
<212> TYPE: PRT
<213> ORGANISM: Artificial Sequence
<220> FEATURE:
<223> OTHER INFORMATION: Synthetic-11A1H10 VL

<400> SEQUENCE: 135

Asp Val Val Met Thr Gln Ser Pro Leu Ser Leu Pro Val Thr Leu Gly
1               5                   10                  15

Gln Pro Ala Ser Ile Ser Cys Arg Ser Ser Gln His Leu Glu Tyr Ser
            20                  25                  30

Asn Gly Tyr Ser Tyr Leu His Trp Tyr Gln Gln Arg Pro Gly Gln Ser
        35                  40                  45

Pro Arg Leu Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Val Glu Ile Lys
            100                 105                 110

<210> SEQ ID NO 136
<211> LENGTH: 112
<212> TYPE: PRT
<213> ORGANISM: Artificial Sequence
<220> FEATURE:
<223> OTHER INFORMATION: Synthetic-11A1H11 VL

<400> SEQUENCE: 136

Asp Val Val Met Thr Gln Ser Pro Leu Ser Leu Pro Val Thr Leu Gly
1               5                   10                  15

Gln Pro Ala Ser Ile Ser Cys Arg Ser Ser Gln His Leu Glu Tyr Ser
            20                  25                  30

Asn Gly Tyr Ser Tyr Leu His Trp Tyr Gln Gln Arg Pro Gly Gln Ser
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Gly
                85                  90                  95

Thr His Val Pro Tyr Thr Phe Gly Gly Gly Thr Lys Val Glu Ile Lys
            100                 105                 110

<210> SEQ ID NO 137
<211> LENGTH: 8
<212> TYPE: PRT
<213> ORGANISM: Artificial Sequence
<220> FEATURE:
<223> OTHER INFORMATION: Synthetic-11A1H5, Synthetic-11A1H7, Synthetic-
    11A1H9, Synthetic-11A1H10, Synthetic-11A1H11 HC-CDR1

<400> SEQUENCE: 137

Gly Tyr Thr Phe Thr Gly Tyr Val
1               5

<210> SEQ ID NO 138
<211> LENGTH: 8
<212> TYPE: PRT
```

<213> ORGANISM: Artificial Sequence
<220> FEATURE:
<223> OTHER INFORMATION: Synthetic-11A1H5, Synthetic-11A1H7, Synthetic-
      11A1H9, Synthetic-11A1H10, Synthetic-11A1H11 HC-CDR2

<400> SEQUENCE: 138

Ile Asn Pro Tyr Asn Gly Gly Thr
1               5

<210> SEQ ID NO 139
<211> LENGTH: 11
<212> TYPE: PRT
<213> ORGANISM: Artificial Sequence
<220> FEATURE:
<223> OTHER INFORMATION: Synthetic-11A1H6, Synthetic-11A1H7 LC-CDR1

<400> SEQUENCE: 139

Gln His Leu Glu Tyr Ser Gln Gly Tyr Ser Tyr
1               5                   10

<210> SEQ ID NO 140
<211> LENGTH: 11
<212> TYPE: PRT
<213> ORGANISM: Artificial Sequence
<220> FEATURE:
<223> OTHER INFORMATION: Synthetic-11A1H8, Synthetic-11A1H9 LC-CDR1

<400> SEQUENCE: 140

Gln His Leu Glu Tyr Ser Thr Gly Tyr Ser Tyr
1               5                   10

<210> SEQ ID NO 141
<211> LENGTH: 3
<212> TYPE: PRT
<213> ORGANISM: Artificial Sequence
<220> FEATURE:
<223> OTHER INFORMATION: Synthetic-11A1H6, Synthetic-11A1H7, Synthetic-
      11A1H8, Synthetic-11A1H9, Synthetic-11A1H10 LC-CDR2

<400> SEQUENCE: 141

Lys Val Ser
1

<210> SEQ ID NO 142
<211> LENGTH: 9
<212> TYPE: PRT
<213> ORGANISM: Artificial Sequence
<220> FEATURE:
<223> OTHER INFORMATION: Synthetic-11A1H11 LC-CDR3

<400> SEQUENCE: 142

Ser Gln Gly Thr His Val Pro Tyr Thr
1               5

<210> SEQ ID NO 143
<211> LENGTH: 25
<212> TYPE: PRT
<213> ORGANISM: Artificial Sequence
<220> FEATURE:
<223> OTHER INFORMATION: Synthetic-11A1H1, Synthetic-11A1H2, Synthetic-
      11A1H3, Synthetic-11A1H4, Synthetic-11A1H5, Synthetic-11A1H6,
      Synthetic-11A1H7, Synthetic-11A1H8, Synthetic-11A1H9, Synthetic-
      11A1H10, Synthetic-11A1H11 HC-FR1

<400> SEQUENCE: 143

Gln Val Gln Leu Val Gln Ser Gly Ala Glu Val Lys Lys Pro Gly Ala
1               5                   10                  15

Ser Val Lys Val Ser Cys Lys Ala Ser
            20              25

<210> SEQ ID NO 144
<211> LENGTH: 17
<212> TYPE: PRT
<213> ORGANISM: Artificial Sequence
<220> FEATURE:
<223> OTHER INFORMATION: Synthetic-11A1H1, Synthetic-11A1H2, Synthetic-
      HC-FR2

<400> SEQUENCE: 144

Ile His Trp Val Arg Gln Ala Pro Gly Lys Gly Leu Glu Trp Met Gly
1               5                   10                  15

Tyr

<210> SEQ ID NO 145
<211> LENGTH: 17
<212> TYPE: PRT
<213> ORGANISM: Artificial Sequence
<220> FEATURE:
<223> OTHER INFORMATION: Synthetic-11A1H3 HC-FR2

<400> SEQUENCE: 145

Met His Trp Val Arg Gln Ala Pro Gly Gln Gly Leu Glu Trp Met Gly
1               5                   10                  15

Tyr

<210> SEQ ID NO 146
<211> LENGTH: 17
<212> TYPE: PRT
<213> ORGANISM: Artificial Sequence
<220> FEATURE:
<223> OTHER INFORMATION: Synthetic-11A1H4, Synthetic-11A1H5, Synthetic-
      11A1H6, Synthetic-11A1H7, Synthetic-11A1H8, Synthetic-11A1H9,
      Synthetic-11A1H10, Synthetic-11A1H11 HC-FR2

<400> SEQUENCE: 146

Ile His Trp Val Arg Gln Ala Pro Gly Gln Gly Leu Glu Trp Met Gly
1               5                   10                  15

Tyr

<210> SEQ ID NO 147
<211> LENGTH: 38
<212> TYPE: PRT
<213> ORGANISM: Artificial Sequence
<220> FEATURE:
<223> OTHER INFORMATION: Synthetic-11A1H1 HC-FR3

<400> SEQUENCE: 147

Lys Ser Asn Glu Lys Phe Lys Gly Arg Val Thr Leu Thr Ser Asp Lys
1               5                   10                  15

Ser Ser Thr Ser Ala Tyr Met Glu Leu Ser Ser Leu Arg Ser Glu Asp
            20                  25                  30

Thr Ala Val Tyr Tyr Cys
        35

<210> SEQ ID NO 148
<211> LENGTH: 38
<212> TYPE: PRT
<213> ORGANISM: Artificial Sequence
<220> FEATURE:
<223> OTHER INFORMATION: Synthetic-11A1H2 HC-FR3

<400> SEQUENCE: 148

```
Lys Ser Asn Glu Lys Phe Lys Gly Arg Val Thr Leu Thr Ser Asp Thr
1               5                   10                  15

Ser Thr Thr Thr Ala Tyr Met Glu Leu Ser Ser Leu Arg Ser Glu Asp
                20                  25                  30

Thr Ala Val Tyr Tyr Cys
            35
```

<210> SEQ ID NO 149
<211> LENGTH: 38
<212> TYPE: PRT
<213> ORGANISM: Artificial Sequence
<220> FEATURE:
<223> OTHER INFORMATION: Synthetic-11A1H3 HC-FR3

<400> SEQUENCE: 149

```
Lys Ser Asn Glu Lys Phe Gln Gly Arg Val Thr Leu Thr Ser Asp Thr
1               5                   10                  15

Ser Thr Ser Thr Ala Tyr Met Glu Leu Ser Ser Leu Arg Ser Glu Asp
                20                  25                  30

Thr Ala Val Tyr Tyr Cys
            35
```

<210> SEQ ID NO 150
<211> LENGTH: 38
<212> TYPE: PRT
<213> ORGANISM: Artificial Sequence
<220> FEATURE:
<223> OTHER INFORMATION: Synthetic-11A1H4, Synthetic-11A1H6, Synthetic-
      11A1H8 HC-FR3

<400> SEQUENCE: 150

```
Lys Tyr Asn Gln Lys Phe Lys Gly Arg Val Thr Leu Thr Ser Asp Thr
1               5                   10                  15

Ser Thr Thr Thr Ala Tyr Met Glu Leu Ser Arg Leu Arg Ser Asp Asp
                20                  25                  30

Thr Ala Val Tyr Tyr Cys
            35
```

<210> SEQ ID NO 151
<211> LENGTH: 38
<212> TYPE: PRT
<213> ORGANISM: Artificial Sequence
<220> FEATURE:
<223> OTHER INFORMATION: Synthetic-11A1H5, Synthetic-11A1H7, Synthetic-
      11A1H9, Synthetic-11A1H10, Synthetic-11A1H11 HC-FR3

<400> SEQUENCE: 151

```
Asn Tyr Ala Gln Lys Phe Lys Gly Arg Val Thr Leu Thr Ser Asp Thr
1               5                   10                  15

Ser Thr Thr Thr Ala Tyr Met Glu Leu Ser Arg Leu Arg Ser Glu Asp
                20                  25                  30

Thr Ala Val Tyr Tyr Cys
            35
```

<210> SEQ ID NO 152
<211> LENGTH: 11
<212> TYPE: PRT
<213> ORGANISM: Artificial Sequence
<220> FEATURE:
<223> OTHER INFORMATION: Synthetic-11A1H1, Synthetic-11A1H2, Synthetic-
      11A1H5, Synthetic-11A1H7, Synthetic-11A1H9, Synthetic-11A1H10,
      Synthetic-11A1H11 HC-FR4

```
<400> SEQUENCE: 152

Trp Gly Gln Gly Thr Leu Val Thr Val Ser Ser
1               5                   10

<210> SEQ ID NO 153
<211> LENGTH: 7
<212> TYPE: PRT
<213> ORGANISM: Artificial Sequence
<220> FEATURE:
<223> OTHER INFORMATION: Synthetic-11A1H3, Synthetic-11A1H4, Synthetic-
      11A1H6, Synthetic-11A1H8 HC-FR4

<400> SEQUENCE: 153

Trp Gly Gln Gly Thr Leu Val
1               5

<210> SEQ ID NO 154
<211> LENGTH: 26
<212> TYPE: PRT
<213> ORGANISM: Artificial Sequence
<220> FEATURE:
<223> OTHER INFORMATION: Synthetic-11A1H1, Synthetic-11A1H2, Synthetic-
      11A1H3, Synthetic-11A1H4, Synthetic-11A1H5, Synthetic-11A1H6,
      Synthetic-11A1H7, Synthetic-11A1H8, Synthetic-11A1H9, 11A1H10,
      11A1H11 LC-FR1

<400> SEQUENCE: 154

Asp Val Val Met Thr Gln Ser Pro Leu Ser Leu Pro Val Thr Leu Gly
1               5                   10                  15

Gln Pro Ala Ser Ile Ser Cys Arg Ser Ser
            20                  25

<210> SEQ ID NO 155
<211> LENGTH: 17
<212> TYPE: PRT
<213> ORGANISM: Artificial Sequence
<220> FEATURE:
<223> OTHER INFORMATION: Synthetic-11A1H1, Synthetic-11A1H2, Synthetic-
      11A1H3, Synthetic-11A1H4, Synthetic-11A1H5, Synthetic-11A1H6,
      Synthetic-11A1H7, Synthetic-11A1H8, Synthetic-11A1H9, Synthetic-
      11A1H10, Synthetic-11A1H11 LC-FR2

<400> SEQUENCE: 155

Leu His Trp Tyr Gln Gln Arg Pro Gly Gln Ser Pro Arg Leu Leu Ile
1               5                   10                  15

Tyr

<210> SEQ ID NO 156
<211> LENGTH: 36
<212> TYPE: PRT
<213> ORGANISM: Artificial Sequence
<220> FEATURE:
<223> OTHER INFORMATION: Synthetic-11A1H1, Synthetic-11A1H2, Synthetic-
      11A1H3, Synthetic-11A1H4, Synthetic-11A1H5, Synthetic-11A1H11
      LC-FR3

<400> SEQUENCE: 156

Asn Arg Phe Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Val Gly
            20                  25                  30

Val Tyr Tyr Cys
        35

<210> SEQ ID NO 157
```

```
<211> LENGTH: 36
<212> TYPE: PRT
<213> ORGANISM: Artificial Sequence
<220> FEATURE:
<223> OTHER INFORMATION: Synthetic-11A1H6, Synthetic-11A1H7, Synthetic-
      11A1H8, Synthetic-11A1H9, Synthetic-11A1H10 LC-FR3

<400> SEQUENCE: 157
```

Asn Arg Asp Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Val Gly
            20                  25                  30

Val Tyr Tyr Cys
        35

```
<210> SEQ ID NO 158
<211> LENGTH: 10
<212> TYPE: PRT
<213> ORGANISM: Artificial Sequence
<220> FEATURE:
<223> OTHER INFORMATION: Synthetic-11A1H1, Synthetic-11A1H2, Synthetic-
      11A1H3, Synthetic-11A1H4, Synthetic-11A1H5, Synthetic-11A1H6,
      Synthetic-11A1H7, Synthetic-11A1H8, Synthetic-11A1H9, Synthetic-
      11A1H10, Synthetic-11A1H11 LC-FR4

<400> SEQUENCE: 158
```

Phe Gly Gly Gly Thr Lys Val Glu Ile Lys
1               5                   10

```
<210> SEQ ID NO 159
<211> LENGTH: 447
<212> TYPE: PRT
<213> ORGANISM: Artificial Sequence
<220> FEATURE:
<223> OTHER INFORMATION: Synthetic-11A1H1 VH-CH1-CH2-CH3

<400> SEQUENCE: 159
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Val Ile His Trp Val Arg Gln Ala Pro Gly Lys Gly Leu Glu Trp Met
        35                  40                  45

Gly Tyr Ile Asn Pro Tyr Asn Asp Gly Thr Lys Ser Asn Glu Lys Phe
    50                  55                  60

Lys Gly Arg Val Thr Leu Thr Ser Asp Lys Ser Ser Thr Ser Ala Tyr
65                  70                  75                  80

Met Glu Leu Ser Ser Leu Arg Ser Glu Asp Thr Ala Val Tyr Tyr Cys
                85                  90                  95

Ala Ser Gly Gly Tyr Tyr Thr Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 160
<211> LENGTH: 219
<212> TYPE: PRT
<213> ORGANISM: Artificial Sequence
<220> FEATURE:
<223> OTHER INFORMATION: Synthetic-11A1H1, Synthetic-11A1H2, Synthetic-
      11A1H3, Synthetic-11A1H4, Synthetic-11A1H5  VL-Ckappa

<400> SEQUENCE: 160

Asp Val Val Met Thr Gln Ser Pro Leu Ser Leu Pro Val Thr Leu Gly
1               5                   10                  15

Gln Pro Ala Ser Ile Ser Cys Arg Ser Ser Gln His Leu Glu Tyr Ser
            20                  25                  30

Asn Gly Tyr Ser Tyr Leu His Trp Tyr Gln Gln Arg Pro Gly Gln Ser
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Val Glu Ile Lys

```
                100                 105                 110
Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 161
<211> LENGTH: 447
<212> TYPE: PRT
<213> ORGANISM: Artificial Sequence
<220> FEATURE:
<223> OTHER INFORMATION: Synthetic-11A1H2 VH-CH1-CH2-CH3

<400> SEQUENCE: 161

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Val Ile His Trp Val Arg Gln Ala Pro Gly Lys Gly Leu Glu Trp Met
        35                  40                  45

Gly Tyr Ile Asn Pro Tyr Asn Asp Gly Thr Lys Ser Asn Glu Lys Phe
    50                  55                  60

Lys Gly Arg Val Thr Leu Thr Ser Asp Thr Ser Thr Thr Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Gly Tyr Tyr Thr Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
```

```
                        245                 250                 255
Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 162
<211> LENGTH: 443
<212> TYPE: PRT
<213> ORGANISM: Artificial Sequence
<220> FEATURE:
<223> OTHER INFORMATION: Synthetic-11A1H3 VH-CH1-CH2-CH3

<400> SEQUENCE: 162

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Asp Gly Thr Lys Ser Asn Glu Lys Phe
    50                  55                  60

Gln Gly Arg Val Thr Leu Thr Ser Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Gly Tyr Tyr Thr Met Asp Tyr Trp Gly Gln Gly Thr Leu
            100                 105                 110

Val Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
```

```
              165                 170                 175
Ser Leu Ser Ser Val Thr Val Pro Ser Ser Leu Gly Thr Gln
            180                 185                 190

Thr Tyr Ile Cys Asn Val Asn His Lys Pro Ser Asn Thr Lys Val Asp
            195                 200                 205

Lys Lys Val Glu Pro Lys Ser Cys Asp Lys Thr His Thr Cys Pro Pro
210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
            275                 280                 285

Glu Glu Gln Tyr Asn Ser Thr Tyr Arg Val Val Ser Val Leu Thr Val
            290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
            325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
            405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
            435                 440

<210> SEQ ID NO 163
<211> LENGTH: 443
<212> TYPE: PRT
<213> ORGANISM: Artificial Sequence
<220> FEATURE:
<223> OTHER INFORMATION: Synthetic-11A1H4, Synthetic-11A1H6, Synthetic-
      11A1H8 VH-CH1-CH2-CH3

<400> SEQUENCE: 163

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Val Ile His Trp Val Arg Gln Ala Pro Gly Gln Gly Leu Glu Trp Met
        35                  40                  45

Gly Tyr Ile Asn Pro Tyr Asn Asp Gly Thr Lys Tyr Asn Gln Lys Phe
    50                  55                  60

Lys Gly Arg Val Thr Leu Thr Ser Asp Thr Ser Thr Thr Thr Ala Tyr
65                  70                  75                  80
```

-continued

```
Met Glu Leu Ser Arg Leu Arg Ser Asp Asp Thr Ala Val Tyr Tyr Cys
                 85                  90                  95

Ala Ser Gly Gly Tyr Tyr Thr Met Asp Tyr Trp Gly Gln Gly Thr Leu
            100                 105                 110

Val Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
            130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
            195                 200                 205

Lys Lys Val Glu Pro Lys Ser Cys Asp Lys Thr His Thr Cys Pro Pro
            210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
            275                 280                 285

Glu Glu Gln Tyr Asn Ser Thr Tyr Arg Val Val Ser Val Leu Thr Val
            290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
            435                 440
```

<210> SEQ ID NO 164
<211> LENGTH: 447
<212> TYPE: PRT
<213> ORGANISM: Artificial Sequence
<220> FEATURE:
<223> OTHER INFORMATION: Synthetic-11A1H5, Synthetic-11A1H7, Synthetic-11A1H9, Synthetic-11A1H10, Synthetic-11A1H11 VH-CH1-CH2-CH3

<400> SEQUENCE: 164

```
Gln Val Gln Leu Val Gln Ser Gly Ala Glu Lys Lys Pro Gly Ala
1               5                   10                  15

Ser Val Lys Val Ser Cys Lys Ala Ser Gly Tyr Thr Phe Thr Gly Tyr
            20                  25                  30

Val Ile His Trp Val Arg Gln Ala Pro Gly Gln Gly Leu Glu Trp Met
            35                  40                  45

Gly Tyr Ile Asn Pro Tyr Asn Gly Gly Thr Asn Tyr Ala Gln Lys Phe
        50                  55                  60

Lys Gly Arg Val Thr Leu Thr Ser Asp Thr Ser Thr Thr Thr Ala Tyr
65                  70                  75                  80

Met Glu Leu Ser Arg Leu Arg Ser Glu Asp Thr Ala Val Tyr Tyr Cys
                85                  90                  95

Ala Ser Gly Gly Tyr Tyr Thr Met Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
                275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
                355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415
```

```
Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
        435                 440                 445

<210> SEQ ID NO 165
<211> LENGTH: 219
<212> TYPE: PRT
<213> ORGANISM: Artificial Sequence
<220> FEATURE:
<223> OTHER INFORMATION: Synthetic-11A1H6, Synthetic-11A1H7 VL-Ckappa

<400> SEQUENCE: 165

Asp Val Val Met Thr Gln Ser Pro Leu Ser Leu Pro Val Thr Leu Gly
1               5                   10                  15

Gln Pro Ala Ser Ile Ser Cys Arg Ser Ser Gln His Leu Glu Tyr Ser
            20                  25                  30

Gln Gly Tyr Ser Tyr Leu His Trp Tyr Gln Gln Arg Pro Gly Gln Ser
        35                  40                  45

Pro Arg Leu Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 166
<211> LENGTH: 219
<212> TYPE: PRT
<213> ORGANISM: Artificial Sequence
<220> FEATURE:
<223> OTHER INFORMATION: Synthetic-11A1H8, Synthetic-11A1H9 VL-Ckappa

<400> SEQUENCE: 166

Asp Val Val Met Thr Gln Ser Pro Leu Ser Leu Pro Val Thr Leu Gly
1               5                   10                  15

Gln Pro Ala Ser Ile Ser Cys Arg Ser Ser Gln His Leu Glu Tyr Ser
            20                  25                  30

Thr Gly Tyr Ser Tyr Leu His Trp Tyr Gln Gln Arg Pro Gly Gln Ser
        35                  40                  45

Pro Arg Leu Leu Ile Tyr Lys Val Ser Asn Arg Asp Ser Gly Val Pro
    50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Val Pro Tyr Thr Phe Gly Gly Gly Thr Lys Val Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
 130                 135                 140

Tyr Pro Arg Glu Ala Lys Val Gln Trp Lys Val Asp Asn Ala Leu Gln
 145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
 210                 215
```

<210> SEQ ID NO 167
<211> LENGTH: 219
<212> TYPE: PRT
<213> ORGANISM: Artificial Sequence
<220> FEATURE:
<223> OTHER INFORMATION: Synthetic-11A1H10 VL-Ckappa

<400> SEQUENCE: 167

```
Asp Val Val Met Thr Gln Ser Pro Leu Ser Leu Pro Val Thr Leu Gly
 1               5                  10                  15

Gln Pro Ala Ser Ile Ser Cys Arg Ser Ser Gln His Leu Glu Tyr Ser
                 20                  25                  30

Asn Gly Tyr Ser Tyr Leu His Trp Tyr Gln Gln Arg Pro Gly Gln Ser
             35                  40                  45

Pro Arg Leu Leu Ile Tyr Lys Val Ser Asn Arg Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Val Pro Tyr Thr Phe Gly Gly Gly Thr Lys Val Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
 130                 135                 140

Tyr Pro Arg Glu Ala Lys Val Gln Trp Lys Val Asp Asn Ala Leu Gln
 145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205
```

```
Pro Val Thr Lys Ser Phe Asn Arg Gly Glu Cys
    210                 215
```

<210> SEQ ID NO 168
<211> LENGTH: 219
<212> TYPE: PRT
<213> ORGANISM: Artificial Sequence
<220> FEATURE:
<223> OTHER INFORMATION: Synthetic-11A1H11 VL-Ckappa

<400> SEQUENCE: 168

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln His Leu Glu Tyr Ser
            20                  25                  30

Asn Gly Tyr Ser Tyr Leu His Trp Tyr Gln Gln Arg Pro Gly Gln Ser
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Gly
                85                  90                  95

Thr His Val Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 169
<211> LENGTH: 8
<212> TYPE: PRT
<213> ORGANISM: Artificial Sequence
<220> FEATURE:
<223> OTHER INFORMATION: Synthetic-11A1H_C HC-CDR1
<220> FEATURE:
<221> NAME/KEY: MISC_FEATURE
<222> LOCATION: (6)..(6)
<223> OTHER INFORMATION: Xaa = N or G

<400> SEQUENCE: 169

```
Gly Tyr Thr Phe Thr Xaa Tyr Val
1               5
```

<210> SEQ ID NO 170
<211> LENGTH: 8
<212> TYPE: PRT
<213> ORGANISM: Artificial Sequence
<220> FEATURE:

```
<223> OTHER INFORMATION: Synthetic-11A1H_C HC-CDR2
<220> FEATURE:
<221> NAME/KEY: MISC_FEATURE
<222> LOCATION: (6)..(6)
<223> OTHER INFORMATION: Xaa = D or G

<400> SEQUENCE: 170

Ile Asn Pro Tyr Asn Xaa Gly Thr
1               5

<210> SEQ ID NO 171
<211> LENGTH: 11
<212> TYPE: PRT
<213> ORGANISM: Artificial Sequence
<220> FEATURE:
<223> OTHER INFORMATION: Synthetic-11A1H_C LC-CDR1
<220> FEATURE:
<221> NAME/KEY: MISC_FEATURE
<222> LOCATION: (7)..(7)
<223> OTHER INFORMATION: Xaa = N, Q or T

<400> SEQUENCE: 171

Gln His Leu Glu Tyr Ser Xaa Gly Tyr Ser Tyr
1               5                   10

<210> SEQ ID NO 172
<211> LENGTH: 3
<212> TYPE: PRT
<213> ORGANISM: Artificial Sequence
<220> FEATURE:
<223> OTHER INFORMATION: Synthetic-11A1H_C LC-CDR2
<220> FEATURE:
<221> NAME/KEY: MISC_FEATURE
<222> LOCATION: (2)..(2)
<223> OTHER INFORMATION: Xaa = I or V

<400> SEQUENCE: 172

Lys Xaa Ser
1

<210> SEQ ID NO 173
<211> LENGTH: 9
<212> TYPE: PRT
<213> ORGANISM: Artificial Sequence
<220> FEATURE:
<223> OTHER INFORMATION: Synthetic-11A1H_C LC-CDR3
<220> FEATURE:
<221> NAME/KEY: MISC_FEATURE
<222> LOCATION: (3)..(3)
<223> OTHER INFORMATION: Xaa = S or G

<400> SEQUENCE: 173

Ser Gln Xaa Thr His Val Pro Tyr Thr
1               5

<210> SEQ ID NO 174
<211> LENGTH: 17
<212> TYPE: PRT
<213> ORGANISM: Artificial Sequence
<220> FEATURE:
<223> OTHER INFORMATION: Synthetic-11A1H_C HC-FR2
<220> FEATURE:
<221> NAME/KEY: MISC_FEATURE
<222> LOCATION: (1)..(1)
<223> OTHER INFORMATION: Xaa = I or M
<220> FEATURE:
<221> NAME/KEY: MISC_FEATURE
<222> LOCATION: (10)..(10)
<223> OTHER INFORMATION: Xaa = Q or K

<400> SEQUENCE: 174
```

```
Xaa His Trp Val Arg Gln Ala Pro Gly Xaa Gly Leu Glu Trp Met Gly
1               5                   10                  15

Tyr

<210> SEQ ID NO 175
<211> LENGTH: 38
<212> TYPE: PRT
<213> ORGANISM: Artificial Sequence
<220> FEATURE:
<223> OTHER INFORMATION: Synthetic-11A1H_C HC-FR3
<220> FEATURE:
<221> NAME/KEY: MISC_FEATURE
<222> LOCATION: (1)..(1)
<223> OTHER INFORMATION: Xaa = K or N
<220> FEATURE:
<221> NAME/KEY: MISC_FEATURE
<222> LOCATION: (2)..(2)
<223> OTHER INFORMATION: Xaa = S or Y
<220> FEATURE:
<221> NAME/KEY: MISC_FEATURE
<222> LOCATION: (3)..(3)
<223> OTHER INFORMATION: Xaa = N or A
<220> FEATURE:
<221> NAME/KEY: MISC_FEATURE
<222> LOCATION: (4)..(4)
<223> OTHER INFORMATION: Xaa = E or Q
<220> FEATURE:
<221> NAME/KEY: MISC_FEATURE
<222> LOCATION: (7)..(7)
<223> OTHER INFORMATION: Xaa = K or Q
<220> FEATURE:
<221> NAME/KEY: MISC_FEATURE
<222> LOCATION: (16)..(16)
<223> OTHER INFORMATION: Xaa = T or K
<220> FEATURE:
<221> NAME/KEY: MISC_FEATURE
<222> LOCATION: (18)..(18)
<223> OTHER INFORMATION: Xaa = T or S
<220> FEATURE:
<221> NAME/KEY: MISC_FEATURE
<222> LOCATION: (20)..(20)
<223> OTHER INFORMATION: Xaa = T or S
<220> FEATURE:
<221> NAME/KEY: MISC_FEATURE
<222> LOCATION: (27)..(27)
<223> OTHER INFORMATION: Xaa = S or R
<220> FEATURE:
<221> NAME/KEY: MISC_FEATURE
<222> LOCATION: (31)..(31)
<223> OTHER INFORMATION: Xaa = E or D

<400> SEQUENCE: 175

Xaa Xaa Xaa Xaa Lys Phe Xaa Gly Arg Val Thr Leu Thr Ser Asp Xaa
1               5                   10                  15

Ser Xaa Ser Xaa Ala Tyr Met Glu Leu Ser Xaa Leu Arg Ser Xaa Asp
            20                  25                  30

Thr Ala Val Tyr Tyr Cys
        35

<210> SEQ ID NO 176
<211> LENGTH: 11
<212> TYPE: PRT
<213> ORGANISM: Artificial Sequence
<220> FEATURE:
<223> OTHER INFORMATION: Synthetic-11A1H_C HC-FR4
<220> FEATURE:
<221> NAME/KEY: MISC_FEATURE
<222> LOCATION: (8)..(8)
<223> OTHER INFORMATION: Xaa = T or absent
<220> FEATURE:
<221> NAME/KEY: MISC_FEATURE
<222> LOCATION: (9)..(9)
```

-continued

```
<223> OTHER INFORMATION: Xaa = V or absent
<220> FEATURE:
<221> NAME/KEY: MISC_FEATURE
<222> LOCATION: (10)..(10)
<223> OTHER INFORMATION: Xaa = S or absent
<220> FEATURE:
<221> NAME/KEY: MISC_FEATURE
<222> LOCATION: (11)..(11)
<223> OTHER INFORMATION: Xaa = S or absent

<400> SEQUENCE: 176

Trp Gly Gln Gly Thr Leu Val Xaa Xaa Xaa Xaa
1               5                   10

<210> SEQ ID NO 177
<211> LENGTH: 36
<212> TYPE: PRT
<213> ORGANISM: Artificial Sequence
<220> FEATURE:
<223> OTHER INFORMATION: Synthetic-11A1H_C LC-FR3
<220> FEATURE:
<221> NAME/KEY: MISC_FEATURE
<222> LOCATION: (3)..(3)
<223> OTHER INFORMATION: Xaa = D or F

<400> SEQUENCE: 177

Asn Arg Xaa Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Val Gly
            20                  25                  30

Val Tyr Tyr Cys
        35

<210> SEQ ID NO 178
<211> LENGTH: 117
<212> TYPE: PRT
<213> ORGANISM: Artificial Sequence
<220> FEATURE:
<223> OTHER INFORMATION: Synthetic-11A1H_C VH
<220> FEATURE:
<221> NAME/KEY: MISC_FEATURE
<222> LOCATION: (31)..(31)
<223> OTHER INFORMATION: Xaa = N or G
<220> FEATURE:
<221> NAME/KEY: MISC_FEATURE
<222> LOCATION: (34)..(34)
<223> OTHER INFORMATION: Xaa = I or M
<220> FEATURE:
<221> NAME/KEY: MISC_FEATURE
<222> LOCATION: (43)..(43)
<223> OTHER INFORMATION: Xaa = Q or K
<220> FEATURE:
<221> NAME/KEY: MISC_FEATURE
<222> LOCATION: (56)..(56)
<223> OTHER INFORMATION: Xaa = D or G
<220> FEATURE:
<221> NAME/KEY: MISC_FEATURE
<222> LOCATION: (59)..(59)
<223> OTHER INFORMATION: Xaa = K or N
<220> FEATURE:
<221> NAME/KEY: MISC_FEATURE
<222> LOCATION: (60)..(60)
<223> OTHER INFORMATION: Xaa = S or Y
<220> FEATURE:
<221> NAME/KEY: MISC_FEATURE
<222> LOCATION: (61)..(61)
<223> OTHER INFORMATION: Xaa = N or A
<220> FEATURE:
<221> NAME/KEY: MISC_FEATURE
<222> LOCATION: (62)..(62)
<223> OTHER INFORMATION: Xaa = E or Q
<220> FEATURE:
<221> NAME/KEY: MISC_FEATURE
```

<222> LOCATION: (65)..(65)
<223> OTHER INFORMATION: Xaa = K or Q
<220> FEATURE:
<221> NAME/KEY: MISC_FEATURE
<222> LOCATION: (74)..(74)
<223> OTHER INFORMATION: Xaa = T or K
<220> FEATURE:
<221> NAME/KEY: MISC_FEATURE
<222> LOCATION: (76)..(76)
<223> OTHER INFORMATION: Xaa = T or S
<220> FEATURE:
<221> NAME/KEY: MISC_FEATURE
<222> LOCATION: (78)..(78)
<223> OTHER INFORMATION: Xaa = T or S
<220> FEATURE:
<221> NAME/KEY: MISC_FEATURE
<222> LOCATION: (85)..(85)
<223> OTHER INFORMATION: Xaa = S or R
<220> FEATURE:
<221> NAME/KEY: MISC_FEATURE
<222> LOCATION: (89)..(89)
<223> OTHER INFORMATION: Xaa = E or D
<220> FEATURE:
<221> NAME/KEY: MISC_FEATURE
<222> LOCATION: (114)..(114)
<223> OTHER INFORMATION: Xaa = T or absent
<220> FEATURE:
<221> NAME/KEY: MISC_FEATURE
<222> LOCATION: (115)..(115)
<223> OTHER INFORMATION: Xaa = V or absent
<220> FEATURE:
<221> NAME/KEY: MISC_FEATURE
<222> LOCATION: (116)..(116)
<223> OTHER INFORMATION: Xaa = S or absent
<220> FEATURE:
<221> NAME/KEY: MISC_FEATURE
<222> LOCATION: (117)..(117)
<223> OTHER INFORMATION: Xaa = S or absent

<400> SEQUENCE: 178

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Xaa Tyr
            20                  25                  30

Val Xaa His Trp Val Arg Gln Ala Pro Gly Xaa Gly Leu Glu Trp Met
        35                  40                  45

Gly Tyr Ile Asn Pro Tyr Asn Xaa Gly Thr Xaa Xaa Xaa Xaa Lys Phe
    50                  55                  60

Xaa Gly Arg Val Thr Leu Thr Ser Asp Xaa Ser Xaa Ser Xaa Ala Tyr
65                  70                  75                  80

Met Glu Leu Ser Xaa Leu Arg Ser Xaa Asp Thr Ala Val Tyr Tyr Cys
                85                  90                  95

Ala Ser Gly Gly Tyr Tyr Thr Met Asp Tyr Trp Gly Gln Gly Thr Leu
            100                 105                 110

Val Xaa Xaa Xaa Xaa
        115

<210> SEQ ID NO 179
<211> LENGTH: 112
<212> TYPE: PRT
<213> ORGANISM: Artificial Sequence
<220> FEATURE:
<223> OTHER INFORMATION: Synthetic-11A1H_C VL
<220> FEATURE:
<221> NAME/KEY: MISC_FEATURE
<222> LOCATION: (33)..(33)
<223> OTHER INFORMATION: Xaa = N, Q or T
<220> FEATURE:
<221> NAME/KEY: MISC_FEATURE
<222> LOCATION: (56)..(56)

```
<223> OTHER INFORMATION: Xaa = I or V
<220> FEATURE:
<221> NAME/KEY: MISC_FEATURE
<222> LOCATION: (60)..(60)
<223> OTHER INFORMATION: Xaa = D or F
<220> FEATURE:
<221> NAME/KEY: MISC_FEATURE
<222> LOCATION: (96)..(96)
<223> OTHER INFORMATION: Xaa = S or G

<400> SEQUENCE: 179

Asp Val Val Met Thr Gln Ser Pro Leu Ser Leu Pro Val Thr Leu Gly
1               5                   10                  15

Gln Pro Ala Ser Ile Ser Cys Arg Ser Ser Gln His Leu Glu Tyr Ser
            20                  25                  30

Xaa Gly Tyr Ser Tyr Leu His Trp Tyr Gln Gln Arg Pro Gly Gln Ser
        35                  40                  45

Pro Arg Leu Leu Ile Tyr Lys Xaa Ser Asn Arg Xaa Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Xaa
                85                  90                  95

Thr His Val Pro Tyr Thr Phe Gly Gly Gly Thr Lys Val Glu Ile Lys
            100                 105                 110
```

CD47 ANTIGEN-BINDING MOLECULES

RELATED APPLICATIONS

This application is a continuation of U.S. patent application Ser. No. 16/760,899, filed on Apr. 30, 2020, which is a national stage filing under 35 U.S.C. 371 of International Patent Application Serial No. PCT/EP2018/079931, filed Nov. 1, 2018, which claims priority to British Application No. GB 1718101.7, filed Nov. 1, 2017, British Application No. GB 1720425.6, filed Dec. 7, 2017 and British Application No. GB 1720426.4, filed Dec. 7, 2017, the contents and elements of each of which are herein incorporated by reference for all purposes.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Jun. 22, 2022, is named H096970002US01-SEQ-AZW and is 193,590 bytes in size.

FIELD OF THE INVENTION

The present invention relates to the fields of molecular biology, more specifically antibody technology. The present invention also relates to methods of medical treatment and prophylaxis.

BACKGROUND TO THE INVENTION

CD47 is the "don't-eat-me" signal and is ubiquitously expressed on normal cells where binding to SIRPα on macrophages inhibits phagocytosis. CD47 is commonly over-expressed in tumors where it correlates with immune evasion and poor prognosis. Blocking CD47-SIRPalpha interaction restores macrophage phagocytosis of tumor cells and anti-CD47 mAbs have shown anti-tumor efficacy in mouse models of solid tumors and hematological malignancies.

WO 2014/087248 A2 discloses monospecific anti-CD47 antibodies having an affinity for human CD47 as high as ~23.6 nM. The high-affinity CD47 antibodies disclosed therein induce substantial hemagglutination (see e.g. Example 8 of WO 2014/087248 A2).

SUMMARY OF THE INVENTION

In a first aspect, the present invention provides an antigen-binding molecule, optionally isolated, which is capable of binding to CD47.

Also provided is an antigen-binding molecule, optionally isolated, which is capable of binding to CD47 in extracellular region 1.

In some embodiments the antigen-binding molecule is capable of binding to the V-type Ig-like domain of CD47. In some embodiments the antigen-binding molecule is capable of binding to a polypeptide comprising or consisting of the amino acid sequence shown in SEQ ID NO:9. In some embodiments the antigen-binding molecule is capable of inhibiting interaction between CD47 and SIRPa. In some embodiments the antigen-binding molecule is capable of increasing phagocytosis of CD47-expressing cells.

In some embodiments the antigen-binding molecule is capable of binding to a peptide or polypeptide comprising or consisting of the amino acid sequence of SEQ ID NO:21. In some embodiments the antigen-binding molecule comprises:

(i) a heavy chain variable (VH) region incorporating the following CDRs:
  HC-CDR1 having the amino acid sequence of SEQ ID NO:169
  HC-CDR2 having the amino acid sequence of SEQ ID NO:170
  HC-CDR3 having the amino acid sequence of SEQ ID NO:26,
  or a variant thereof in which one or two or three amino acids in one or more of HC-CDR1, HC-CDR2, or HC-CDR3 are substituted with another amino acid; and
(ii) a light chain variable (VL) region incorporating the following CDRs:
  LC-CDR1 having the amino acid sequence of SEQ ID NO:171
  LC-CDR2 having the amino acid sequence of SEQ ID NO:172
  LC-CDR3 having the amino acid sequence of SEQ ID NO:173;
or a variant thereof in which one or two or three amino acids in one or more of LC-CDR1, LC-CDR2 or LC-CDR3 are substituted with another amino acid.

In some embodiments the antigen-binding molecule comprises:

(a)
  (i) a heavy chain variable (VH) region incorporating the following CDRs:
    HC-CDR1 having the amino acid sequence of SEQ ID NO:24
    HC-CDR2 having the amino acid sequence of SEQ ID NO:25
    HC-CDR3 having the amino acid sequence of SEQ ID NO:26,
    or a variant thereof in which one or two or three amino acids in one or more of HC-CDR1, HC-CDR2, or HC-CDR3 are substituted with another amino acid; and
  (ii) a light chain variable (VL) region incorporating the following CDRs:
    LC-CDR1 having the amino acid sequence of SEQ ID NO:32
    LC-CDR2 having the amino acid sequence of SEQ ID NO:33
    LC-CDR3 having the amino acid sequence of SEQ ID NO:34;
  or a variant thereof in which one or two or three amino acids in one or more of LC-CDR1, LC-CDR2 or LC-CDR3 are substituted with another amino acid;
or
(b)
  (i) a heavy chain variable (VH) region incorporating the following CDRs:
    HC-CDR1 having the amino acid sequence of SEQ ID NO:137
    HC-CDR2 having the amino acid sequence of SEQ ID NO:138
    HC-CDR3 having the amino acid sequence of SEQ ID NO:26,
    or a variant thereof in which one or two or three amino acids in one or more of HC-CDR1, HC-CDR2, or HC-CDR3 are substituted with another amino acid; and
  (ii) a light chain variable (VL) region incorporating the following CDRs:
    LC-CDR1 having the amino acid sequence of SEQ ID NO:32

LC-CDR2 having the amino acid sequence of SEQ ID NO:33
LC-CDR3 having the amino acid sequence of SEQ ID NO:34;
or a variant thereof in which one or two or three amino acids in one or more of LC-CDR1, LC-CDR2 or LC-CDR3 are substituted with another amino acid;
or
(c)
  (i) a heavy chain variable (VH) region incorporating the following CDRs:
    HC-CDR1 having the amino acid sequence of SEQ ID NO:24
    HC-CDR2 having the amino acid sequence of SEQ ID NO:25
    HC-CDR3 having the amino acid sequence of SEQ ID NO:26,
    or a variant thereof in which one or two or three amino acids in one or more of HC-CDR1, HC-CDR2, or HC-CDR3 are substituted with another amino acid; and
  (ii) a light chain variable (VL) region incorporating the following CDRs:
    LC-CDR1 having the amino acid sequence of SEQ ID NO:139
    LC-CDR2 having the amino acid sequence of SEQ ID NO:141
    LC-CDR3 having the amino acid sequence of SEQ ID NO:34;
    or a variant thereof in which one or two or three amino acids in one or more of LC-CDR1, LC-CDR2 or LC-CDR3 are substituted with another amino acid;
or
(d)
  (i) a heavy chain variable (VH) region incorporating the following CDRs:
    HC-CDR1 having the amino acid sequence of SEQ ID NO:137
    HC-CDR2 having the amino acid sequence of SEQ ID NO:138
    HC-CDR3 having the amino acid sequence of SEQ ID NO:26,
    or a variant thereof in which one or two or three amino acids in one or more of HC-CDR1, HC-CDR2, or HC-CDR3 are substituted with another amino acid; and
  (ii) a light chain variable (VL) region incorporating the following CDRs:
    LC-CDR1 having the amino acid sequence of SEQ ID NO:139
    LC-CDR2 having the amino acid sequence of SEQ ID NO:141
    LC-CDR3 having the amino acid sequence of SEQ ID NO:34;
    or a variant thereof in which one or two or three amino acids in one or more of LC-CDR1, LC-CDR2 or LC-CDR3 are substituted with another amino acid;
or
(e)
  (i) a heavy chain variable (VH) region incorporating the following CDRs:
    HC-CDR1 having the amino acid sequence of SEQ ID NO:24
    HC-CDR2 having the amino acid sequence of SEQ ID NO:25
    HC-CDR3 having the amino acid sequence of SEQ ID NO:26,
    or a variant thereof in which one or two or three amino acids in one or more of HC-CDR1, HC-CDR2, or HC-CDR3 are substituted with another amino acid; and
  (ii) a light chain variable (VL) region incorporating the following CDRs:
    LC-CDR1 having the amino acid sequence of SEQ ID NO:140
    LC-CDR2 having the amino acid sequence of SEQ ID NO:141
    LC-CDR3 having the amino acid sequence of SEQ ID NO:34;
    or a variant thereof in which one or two or three amino acids in one or more of LC-CDR1, LC-CDR2 or LC-CDR3 are substituted with another amino acid;
or
(f)
  (i) a heavy chain variable (VH) region incorporating the following CDRs:
    HC-CDR1 having the amino acid sequence of SEQ ID NO:137
    HC-CDR2 having the amino acid sequence of SEQ ID NO:138
    HC-CDR3 having the amino acid sequence of SEQ ID NO:26,
    or a variant thereof in which one or two or three amino acids in one or more of HC-CDR1, HC-CDR2, or HC-CDR3 are substituted with another amino acid; and
  (ii) a light chain variable (VL) region incorporating the following CDRs:
    LC-CDR1 having the amino acid sequence of SEQ ID NO:140
    LC-CDR2 having the amino acid sequence of SEQ ID NO:141
    LC-CDR3 having the amino acid sequence of SEQ ID NO:34;
    or a variant thereof in which one or two or three amino acids in one or more of LC-CDR1, LC-CDR2 or LC-CDR3 are substituted with another amino acid;
or
(g)
  (i) a heavy chain variable (VH) region incorporating the following CDRs:
    HC-CDR1 having the amino acid sequence of SEQ ID NO:137
    HC-CDR2 having the amino acid sequence of SEQ ID NO:138
    HC-CDR3 having the amino acid sequence of SEQ ID NO:26,
    or a variant thereof in which one or two or three amino acids in one or more of HC-CDR1, HC-CDR2, or HC-CDR3 are substituted with another amino acid; and
  (ii) a light chain variable (VL) region incorporating the following CDRs:
    LC-CDR1 having the amino acid sequence of SEQ ID NO:32
    LC-CDR2 having the amino acid sequence of SEQ ID NO:141
    LC-CDR3 having the amino acid sequence of SEQ ID NO:34;
    or a variant thereof in which one or two or three amino acids in one or more of LC-CDR1, LC-CDR2 or LC-CDR3 are substituted with another amino acid;
or
(h)
  (i) a heavy chain variable (VH) region incorporating the following CDRs:

HC-CDR1 having the amino acid sequence of SEQ ID NO:137
HC-CDR2 having the amino acid sequence of SEQ ID NO:138
HC-CDR3 having the amino acid sequence of SEQ ID NO:26,
or a variant thereof in which one or two or three amino acids in one or more of HC-CDR1, HC-CDR2, or HC-CDR3 are substituted with another amino acid; and
(ii) a light chain variable (VL) region incorporating the following CDRs:
LC-CDR1 having the amino acid sequence of SEQ ID NO:32
LC-CDR2 having the amino acid sequence of SEQ ID NO:33
LC-CDR3 having the amino acid sequence of SEQ ID NO:142;
or a variant thereof in which one or two or three amino acids in one or more of LC-CDR1, LC-CDR2 or LC-CDR3 are substituted with another amino acid.

In some embodiments the antigen-binding molecule comprises:

(a)
(i) a heavy chain variable (VH) region incorporating the following CDRs:
HC-CDR1 having the amino acid sequence of SEQ ID NO:24
HC-CDR2 having the amino acid sequence of SEQ ID NO:25
HC-CDR3 having the amino acid sequence of SEQ ID NO:26; and
(ii) a light chain variable (VL) region incorporating the following CDRs:
LC-CDR1 having the amino acid sequence of SEQ ID NO:32
LC-CDR2 having the amino acid sequence of SEQ ID NO:33
LC-CDR3 having the amino acid sequence of SEQ ID NO:34;
or
(b)
(i) a heavy chain variable (VH) region incorporating the following CDRs:
HC-CDR1 having the amino acid sequence of SEQ ID NO:137
HC-CDR2 having the amino acid sequence of SEQ ID NO:138
HC-CDR3 having the amino acid sequence of SEQ ID NO:26; and
(ii) a light chain variable (VL) region incorporating the following CDRs:
LC-CDR1 having the amino acid sequence of SEQ ID NO:32
LC-CDR2 having the amino acid sequence of SEQ ID NO:33
LC-CDR3 having the amino acid sequence of SEQ ID NO:34;
or
(c)
(i) a heavy chain variable (VH) region incorporating the following CDRs:
HC-CDR1 having the amino acid sequence of SEQ ID NO:24
HC-CDR2 having the amino acid sequence of SEQ ID NO:25
HC-CDR3 having the amino acid sequence of SEQ ID NO:26; and
(ii) a light chain variable (VL) region incorporating the following CDRs:
LC-CDR1 having the amino acid sequence of SEQ ID NO:139
LC-CDR2 having the amino acid sequence of SEQ ID NO:141
LC-CDR3 having the amino acid sequence of SEQ ID NO:34;
or
(d)
(i) a heavy chain variable (VH) region incorporating the following CDRs:
HC-CDR1 having the amino acid sequence of SEQ ID NO:137
HC-CDR2 having the amino acid sequence of SEQ ID NO:138
HC-CDR3 having the amino acid sequence of SEQ ID NO:26; and
(ii) a light chain variable (VL) region incorporating the following CDRs:
LC-CDR1 having the amino acid sequence of SEQ ID NO:139
LC-CDR2 having the amino acid sequence of SEQ ID NO:141
LC-CDR3 having the amino acid sequence of SEQ ID NO:34;
or
(e)
(i) a heavy chain variable (VH) region incorporating the following CDRs:
HC-CDR1 having the amino acid sequence of SEQ ID NO:24
HC-CDR2 having the amino acid sequence of SEQ ID NO:25
HC-CDR3 having the amino acid sequence of SEQ ID NO:26; and
(ii) a light chain variable (VL) region incorporating the following CDRs:
LC-CDR1 having the amino acid sequence of SEQ ID NO:140
LC-CDR2 having the amino acid sequence of SEQ ID NO:141
LC-CDR3 having the amino acid sequence of SEQ ID NO:34;
or
(f)
(i) a heavy chain variable (VH) region incorporating the following CDRs:
HC-CDR1 having the amino acid sequence of SEQ ID NO:137
HC-CDR2 having the amino acid sequence of SEQ ID NO:138
HC-CDR3 having the amino acid sequence of SEQ ID NO:26; and
(ii) a light chain variable (VL) region incorporating the following CDRs:
LC-CDR1 having the amino acid sequence of SEQ ID NO:140
LC-CDR2 having the amino acid sequence of SEQ ID NO:141
LC-CDR3 having the amino acid sequence of SEQ ID NO:34;
or
(g)
(i) a heavy chain variable (VH) region incorporating the following CDRs:

HC-CDR1 having the amino acid sequence of SEQ ID NO:137
HC-CDR2 having the amino acid sequence of SEQ ID NO:138
HC-CDR3 having the amino acid sequence of SEQ ID NO:26; and
(ii) a light chain variable (VL) region incorporating the following CDRs:
LC-CDR1 having the amino acid sequence of SEQ ID NO:32
LC-CDR2 having the amino acid sequence of SEQ ID NO:141
LC-CDR3 having the amino acid sequence of SEQ ID NO:34;
or
(h)
(i) a heavy chain variable (VH) region incorporating the following CDRs:
HC-CDR1 having the amino acid sequence of SEQ ID NO:137
HC-CDR2 having the amino acid sequence of SEQ ID NO:138
HC-CDR3 having the amino acid sequence of SEQ ID NO:26; and
(ii) a light chain variable (VL) region incorporating the following CDRs:
LC-CDR1 having the amino acid sequence of SEQ ID NO:32
LC-CDR2 having the amino acid sequence of SEQ ID NO:33
LC-CDR3 having the amino acid sequence of SEQ ID NO:142.

In some embodiments the antigen-binding molecule comprises:
a VH region comprising an amino acid sequence having at least 70% sequence identity to the amino acid sequence of SEQ ID NO:23, 39, 178, 127, 129, 130, 131 or 132; and
a VL region comprising an amino acid sequence having at least 70% sequence identity to the amino acid sequence of SEQ ID NO:31, 44, 179, 128, 133, 134, 135 or 136.

In some embodiments the antigen-binding molecule comprises:
(i) a VH region comprising an amino acid sequence having at least 70% sequence identity to the amino acid sequence of SEQ ID NO:23; and
a VL region comprising an amino acid sequence having at least 70% sequence identity to the amino acid sequence of SEQ ID NO:31;
or
(ii) a VH region comprising an amino acid sequence having at least 70% sequence identity to the amino acid sequence of SEQ ID NO:39; and
a VL region comprising an amino acid sequence having at least 70% sequence identity to the amino acid sequence of SEQ ID NO:44;
or
(iii) a VH region comprising an amino acid sequence having at least 70% sequence identity to the amino acid sequence of SEQ ID NO:178; and
a VL region comprising an amino acid sequence having at least 70% sequence identity to the amino acid sequence of SEQ ID NO:179;
or
(iv) a VH region comprising an amino acid sequence having at least 70% sequence identity to the amino acid sequence of SEQ ID NO:127; and
a VL region comprising an amino acid sequence having at least 70% sequence identity to the amino acid sequence of SEQ ID NO:128;
or
(v) a VH region comprising an amino acid sequence having at least 70% sequence identity to the amino acid sequence of SEQ ID NO:129; and
a VL region comprising an amino acid sequence having at least 70% sequence identity to the amino acid sequence of SEQ ID NO:128;
or
(vi) a VH region comprising an amino acid sequence having at least 70% sequence identity to the amino acid sequence of SEQ ID NO:130; and
a VL region comprising an amino acid sequence having at least 70% sequence identity to the amino acid sequence of SEQ ID NO:128;
or
(vii) a VH region comprising an amino acid sequence having at least 70% sequence identity to the amino acid sequence of SEQ ID NO:131; and
a VL region comprising an amino acid sequence having at least 70% sequence identity to the amino acid sequence of SEQ ID NO:128;
or
(viii) a VH region comprising an amino acid sequence having at least 70% sequence identity to the amino acid sequence of SEQ ID NO:132; and
a VL region comprising an amino acid sequence having at least 70% sequence identity to the amino acid sequence of SEQ ID NO:128;
or
(ix) a VH region comprising an amino acid sequence having at least 70% sequence identity to the amino acid sequence of SEQ ID NO:131; and
a VL region comprising an amino acid sequence having at least 70% sequence identity to the amino acid sequence of SEQ ID NO:133;
or
(x) a VH region comprising an amino acid sequence having at least 70% sequence identity to the amino acid sequence of SEQ ID NO:132; and
a VL region comprising an amino acid sequence having at least 70% sequence identity to the amino acid sequence of SEQ ID NO:133;
or
(xi) a VH region comprising an amino acid sequence having at least 70% sequence identity to the amino acid sequence of SEQ ID NO:131; and
a VL region comprising an amino acid sequence having at least 70% sequence identity to the amino acid sequence of SEQ ID NO:134;
or
(xii) a VH region comprising an amino acid sequence having at least 70% sequence identity to the amino acid sequence of SEQ ID NO:132; and
a VL region comprising an amino acid sequence having at least 70% sequence identity to the amino acid sequence of SEQ ID NO:134;
or
(xiii) a VH region comprising an amino acid sequence having at least 70% sequence identity to the amino acid sequence of SEQ ID NO:132; and
a VL region comprising an amino acid sequence having at least 70% sequence identity to the amino acid sequence of SEQ ID NO:135;

or
(xiv) a VH region comprising an amino acid sequence having at least 70% sequence identity to the amino acid sequence of SEQ ID NO:132; and
a VL region comprising an amino acid sequence having at least 70% sequence identity to the amino acid sequence of SEQ ID NO:136.

In some embodiments the antigen-binding molecule is capable of binding to a peptide or polypeptide comprising or consisting of the amino acid sequence of SEQ ID NO:22.

In some embodiments the antigen-binding molecule comprises:
(i) a heavy chain variable (VH) region incorporating the following CDRs:
HC-CDR1 having the amino acid sequence of SEQ ID NO:50
HC-CDR2 having the amino acid sequence of SEQ ID NO:51
HC-CDR3 having the amino acid sequence of SEQ ID NO:52,
or a variant thereof in which one or two or three amino acids in one or more of HC-CDR1, HC-CDR2, or HC-CDR3 are substituted with another amino acid; and
(ii) a light chain variable (VL) region incorporating the following CDRs:
LC-CDR1 having the amino acid sequence of SEQ ID NO:58
LC-CDR2 having the amino acid sequence of SEQ ID NO:59
LC-CDR3 having the amino acid sequence of SEQ ID NO:60;
or a variant thereof in which one or two or three amino acids in one or more of LC-CDR1, LC-CDR2 or LC-CDR3 are substituted with another amino acid.

In some embodiments the antigen-binding molecule comprises:
(i) a heavy chain variable (VH) region incorporating the following CDRs:
HC-CDR1 having the amino acid sequence of SEQ ID NO:50
HC-CDR2 having the amino acid sequence of SEQ ID NO:51
HC-CDR3 having the amino acid sequence of SEQ ID NO:52; and
(ii) a light chain variable (VL) region incorporating the following CDRs:
LC-CDR1 having the amino acid sequence of SEQ ID NO:58
LC-CDR2 having the amino acid sequence of SEQ ID NO:59
LC-CDR3 having the amino acid sequence of SEQ ID NO:60.

In some embodiments the antigen-binding molecule comprises:
a VH region comprising an amino acid sequence having at least 70% sequence identity to the amino acid sequence of SEQ ID NO:49; and
a VL region comprising an amino acid sequence having at least 70% sequence identity to the amino acid sequence of SEQ ID NO:57.

In some embodiments the antigen-binding molecule comprises:
(i) a heavy chain variable (VH) region incorporating the following CDRs:
HC-CDR1 having the amino acid sequence of SEQ ID NO:66
HC-CDR2 having the amino acid sequence of SEQ ID NO:67
HC-CDR3 having the amino acid sequence of SEQ ID NO:68,
or a variant thereof in which one or two or three amino acids in one or more of HC-CDR1, HC-CDR2, or HC-CDR3 are substituted with another amino acid; and
(ii) a light chain variable (VL) region incorporating the following CDRs:
LC-CDR1 having the amino acid sequence of SEQ ID NO:74
LC-CDR2 having the amino acid sequence of SEQ ID NO:75
LC-CDR3 having the amino acid sequence of SEQ ID NO:76;
or a variant thereof in which one or two or three amino acids in one or more of LC-CDR1, LC-CDR2 or LC-CDR3 are substituted with another amino acid.

In some embodiments the antigen-binding molecule comprises:
(i) a heavy chain variable (VH) region incorporating the following CDRs:
HC-CDR1 having the amino acid sequence of SEQ ID NO:66
HC-CDR2 having the amino acid sequence of SEQ ID NO:67
HC-CDR3 having the amino acid sequence of SEQ ID NO:68; and
(ii) a light chain variable (VL) region incorporating the following CDRs:
LC-CDR1 having the amino acid sequence of SEQ ID NO:74
LC-CDR2 having the amino acid sequence of SEQ ID NO:75
LC-CDR3 having the amino acid sequence of SEQ ID NO:76.

In some embodiments the antigen-binding molecule comprises:
a VH region comprising an amino acid sequence having at least 70% sequence identity to the amino acid sequence of SEQ ID NO:65; and
a VL region comprising an amino acid sequence having at least 70% sequence identity to the amino acid sequence of SEQ ID NO:73.

In another aspect the present invention provides an antigen-binding molecule, optionally isolated, comprising (i) an antigen-binding molecule according to the invention, and (ii) an antigen-binding molecule capable of binding to an antigen other than CD47.

In some embodiments the antigen-binding molecule is capable of binding to cells expressing CD47 at the cell surface.

In some embodiments the antigen-binding molecule is capable of inhibiting interaction between CD47 and SIRPα.

In some embodiments the antigen-binding molecule is capable of increasing phagocytosis of CD47-expressing cells.

In another aspect the present invention provides a chimeric antigen receptor (CAR) comprising an antigen-binding molecule according to the invention.

In another aspect the present invention provides a nucleic acid, or a plurality of nucleic acids, optionally isolated, encoding an antigen-binding molecule or a CAR according to the invention.

In another aspect the present invention provides an expression vector, or a plurality of expression vectors, comprising a nucleic acid or a plurality of nucleic acids according to the invention.

In another aspect the present invention provides a cell comprising an antigen-binding molecule, a CAR, a nucleic acid or a plurality of nucleic acids, or an expression vector or a plurality of expression vectors according to the invention.

In another aspect the present invention provides a method comprising culturing a cell comprising a nucleic acid or a plurality of nucleic acids, or an expression vector or a plurality of expression vectors according to the invention, under conditions suitable for expression of the antigen-binding molecule or CAR from the nucleic acid(s) or expression vector(s).

In another aspect the present invention provides a composition comprising an antigen-binding molecule, a CAR, a nucleic acid or a plurality of nucleic acids, an expression vector or a plurality of expression vectors, or a cell according to the invention.

In another aspect the present invention provides an antigen-binding molecule, a CAR, a nucleic acid or a plurality of nucleic acids, an expression vector or a plurality of expression vectors, a cell, or a composition according to the invention for use in a method of medical treatment or prophylaxis.

In another aspect the present invention provides an antigen-binding molecule, a CAR, a nucleic acid or a plurality of nucleic acids, an expression vector or a plurality of expression vectors, a cell, or a composition according to the invention for use in a method of treatment or prevention of a cancer.

In another aspect the present invention provides the use of an antigen-binding molecule, a CAR, a nucleic acid or a plurality of nucleic acids, an expression vector or a plurality of expression vectors, a cell, or a composition according to the invention in the manufacture of a medicament for use in a method of treatment or prevention of a cancer.

In another aspect the present invention provides a method of treating or preventing a cancer, comprising administering to a subject a therapeutically or prophylactically effective amount of an antigen-binding molecule, a CAR, a nucleic acid or a plurality of nucleic acids, an expression vector or a plurality of expression vectors, a cell, or a composition according to the invention.

In another aspect the present invention provides a method for increasing phagocytosis of CD47-expressing cells, comprising contacting CD47-expressing cells with an antigen-binding molecule according to the invention.

In another aspect the present invention provides an in vitro complex, optionally isolated, comprising an antigen-binding molecule according to the invention bound to CD47.

In another aspect the present invention provides a method comprising contacting a sample containing, or suspected to contain, CD47 with an antigen-binding molecule according to the invention, and detecting the formation of a complex of the antigen-binding molecule with CD47.

In another aspect the present invention provides a subject for treatment with a CD47-targeted agent, the method comprising contacting, in vitro, a sample from the subject with an antigen-binding molecule according to the invention and detecting the formation of a complex of the antigen-binding molecule with CD47.

In another aspect the present invention provides the use of an antigen-binding molecule according to the invention as an in vitro or in vivo diagnostic or prognostic agent.

In some embodiments in connection with various aspects of the present invention the cancer is selected from: a hematologic malignancy, a myeloid hematologic malignancy, a lymphoblastic hematologic malignancy, myelodysplastic syndrome (MDS), acute myeloid leukemia (AML), chronic myeloid leukemia (CML), acute lymphoblastic leukemia (ALL), non-Hodgkin's lymphoma (NHL), multiple myeloma (MM), bladder cancer, brain cancer, glioblastoma, ovarian cancer, breast cancer, colon cancer, liver cancer, hepatocellular carcinoma, prostate cancer, lung cancer, Non-small Cell Lung Cancer (NSCLC), skin cancer and melanoma.

DESCRIPTION

The present invention provides antigen-binding molecules having combinations of desirable biophysical and/or functional properties as compared to antigen-binding molecules disclosed in the prior art.

Aspects of the present invention relate to antigen-binding molecules capable of binding to CD47.

In aspects described herein antigen-binding molecules are provided which bind to human CD47 with high affinity, which are cross-reactive with non-human primate CD47, and which display potent inhibition of interaction between CD47 and SIRPα.

In particular, the antigen-binding molecules described herein bind to CD47 with greater affinity than prior art anti-CD47 antibodies, and are more potent as a CD47-targeted therapeutic agents.

Also, the antigen-binding molecules described herein bind to a particular epitope of CD47 that provides for more effective inhibition of the interaction between CD47 and SIPRa as compared to prior art anti-CD47 antibodies. The antigen-binding molecules described herein are thus more effective at enhancing phagocytosis of cells expressing CD47 than prior art anti-CD47 antibodies.

CD47

Human CD47 (also known as IAP, MER6 and OA3) is the protein identified by UniProt Q08722. Alternative splicing of mRNA encoded by the human CD47 gene yields four isoforms which differ in the sequence of the C-terminal cytoplasmic tail region: isoform OA3-323 (UniProt: Q08722-1, v1; SEQ ID NO:1); isoform OA3-293 (UniProt: Q08722-2; SEQ ID NO:2), which lacks the amino acid sequence corresponding to positions 293 to 323 of SEQ ID NO:1; isoform OA3-305 (UniProt: Q08722-3; SEQ ID NO:3), which comprises the substitutions K304N and A305N relative to SEQ ID NO:1, and which lacks the amino acid sequence corresponding to positions 306 to 323 of SEQ ID NO:1; and isoform OA3-312 (UniProt: Q08722-4; SEQ ID NO:4), which lacks the amino acid sequence corresponding to positions 312 to 323 of SEQ ID NO:1.

The N-terminal 18 amino acids of SEQ ID NOs:1 to 4 constitute a signal peptide, and so the mature form of isoforms OA3-323, OA3-293, OA3-305 and OA3-312 (i.e. after processing to remove the signal peptide) have the amino acid sequences shown in SEQ ID NOs:5 to 8, respectively.

The structure and function of CD47 is reviewed e.g. in Sick et al., Br J Pharmacol. (2012) 167(7): 1415-1430 and Willingham et al. Proc Natl Acad Sci USA. (2012) 109(17): 6662-6667, both of which are hereby incorporated by reference in its entirety. CD47 is a ubiquitously-expressed ~50 kDa multi-pass membrane receptor that belongs to the immunoglobulin superfamily, comprising an N-terminal extracellular region (SEQ ID NO:10) having a V-type Ig-like domain (SEQ ID NO:9), five transmembrane domains (SEQ ID NOs:11, 13, 15, 17 and 19), and a short C-terminal intracellular tail (SEQ ID NO:20).

CD47 is involved in cell-to-cell communication through ligating to the transmembrane signal-regulatory proteins (SIRPs) SIRPα and SIRPγ and integrins (e.g. αvβ3 integrin), and also mediates cell-extracellular matrix interactions through binding to thrombospondin-1 (TSP-1). CD47 is involved in a wide range of cellular processes including adhesion, migration, proliferation and apoptosis, and plays a key role in immune processes and angiogenesis.

CD47 is the ligand for SIRPα, which expressed on macrophages and dendritic cells. Binding of CD47 to SIRPα on the surface of phagocytic cells, triggers SIRPα ITIM signalling, inhibiting phagocytosis of the CD47 expressing cell. CD47 is a multi-pass transmembrane protein, whereas SIRPα consists of 4 extracellular domains and an intracellular ITIM-domain. The terminal V-set domain of SIRPα interacts with the Ig V-like domain of CD47.

Upon binding CD47, SIRPα initiates a signalling cascade that results in the inhibition of phagocytosis of the CD47-expressing cell. This "don't eat me" signal is transmitted by phosphorylation by Src kinases of immunoreceptor tyrosine-based inhibitor motifs (ITIMs) in the cytoplasmic domain of SIRPα. Subsequent binding and activation of Src homology-2 (SH2) domain-containing tyrosine phosphatases SHP-1 and SHP-2 blocks phagocytosis, potentially through preventing the accumulation of myosin-IIA at the phagocytic synapse. Disrupting the interaction along the antiparallel beta sheets of CD47 prevents downstream ITIM-mediated signalling, enabling phagocytes to 'eat' and destroy cancer cells.

Aberrant CD47 expression/activity is implicated in the development and progression of many cancers, and accumulating evidence suggests that cell-surface expression of CD47 is a common mechanism by which cancer cells protect themselves from phagocytosis.

In this specification "CD47" refers to CD47 from any species and includes CD47 isoforms, fragments, variants or homologues from any species.

As used herein, a "fragment", "variant" or "homologue" of a protein may optionally be characterised as having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of the reference protein (e.g. a reference isoform). In some embodiments fragments, variants, isoforms and homologues of a reference protein may be characterised by ability to perform a function performed by the reference protein.

A "fragment" generally refers to a fraction of the reference protein. A "variant" generally refers to a protein having an amino acid sequence comprising one or more amino acid substitutions, insertions, deletions or other modifications relative to the amino acid sequence of the reference protein, but retaining a considerable degree of sequence identity (e.g. at least 60%) to the amino acid sequence of the reference protein. An "isoform" generally refers to a variant of the reference protein expressed by the same species as the species of the reference protein (e.g. OA3-323, OA3-293, OA3-305 and OA3-312 are all isoforms of one another). A "homologue" generally refers to a variant of the reference protein produced by a different species as compared to the species of the reference protein. For example, human CD47 isoform OA3-323 (008722-1, v1; SEQ ID NO:1) and Rhesus macaque CD47 (UniProt: F7F5Y9-1, v2; SEQ ID NO:117) are homologues of one another. Homologues include orthologues.

A "fragment" of a reference protein may be of any length (by number of amino acids), although may optionally be at least 25% of the length of the reference protein (that is, the protein from which the fragment is derived) and may have a maximum length of one of 50%, 75%, 80%, 85%, 90%, 91%, 92%, 93%, 94%, 95%, 96%, 97%, 98%, or 99% of the length of the reference protein.

A fragment of CD47 may have a minimum length of one of 10, 20, 30, 40, 50, 100, 150, 200, 250 or 300 amino acids, and may have a maximum length of one of 20, 30, 40, 50, 100, 150, 200, 250 or 300 amino acids.

In some embodiments, the CD47 is CD47 from a mammal (e.g. a primate (rhesus, cynomolgous, non-human primate or human) and/or a rodent (e.g. rat or murine) CD47). Isoforms, fragments, variants or homologues of CD47 may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of an immature or mature CD47 isoform from a given species, e.g. human.

Isoforms, fragments, variants or homologues may optionally be functional isoforms, fragments, variants or homologues, e.g. having a functional property/activity of the reference CD47 (e.g. human CD47 isoform OA3-323), as determined by analysis by a suitable assay for the functional property/activity. For example, an isoform, fragment, variant or homologue of CD47 may display association with one or more of: SIRPα, SIRPγ, TSP-1 and αvβ3 integrin.

In some embodiments, the CD47 comprises, or consists of, an amino acid sequence having at least 70%, preferably one of 80%, 85%, 90%, 91%, 92%, 93%, 94%, 95%, 96%, 97%, 98%, 99% or 100% amino acid sequence identity to one of SEQ ID NOs:1 to 8.

In some embodiments, a fragment of CD47 comprises, or consists of, an amino acid sequence having at least 70%, preferably one of 80%, 85%, 90%, 91%, 92%, 93%, 94%, 95%, 96%, 97%, 98%, 99% or 100% amino acid sequence identity to one of SEQ ID NOs:9 or 10.

CD47 is an attractive therapeutic target. CD47 is usually expressed on the surface of normal healthy cells and migrating hematopoietic stem cells to prevent phagocytosis, and is upregulated in nearly all hematological and solid tumors, to evade immune surveillance and escape phagocytosis. Disrupting the interaction between CD47 and SIRPα enables phagocytes to "eat" and destroy cancer cells. CD47 blockade repolarises tumor-associated macrophages into a pro-inflammatory, anti-tumor state, and clearance of malignant cells by phagocytic cells offers an additional route for neo-antigen presentation to adaptive immune system.

Antigen-Binding Molecules

The present invention provides antigen-binding molecules capable of binding to CD47.

An "antigen-binding molecule" refers to a molecule which is capable of binding to a target antigen, and encompasses monoclonal antibodies, polyclonal antibodies, monospecific and multispecific antibodies (e.g., bispecific antibodies), and antibody fragments (e.g. Fv, scFv, Fab, scFab, F(ab')$_2$, Fab$_2$, diabodies, triabodies, scFv-Fc, minibodies, single domain antibodies (e.g. VhH), etc.), as long as they display binding to the relevant target molecule(s).

The antigen-binding molecule of the present invention comprises a moiety or moieties capable of binding to a target antigen(s). In some embodiments, the moiety capable of binding to a target antigen comprises an antibody heavy chain variable region (VH) and an antibody light chain variable region (VL) of an antibody capable of specific binding to the target antigen. In some embodiments, the moiety capable of binding to a target antigen comprises or consists of an aptamer capable of binding to the target antigen, e.g. a nucleic acid aptamer (reviewed, for example, in Zhou and Rossi Nat Rev Drug Discov. 2017 16(3):181-202). In some embodiments, the moiety capable of binding to a target antigen comprises or consists of a antigen-binding peptide/polypeptide, e.g. a peptide aptamer, thioredoxin, monobody, anticalin, Kunitz domain, avimer, knottin, fynomer, atrimer, DARPin, affibody, nanobody (i.e. a single-domain antibody (sdAb)) affilin, armadillo repeat protein (ArmRP), OBody or fibronectin—reviewed e.g. in Reverdatto et al., Curr Top Med Chem. 2015; 15(12): 1082-1101, which is hereby incorporated by reference in its entirety (see also e.g. Boersma et al., J Biol Chem (2011) 286:41273-85 and Emanuel et al., Mabs (2011) 3:38-48).

The antigen-binding molecules of the present invention generally comprise an antigen-binding domain comprising a VH and a VL of an antibody capable of specific binding to the target antigen. The antigen-binding domain formed by a VH and a VL may also be referred to herein as an Fv region.

An antigen-binding molecule may be, or may comprise, an antigen-binding polypeptide, or an antigen-binding polypeptide complex. An antigen-binding molecule may comprise more than one polypeptide which together form an antigen-binding domain. The polypeptides may associate covalently or non-covalently. In some embodiments the polypeptides form part of a larger polypeptide comprising the polypeptides (e.g. in the case of scFv comprising VH and VL, or in the case of scFab comprising VH-CH1 and VL-CL).

An antigen-binding molecule may refer to a non-covalent or covalent complex of more than one polypeptide (e.g. 2, 3, 4, 6, or 8 polypeptides), e.g. an IgG-like antigen-binding molecule comprising two heavy chain polypeptides and two light chain polypeptides.

The antigen-binding molecules of the present invention may be designed and prepared using the sequences of monoclonal antibodies (mAbs) capable of binding to CD47. Antigen-binding regions of antibodies, such as single chain variable fragment (scFv), Fab and F(ab')$_2$ fragments may also be used/provided. An "antigen-binding region" is any fragment of an antibody which is capable of binding to the target for which the given antibody is specific.

Antibodies generally comprise six complementarity-determining regions CDRs; three in the heavy chain variable (VH) region: HC-CDR1, HC-CDR2 and HC-CDR3, and three in the light chain variable (VL) region: LC-CDR1, LC-CDR2, and LC-CDR3. The six CDRs together define the paratope of the antibody, which is the part of the antibody which binds to the target antigen.

The VH region and VL region comprise framework regions (FRs) either side of each CDR, which provide a scaffold for the CDRs. From N-terminus to C-terminus, VH regions comprise the following structure: N term-[HC-FR1]-[HC-CDR1HHC-FR2HHC-CDR2HHC-FR3HHC-CDR3HHC-FR4]-C term; and VL regions comprise the following structure: N term-[LC-FR1]-[LC-CDR1]-[LC-FR2]-[LC-CDR2]-[LC-FR3]-[LC-CDR3]-[LC-FR4]-C term.

There are several different conventions for defining antibody CDRs and FRs, such as those described in Kabat et al., Sequences of Proteins of Immunological Interest, 5th Ed. Public Health Service, National Institutes of Health, Bethesda, Md. (1991), Chothia et al., J. Mol. Biol. 196:901-917 (1987), and VBASE2, as described in Retter et al., Nucl. Acids Res. (2005) 33 (suppl 1): D671-D674. The CDRs and FRs of the VH regions and VL regions of the antibody clones described herein were defined according to the international IMGT (ImMunoGeneTics) information system (LeFranc et al., Nucleic Acids Res. (2015) 43 (Database issue):D413-22), which uses the IMGT V-DOMAIN numbering rules as described in Lefranc et al., Dev. Comp. Immunol. (2003) 27:55-77.

In some embodiments, the antigen-binding molecule comprises the CDRs of an antigen-binding molecule which is capable of binding to CD47. In some embodiments, the antigen-binding molecule comprises the FRs of an antigen-binding molecule which is capable of binding to CD47. In some embodiments, the antigen-binding molecule comprises the CDRs and the FRs of an antigen-binding molecule which is capable of binding to CD47. That is, in some embodiments the antigen-binding molecule comprises the VH region and the VL region of an antigen-binding molecule which is capable of binding to CD47.

In some embodiments the antigen-binding molecule comprises a VH region and a VL region which is, or which is derived from, the VH/VL region of a CD47-binding antibody clone described herein (i.e. anti-CD47 antibody clones 1-1-A1_BM, 1-1-A1, 5-48-A6, 5-48-D2, 11A1H1, 11A1H2, 11A1H3, 11A1H4, 11A1H5, 11A1H6, 11A1H7, 11A1H8, 11A1H9, 11A1H10 or 11A1H11).

In some embodiments the antigen-binding molecule comprises a VH region according to one of (1) to (4) below:
(1) a VH region incorporating the following CDRs:
  HC-CDR1 having the amino acid sequence of SEQ ID NO:24
  HC-CDR2 having the amino acid sequence of SEQ ID NO:25
  HC-CDR3 having the amino acid sequence of SEQ ID NO:26,
  or a variant thereof in which one or two or three amino acids in one or more of HC-CDR1, HC-CDR2, or HC-CDR3 are substituted with another amino acid.
(2) a VH region incorporating the following CDRs:
  HC-CDR1 having the amino acid sequence of SEQ ID NO:50
  HC-CDR2 having the amino acid sequence of SEQ ID NO:51
  HC-CDR3 having the amino acid sequence of SEQ ID NO:52,
  or a variant thereof in which one or two or three amino acids in one or more of HC-CDR1, HC-CDR2, or HC-CDR3 are substituted with another amino acid.
(3) a VH region incorporating the following CDRs:
  HC-CDR1 having the amino acid sequence of SEQ ID NO:66
  HC-CDR2 having the amino acid sequence of SEQ ID NO:67
  HC-CDR3 having the amino acid sequence of SEQ ID NO:68,
  or a variant thereof in which one or two or three amino acids in one or more of HC-CDR1, HC-CDR2, or HC-CDR3 are substituted with another amino acid.
(4) a VH region incorporating the following CDRs:
  HC-CDR1 having the amino acid sequence of SEQ ID NO:169
  HC-CDR2 having the amino acid sequence of SEQ ID NO:170
  HC-CDR3 having the amino acid sequence of SEQ ID NO:26,
  or a variant thereof in which one or two or three amino acids in one or more of HC-CDR1, HC-CDR2, or HC-CDR3 are substituted with another amino acid.

(5) a VH region incorporating the following CDRs:
- HC-CDR1 having the amino acid sequence of SEQ ID NO:137
- HC-CDR2 having the amino acid sequence of SEQ ID NO:138
- HC-CDR3 having the amino acid sequence of SEQ ID NO:26,
- or a variant thereof in which one or two or three amino acids in one or more of HC-CDR1, HC-CDR2, or HC-CDR3 are substituted with another amino acid.

In some embodiments the antigen-binding molecule comprises a VH region according to one of (6) to (15) below:

(6) a VH region incorporating the following FRs:
- HC-FR1 having the amino acid sequence of SEQ ID NO:27
- HC-FR2 having the amino acid sequence of SEQ ID NO:28
- HC-FR3 having the amino acid sequence of SEQ ID NO:29
- HC-FR4 having the amino acid sequence of SEQ ID NO:30,
- or a variant thereof in which one or two or three amino acids in one or more of HC-FR1, HC-FR2, HC-FR3, or HC-FR4 are substituted with another amino acid.

(7) a VH region incorporating the following FRs:
- HC-FR1 having the amino acid sequence of SEQ ID NO:40
- HC-FR2 having the amino acid sequence of SEQ ID NO:41
- HC-FR3 having the amino acid sequence of SEQ ID NO:42
- HC-FR4 having the amino acid sequence of SEQ ID NO:43,
- or a variant thereof in which one or two or three amino acids in one or more of HC-FR1, HC-FR2, HC-FR3, or HC-FR4 are substituted with another amino acid.

(8) a VH region incorporating the following FRs:
- HC-FR1 having the amino acid sequence of SEQ ID NO:53
- HC-FR2 having the amino acid sequence of SEQ ID NO:54
- HC-FR3 having the amino acid sequence of SEQ ID NO:55
- HC-FR4 having the amino acid sequence of SEQ ID NO:56,
- or a variant thereof in which one or two or three amino acids in one or more of HC-FR1, HC-FR2, HC-FR3, or HC-FR4 are substituted with another amino acid.

(9) a VH region incorporating the following FRs:
- HC-FR1 having the amino acid sequence of SEQ ID NO:69
- HC-FR2 having the amino acid sequence of SEQ ID NO:70
- HC-FR3 having the amino acid sequence of SEQ ID NO:71
- HC-FR4 having the amino acid sequence of SEQ ID NO:72,
- or a variant thereof in which one or two or three amino acids in one or more of HC-FR1, HC-FR2, HC-FR3, or HC-FR4 are substituted with another amino acid.

(10) a VH region incorporating the following FRs:
- HC-FR1 having the amino acid sequence of SEQ ID NO:143
- HC-FR2 having the amino acid sequence of SEQ ID NO:174
- HC-FR3 having the amino acid sequence of SEQ ID NO:175
- HC-FR4 having the amino acid sequence of SEQ ID NO:176,
- or a variant thereof in which one or two or three amino acids in one or more of HC-FR1, HC-FR2, HC-FR3, or HC-FR4 are substituted with another amino acid.

(11) a VH region incorporating the following FRs:
- HC-FR1 having the amino acid sequence of SEQ ID NO:143
- HC-FR2 having the amino acid sequence of SEQ ID NO:144
- HC-FR3 having the amino acid sequence of SEQ ID NO:147
- HC-FR4 having the amino acid sequence of SEQ ID NO:152,
- or a variant thereof in which one or two or three amino acids in one or more of HC-FR1, HC-FR2, HC-FR3, or HC-FR4 are substituted with another amino acid.

(12) a VH region incorporating the following FRs:
- HC-FR1 having the amino acid sequence of SEQ ID NO:143
- HC-FR2 having the amino acid sequence of SEQ ID NO:144
- HC-FR3 having the amino acid sequence of SEQ ID NO:148
- HC-FR4 having the amino acid sequence of SEQ ID NO:152,
- or a variant thereof in which one or two or three amino acids in one or more of HC-FR1, HC-FR2, HC-FR3, or HC-FR4 are substituted with another amino acid.

(13) a VH region incorporating the following FRs:
- HC-FR1 having the amino acid sequence of SEQ ID NO:143
- HC-FR2 having the amino acid sequence of SEQ ID NO:145
- HC-FR3 having the amino acid sequence of SEQ ID NO:149
- HC-FR4 having the amino acid sequence of SEQ ID NO:153,
- or a variant thereof in which one or two or three amino acids in one or more of HC-FR1, HC-FR2, HC-FR3, or HC-FR4 are substituted with another amino acid.

(14) a VH region incorporating the following FRs:
- HC-FR1 having the amino acid sequence of SEQ ID NO:143
- HC-FR2 having the amino acid sequence of SEQ ID NO:146
- HC-FR3 having the amino acid sequence of SEQ ID NO:150
- HC-FR4 having the amino acid sequence of SEQ ID NO:153,
- or a variant thereof in which one or two or three amino acids in one or more of HC-FR1, HC-FR2, HC-FR3, or HC-FR4 are substituted with another amino acid.

(15) a VH region incorporating the following FRs:
- HC-FR1 having the amino acid sequence of SEQ ID NO:143
- HC-FR2 having the amino acid sequence of SEQ ID NO:146
- HC-FR3 having the amino acid sequence of SEQ ID NO:151
- HC-FR4 having the amino acid sequence of SEQ ID NO:152,
- or a variant thereof in which one or two or three amino acids in one or more of HC-FR1, HC-FR2, HC-FR3, or HC-FR4 are substituted with another amino acid.

In some embodiments the antigen-binding molecule comprises a VH region comprising the CDRs according to one of (1), (2), (3), (4) or (5) above, and the FRs according to one of (5), (6), (7), (8), (9), (10), (11), (12), (13), (14) or (15) above.

In some embodiments the antigen-binding molecule comprises a VH region according to one of (16) to (25) below:
(16) a VH region comprising the CDRs according to (1) and the FRs according to (6).
(17) a VH region comprising the CDRs according to (1) and the FRs according to (7).
(18) a VH region comprising the CDRs according to (2) and the FRs according to (8).
(19) a VH region comprising the CDRs according to (3) and the FRs according to (9).
(20) a VH region comprising the CDRs according to (4) and the FRs according to (10).
(21) a VH region comprising the CDRs according to (1) and the FRs according to (11).
(22) a VH region comprising the CDRs according to (1) and the FRs according to (12).
(23) a VH region comprising the CDRs according to (1) and the FRs according to (13).
(24) a VH region comprising the CDRs according to (1) and the FRs according to (14).
(25) a VH region comprising the CDRs according to (5) and the FRs according to (15).

In some embodiments the antigen-binding molecule comprises a VH region according to one of (26) to (34) below:
(26) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:23.
(27) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:39.
(28) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:49.
(29) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:65.
(31) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:178.
(31) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:127.
(32) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:129.
(33) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:130.
(34) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:131.
(35) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:132.

In some embodiments the antigen-binding molecule comprises a VL region according to one of (36) to (43) below:
(36) a VL region incorporating the following CDRs:
LC-CDR1 having the amino acid sequence of SEQ ID NO:32
LC-CDR2 having the amino acid sequence of SEQ ID NO:33
LC-CDR3 having the amino acid sequence of SEQ ID NO:34;
or a variant thereof in which one or two or three amino acids in one or more of LC-CDR1, LC-CDR2 or LC-CDR3 are substituted with another amino acid.
(37) a VL region incorporating the following CDRs:
LC-CDR1 having the amino acid sequence of SEQ ID NO:58
LC-CDR2 having the amino acid sequence of SEQ ID NO:59
LC-CDR3 having the amino acid sequence of SEQ ID NO:60;
or a variant thereof in which one or two or three amino acids in one or more of LC-CDR1, LC-CDR2 or LC-CDR3 are substituted with another amino acid.
(38) a VL region incorporating the following CDRs:
LC-CDR1 having the amino acid sequence of SEQ ID NO:74
LC-CDR2 having the amino acid sequence of SEQ ID NO:75
LC-CDR3 having the amino acid sequence of SEQ ID NO:76;
or a variant thereof in which one or two or three amino acids in one or more of LC-CDR1, LC-CDR2 or LC-CDR3 are substituted with another amino acid.
(39) a VL region incorporating the following CDRs:
LC-CDR1 having the amino acid sequence of SEQ ID NO:171
LC-CDR2 having the amino acid sequence of SEQ ID NO:172
LC-CDR3 having the amino acid sequence of SEQ ID NO:173;
or a variant thereof in which one or two or three amino acids in one or more of LC-CDR1, LC-CDR2 or LC-CDR3 are substituted with another amino acid.
(40) a VL region incorporating the following CDRs:
LC-CDR1 having the amino acid sequence of SEQ ID NO:139

LC-CDR2 having the amino acid sequence of SEQ ID NO:141
LC-CDR3 having the amino acid sequence of SEQ ID NO:34;
or a variant thereof in which one or two or three amino acids in one or more of LC-CDR1, LC-CDR2 or LC-CDR3 are substituted with another amino acid.
(41) a VL region incorporating the following CDRs:
LC-CDR1 having the amino acid sequence of SEQ ID NO:140
LC-CDR2 having the amino acid sequence of SEQ ID NO:141
LC-CDR3 having the amino acid sequence of SEQ ID NO:34;
or a variant thereof in which one or two or three amino acids in one or more of LC-CDR1, LC-CDR2 or LC-CDR3 are substituted with another amino acid.
(42) a VL region incorporating the following CDRs:
LC-CDR1 having the amino acid sequence of SEQ ID NO:32
LC-CDR2 having the amino acid sequence of SEQ ID NO:141
LC-CDR3 having the amino acid sequence of SEQ ID NO:34;
or a variant thereof in which one or two or three amino acids in one or more of LC-CDR1, LC-CDR2 or LC-CDR3 are substituted with another amino acid.
(43) a VL region incorporating the following CDRs:
LC-CDR1 having the amino acid sequence of SEQ ID NO:32
LC-CDR2 having the amino acid sequence of SEQ ID NO:33
LC-CDR3 having the amino acid sequence of SEQ ID NO:142;
or a variant thereof in which one or two or three amino acids in one or more of LC-CDR1, LC-CDR2 or LC-CDR3 are substituted with another amino acid.

In some embodiments the antigen-binding molecule comprises a VL region according to one of (44) to (50) below:
(44) a VL region incorporating the following FRs:
LC-FR1 having the amino acid sequence of SEQ ID NO:35
LC-FR2 having the amino acid sequence of SEQ ID NO:36
LC-FR3 having the amino acid sequence of SEQ ID NO:37
LC-FR4 having the amino acid sequence of SEQ ID NO:38,
or a variant thereof in which one or two or three amino acids in one or more of LC-FR1, LC-FR2, LC-FR3, or LC-FR4 are substituted with another amino acid.
(45) a VL region incorporating the following FRs:
LC-FR1 having the amino acid sequence of SEQ ID NO:45
LC-FR2 having the amino acid sequence of SEQ ID NO:46
LC-FR3 having the amino acid sequence of SEQ ID NO:47
LC-FR4 having the amino acid sequence of SEQ ID NO:48,
or a variant thereof in which one or two or three amino acids in one or more of LC-FR1, LC-FR2, LC-FR3, or LC-FR4 are substituted with another amino acid.
(46) a VL region incorporating the following FRs:
LC-FR1 having the amino acid sequence of SEQ ID NO:61
LC-FR2 having the amino acid sequence of SEQ ID NO:62
LC-FR3 having the amino acid sequence of SEQ ID NO:63
LC-FR4 having the amino acid sequence of SEQ ID NO:64,
or a variant thereof in which one or two or three amino acids in one or more of LC-FR1, LC-FR2, LC-FR3, or LC-FR4 are substituted with another amino acid.
(47) a VL region incorporating the following FRs:
LC-FR1 having the amino acid sequence of SEQ ID NO:77
LC-FR2 having the amino acid sequence of SEQ ID NO:78
LC-FR3 having the amino acid sequence of SEQ ID NO:79
LC-FR4 having the amino acid sequence of SEQ ID NO:80,
or a variant thereof in which one or two or three amino acids in one or more of LC-FR1, LC-FR2, LC-FR3, or LC-FR4 are substituted with another amino acid.
(48) a VL region incorporating the following FRs:
LC-FR1 having the amino acid sequence of SEQ ID NO:154
LC-FR2 having the amino acid sequence of SEQ ID NO:155
LC-FR3 having the amino acid sequence of SEQ ID NO:177
LC-FR4 having the amino acid sequence of SEQ ID NO:158,
or a variant thereof in which one or two or three amino acids in one or more of LC-FR1, LC-FR2, LC-FR3, or LC-FR4 are substituted with another amino acid.
(49) a VL region incorporating the following FRs:
LC-FR1 having the amino acid sequence of SEQ ID NO:154
LC-FR2 having the amino acid sequence of SEQ ID NO:155
LC-FR3 having the amino acid sequence of SEQ ID NO:156
LC-FR4 having the amino acid sequence of SEQ ID NO:158,
or a variant thereof in which one or two or three amino acids in one or more of LC-FR1, LC-FR2, LC-FR3, or LC-FR4 are substituted with another amino acid.
(50) a VL region incorporating the following FRs:
LC-FR1 having the amino acid sequence of SEQ ID NO:154
LC-FR2 having the amino acid sequence of SEQ ID NO:155
LC-FR3 having the amino acid sequence of SEQ ID NO:157
LC-FR4 having the amino acid sequence of SEQ ID NO:158,
or a variant thereof in which one or two or three amino acids in one or more of LC-FR1, LC-FR2, LC-FR3, or LC-FR4 are substituted with another amino acid.

In some embodiments the antigen-binding molecule comprises a VL region comprising the CDRs according to one of (36), (37), (38), (39), (40), (41), (42) or (43) above, and the FRs according to one of (44), (45), (46), (47), (48), (49) or (50) above.

In some embodiments the antigen-binding molecule comprises a VL region according to one of (51) to (60) below:
(51) a VL region comprising the CDRs according to (36) and the FRs according to (43).

52) a VL region comprising the CDRs according to (36) and the FRs according to (44).
53) a VL region comprising the CDRs according to (37) and the FRs according to (45).
54) a VL region comprising the CDRs according to (38) and the FRs according to (46).
55) a VL region comprising the CDRs according to (39) and the FRs according to (48).
56) a VL region comprising the CDRs according to (36) and the FRs according to (49).
57) a VL region comprising the CDRs according to (40) and the FRs according to (50).
58) a VL region comprising the CDRs according to (41) and the FRs according to (50).
59) a VL region comprising the CDRs according to (42) and the FRs according to (50).
60) a VL region comprising the CDRs according to (43) and the FRs according to (49).

In some embodiments the antigen-binding molecule comprises a VL region according to one of (61) to (70) below:
(61) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:31.
(62) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:44.
(63) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:57.
(64) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:73.
(65) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:179.
(66) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:128.
(67) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:133.
(68) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:134.
(69) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:135.
(70) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:136.

In some embodiments the antigen-binding molecule comprises a VH region according to any one of (1) to (35) above, and a VL region according to any one of (36) to (70) above.

In embodiments in accordance with the present invention in which one or more amino acids are substituted with another amino acid, the substitutions may conservative substitutions, for example according to the following Table. In some embodiments, amino acids in the same block in the middle column are substituted. In some embodiments, amino acids in the same line in the rightmost column are substituted:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

In some embodiments, substitution(s) may be functionally conservative. That is, in some embodiments the substitution may not affect (or may not substantially affect) one or more functional properties (e.g. target binding) of the antigen-binding molecule comprising the substitution as compared to the equivalent unsubstituted molecule.

The VH and VL region of an antigen-binding region of an antibody together constitute the Fv region. In some embodiments, the antigen-binding molecule according to the present invention comprises, or consists of, an Fv region which binds to CD47. In some embodiments the VH and VL regions of the Fv are provided as single polypeptide joined by a linker region, i.e. a single chain Fv (scFv).

In some embodiments the antigen-binding molecule of the present invention comprises one or more regions of an immunoglobulin heavy chain constant sequence. In some embodiments the immunoglobulin heavy chain constant sequence is, or is derived from, the heavy chain constant sequence of an IgG (e.g. IgG1, IgG2, IgG3, IgG4), IgA (e.g. IgA1, IgA2), IgD, IgE or IgM.

In some embodiments the immunoglobulin heavy chain constant sequence is human immunoglobulin G 1 constant (IGHG1; UniProt: P01857-1, v1; SEQ ID NO:118). Positions 1 to 98 of SEQ ID NO:118 form the CH1 region (SEQ ID NO:119). Positions 99 to 110 of SEQ ID NO:118 form a hinge region between CH1 and CH2 regions (SEQ ID NO:120). Positions 111 to 223 of SEQ ID NO:118 form the CH2 region (SEQ ID NO:121). Positions 224 to 330 of SEQ ID NO:118 form the CH3 region (SEQ ID NO:122).

The exemplified antigen-binding molecules were prepared using pFUSE-CHIg-hG1, which comprises the substitutions D356E, L358M (positions numbered according to EU numbering) in the CH3 region relative to SEQ ID NO:118. The amino acid sequence of the CH3 region encoded by pFUSE-CHIg-hG1 is shown in SEQ ID NO:123. It will be appreciated that CH3 regions may be provided with further substitutions in accordance with modification to an Fc region of the antigen-binding molecule as described herein.

In some embodiments a CH1 region comprises or consists of the sequence of SEQ ID NO:119, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:119. In some embodiments a CH1-CH2 hinge region comprises or consists of the sequence of SEQ ID NO:120, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:120. In some embodiments a CH2 region comprises or consists of the sequence of SEQ ID NO:121, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:121. In some embodiments a CH3 region comprises or consists of the sequence of SEQ ID NO:122 or 123, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:122 or 123.

In some embodiments the antigen-binding molecule of the present invention comprises one or more regions of an immunoglobulin light chain constant sequence. In some embodiments the immunoglobulin light chain constant sequence is human immunoglobulin kappa constant (IGKC; Cκ; UniProt: P01834-1, v2; SEQ ID NO:124). In some embodiments the immunoglobulin light chain constant sequence is a human immunoglobulin lambda constant (IGLC; Cλ), e.g. IGLC1, IGLC2, IGLC3, IGLC6 or IGLC7. In some embodiments a CL region comprises or consists of the sequence of SEQ ID NO:124, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:124.

The VL and light chain constant (CL) region, and the VH region and heavy chain constant 1 (CH1) region of an antigen-binding region of an antibody together constitute the Fab region. In some embodiments the antigen-binding molecule comprises a Fab region comprising a VH, a CH1, a VL and a CL (e.g. Cκ or Cλ). In some embodiments the Fab region comprises a polypeptide comprising a VH and a CH1 (e.g. a VH-CH1 fusion polypeptide), and a polypeptide comprising a VL and a CL (e.g. a VL-CL fusion polypeptide). In some embodiments the Fab region comprises a polypeptide comprising a VH and a CL (e.g. a VH-CL fusion polypeptide) and a polypeptide comprising a VL and a CH (e.g. a VL-CH1 fusion polypeptide); that is, in some embodiments the Fab region is a CrossFab region. In some embodiments the VH, CH1, VL and CL regions of the Fab or CrossFab are provided as single polypeptide joined by linker regions, i.e. as a single chain Fab (scFab) or a single chain CrossFab (scCrossFab).

In some embodiments, the antigen-binding molecule of the present invention comprises, or consists of, a Fab region which binds to CD47.

In some embodiments, the antigen-binding molecule described herein comprises, or consists of, a whole antibody which binds to CD47. As used herein, "whole antibody" refers to an antibody having a structure which is substantially similar to the structure of an immunoglobulin (Ig). Different kinds of immunoglobulins and their structures are described e.g. in Schroeder and Cavacini J Allergy Clin Immunol. (2010) 125(202): S41-S52, which is hereby incorporated by reference in its entirety.

Immunoglobulins of type G (i.e. IgG) are ~150 kDa glycoproteins comprising two heavy chains and two light chains. From N- to C-terminus, the heavy chains comprise a VH followed by a heavy chain constant region comprising three constant domains (CH1, CH2, and CH3), and similarly the light chain comprise a VL followed by a CL. Depending on the heavy chain, immunoglobulins may be classed as IgG (e.g. IgG1, IgG2, IgG3, IgG4), IgA (e.g. IgA1, IgA2), IgD, IgE, or IgM. The light chain may be kappa (κ) or lambda (λ).

In some embodiments, the antigen-binding molecule described herein comprises, or consists of, an IgG (e.g. IgG1, IgG2, IgG3, IgG4), IgA (e.g. IgA1, IgA2), IgD, IgE, or IgM which binds to CD47. Aspects of the present invention relate to multispecific antigen-binding molecules. By "multispecific" it is meant that the antigen-binding molecule displays specific binding to more than one target. In some embodiments the antigen-binding molecule is a bispecific antigen-binding molecule. In some embodiments the antigen-binding molecule comprises at least two different antigen-binding domains (i.e. at least two antigen-binding domains, e.g. comprising non-identical VHs and VLs).

In some embodiments the antigen-binding molecule binds to CD47 and an antigen other than CD47, and so is at least bispecific. The term "bispecific" means that the antigen-binding molecule is able to bind specifically to at least two distinct antigenic determinants.

It will be appreciated that an antigen-binding molecule according to the present invention (e.g. a multispecific antigen-binding molecule) may comprise antigen-binding molecules capable of binding to the targets for which the antigen-binding molecule is specific. For example, an antigen-binding molecule which is capable of binding to CD47 and an antigen other than CD47 may comprise: (i) an antigen-binding molecule which is capable of binding to CD47, and (ii) an antigen-binding molecule which is capable of binding to an antigen other than CD47. By way of illustration, an antigen-binding molecule which is capable of binding to CD47 and an antigen other than CD47 may comprise (i) an antigen-binding molecule which is capable of binding to CD47, (e.g. a CD47-binding Fab or scFv), and (ii) an antigen-binding molecule which is capable of binding to an antigen other than CD47 (e.g. a Fab or scFv specific for the antigen other than CD47).

It will also be appreciated that an antigen-binding molecule according to the present invention (e.g. a multispecific antigen-binding molecule) may comprise antigen-binding polypeptides or antigen-binding polypeptide complexes capable of binding to the targets for which the antigen-binding molecule is specific.

In some embodiments, a component antigen-binding molecule of a larger antigen-binding molecule (e.g. a multispecific antigen-binding molecule) may be referred to e.g. as an "antigen-binding domain" or "antigen-binding region" of the larger antigen-binding molecule.

In some embodiments the antigen-binding molecule comprises an antigen-binding molecule capable of binding to CD47, and an antigen-binding molecule capable of binding to an antigen other than CD47. In some embodiments, the antigen other than CD47 is an immune cell surface molecule. In some embodiments, the antigen other than CD47 is a cancer cell antigen. In some embodiments the antigen other than CD47 is a receptor molecule, e.g. a cell surface receptor. In some embodiments the antigen other than CD47 is a cell signalling molecule, e.g. a cytokine, chemokine, interferon, interleukin or lymphokine. In some embodiments the antigen other than CD47 is a growth factor or a hormone.

A cancer cell antigen is an antigen which is expressed or over-expressed by a cancer cell. A cancer cell antigen may be any peptide/polypeptide, glycoprotein, lipoprotein, glycan, glycolipid, lipid, or fragment thereof. A cancer cell antigen's expression may be associated with a cancer. A cancer cell antigen may be abnormally expressed by a cancer cell (e.g. the cancer cell antigen may be expressed with abnormal localisation), or may be expressed with an abnormal structure by a cancer cell. A cancer cell antigen may be capable of eliciting an immune response. In some embodiments, the antigen is expressed at the cell surface of the cancer cell (i.e. the cancer cell antigen is a cancer cell surface antigen). In some embodiments, the part of the antigen which is bound by the antigen-binding molecule described herein is displayed on the external surface of the cancer cell (i.e. is extracellular). The cancer cell antigen may be a cancer-associated antigen. In some embodiments the cancer cell antigen is an antigen whose expression is associated with the development, progression or severity of symptoms of a cancer. The cancer-associated antigen may be associated with the cause or pathology of the cancer, or may be expressed abnormally as a consequence of the cancer. In some embodiments, the cancer cell antigen is an antigen whose expression is upregulated (e.g. at the RNA and/or protein level) by cells of a cancer, e.g. as compared to the level of expression of by comparable non-cancerous cells (e.g. non-cancerous cells derived from the same tissue/cell type). In some embodiments, the cancer-associated antigen may be preferentially expressed by cancerous cells, and not expressed by comparable non-cancerous cells (e.g. non-cancerous cells derived from the same tissue/cell type). In some embodiments, the cancer-associated antigen may be the product of a mutated oncogene or mutated tumor suppressor gene. In some embodiments, the cancer-associated antigen may be the product of an overexpressed cellular protein, a cancer antigen produced by an oncogenic virus, an oncofetal antigen, or a cell surface glycolipid or glycoprotein.

An immune cell surface molecule may be any peptide/polypeptide, glycoprotein, lipoprotein, glycan, glycolipid, lipid, or fragment thereof expressed at or on the cell surface of an immune cell. In some embodiments, the part of the immune cell surface molecule which is bound by the antigen-binding molecule of the present invention is on the external surface of the immune cell (i.e. is extracellular). The immune cell surface molecule may be expressed at the cell surface of any immune cell. In some embodiments, the immune cell may be a cell of hematopoietic origin, e.g. a neutrophil, eosinophil, basophil, dendritic cell, lymphocyte, or monocyte. The lymphocyte may be e.g. a T cell, B cell, natural killer (NK) cell, NKT cell or innate lymphoid cell (ILC), or a precursor thereof (e.g. a thymocyte or pre-B cell).

In some embodiments the antigen other than CD47 is an antigen expressed by cells of a hematologic malignancy, a myeloid hematologic malignancy, a lymphoblastic hematologic malignancy, myelodysplastic syndrome (MDS), acute myeloid leukemia (AML), chronic myeloid leukemia, acute lymphoblastic leukemia (ALL), non-Hodgkin's lymphoma, multiple myeloma, bladder cancer or brain cancer.

In some embodiments the antigen other than CD47 is an antigen expressed by cells of AML, e.g. as described in Hoseini and Cheung Blood Cancer J. (2017) 7(2):e522, which is hereby incorporated by reference in its entirety. In some embodiments the antigen other than CD47 is selected from: CD33, CD123, Wilms' tumor protein (WT1), CD13, CD15, CD30, CD45, C-type lectin-like molecule 1 (CLL1), Fms-like tyrosine kinase 3 (FLT-3), VEGF and angiopoietin-2 (Ang-2). In some embodiments the antigen other than CD47 is CD33.

Multispecific antigen-binding molecules described herein display at least monovalent binding with respect to CD47, and also display at least monovalent binding with respect to the antigen other than CD47.

In some embodiments the antigen-binding molecule comprises an antigen-binding region (e.g. an Fv, Fab or antibody) capable of binding to CD47, and an antigen-binding region (e.g. an Fv, Fab or antibody) capable of binding to an antigen other than CD47. In some embodiments the antigen-binding molecule comprises the VH and VL of an antibody capable of binding to CD47, and the VH and VL of an antibody capable of binding to an antigen other than CD47.

Binding valency refers to the number of binding sites in an antigen-binding molecule for a given antigenic determinant. For example, in the IgG1 format described herein the anti-CD47 antibody is bivalent with respect to binding to CD47.

Multispecific antigen-binding molecules according to the invention may be provided in any suitable format, such as those formats described in described in Brinkmann and Kontermann MAbs (2017) 9(2): 182-212, which is hereby incorporated by reference in its entirety. Suitable formats include those shown in FIG. 2 of Brinkmann and Kontermann MAbs (2017) 9(2): 182-212: antibody conjugates, e.g. IgG2, F(ab')2 or CovX-Body; IgG or IgG-like molecules, e.g. IgG, chimeric IgG, κλ-body common HC; CH1/CL fusion proteins, e.g. scFv2-CH1/CL, VHH2-CH1/CL; 'variable domain only' bispecific antigen-binding molecules, e.g. tandem scFv (taFV), triplebodies, diabodies (db), dsDb, db(kih), DART, scDB, dsFv-dsFv, tandAbs, triple heads, tandem dAbNHH, tertravalent dAb.VHH; Non-Ig fusion proteins, e.g. scFv$_2$-albumin, scDb-albumin, taFv-albumin, taFv-toxin, miniantibody, DNL-Fab$_2$, DNL-Fab$_2$-scFv, DNL-Fab$_2$-IgG-cytokine$_2$, ImmTAC (TCR-scFv); modified Fc and CH3 fusion proteins, e.g. scFv-Fc(kih), scFv-Fc(CH3 charge pairs), scFv-Fc (EW-RVT), scFv-fc (HA-TF), scFv-Fc (SEEDbody), taFv-Fc(kih), scFv-Fc(kih)-Fv, Fab-Fc (kih)-scFv, Fab-scFv-Fc(kih), Fab-scFv-Fc(BEAT), Fab-scFv-Fc (SEEDbody), DART-Fc, scFv-CH3(kih), TriFabs; Fc fusions, e.g. Di-diabody, scDb-Fc, taFv-Fc, scFv-Fc-scFv, HCAb-VHH, Fab-scFv-Fc, scFv$_4$-Ig, scFv$_2$-Fcab; CH3 fusions, e.g. Dia-diabody, scDb-CH3; IgE/IgM CH2 fusions, e.g. scFv-EHD2-scFv, scFvMHD$_2$-scFv; Fab fusion proteins, e.g. Fab-scFv (bibody), Fab-scFv$_2$ (tribody), Fab-Fv, Fab-dsFv, Fab-VHH, orthogonal Fab-Fab; non-Ig fusion proteins, e.g. DNL-Fab$_3$, DNL-Fab$_2$-scFv, DNL-Fab$_2$-IgG-cytokine2; asymmetric IgG or IgG-like molecules, e.g. IgG (kih), IgG(kih) common LC, ZW1 IgG common LC, Biclonics common LC, CrossMab, CrossMab(kih), scFab-IgG (kih), Fab-scFab-IgG(kih), orthogonal Fab IgG(kih), DuetMab, CH3 charge pairs+CH1/CL charge pairs, hinge/CH3 charge pairs, SEED-body, Duobody, four-in-one-CrossMab(kih), LUZ-Y common LC; LUZ-Y scFab-IgG, FcFc*; appended and Fc-modified IgGs, e.g. IgG(kih)-Fv, IgG HA-TF-Fv, IgG(kih)scFab, scFab-Fc(kih)-scFv2, scFab-Fc(kih)-scFv, half DVD-Ig, DVI-Ig (four-in-one), CrossMab-Fab; modified Fc and CH3 fusion proteins, e.g.

Fab-Fc(kih)-scFv, Fab-scFv-Fc(kih), Fab-scFv-Fc(BEAT), Fab-scFv-Fc-SEEDbody, Tri Fab; appended IgGs-HC fusions, e.g. IgG-HC, scFv, IgG-dAb, IgG-taFV, IgG-Cross-Fab, IgG-orthogonal Fab, IgG-(CαCβ) Fab, scFv-HC-IgG, tandem Fab-IgG (orthogonal Fab) Fab-IgG(CαCβ Fab), Fab-IgG(CR3), Fab-hinge-IgG(CR3); appended IgGs-LC fusions, e.g. IgG-scFv(LC), scFv(LC)-IgG, dAb-IgG; appended IgGs-HC and LC fusions, e.g. DVD-Ig, TVD-Ig, CODV-Ig, scFv$_4$-IgG, Zybody; Fc fusions, e.g. Fab-scFv-Fc, scFv$_4$-Ig; F(ab')2 fusions, e.g. F(ab')2-scFv$_2$; CH1/CL fusion proteins e.g. scFv$_2$-CH1-hinge/CL; modified IgGs, e.g. DAF (two-in one-IgG), DutaMab, Mab$^2$; and non-Ig fusions, e.g. DNL-Fab$_4$-IgG.

The skilled person is able to design and prepare bispecific antigen-binding molecules. Methods for producing bispecific antigen-binding molecules include chemically cross-linking of antigen-binding molecules or antibody fragments, e.g. with reducible disulphide or non-reducible thioether bonds, for example as described in Segal and Bast, 2001. Production of Bispecific Antigen-binding molecules. Current Protocols in Immunology. 14:IV:2.13:2.13.1-2.13.16, which is hereby incorporated by reference in its entirety. For example, N-succinimidyl-3-(-2-pyridyldithio)-propionate (SPDP) can be used to chemically crosslink e.g. Fab fragments via hinge region SH-groups, to create disulfide-linked bispecific F(ab)$_2$ heterodimers.

Other methods for producing bispecific antigen-binding molecules include fusing antibody-producing hybridomas e.g. with polyethylene glycol, to produce a quadroma cell capable of secreting bispecific antibody, for example as described in D. M. and Bast, B. J. 2001. Production of Bispecific Antigen-binding molecules. Current Protocols in Immunology. 14:IV:2.13:2.13.1-2.13.16.

Bispecific antigen-binding molecules according to the present invention can also be produced recombinantly, by expression from e.g. a nucleic acid construct encoding polypeptides for the antigen-binding molecules, for example as described in Antibody Engineering: Methods and Protocols, Second Edition (Humana Press, 2012), at Chapter 40: Production of Bispecific Antigen-binding molecules: Diabodies and Tandem scFv (Hornig and Farber-Schwarz), or French, How to make bispecific antigen-binding molecules, Methods Mol. Med. 2000; 40:333-339, the entire contents of both of which are hereby incorporated by reference.

For example, a DNA construct encoding the light and heavy chain variable domains for the two antigen-binding fragments (i.e. the light and heavy chain variable domains for the antigen-binding fragment capable of binding CD47, and the light and heavy chain variable domains for the antigen-binding fragment capable of binding to another target protein), and including sequences encoding a suitable linker or dimerization domain between the antigen-binding fragments can be prepared by molecular cloning techniques. Recombinant bispecific antibody can thereafter be produced by expression (e.g. in vitro) of the construct in a suitable host cell (e.g. a mammalian host cell), and expressed recombinant bispecific antibody can then optionally be purified.

Fc Regions

In some embodiments the antigen-binding molecules of the present invention comprise an Fc region.

An Fc region is composed of CH2 and CH3 regions from one polypeptide, and CH2 and CH3 regions from another polypeptide. The CH2 and CH3 regions from the two polypeptides together form the Fc region.

In some embodiments, the antigen-binding molecule of the present invention comprises an Fc region comprising modification in one or more of the CH2 and CH3 regions promoting association of the Fc region. Recombinant co-expression of constituent polypeptides of an antigen-binding molecule and subsequent association leads to several possible combinations. To improve the yield of the desired combinations of polypeptides in antigen-binding molecules in recombinant production, it is advantageous to introduce in the Fc regions modification(s) promoting association of the desired combination of heavy chain polypeptides. Modifications may promote e.g. hydrophobic and/or electrostatic interaction between CH2 and/or CH3 regions of different polypeptide chains. Suitable modifications are described e.g. in Ha et al., Front. Immnol (2016) 7:394, which is hereby incorporated by reference in its entirety.

In some embodiments the antigen antigen-binding molecule of the present invention comprises an Fc region comprising paired substitutions in the CH3 regions of the Fc region according to one of the following formats, as shown in Table 1 of Ha et al., Front. Immnol (2016) 7:394: KiH, KiH$_{s-s}$, HA-TF, ZW1, 7.8.60, DD-KK, EW-RVT, EW-RVT$_{s-s}$, SEED or A107.

In some embodiments, the Fc region comprises the "knob-into-hole" or "KiH" modification, e.g. as described e.g. in U.S. Pat. No. 7,695,936 and Carter, J Immunol Meth 248, 7-15 (2001). In such embodiments, one of the CH3 regions of the Fc region comprises a "knob" modification, and the other CH3 region comprises a "hole" modification. The "knob" and "hole" modifications are positioned within the respective CH3 regions so that the "knob" can be positioned in the "hole" in order to promote heterodimerisation (and inhibit homodimerisation) of the polypeptides and/or stabilise heterodimers. Knobs are constructed by substituting amino acids having small chains with those having larger side chains (e.g. tyrosine or tryptophan). Holes are created by substituting amino acids having large side chains with those having smaller side chains (e.g. alanine or threonine).

In some embodiments, one of the CH3 regions of the Fc region of the antigen-binding molecule of the present invention comprises the substitution (numbering of positions/substitutions in the Fc, CH2 and CH3 regions herein is according to the EU numbering system as described in Kabat et al., Sequences of Proteins of Immunological Interest, 5th Ed. Public Health Service, National Institutes of Health, Bethesda, Md., 1991) T366W, and the other CH3 region of the Fc region comprises the substitution Y407V. In some embodiments, one of the CH3 regions of the Fc region of the antigen-binding molecule comprises the substitution T366W, and the other CH3 region of the Fc region comprises the substitutions T366S and L368A. In some embodiments, one of the CH3 regions of the Fc region of the antigen-binding molecule comprises the substitution T366W, and the other CH3 region of the Fc region comprises the substitutions Y407V, T366S and L368A.

In some embodiments, the Fc region comprises the "DD-KK" modification as described e.g. in WO 2014/131694 A1. In some embodiments, one of the CH3 regions comprises the substitutions K392D and K409D, and the other CH3 region of the Fc region comprises the substitutions E356K and D399K. The modifications promote electrostatic interaction between the CH3 regions.

In some embodiments, the antigen-binding molecule of the present invention comprises an Fc region modified as described in Labrijn et al., Proc Natl Acad Sci USA. (2013) 110(13):5145-50, referred to as 'Duobody' format. In some embodiments one of the CH3 regions comprises the substitution K409R, and the other CH3 region of the Fc region comprises the substitution K405L.

In some embodiments, the antigen-binding molecule of the present invention comprises an Fc region comprising the "EEE-RRR" modification as described in Strop et al., J Mol Biol. (2012) 420(3):204-19. In some embodiments one of the CH3 regions comprises the substitutions D221E, P228E and L368E, and the other CH3 region of the Fc region comprises the substitutions D221R, P228R and K409R.

In some embodiments, the antigen-binding molecule comprises an Fc region comprising the "EW-RVT" modification described in Choi et al., Mol Cancer Ther (2013) 12(12):2748-59. In some embodiments one of the CH3 regions comprises the substitutions K360E and K409W, and the other CH3 region of the Fc region comprises the substitutions Q347R, D399V and F405T.

In some embodiments, one of the CH3 regions comprises the substitution S354C, and the other CH3 region of the Fc region comprises the substitution Y349C. Introduction of these cysteine residues results in formation of a disulphide bridge between the two CH3 regions of the Fc region, further stabilizing the heterodimer (Carter (2001), J Immunol Methods 248, 7-15).

In some embodiments, the Fc region comprises the "KiH$_{s-s}$" modification. In some embodiments one of the CH3 regions comprises the substitutions T366W and S354C, and the other CH3 region of the Fc region comprises the substitutions T366S, L368A, Y407V and Y349C.

In some embodiments, the antigen-binding molecule of the present invention comprises an Fc region comprising the "SEED" modification as described in Davis et al., Protein Eng Des Sel (2010) 23(4):195-202, in which β-strand segments of human IgG1 CH3 and IgA CH3 are exchanged.

In some embodiments, one of the CH3 regions comprises the substitutions S364H and F405A, and the other CH3 region of the Fc region comprises the substitutions Y349T and T394F (see e.g. Moore et al., MAbs (2011) 3(6):546-57).

In some embodiments, one of the CH3 regions comprises the substitutions T350V, L351Y, F405A and Y407V, and the other CH3 region of the Fc region comprises the substitutions T350V, T366L, K392L and T394W (see e.g. Von Kreudenstein et al., MAbs (2013) 5(5):646-54).

In some embodiments, one of the CH3 regions comprises the substitutions K360D, D399M and Y407A, and the other CH3 region of the Fc region comprises the substitutions E345R, Q347R, T366V and K409V (see e.g. Leaver-Fay et al., Structure (2016) 24(4):641-51).

In some embodiments, one of the CH3 regions comprises the substitutions K370E and K409W, and the other CH3 region of the Fc region comprises the substitutions E357N, D399V and F405T (see e.g. Choi et al., PLoS One (2015) 10(12):e0145349).

Polypeptides

The present invention also provides polypeptide constituents of antigen-binding molecules. The polypeptides may be provided in isolated or substantially purified form.

The antigen-binding molecule of the present invention may be, or may comprise, a complex of polypeptides.

In the present specification where a polypeptide comprises more than one domain or region, it will be appreciated that the plural domains/regions are preferably present in the same polypeptide chain. That is, the polypeptide comprises more than one domain or region is a fusion polypeptide comprising the domains/regions.

In some embodiments a polypeptide according to the present invention comprises, or consists of, a VH as described herein. In some embodiments a polypeptide according to the present invention comprises, or consists of, a VL as described herein.

In some embodiments, the polypeptide additionally comprises one or more antibody heavy chain constant regions (CH). In some embodiments, the polypeptide additionally comprises one or more antibody light chain constant regions (CL). In some embodiments, the polypeptide comprises a CH1, CH2 region and/or a CH3 region of an immunoglobulin (Ig).

In some embodiments the polypeptide comprises one or more regions of an immunoglobulin heavy chain constant sequence. In some embodiments the polypeptide comprises a CH1 region as described herein. In some embodiments the polypeptide comprises a CH1-CH2 hinge region as described herein. In some embodiments the polypeptide comprises a CH2 region as described herein. In some embodiments the polypeptide comprises a CH3 region as described herein.

In some embodiments the polypeptide comprises a CH3 region comprising any one of the following amino acid substitutions/combinations of amino acid substitutions (shown e.g. in Table 1 of Ha et al., Front. Immnol (2016) 7:394, incorporated by reference hereinabove): T366W; T366S, L368A and Y407V; T366W and S354C; T366S, L368A, Y407V and Y3490; S364H and F405A; Y349T and T394F; T350V, L351Y, F405A and Y407V; T350V, T366L, K392L and T394W; K360D, D399M and Y407A; E345R, Q347R, T366V and K409V; K409D and K392D; D399K and E356K; K360E and K409W; Q347R, D399V and F405T; K360E, K409W and Y3490; Q347R, D399V, F405T and S354C; K370E and K409W; and E357N, D399V and F405T.

In some embodiments the CH2 and/or CH3 regions of the polypeptide comprise one or more amino acid substitutions for promoting association of the polypeptide with another polypeptide comprising a CH2 and/or CH3 region.

In some embodiments the polypeptide comprises one or more regions of an immunoglobulin light chain constant sequence. In some embodiments the polypeptide comprises a CL region as described herein.

In some embodiments, the polypeptide according to the present invention comprises a structure from N- to C-terminus according to one of the following:
 (i) VH
 (ii) VL
 (iii) VH-CH1
 (iv) VL-CL
 (v) VL-CH1
 (vi) VH-CL
 (vii) VH-CH1-CH2-CH3
 (viii) VL-CL-CH2-CH3
 (ix) VL-CH1-CH2-CH3
 (x) VH-CL-CH2-CH3

Also provided by the present invention are antigen-binding molecules composed of the polypeptides of the present invention. In some embodiments, the antigen-binding molecule of the present invention comprises one of the following combinations of polypeptides:
 (A) VH+VL
 (B) VH-CH1+VL-CL
 (C) VL-CH1+VH-CL
 (D) VH-CH1-CH2-CH3+VL-CL
 (E) VH-CL-CH2-CH3+VL-CH1
 (F) VL-CH1-CH2-CH3+VH-CL (G) VL-CL-CH2-CH3+VH-CH1
(H) VH-CH1-CH2-CH3+VL-CL-CH2-CH3
(I) VH-CL-CH2-CH3+VL-CH1-CH2-CH3

In some embodiments the antigen-binding molecule comprises more than one of a polypeptide of the combinations shown in (A) to (I) above. By way of example, with reference to (D) above, in some embodiments the antigen-binding molecule comprises two polypeptides comprising the structure VH-CH1-CH2-CH3, and two polypeptides comprising the structure VL-CL.

In some embodiments, the antigen-binding molecule of the present invention comprises one of the following combinations of polypeptides:

(J) VH (anti-CD47)+VL (anti-CD47)
(K) VH (anti-CD47)-CH1+VL (anti-CD47)-CL
(L) VL (anti-CD47)-CH1+VH (anti-CD47)-CL
(M) VH (anti-CD47)-CH1-CH2-CH3+VL (anti-CD47)-CL
(N) VH (anti-CD47)-CL-CH2-CH3+VL (anti-CD47)-CH1
(O) VL (anti-CD47)-CH1-CH2-CH3+VH (anti-CD47)-CL
(P) VL (anti-CD47)-CL-CH2-CH3+VH (anti-CD47)-CH1
(Q) VH (anti-CD47)-CH1-CH2-CH3+VL (anti-CD47)-CL-CH2-CH3
(R) VH (anti-CD47)-CL-CH2-CH3+VL (anti-CD47)-CH1-CH2-CH3

Wherein: "VH(anti-CD47)" refers to the VH of an antigen-binding molecule capable of binding to CD47 as described herein, e.g. as defined in one of (1) to (35); and "VL(anti-CD47)" refers to the VL of an antigen-binding molecule capable of binding to CD47 as described herein, e.g. as defined in one of (36) to (70); In some embodiments the polypeptide comprises or consists of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of one of SEQ ID NOs:23, 31, 39, 44, 49, 57, 65, 73, 178, 179, 127, 128, 129, 130, 131, 132, 133, 134, 135 or 136.

In some embodiments the polypeptide comprises or consists of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of one of SEQ ID NOs:107, 108, 109, 110, 111, 112, 113, 114, 159, 160, 161, 162, 163, 164, 165, 166, 167 or 168.

Linkers and Additional Sequences

In some embodiments the antigen-binding molecules and polypeptides of the present invention comprise a hinge region. In some embodiments a hinge region is provided between a CH1 region and a CH2 region. In some embodiments a hinge region is provided between a CL region and a CH2 region. In some embodiments the hinge region comprises, or consists of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:120.

In some embodiments the antigen-binding molecules and polypeptides of the present invention comprise one or more linker sequences between amino acid sequences. A linker sequence may be provided at one or both ends of one or more of a VH, VL, CH1-CH2 hinge region, CH2 region and a CH3 region of the antigen-binding molecule/polypeptide.

Linker sequences are known to the skilled person, and are described, for example in Chen et al., Adv Drug Deliv Rev (2013) 65(10): 1357-1369, which is hereby incorporated by reference in its entirety. In some embodiments, a linker sequence may be a flexible linker sequence. Flexible linker sequences allow for relative movement of the amino acid sequences which are linked by the linker sequence. Flexible linkers are known to the skilled person, and several are identified in Chen et al., Adv Drug Deliv Rev (2013) 65(10): 1357-1369. Flexible linker sequences often comprise high proportions of glycine and/or serine residues.

In some embodiments, the linker sequence comprises at least one glycine residue and/or at least one serine residue. In some embodiments the linker sequence consists of glycine and serine residues. In some embodiments, the linker sequence has a length of 1-2, 1-3, 1-4, 1-5 or 1-10 amino acids.

The antigen-binding molecules and polypeptides of the present invention may additionally comprise further amino acids or sequences of amino acids. For example, the antigen-binding molecules and polypeptides may comprise amino acid sequence(s) to facilitate expression, folding, trafficking, processing, purification or detection of the antigen-binding molecule/polypeptide. For example, the antigen-binding molecule/polypeptide may comprise a sequence encoding a His, (e.g. 6×His), Myc, GST, MBP, FLAG, HA, E, or Biotin tag, optionally at the N- or C-terminus of the antigen-binding molecule/polypeptide. In some embodiments the antigen-binding molecule/polypeptide comprises a detectable moiety, e.g. a fluorescent, luminescent, immuno-detectable, radio, chemical, nucleic acid or enzymatic label.

The antigen-binding molecules and polypeptides of the present invention may additionally comprise a signal peptide (also known as a leader sequence or signal sequence). Signal peptides normally consist of a sequence of 5-30 hydrophobic amino acids, which form a single alpha helix. Secreted proteins and proteins expressed at the cell surface often comprise signal peptides.

The signal peptide may be present at the N-terminus of the antigen-binding molecule/polypeptide, and may be present in the newly synthesised antigen-binding molecule/polypeptide. The signal peptide provides for efficient trafficking and secretion of the antigen-binding molecule/polypeptide. Signal peptides are often removed by cleavage, and thus are not comprised in the mature antigen-binding molecule/polypeptide secreted from the cell expressing the antigen-binding molecule/polypeptide.

Signal peptides are known for many proteins, and are recorded in databases such as GenBank, UniProt, Swiss-Prot, TrEMBL, Protein Information Resource, Protein Data Bank, Ensembl, and InterPro, and/or can be identified/predicted e.g. using amino acid sequence analysis tools such as SignalP (Petersen et al., 2011 Nature Methods 8: 785-786) or Signal-BLAST (Frank and Sippl, 2008 Bioinformatics 24: 2172-2176).

In some embodiments, the signal peptide of the antigen-binding molecule/polypeptide of the present invention comprises, or consists of, an amino acid sequence having at least 80%, 85% 86%, 87%, 88%, 89%, 90%, 91%, 92%, 93%, 94%, 95%, 96%, 97%, 98%, 99%, or 100% sequence identity to the amino acid sequence of one of SEQ ID NOs:81 to 86.

Labels and Conjugates

In some embodiments the antigen-binding molecules of the present invention additionally comprise a detectable moiety.

In some embodiments the antigen-binding molecule comprises a detectable moiety, e.g. a fluorescent label, phosphorescent label, luminescent label, immuno-detectable label (e.g. an epitope tag), radiolabel, chemical, nucleic acid or enzymatic label. The antigen-binding molecule may be covalently or non-covalently labelled with the detectable moiety.

Fluorescent labels include e.g. fluorescein, rhodamine, allophycocyanin, eosine and NDB, green fluorescent protein (GFP) chelates of rare earths such as europium (Eu), terbium (Tb) and samarium (Sm), tetramethyl rhodamine, Texas Red, 4-methyl umbelliferone, 7-amino-4-methyl coumarin, Cy3, and Cy5. Radiolabels include radioisotopes such as Iodine$^{123}$, Iodine$^{125}$, Iodine$^{126}$, Iodine$^{131}$, Iodine$^{133}$, Bromine$^{77}$, Technetium$^{99m}$, Indium$^{113m}$, Gallium$^{67}$, Gallium$^{68}$, Ruthenium$^{95}$, Ruthenium$^{97}$, Ruthenium$^{103}$, Ruthenium$^{105}$, Mercury$^{207}$, Mercury$^{203}$, Rhenium$^{99m}$, Rhenium$^{101}$, Rhenium$^{105}$, Scandium$^{47}$, Tellurium$^{121m}$, Tellurium$^{122m}$, TelluriuM$^{125m}$, Thulium$^{165}$, Thulium$^{167}$, Thulium$^{168}$, Copper$^{67}$, Fluorine$^{18}$, Yttrium$^{90}$, Palladium$^{100}$, Bismuth$^{217}$ and Antimony$^{211}$. Luminescent labels include as radioluminescent, chemiluminescent (e.g. acridinium ester, luminol, isoluminol) and bioluminescent labels. Immuno-detectable labels include haptens, peptides/polypeptides, antibodies, receptors and ligands such as biotin, avidin, streptavidin or digoxigenin. Nucleic acid labels include aptamers. Enzymatic labels include e.g. peroxidase, alkaline phosphatase, glucose oxidase, beta-galactosidase and luciferase.

In some embodiments the antigen-binding molecules of the present invention are conjugated to a chemical moiety. The chemical moiety may be a moiety for providing a therapeutic effect. Antibody-drug conjugates are reviewed e.g. in Parslow et al., Biomedicines. 2016 Sep; 4(3):14. In some embodiments, the chemical moiety may be a drug moiety (e.g. a cytotoxic agent). In some embodiments, the drug moiety may be a chemotherapeutic agent. In some embodiments, the drug moiety is selected from calicheamicin, DM1, DM4, monomethylauristatin E (MMAE), monomethylauristatin F (MMAF), SN-38, doxorubicin, duocarmycin, D6.5 and PBD.

Particular Exemplary Embodiments of the Antigen-Binding Molecules

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:107; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:108.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:109; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:110.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:111; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:112.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:113; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:114.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:159; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:160.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:161; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:160.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:162; and (ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:160.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:163; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:160.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:164; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:160.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:163; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:165.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:164; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:165.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:163; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:166.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:164; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:166.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:164; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:167.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:164; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:168.

Functional Properties of the Antigen-Binding Molecules

The antigen-binding molecules described herein may be characterised by reference to certain functional properties. In some embodiments, the antigen-binding molecule described herein may possess one or more of the following properties:
  binds to CD47;
  binds to CD47-expressing cells;
  inhibits interaction between CD47 and SIRPα;
  inhibits SIRPα-mediated signalling;
  increases phagocytosis of CD47-expressing cells by phagocytic cells (e.g. macrophages);
  increases the number/proportion of cancer antigen-specific immune cells does not cause substantial hemagglutination;

causes less hemagglutination as compared to a reference anti-CD47 antibody;
increases killing of cancer cells;
inhibits the development/progression of cancer.

The antigen-binding molecules and antigen-binding domains described herein preferably display specific binding to the relevant target antigen(s) (e.g. CD47). As used herein, "specific binding" refers to binding which is selective for the antigen, and which can be discriminated from non-specific binding to non-target antigen. An antigen-binding molecule/domain that specifically binds to a target molecule preferably binds the target with greater affinity, and/or with greater duration than it binds to other, non-target molecules.

The ability of a given polypeptide to bind specifically to a given molecule can be determined by analysis according to methods known in the art, such as by ELISA, Surface Plasmon Resonance (SPR; see e.g. Hearty et al., Methods Mol Biol (2012) 907:411-442), Bio-Layer Interferometry (see e.g. Lad et al., (2015) J Biomol Screen 20(4): 498-507), flow cytometry, or by a radiolabeled antigen-binding assay (RIA) enzyme-linked immunosorbent assay. Through such analysis binding to a given molecule can be measured and quantified. In some embodiments, the binding may be the response detected in a given assay.

In some embodiments, the extent of binding of the antigen-binding molecule to an non-target molecule is less than about 10% of the binding of the antibody to the target molecule as measured, e.g. by ELISA, SPR, Bio-Layer Interferometry or by RIA. Alternatively, binding specificity may be reflected in terms of binding affinity where the antigen-binding molecule binds with a dissociation constant (KD) that is at least 0.1 order of magnitude (i.e. $0.1 \times 10^n$, where n is an integer representing the order of magnitude) greater than the KD of the antigen-binding molecule towards a non-target molecule. This may optionally be one of at least 0.2, 0.3, 0.4, 0.5, 0.6, 0.7, 0.8, 0.9, 1.0, 1.5, or 2.0.

In some embodiments, the antigen-binding molecule described herein binds to CD47 with a KD of 10 µM or less, preferably one of ≤5 µM, ≤2 µM, ≤1 µM, ≤500 nM, ≤100 nM, ≤75 nM, ≤50 nM, ≤40 nM, ≤30 nM, ≤20 nM, ≤15 nM, ≤12.5 nM, ≤10 nM, ≤9 nM, ≤8 nM, ≤7 nM, ≤6 nM, ≤5 nM, ≤4 nM ≤3 nM, ≤2 nM, ≤1 nM or ≤500 pM. In some embodiments, the antigen-binding molecule binds to CD47 with an affinity of $K_D$=≤10 nM, ≤9 nM, ≤8 nM, ≤7 nM or ≤6 nM, e.g. ~5 nM.

In some embodiments, the antigen-binding molecule binds to CD47 with an affinity of binding (e.g. as determined by ELISA) of EC50=100 µg/ml or less, preferably one of ≤90 µg/ml, ≤80 µg/ml, ≤70 µg/ml, ≤60 µg/ml, ≤50 µg/ml, µ40 g/ml, ≤30 µg/ml, ≤20 µg/ml, ≤10 µg/ml, ≤9 µg/ml, ≤8 µg/ml, ≤7 µg/ml, ≤6 µg/ml, ≤5 µg/ml, ≤4 µg/ml, ≤3 µg/ml, ≤2 µg/ml, ≤1.5 µg/ml, ≤1 µg/ml, ≤0.5 µg/ml, ≤0.25 µg/ml, or ≤0.1 µg/ml.

The antigen-binding molecules of the present invention may bind to a particular region of interest of the target antigen(s). The antigen-binding region of an antigen-binding molecule according to the present domain may bind to linear epitope of a target antigen (e.g. CD47), consisting of a contiguous sequence of amino acids (i.e. an amino acid primary sequence). In some embodiments, the antigen-binding region molecule may bind to a conformational epitope of a target antigen (i.e. CD47), consisting of a discontinuous sequence of amino acids of the amino acid sequence.

In some embodiments, the antigen-binding molecule of the present invention is capable of binding to CD47. In some embodiments, the antigen-binding molecule is capable of binding to CD47 in an extracellular region of CD47. In some embodiments, the antigen-binding molecule is capable of binding to CD47 in extracellular region 1 of CD47 (e.g. the region shown in SEQ ID NO:10). In some embodiments, the antigen-binding molecule is capable of binding to the V-type Ig-like domain of CD47 (e.g. the region shown in SEQ ID NO:9).

In some embodiments the antigen-binding molecule is capable of binding to a polypeptide comprising or consisting of the amino acid sequence shown in SEQ ID NO:10. In some embodiments the antigen-binding molecule is capable of binding to a polypeptide comprising or consisting of the amino acid sequence shown in SEQ ID NO:9. In some embodiments the antigen-binding molecule is capable of binding to a polypeptide comprising or consisting of the amino acid sequence shown in SEQ ID NO:9. In some embodiments the antigen-binding molecule is capable of binding to a peptide or polypeptide comprising or consisting of the amino acid sequence shown in SEQ ID NO:21. In some embodiments the antigen-binding molecule is capable of binding to a peptide or polypeptide comprising or consisting of the amino acid sequence shown in SEQ ID NO:22.

As used herein, a "peptide" refers to a chain of two or more amino acid monomers linked by peptide bonds. A peptide typically has a length in the region of about 2 to 50 amino acids. A "polypeptide" is a polymer chain of two or more peptides. Polypeptides typically have a length greater than about 50 amino acids.

The ability of an antigen-binding molecule to bind to a given peptide/polypeptide can be analysed by methods well known to the skilled person, including analysis by ELISA, immunoblot (e.g. western blot), immunoprecipitation, surface plasmon resonance and biolayer interferometry.

In some embodiments the antigen-binding molecule is capable of binding the same region of CD47, or an overlapping region of CD47, to the region of CD47 which is bound by an antibody comprising the VH and VL sequences of one of clones 1-1-A1 BM, 1-1-A1, 5-48-A6, 5-48-D2, 11A1H1, 11A1H2, 11A1H3, 11A1H4, 11A1H5, 11A1H6, 11A1H7, 11A1H8, 11A1H9, 11A1H10 or 11A1H11.

The region of a peptide/polypeptide to which an antibody binds can be determined by the skilled person using various methods well known in the art, including X-ray co-crystallography analysis of antibody-antigen complexes, peptide scanning, mutagenesis mapping, hydrogen-deuterium exchange analysis by mass spectrometry, phage display, competition ELISA and proteolysis-based 'protection' methods. Such methods are described, for example, in Gershoni et al., BioDrugs, 2007, 21(3):145-156, which is hereby incorporated by reference in its entirety.

In some embodiments the antigen-binding molecule of the present invention displays cross-reactivity with CD47 of a non-human primate. That is, in some embodiments the antigen-binding molecule binds to both human CD47 and CD47 from a non-human primate. In some embodiments the non-human primate is rhesus macaque (*Macaca mulatta*).

In some embodiments the antigen-binding molecule of the present invention binds to CD47 in a region which is accessible to an antigen-binding molecule (i.e., an extracellular antigen-binding molecule) when CD47 is expressed at the cell surface (i.e. in or at the cell membrane). In some embodiments the antigen-binding molecule is capable of binding to CD47 expressed at the cell surface of a cell expressing CD47. In some embodiments the antigen-binding molecule is capable of binding to CD47-expressing cells (e.g. myeloid cells, myeloid leukemia cells, HL-60 cells, HMC-1 cells, HEL cells or Raji cells).

The ability of an antigen-binding molecule to bind to a given cell type can be analysed by contacting cells with the antigen-binding molecule, and detecting antigen-binding molecule bound to the cells, e.g. after a washing step to remove unbound antigen-binding molecule. The ability of an antigen-binding molecule to bind to immune cell surface molecule-expressing cells and/or cancer cell antigen-expressing cells can be analysed by methods such as flow cytometry and immunofluorescence microscopy.

The antigen-binding molecule of the present invention may be an antagonist of CD47. In some embodiments, the antigen-binding molecule is capable of inhibiting a function or process (e.g. interaction, signalling or other activity) mediated by CD47. Herein, 'inhibition' refers to a reduction, decrease or lessening relative to a control condition.

In some embodiments the antigen-binding molecule of the present invention is capable of inhibiting interaction between CD47 and a ligand for CD47. In some embodiments the antigen-binding molecule of the present invention is capable of inhibiting interaction between CD47 and SIRPα.

The ability of an antigen-binding molecule to inhibit interaction between two factors can be determined for example by analysis of interaction in the presence of, or following incubation of one or both of the interaction partners with, the antibody/fragment. An example of a suitable assay to determine whether a given antigen-binding molecule is capable of inhibiting interaction between two interaction partners is a competition ELISA assay.

An antigen-binding molecule which is capable of inhibiting a given interaction (e.g. between CD47 and SIRPα) is identified by the observation of a reduction/decrease in the level of interaction between the interaction partners in the presence of—or following incubation of one or both of the interaction partners with—the antigen-binding molecule, as compared to the level of interaction in the absence of the antigen-binding molecule (or in the presence of an appropriate control antigen-binding molecule). Suitable analysis can be performed in vitro, e.g. using recombinant interaction partners or using cells expressing the interaction partners. Cells expressing interaction partners may do so endogenously, or may do so from nucleic acid introduced into the cell. For the purposes of such assays, one or both of the interaction partners and/or the antigen-binding molecule may be labelled or used in conjunction with a detectable entity for the purposes of detecting and/or measuring the level of interaction.

The ability of an antigen-binding molecule to inhibit interaction between two binding partners can also be determined by analysis of the downstream functional consequences of such interaction. For example, downstream functional consequences of interaction between CD47 and SIRPα may include SIRPα-mediated signalling. For example, the ability of an antigen-binding molecule to inhibit interaction of CD47 and SIRPα may be determined by analysis of SIRPα ITIM phosphorylation, or analysis of phagocytosis of CD47-expressing cell by a SIRPα-expressing cell.

In some embodiments, the antigen-binding molecule of the present invention is capable of inhibiting interaction between CD47 and SIRPα to less than less than 1 times, e.g. ≤0.99 times, ≤0.95 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times, ≤0.05 times, or ≤0.01 times the level of interaction between CD47 and SIRPα in the absence of the antigen-binding molecule (or in the presence of an appropriate control antigen-binding molecule).

In some embodiments, the antigen-binding molecule inhibits interaction between CD47 and SIRPα with an IC50 (e.g. as determined by ELISA) of 100 µg/ml or less, preferably one of ≤90 µg/ml, ≤80 µg/ml, ≤70 µg/ml, ≤60 µg/ml, ≤50 µg/ml, ≤40 µg/ml, ≤30 µg/ml, ≤20 µg/ml, ≤10 µg/ml, ≤9 µg/ml, ≤8 µg/ml, ≤7 µg/ml, ≤6 µg/ml, ≤5 µg/ml, ≤4 µg/ml, ≤3 µg/ml, ≤2 µg/ml, ≤1.5 µg/ml, ≤1 µg/ml, ≤0.5 µg/ml, ≤0.25 µg/ml, or ≤0.1 µg/ml.

In some embodiments the antigen-binding molecule inhibits SIRPα-mediated signalling. SIRPα-mediated signalling can be analysed using SIRPα-expressing cells e.g. using an assay for detecting and/or quantifying SIRPα ITIM phosphorylation, or using in vitro assay of phagocytosis of CD47-expressing cells (e.g. Raji cells) by SIRPα-expressing cells (e.g. macrophages). For example, an in vitro assay of phagocytosis of CD47-expressing cells by SIRPα-expressing cells may be performed as described in Feng et al., Proc Natl Acad Sci USA. (2015) 112(7): 2145-2150 (hereby incorporated by reference in its entirety), or as described in the experimental examples herein.

In some embodiments, the antigen-binding molecule of the present invention is capable of inhibiting SIRPα-mediated signalling to less than 1 times, e.g. ≤0.99 times, ≤0.95 times, ≤0.9 times, ≤0.85 times, ≤0.8 times, ≤0.75 times, ≤0.17 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times, ≤0.05 times, or ≤0.01 times the level of SIRPα-mediated signalling in the absence of the antigen-binding molecule (or in the presence of an appropriate control antigen-binding molecule).

In some embodiments, the antigen-binding molecule of the present invention is capable of increasing phagocytosis of CD47-expressing cells. In some embodiments, the antigen-binding molecule of the present invention is capable of increasing phagocytosis of CD47-expressing cells (e.g. Raji cells) by SIRPα-expressing cells (e.g. macrophages).

An antigen-binding molecule which is capable of increasing phagocytosis of CD47-expressing cells by SIRPα-expressing cells is identified by the observation of an increased level of phagocytosis of the CD47-expressing cells by the SIRPα-expressing cells in the presence of—or following incubation of the CD47-expressing cells with—the antigen-binding molecule, as compared to the level of phagocytosis detected in the absence of the antigen-binding molecule (or in the presence of an appropriate control antigen-binding molecule).

In some embodiments, the antigen-binding molecule of the present invention is capable of increasing phagocytosis of CD47-expressing cells (e.g. Raji cells) by SIRPα-expressing cells (e.g. macrophages) to more than 1 times, e.g. ≥1.01 times, ≥1.02 times, ≥1.03 times, ≥1.04 times, ≥1.05 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥3 times, ≥4 times, ≥5 times, ≥6 times, ≥7 times, ≥8 times, ≥9 times or ≥10 times the level phagocytosis of the CD47-expressing cells by the SIRPα-expressing cells in the absence of the antigen-binding molecule (or in the presence of an appropriate control antigen-binding molecule).

In some embodiments, the antigen-binding molecule of the present invention is capable of increasing the number/proportion of cancer antigen-specific immune cells (e.g. CD8+ T cells or CD8+CTLs) relative to a negative control condition, e.g. in an appropriate in vitro assay, or in vivo. Tseng et al., Proc Natl Acad Sci USA. (2013) 110(27): 11103-11108 (hereby incorporated by reference in its entirety) demonstrated that increased phagocytosis of CD47-expressing cancer cells by macrophages in the presence of an anti-CD47 antibody was associated with increased priming of cancer antigen-specific CD8+ T cells. Antigen-binding molecules capable of causing an increase in the number/proportion of cancer antigen-specific immune cells can be identified using a T cell priming assay e.g. as described in Tseng et al., Proc Natl Acad Sci USA. (2013) 110(27): 11103-11108.

In some embodiments, the antigen-binding molecule of the present invention does not cause substantial hemagglutination (e.g. at concentrations of up to 400 µg/ml). Hemagglutination refers to agglutination of red blood cells (erythrocytes).

An agent which causes hemagglutination may be referred to as a hemagglutinin. In some embodiments the antigen-binding molecule of the present invention is not a hemagglutinin.

The ability of an antibody to cause hemagglutination can be analysed e.g. using an in vitro hemagglutination assay. A suitable assay of hemagglutination for the purposes of such analysis is described e.g. in Example 5 of WO 2013/119714 A1 (hereby incorporated by reference in its entirety), or the assay of hemagglutination described in the experimental examples herein. "Substantial" hemagglutination may be a level of hemagglutination which is more than 2 times, e.g. more than 3, 4, 5, 6, 7, 8, 9 or 10 times the level of hemagglutination detected in the absence of the antigen-binding molecule (or in the presence of an appropriate control antigen-binding molecule which does not cause hemagglutination).

In some embodiments, the antigen-binding molecule of the present invention causes less hemagglutination as compared to a reference anti-CD47 antibody (e.g. a prior art anti-CD47 antibody). In some embodiments, the antigen-binding molecule of the present invention causes less than 1 times, e.g. ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times, ≤0.05 times, or ≤0.01 times the level of hemagglutination as compared to a reference anti-CD47 antibody (e.g. a prior art anti-CD47 antibody), e.g. as determined using an in vitro assay of hemagglutination.

In some embodiments the antigen-binding molecule of the present invention increases killing of cancer cells. In some embodiments the antigen-binding molecule of the present invention causes a reduction in the number of cancer cells in vivo, e.g. as compared to an appropriate control condition. The cancer may be a cancer expressing CD47, or may comprise cells expressing CD47 (e.g. the CD47+AML cell line, HL-60). The antigen-binding molecule of the present invention may be analysed for anticancer activity in an appropriate in vivo model, e.g. an AML cell line-derived xenograft model.

In some embodiments the antigen-binding molecule of the present invention causes a greater reduction of the number of cancer cells in vivo in a AML cell line-derived xenograft model as compared to a reference anti-CD47 antibody (e.g. a prior art anti-CD47 antibody).

In some embodiments, administration of an antigen-binding molecule according to the present invention may cause one or more of: inhibition of the development/progression of the cancer, a delay to/prevention of onset of the cancer, a reduction in/delay to/prevention of tumor growth, a reduction in/delay to/prevention of metastasis, a reduction in the severity of the symptoms of the cancer, a reduction in the number of cancer cells, a reduction in tumour size/volume, and/or an increase in survival (e.g. progression free survival), e.g. as determined in an AML cell line-derived xenograft model.

Chimeric Antigen Receptors (CARs)

The present invention also provides Chimeric Antigen Receptors (CARs) comprising the antigen-binding polypeptides or polypeptides of the present invention.

CARs are recombinant receptors that provide both antigen-binding and T cell activating functions. CAR structure and engineering is reviewed, for example, in Dotti et al., Immunol Rev (2014) 257(1), hereby incorporated by reference in its entirety. CARs comprise an antigen-binding region linked to a cell membrane anchor region and a signalling region. An optional hinge region may provide separation between the antigen-binding region and cell membrane anchor region, and may act as a flexible linker.

The CAR of the present invention comprises an antigen-binding region which comprises or consists of the antigen-binding molecule of the present invention, or which comprises or consists of a polypeptide according to the invention.

The cell membrane anchor region is provided between the antigen-binding region and the signalling region of the CAR and provides for anchoring the CAR to the cell membrane of a cell expressing a CAR, with the antigen-binding region in the extracellular space, and signalling region inside the cell. In some embodiments, the CAR comprises a cell membrane anchor region comprising or consisting of an amino acid sequence which comprises, consists of, or is derived from, the transmembrane region amino acid sequence for one of CD3-ζ, CD4, CD8 or CD28. As used herein, a region which is 'derived from' a reference amino acid sequence comprises an amino acid sequence having at least 60%, e.g. one of at least 65%, 70%, 75%, 80%, 85%, 90%, 91%, 92%, 93%, 94%, 95%, 96%, 97%, 98%, 99% or 100% sequence identity to the reference sequence.

The signalling region of a CAR allows for activation of the T cell. The CAR signalling regions may comprise the amino acid sequence of the intracellular domain of CD3-, which provides immunoreceptor tyrosine-based activation motifs (ITAMs) for phosphorylation and activation of the CAR-expressing T cell. Signalling regions comprising sequences of other ITAM-containing proteins such as FcγRI have also been employed in CARs (Haynes et al., 2001 J Immunol 166(1):182-187). Signalling regions of CARs may also comprise co-stimulatory sequences derived from the signalling region of co-stimulatory molecules, to facilitate activation of CAR-expressing T cells upon binding to the target protein. Suitable co-stimulatory molecules include CD28, OX40, 4-1 BB, ICOS and CD27. In some cases CARs are engineered to provide for co-stimulation of different intracellular signalling pathways. For example, signalling associated with CD28 costimulation preferentially activates the phosphatidylinositol 3-kinase (P13K) pathway, whereas the 4-1 BB-mediated signalling is through TNF receptor associated factor (TRAF) adaptor proteins. Signalling regions of CARs therefore sometimes contain co-stimulatory sequences derived from signalling regions of more than one co-stimulatory molecule. In some embodiments, the CAR of the present invention comprises one or more co-stimulatory sequences comprising or consisting of an amino acid sequence which comprises, consists of, or is derived from, the amino acid sequence of the intracellular domain of one or more of CD28, OX40, 4-1 BB, ICOS and CD27.

An optional hinge region may provide separation between the antigen-binding domain and the transmembrane domain, and may act as a flexible linker. Hinge regions may be derived from IgG1. In some embodiments, the CAR of the present invention comprises a hinge region comprising or consisting of an amino acid sequence which comprises, consists of, or is derived from, the amino acid sequence of the hinge region of IgG1.

Also provided is a cell comprising a CAR according to the invention. The CAR according to the present invention may be used to generate CAR-expressing immune cells, e.g. CAR-T or CAR-NK cells. Engineering of CARs into immune cells may be performed during culture, in vitro.

The antigen-binding region of the CAR of the present invention may be provided with any suitable format, e.g. scFv, scFab, etc.

Nucleic Acids and Vectors

The present invention provides a nucleic acid, or a plurality of nucleic acids, encoding an antigen-binding molecule, polypeptide or CAR according to the present invention.

In some embodiments, the nucleic acid is purified or isolated, e.g. from other nucleic acid, or naturally-occurring biological material. In some embodiments the nucleic acid(s) comprise or consist of DNA and/or RNA.

The present invention also provides a vector, or plurality of vectors, comprising the nucleic acid or plurality of nucleic acids according to the present invention.

The nucleotide sequence may be contained in a vector, e.g. an expression vector. A "vector" as used herein is a nucleic acid molecule used as a vehicle to transfer exogenous nucleic acid into a cell. The vector may be a vector for expression of the nucleic acid in the cell. Such vectors may include a promoter sequence operably linked to the nucleotide sequence encoding the sequence to be expressed. A vector may also include a termination codon and expression enhancers. Any suitable vectors, promoters, enhancers and termination codons known in the art may be used to express a peptide or polypeptide from a vector according to the invention.

The term "operably linked" may include the situation where a selected nucleic acid sequence and regulatory nucleic acid sequence (e.g. promoter and/or enhancer) are covalently linked in such a way as to place the expression of nucleic acid sequence under the influence or control of the regulatory sequence (thereby forming an expression cassette). Thus a regulatory sequence is operably linked to the selected nucleic acid sequence if the regulatory sequence is capable of effecting transcription of the nucleic acid sequence. The resulting transcript(s) may then be translated into a desired peptide(s)/polypeptide(s).

Suitable vectors include plasmids, binary vectors, DNA vectors, mRNA vectors, viral vectors (e.g. gammaretroviral vectors (e.g. murine Leukemia virus (MLV)-derived vectors), lentiviral vectors, adenovirus vectors, adeno-associated virus vectors, vaccinia virus vectors and herpesvirus vectors), transposon-based vectors, and artificial chromosomes (e.g. yeast artificial chromosomes).

In some embodiments, the vector may be a eukaryotic vector, e.g. a vector comprising the elements necessary for expression of protein from the vector in a eukaryotic cell. In some embodiments, the vector may be a mammalian vector, e.g. comprising a cytomegalovirus (CMV) or SV40 promoter to drive protein expression.

Constituent polypeptides of an antigen-binding molecule according to the present invention may be encoded by different nucleic acids of the plurality of nucleic acids, or by different vectors of the plurality of vectors.

Cells Comprising/Expressing the Antigen-Binding Molecules and Polypeptides

The present invention also provides a cell comprising or expressing an antigen-binding molecule, polypeptide or CAR according to the present invention. Also provided is a cell comprising or expressing a nucleic acid, a plurality of nucleic acids, a vector or a plurality of vectors according to the invention.

The cell may be a eukaryotic cell, e.g. a mammalian cell. The mammal may be a primate (rhesus, cynomolgous, non-human primate or human) or a non-human mammal (e.g. rabbit, guinea pig, rat, mouse or other rodent (including any animal in the order Rodentia), cat, dog, pig, sheep, goat, cattle (including cows, e.g. dairy cows, or any animal in the order Bos), horse (including any animal in the order Equidae), donkey, and non-human primate).

The present invention also provides a method for producing a cell comprising a nucleic acid(s) or vector(s) according to the present invention, comprising introducing a nucleic acid, a plurality of nucleic acids, a vector or a plurality of vectors according to the present invention into a cell. In some embodiments, introducing an isolated nucleic acid(s) or vector(s) according to the invention into a cell comprises transformation, transfection, electroporation or transduction (e.g. retroviral transduction).

The present invention also provides a method for producing a cell expressing/comprising an antigen-binding molecule, polypeptide or CAR according to the present invention, comprising introducing a nucleic acid, a plurality of nucleic acids, a vector or a plurality of vectors according to the present invention in a cell. In some embodiments, the methods additionally comprise culturing the cell under conditions suitable for expression of the nucleic acid(s) or vector(s) by the cell. In some embodiments, the methods are performed in vitro.

The present invention also provides cells obtained or obtainable by the methods according to the present invention.

Producing the Antigen-Binding Molecules and Polypeptides

Antigen-binding molecules and polypeptides according to the invention may be prepared according to methods for the production of polypeptides known to the skilled person.

Polypeptides may be prepared by chemical synthesis, e.g. liquid or solid phase synthesis. For example, peptides/polypeptides can by synthesised using the methods described in, for example, Chandrudu et al., Molecules (2013), 18: 4373-4388, which is hereby incorporated by reference in its entirety.

Alternatively, antigen-binding molecules and polypeptides may be produced by recombinant expression. Molecular biology techniques suitable for recombinant production of polypeptides are well known in the art, such as those set out in Green and Sambrook, Molecular Cloning: A Laboratory Manual (4th Edition), Cold Spring Harbor Press, 2012, and in Nat Methods. (2008); 5(2): 135-146 both of which are hereby incorporated by reference in their entirety. Methods for the recombinant production of antigen-binding molecules are also described in Frenzel et al., Front Immunol. (2013); 4: 217 and Kunert and Reinhart, Appl Microbiol Biotechnol. (2016) 100: 3451-3461, both of which are hereby incorporated by reference in their entirety.

In some cases the antigen-binding molecule of the present invention are comprised of more than one polypeptide chain.

In such cases, production of the antigen-binding molecules may comprise transcription and translation of more than one polypeptide, and subsequent association of the polypeptide chains to form the antigen-binding molecule.

For recombinant production according to the invention, any cell suitable for the expression of polypeptides may be used. The cell may be a prokaryote or eukaryote. In some embodiments the cell is a prokaryotic cell, such as a cell of archaea or bacteria. In some embodiments the bacteria may be Gram-negative bacteria such as bacteria of the family Enterobacteriaceae, for example *Escherichia coli*. In some embodiments, the cell is a eukaryotic cell such as a yeast cell, a plant cell, insect cell or a mammalian cell, e.g. CHO, HEK (e.g. HEK293), HeLa or COS cells.

In some cases the cell is not a prokaryotic cell because some prokaryotic cells do not allow for the same folding or post-translational modifications as eukaryotic cells. In addition, very high expression levels are possible in eukaryotes and proteins can be easier to purify from eukaryotes using appropriate tags. Specific plasmids may also be utilised which enhance secretion of the protein into the media.

In some embodiments polypeptides may be prepared by cell-free-protein synthesis (CFPS), e.g. according using a system described in Zemella et al. Chembiochem (2015) 16(17): 2420-2431, which is hereby incorporated by reference in its entirety.

Production may involve culture or fermentation of a eukaryotic cell modified to express the polypeptide(s) of interest. The culture or fermentation may be performed in a bioreactor provided with an appropriate supply of nutrients, air/oxygen and/or growth factors. Secreted proteins can be collected by partitioning culture media/fermentation broth from the cells, extracting the protein content, and separating individual proteins to isolate secreted polypeptide(s). Culture, fermentation and separation techniques are well known to those of skill in the art, and are described, for example, in Green and Sambrook, Molecular Cloning: A Laboratory Manual (4th Edition; incorporated by reference herein above).

Bioreactors include one or more vessels in which cells may be cultured. Culture in the bioreactor may occur continuously, with a continuous flow of reactants into, and a continuous flow of cultured cells from, the reactor. Alternatively, the culture may occur in batches. The bioreactor monitors and controls environmental conditions such as pH, oxygen, flow rates into and out of, and agitation within the vessel such that optimum conditions are provided for the cells being cultured.

Following culturing the cells that express the antigen-binding molecule/polypeptide(s), the polypeptide(s) of interest may be isolated. Any suitable method for separating proteins from cells known in the art may be used. In order to isolate the polypeptide it may be necessary to separate the cells from nutrient medium. If the polypeptide(s) are secreted from the cells, the cells may be separated by centrifugation from the culture media that contains the secreted polypeptide(s) of interest. If the polypeptide(s) of interest collect within the cell, protein isolation may comprise centrifugation to separate cells from cell culture medium, treatment of the cell pellet with a lysis buffer, and cell disruption e.g. by sonification, rapid freeze-thaw or osmotic lysis.

It may then be desirable to isolate the polypeptide(s) of interest from the supernatant or culture medium, which may contain other protein and non-protein components. A common approach to separating protein components from a supernatant or culture medium is by precipitation. Proteins of different solubilities are precipitated at different concentrations of precipitating agent such as ammonium sulfate. For example, at low concentrations of precipitating agent, water soluble proteins are extracted. Thus, by adding different increasing concentrations of precipitating agent, proteins of different solubilities may be distinguished. Dialysis may be subsequently used to remove ammonium sulfate from the separated proteins.

Other methods for distinguishing different proteins are known in the art, for example ion exchange chromatography and size chromatography. These may be used as an alternative to precipitation, or may be performed subsequently to precipitation.

Once the polypeptide(s) of interest have been isolated from culture it may be desired or necessary to concentrate the polypeptide(s). A number of methods for concentrating proteins are known in the art, such as ultrafiltration or lyophilisation.

Compositions

The present invention also provides compositions comprising the antigen-binding molecules, polypeptides, CARs, nucleic acids, expression vectors and cells described herein.

The antigen-binding molecules, polypeptides, CARs, nucleic acids, expression vectors and cells described herein may be formulated as pharmaceutical compositions or medicaments for clinical use and may comprise a pharmaceutically acceptable carrier, diluent, excipient or adjuvant. The composition may be formulated for topical, parenteral, systemic, intracavitary, intravenous, intra-arterial, intramuscular, intrathecal, intraocular, intraconjunctival, intratumoral, subcutaneous, intradermal, intrathecal, oral or transdermal routes of administration which may include injection or infusion.

Suitable formulations may comprise the antigen-binding molecule in a sterile or isotonic medium. Medicaments and pharmaceutical compositions may be formulated in fluid, including gel, form. Fluid formulations may be formulated for administration by injection or infusion (e.g. via catheter) to a selected region of the human or animal body.

In some embodiments the composition is formulated for injection or infusion, e.g. into a blood vessel or tumor.

In accordance with the invention described herein methods are also provided for the production of pharmaceutically useful compositions, such methods of production may comprise one or more steps selected from: producing an antigen-binding molecule, polypeptide, CAR, nucleic acid (or plurality thereof), expression vector (or plurality thereof) or cell described herein; isolating an antigen-binding molecule, polypeptide, CAR, nucleic acid (or plurality thereof), expression vector (or plurality thereof) or cell described herein; and/or mixing antigen-binding molecule, polypeptide, CAR, nucleic acid (or plurality thereof), expression vector (or plurality thereof) or cell described herein with a pharmaceutically acceptable carrier, adjuvant, excipient or diluent.

For example, a further aspect the invention described herein relates to a method of formulating or producing a medicament or pharmaceutical composition for use in the treatment of a disease/condition (e.g. a cancer), the method comprising formulating a pharmaceutical composition or medicament by mixing an antigen-binding molecule, polypeptide, CAR, nucleic acid (or plurality thereof), expression vector (or plurality thereof) or cell described herein with a pharmaceutically acceptable carrier, adjuvant, excipient or diluent.

Therapeutic and Prophylactic Applications

The antigen-binding molecules, polypeptides, CARs, nucleic acids, expression vectors, cells and compositions described herein find use in therapeutic and prophylactic methods.

The present invention provides an antigen-binding molecule, polypeptide, CAR, nucleic acid (or plurality thereof), expression vector (or plurality thereof), cell or composition described herein for use in a method of medical treatment or prophylaxis. Also provided is the use of an antigen-binding molecule, polypeptide, CAR, nucleic acid (or plurality thereof), expression vector (or plurality thereof), cell or composition described herein in the manufacture of a medicament for treating or preventing a disease or condition. Also provided is a method of treating or preventing a disease or condition, comprising administering to a subject a therapeutically or prophylactically effective amount of an antigen-binding molecule, polypeptide, CAR, nucleic acid (or plurality thereof), expression vector (or plurality thereof), cell or composition described herein.

The methods may be effective to reduce the development or progression of a disease/condition, alleviation of the symptoms of a disease/condition or reduction in the pathology of a disease/condition. The methods may be effective to prevent progression of the disease/condition, e.g. to prevent worsening of, or to slow the rate of development of, the disease/condition. In some embodiments the methods may lead to an improvement in the disease/condition, e.g. a reduction in the symptoms of the disease/condition or reduction in some other correlate of the severity/activity of the disease/condition. In some embodiments the methods may prevent development of the disease/condition a later stage (e.g. a chronic stage or metastasis).

It will be appreciated that the articles of the present invention may be used for the treatment/prevention of any disease/condition that would derived therapeutic or prophylactic benefit from a reduction in the number and/or activity of cells expressing CD47. For example, the disease/condition may be a disease/condition in which cells expressing CD47 are pathologically implicated, e.g. a disease/condition in which an increased number/proportion of cells expressing CD47 is positively associated with the onset, development or progression of the disease/condition, and/or severity of one or more symptoms of the disease/condition, or for which an increased number/proportion of cells expressing CD47, is a risk factor for the onset, development or progression of the disease/condition.

In some embodiments, the disease/condition to be treated/prevented in accordance with the present invention is a disease/condition characterised by an increase in the number/proportion/activity of cells expressing CD47, e.g. as compared to the number/proportion/activity of cells expressing CD47 in the absence of the disease/condition.

In some embodiments the disease/condition to be treated/prevented is a cancer. CD47 has been proposed to be a cell-surface marker expressed by all human cancers (Willingham et al. Proc Natl Acad Sci USA. (2012) 109(17): 6662-6667)

The cancer may be any unwanted cell proliferation (or any disease manifesting itself by unwanted cell proliferation), neoplasm or tumor. The cancer may be benign or malignant and may be primary or secondary (metastatic). A neoplasm or tumor may be any abnormal growth or proliferation of cells and may be located in any tissue. The cancer may be of tissues/cells derived from e.g. the adrenal gland, adrenal medulla, anus, appendix, bladder, blood, bone, bone marrow, brain, breast, cecum, central nervous system (including or excluding the brain) cerebellum, cervix, colon, duodenum, endometrium, epithelial cells (e.g. renal epithelia), gallbladder, oesophagus, glial cells, heart, ileum, jejunum, kidney, lacrimal glad, larynx, liver, lung, lymph, lymph node, lymphoblast, maxilla, mediastinum, mesentery, myometrium, nasopharynx, omentum, oral cavity, ovary, pancreas, parotid gland, peripheral nervous system, peritoneum, pleura, prostate, salivary gland, sigmoid colon, skin, small intestine, soft tissues, spleen, stomach, testis, thymus, thyroid gland, tongue, tonsil, trachea, uterus, vulva, white blood cells.

Tumors to be treated may be nervous or non-nervous system tumors. Nervous system tumors may originate either in the central or peripheral nervous system, e.g. glioma, medulloblastoma, meningioma, neurofibroma, ependymoma, Schwannoma, neurofibrosarcoma, astrocytoma and oligodendroglioma. Non-nervous system cancers/tumors may originate in any other non-nervous tissue, examples include melanoma, mesothelioma, lymphoma, myeloma, leukemia, Non-Hodgkin's lymphoma (NHL), Hodgkin's lymphoma, chronic myelogenous leukemia (CML), acute myeloid leukemia (AML), myelodysplastic syndrome (MDS), cutaneous T-cell lymphoma (CTCL), chronic lymphocytic leukemia (CLL), hepatoma, epidermoid carcinoma, prostate carcinoma, breast cancer, lung cancer, colon cancer, ovarian cancer, pancreatic cancer, thymic carcinoma, NSCLC, hematologic cancer and sarcoma.

The treatment/prevention may be aimed at one or more of: delaying/preventing the onset/progression of symptoms of the cancer, reducing the severity of symptoms of the cancer, reducing the survival/growth/invasion/metastasis of cells of the cancer, reducing the number of cells of the cancer and/or increasing survival of the subject.

In some embodiments, the cancer to be treated/prevented comprises cells expressing CD47. In some embodiments, the cancer to be treated/prevented is a cancer which is positive for CD47. In some embodiments, the cancer over-expresses CD47. Overexpression of CD47 can be determined by detection of a level of expression of CD47 which is greater than the level of expression by equivalent non-cancerous cells/non-tumor tissue.

CD47 expression may be determined by any suitable means. Expression may be gene expression or protein expression. Gene expression can be determined e.g. by detection of mRNA encoding CD47, for example by quantitative real-time PCR (qRT-PCR). Protein expression can be determined e.g. by detection of CD47, for example by antibody-based methods, for example by western blot, immunohistochemistry, immunocytochemistry, flow cytometry, or ELISA.

In some embodiments, a patient may be selected for treatment described herein based on the detection of a cancer expressing CD47, or overexpressing CD47, e.g. in a sample obtained from the subject.

The role of CD47 in the development and progression of various cancers is reviewed e.g. in Sick et al. Br J Pharmacol. (2012) 167(7): 1415-1430 and Chao et al., Curr Opin Immunol. 2012 April; 24(2): 225-232 (hereby incorporated by reference in its entirety). Elevated CD47 expression is a negative prognostic indicator for several cancers, and may contribute to cancer development/progression by reducing killing of cancer cells and by increasing proliferation, migration and/or invasion of cancer cells. CD47 has been shown to suppress innate macrophage and NK cell-mediated anticancer responses (Soto-Pantoja et al., Expert Opin Ther Targets. (2013) 17(1): 89-103, which is hereby incorporated by reference in its entirety).

CD47 is expressed by acute myeloid leukemia (AML), chronic myeloid leukemia (CML), acute lymphoblastic leukemia (ALL), non-Hodgkin's lymphoma (NHL), multiple myeloma (MM), bladder cancer, brain cancer and ovarian cancer cells. Willingham et al. Proc Natl Acad Sci USA. (2012) 109(17): 6662-6667 reported expression of CD47 on cells of ovarian, breast, colon, bladder, glioblastoma, hepatocellular carcinoma, and prostate tumors, and CD47 has recently been shown to promote tumor invasion and metastasis in Non-small Cell Lung Cancer (NSCLC; Zhao et al., Sci Rep. (2016) 6: 29719) and melanoma (Ngo et al., Cell Reports (2016) 16, 1701-1716).

Accordingly, in some embodiments the cancer to be treated/prevented in accordance with the present invention is selected from: a hematologic malignancy, a myeloid hematologic malignancy, a lymphoblastic hematologic malignancy, myelodysplastic syndrome (MDS), acute myeloid leukemia (AML), chronic myeloid leukemia (CML), acute lymphoblastic leukemia (ALL), non-Hodgkin's lymphoma (NHL), multiple myeloma (MM), bladder cancer, brain cancer, glioblastoma, ovarian cancer, breast cancer, colon cancer, liver cancer, hepatocellular carcinoma, prostate cancer, lung cancer, Non-small Cell Lung Cancer (NSCLC), skin cancer and melanoma.

CD47 is a particularly attractive therapeutic targets for AML because it is highly expressed in all characterised AML cell lines, and play functional roles which therefore reduce risk of antigen loss. The large population of tissue-resident macrophages in the liver (Kupffer cells) represents an attractive therapeutic mechanism for hematological malignancies, and macrophage-driven clearance of malignant cells offers a further route for neo-antigen presentation to adaptive immune system.

CD47 is also implicated in the pathogenesis of autoimmune diseases, inflammatory diseases, ischemia-reperfusion injury (IRI) and cardiovascular diseases (see e.g. Soto-Pantoja et al., Expert Opin Ther Targets. (2013) 17(1): 89-103). The CD47-SIRPα axis has been implicated in type I diabetes (Dugas et al., J Autoimmun. (2010) 35(1):23-32). Thrombospondin-1 has been shown to act via CD47 to inhibit nitric oxide signaling throughout the vascular system, and blocking TSP1-CD47 interaction alleviates tissue ischemia (Isenberg et al., Arterioscler Thromb Vasc Biol. (2008) 28(4): 615-621) and reduces ischemia-reperfusion injury (IRI) (Xiao et al., Liver Transpl. (2015) 21(4): 468-477).

Accordingly, in some embodiments the disease/disorder to be treated/prevented is a cancer, an autoimmune disease (e.g. type I diabetes), an inflammatory disease, ischemia-reperfusion injury (IRI) or cardiovascular disease.

Administration of the articles of the present invention is preferably in a "therapeutically effective" or "prophylactically effective" amount, this being sufficient to show therapeutic or prophylactic benefit to the subject. The actual amount administered, and rate and time-course of administration, will depend on the nature and severity of the disease/condition and the particular article administered. Prescription of treatment, e.g. decisions on dosage etc., is within the responsibility of general practitioners and other medical doctors, and typically takes account of the disease/disorder to be treated, the condition of the individual subject, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Administration may be alone or in combination with other treatments, either simultaneously or sequentially dependent upon the condition to be treated. The antigen-binding molecule or composition described herein and a therapeutic agent may be administered simultaneously or sequentially.

In some embodiments, the methods comprise additional therapeutic or prophylactic intervention, e.g. for the treatment/prevention of a cancer. In some embodiments, the therapeutic or prophylactic intervention is selected from chemotherapy, immunotherapy, radiotherapy, surgery, vaccination and/or hormone therapy. In some embodiments, the therapeutic or prophylactic intervention comprises leukapheresis. In some embodiments the therapeutic or prophylactic intervention comprises a stem cell transplant.

The antigen-binding molecules of the present invention are particularly suitable for use in conjunction with radiotherapy. Antagonism of CD47 has previously been shown to help maintain the viability of normal tissues after irradiation, while increasing the radiosensitivity of tumors (Maxhimer et al., Science Translational Medicine (2009) 1(3): 3ra7).

Simultaneous administration refers to administration of the antigen-binding molecule, polypeptide, CAR, nucleic acid (or plurality thereof), expression vector (or plurality thereof), cell or composition and therapeutic agent together, for example as a pharmaceutical composition containing both agents (combined preparation), or immediately after each other and optionally via the same route of administration, e.g. to the same artery, vein or other blood vessel. Sequential administration refers to administration of one of the antigen-binding molecule/composition or therapeutic agent followed after a given time interval by separate administration of the other agent. It is not required that the two agents are administered by the same route, although this is the case in some embodiments. The time interval may be any time interval.

Chemotherapy and radiotherapy respectively refer to treatment of a cancer with a drug or with ionising radiation (e.g. radiotherapy using X-rays or γ-rays). The drug may be a chemical entity, e.g. small molecule pharmaceutical, antibiotic, DNA intercalator, protein inhibitor (e.g. kinase inhibitor), or a biological agent, e.g. antibody, antibody fragment, aptamer, nucleic acid (e.g. DNA, RNA), peptide, polypeptide, or protein. The drug may be formulated as a pharmaceutical composition or medicament. The formulation may comprise one or more drugs (e.g. one or more active agents) together with one or more pharmaceutically acceptable diluents, excipients or carriers.

A treatment may involve administration of more than one drug. A drug may be administered alone or in combination with other treatments, either simultaneously or sequentially dependent upon the condition to be treated. For example, the chemotherapy may be a co-therapy involving administration of two drugs, one or more of which may be intended to treat the cancer.

The chemotherapy may be administered by one or more routes of administration, e.g. parenteral, intravenous injection, oral, subcutaneous, intradermal or intratumoral.

The chemotherapy may be administered according to a treatment regime. The treatment regime may be a pre-determined timetable, plan, scheme or schedule of chemotherapy administration which may be prepared by a physician or medical practitioner and may be tailored to suit the patient requiring treatment. The treatment regime may indicate one or more of: the type of chemotherapy to administer to the patient; the dose of each drug or radiation; the time interval between administrations; the length of each treatment; the number and nature of any treatment holidays, if any etc. For a co-therapy a single treatment regime may be provided which indicates how each drug is to be administered.

Chemotherapeutic drugs may be selected from: Abemaciclib, Abiraterone Acetate, Abitrexate (Methotrexate), Abraxane (Paclitaxel Albumin-stabilized Nanoparticle Formulation), ABVD, ABVE, ABVE-PC, AC, Acalabrutinib, AC-T, Adcetris (Brentuximab Vedotin), ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), Aliqopa (Copanlisib Hydrochloride), Alkeran for Injection (Melphalan Hydrochloride), Alkeran Tablets (Melphalan), Aloxi (Palonosetron Hydrochloride), Alunbrig (Brigatinib), Ambochlorin (Chlorambucil), Amboclorin (Chlorambucil), Amifostine, Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Atezolizumab, Avastin (Bevacizumab), Avelumab, Axicabtagene Ciloleucel, Axitinib, Azacitidine, Bavencio (Avelumab), BEACOPP, Becenum (Carmustine), Beleodaq (Belinostat), Belinostat, Bendamustine Hydrochloride, BEP, Besponsa (Inotuzumab Ozogamicin), Bevacizumab, Bexarotene, Bexxar (Tositumomab and Iodine 1131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Brigatinib, BuMel, Busulfan, Busulfex (Busulfan), Cabazitaxel, Cabometyx (Cabozantinib-S-Malate), Cabozantinib-S-Malate, CAF, Calquence (Acalabrutinib), Campath (Alemtuzumab), Camptosar (Irinotecan Hydrochloride), Capecitabine, CAPDX, Carac (Fluorouracil-Topical), Carboplatin, CARBOPLATIN-TAXOL, Carfilzomib, Carmubris (Carmustine), Carmustine, Carmustine Implant, Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, CHLORAMBUCIL-PREDNISONE, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), Copanlisib Hydrochloride, COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Daunorubicin Hydrochloride and Cytarabine Liposome, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Efudex (Fluorouracil-Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enasidenib Mesylate, Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Ethyol (Amifostine), Etopophos (Etoposide Phosphate), Etoposide, Etoposide Phosphate, Evacet (Doxorubicin Hydrochloride Liposome), Everolimus, Evista (Raloxifene Hydrochloride), Evomela (Melphalan Hydrochloride), Exemestane, 5-FU (Fluorouracil Injection), 5-FU (Fluorouracil-Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil-Topical), Fluorouracil Injection, Fluorouracil-Topical, Flutamide, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Idhifa (Enasidenib Mesylate), Ifex (Ifosfamide), Ifosfamide, Ifosfamidum (Ifosfamide), IL-2 (Aldesleukin), Imatinib Mesylate, Imbruvica (Ibrutinib), Imfinzi (Durvalumab), Imiquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Iodine 1131 Tositumomab and Tositumomab, Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), JEB, Jevtana (Cabazitaxel), Kadcyla (Ado-Trastuzumab Emtansine), Keoxifene (Raloxifene Hydrochloride), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), Margibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nolvadex (Tamoxifen Citrate), Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), [No Entries], Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EPOCH, Revlimid (Lenalidomide), Rheumatrex (Methotrexate), Ribociclib, R-ICE, Rituxan (Rituximab), Rituxan Hycela (Rituximab and Hyaluronidase Human), Rituximab, Rituximab and Hyaluronidase Human, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Tecentriq (Atezolizumab), Temodar (Temozolomide), Temozolomide, Temsirolimus, Thalidomide, Thalomid (Thalidomide), Thioguanine, Thiotepa, Tisagenlecleucel, Tolak (Fluorouracil-Topical), Topotecan Hydrochloride, Toremifene, Torisel (Temsirolimus), Tositumomab and Iodine I 131 Tositumomab, Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Valrubicin, Valstar (Valrubicin), Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, Venclexta (Venetoclax), Venetoclax, Verzenio (Abemaciclib), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Vyxeos (Daunorubicin Hydrochloride and Cytarabine Liposome), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yescarta (Axicabtagene Ciloleucel), Yondelis (Trabectedin), Zaltrap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib) and Zytiga (Abiraterone Acetate).

In some embodiments the chemotherapeutic agent is selected from one or more of: cytarabine, 5-azacytidine (5-AZA), valproic acid (VPA), all-trans retinoic acid (ATRA), decitabine, sodium phenylbutyrate, hydrozyurea, 6-mercaptopurine (6-MP), 6-thioguanine (6-TG), Mocetinostat (MGCD0103), Panobinostat (LBH-589), romidepsin, an antracycline, daunorubicin, daunomycin, idarubicin, cladribine (Leustatin, 2-CdA), midostaurin, fludarabine (Fludara) and topotecan.

In some embodiments the chemotherapeutic agent is histone deacetylase (HDAC) inhibitor, e.g. a HDAC inhibitor described in Fredly et al., Clin Epigenetics. (2013) 5(1):12 (hereby incorporated by reference in its entirety). In some embodiments the chemotherapeutic agent is cytarabine.

Multiple doses of the producing an antigen-binding molecule, polypeptide, CAR, nucleic acid (or plurality thereof), expression vector (or plurality thereof), cell or composition may be provided. One or more, or each, of the doses may be accompanied by simultaneous or sequential administration of another therapeutic agent.

Multiple doses may be separated by a predetermined time interval, which may be selected to be one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days, or 1, 2, 3, 4, 5, or 6 months. By way of example, doses may be given once every 7, 14, 21 or 28 days (plus or minus 3, 2, or 1 days).

Methods of Detection

The invention also provides the articles of the present invention for use in methods for detecting, localizing or imaging CD47, or cells expressing CD47.

The antigen-binding molecules described herein may be used in methods that involve the antigen-binding molecule to CD47. Such methods may involve detection of the bound complex of the antigen-binding molecule and CD47.

As such, a method is provided, comprising contacting a sample containing, or suspected to contain, CD47, and detecting the formation of a complex of the antigen-binding molecule and CD47. Also provided is a method comprising contacting a sample containing, or suspected to contain, a cell expressing CD47, and detecting the formation of a complex of the antigen-binding molecule and a cell expressing CD47.

Suitable method formats are well known in the art, including immunoassays such as sandwich assays, e.g. ELISA. The methods may involve labelling the antigen-binding molecule, or target(s), or both, with a detectable moiety, e.g. a fluorescent label, phosphorescent label, luminescent label, immuno-detectable label, radiolabel, chemical, nucleic acid or enzymatic label as described herein. Detection techniques are well known to those of skill in the art and can be selected to correspond with the labelling agent.

Methods of this kind may provide the basis of methods for the diagnostic and/or prognostic evaluation of a disease or condition, e.g. a cancer. Such methods may be performed in vitro on a patient sample, or following processing of a patient sample. Once the sample is collected, the patient is not required to be present for the in vitro method to be performed, and therefore the method may be one which is not practised on the human or animal body. In some embodiments the method is performed in vivo.

Detection in a sample may be used for the purpose of diagnosis of a disease/condition (e.g. a cancer), predisposition to a disease/condition, or for providing a prognosis (prognosticating) for a disease/condition, e.g. a disease/condition described herein. The diagnosis or prognosis may relate to an existing (previously diagnosed) disease/condition.

Such methods may involve detecting or quantifying one or more of CD47 or cells expressing CD47, e.g. in a patient sample. Where the method comprises quantifying the relevant factor, the method may further comprise comparing the determined amount against a standard or reference value as part of the diagnostic or prognostic evaluation. Other diagnostic/prognostic tests may be used in conjunction with those described herein to enhance the accuracy of the diagnosis or prognosis or to confirm a result obtained by using the tests described herein.

A sample may be taken from any tissue or bodily fluid. The sample may comprise or may be derived from: a quantity of blood; a quantity of serum derived from the individual's blood which may comprise the fluid portion of the blood obtained after removal of the fibrin clot and blood cells; a tissue sample or biopsy; pleural fluid; cerebrospinal fluid (CSF); or cells isolated from said individual. In some embodiments, the sample may be obtained or derived from a tissue or tissues which are affected by the disease/condition (e.g. tissue or tissues in which symptoms of the disease manifest, or which are involved in the pathogenesis of the disease/condition).

The present invention also provides methods for selecting/stratifying a subject for treatment with a CD47-targeted agent. In some embodiments a subject is selected for treatment/prevention in accordance with the invention, or is identified as a subject which would benefit from such treatment/prevention, based on detection/quantification of CD47, or cells expressing CD47, e.g. in a sample obtained from the individual.

Subjects

The subject in accordance with aspects the invention described herein may be any animal or human. The subject is preferably mammalian, more preferably human. The subject may be a non-human mammal, but is more preferably human. The subject may be male or female. The subject may be a patient. A subject may have been diagnosed with a disease or condition requiring treatment (e.g. a cancer), may be suspected of having such a disease/condition, or may be at risk of developing/contracting such a disease/condition.

In embodiments according to the present invention the subject is preferably a human subject. In some embodiments, the subject to be treated according to a therapeutic or prophylactic method of the invention herein is a subject having, or at risk of developing, a cancer. In embodiments according to the present invention, a subject may be selected for treatment according to the methods based on characterisation for certain markers of such disease/condition.

Kits

In some aspects of the invention described herein a kit of parts is provided. In some embodiments the kit may have at least one container having a predetermined quantity of an antigen-binding molecule, polypeptide, CAR, nucleic acid (or plurality thereof), expression vector (or plurality thereof), cell or composition described herein.

In some embodiments, the kit may comprise materials for producing an antigen-binding molecule, polypeptide, CAR, nucleic acid (or plurality thereof), expression vector (or plurality thereof), cell or composition described herein.

The kit may provide the antigen-binding molecule, polypeptide, CAR, nucleic acid (or plurality thereof), expression vector (or plurality thereof), cell or composition together with instructions for administration to a patient in order to treat a specified disease/condition.

In some embodiments the kit may further comprise at least one container having a predetermined quantity of another therapeutic agent (e.g. anti-infective agent or chemotherapy agent). In such embodiments, the kit may also comprise a second medicament or pharmaceutical composition such that the two medicaments or pharmaceutical compositions may be administered simultaneously or separately such that they provide a combined treatment for the specific disease or condition. The therapeutic agent may also be formulated so as to be suitable for injection or infusion to a tumor or to the blood.

Sequence Identity

As used herein, "sequence identity" refers to the percent of nucleotides/amino acid residues in a subject sequence that are identical to nucleotides/amino acid residues in a reference sequence, after aligning the sequences and, if necessary, introducing gaps, to achieve the maximum percent sequence identity between the sequences. Pairwise and multiple sequence alignment for the purposes of determining percent sequence identity between two or more amino acid or nucleic acid sequences can be achieved in various ways known to a person of skill in the art, for instance, using publicly available computer software such as ClustalOmega (Söding, J. 2005, Bioinformatics 21, 951-960), T-coffee (Notredame et al. 2000, J. Mol. Biol. (2000) 302, 205-217), Kalign (Lassmann and Sonnhammer 2005, BMC Bioinformatics, 6(298)) and MAFFT (Katoh and Standley 2013, Molecular Biology and Evolution, 30(4) 772-780 software. When using such software, the default parameters, e.g. for gap penalty and extension penalty, are preferably used.

Sequences

| SEQ ID NO: | DESCRIPTION | SEQUENCE |
|---|---|---|
| 1 | Human CD47 isoform OA3-323 (UniProt: Q08722-1, v1) | MWPLVAALLLGSACCGSAQLLFNKTKSVEFTFCNDTVVIPCFVTNMEAQNTTEVYVKWKFKGRDI YTFDGALNKSTVPTDFSSAKIEVSQLLKGDASLKMDKSDAVSHTGNYTCEVTELTREGETIIELKYR VVSWFSPNENILIVIFPIFAILLFWGQFGIKTLKYRSGGMDEKTIALLVAGLVITVIVIVGAILFVPGEYS LKNATGLGLIVTSTGILILLHYYVFSTAIGLTSFVIAILVIQVIAYILAVVGLSLCIAACIPMHGPLLISGLSI LALAQLLGLVYMKFVASNQKTIQPPRKAVEEPLNAFKESKGMMNDE |
| 2 | Human CD47 isoform OA3-293 (UniProt: Q08722-2) | MWPLVAALLLGSACCGSAQLLFNKTKSVEFTFCNDTVVIPCFVTNMEAQNTTEVYVKWKFKGRDI YTFDGALNKSTVPTDFSSAKIEVSQLLKGDASLKMDKSDAVSHTGNYTCEVTELTREGETIIELKYR VVSWFSPNENILIVIFPIFAILLFWGQFGIKTLKYRSGGMDEKTIALLVAGLVITVIVIVGAILFVPGEYS LKNATGLGLIVTSTGILILLHYYVFSTAIGLTSFVIAILVIQVIAYILAVVGLSLCIAACIPMHGPLLISGLSI LALAQLLGLVYMKFV |
| 3 | Human CD47 isoform OA3-305 (UniProt: Q08722-3) | MWPLVAALLLGSACCGSAQLLFNKTKSVEFTFCNDTVVIPCFVTNMEAQNTTEVYVKWKFKGRDI YTFDGALNKSTVPTDFSSAKIEVSQLLKGDASLKMDKSDAVSHTGNYTCEVTELTREGETIIELKYR VVSWFSPNENILIVIFPIFAILLFWGQFGIKTLKYRSGGMDEKTIALLVAGLVITVIVIVGAILFVPGEYS LKNATGLGLIVTSTGILILLHYYVFSTAIGLTSFVIAILVIQVIAYILAVVGLSLCIAACIPMHGPLLISGLSI LALAQLLGLVYMKFVASNQKTIQPPRNN |
| 4 | Human CD47 isoform OA3-312 (UniProt: Q08722-4) | MWPLVAALLLGSACCGSAQLLFNKTKSVEFTFCNDTVVIPCFVTNMEAQNTTEVYVKWKFKGRDI YTFDGALNKSTVPTDFSSAKIEVSQLLKGDASLKMDKSDAVSHTGNYTCEVTELTREGETIIELKYR VVSWFSPNENILIVIFPIFAILLFWGQFGIKTLKYRSGGMDEKTIALLVAGLVITVIVIVGAILFVPGEYS LKNATGLGLIVTSTGILILLHYYVFSTAIGLTSFVIAILVIQVIAYILAVVGLSLCIAACIPMHGPLLISGLSI LALAQLLGLVYMKFVASNQKTIQPPRKAVEEPLN |
| 5 | Mature human CD47 isoform OA3-323 (UniProt: Q08722-1, v1 positions 19-323) | QLLFNKTKSVEFTFCNDTVVIPCFVTNMEAQNTTEVYVKWKFKGRDIYTFDGALNKSTVPTDFSSA KIEVSQLLKGDASLKMDKSDAVSHTGNYTCEVTELTREGETIIELKYRVVSWFSPNENILIVIFPIFAI LLFWGQFGIKTLKYRSGGMDEKTIALLVAGLVITVIVIVGAILFVPGEYSLKNATGLGLIVTSTGILILL HYYVFSTAIGLTSFVIAILVIQVIAYILAVVGLSLCIAACIPMHGPLLISGLSILALAQLLGLVYMKFVAS NQKTIQPPRKAVEEPLNAFKESKGMMNDE |
| 6 | Mature human CD47 isoform OA3-293 (UniProt: Q08722-2 positions 19-292) | QLLFNKTKSVEFTFCNDTVVIPCFVTNMEAQNTTEVYVKWKFKGRDIYTFDGALNKSTVPTDFSSA KIEVSQLLKGDASLKMDKSDAVSHTGNYTCEVTELTREGETIIELKYRVVSWFSPNENILIVIFPIFAI LLFWGQFGIKTLKYRSGGMDEKTIALLVAGLVITVIVIVGAILFVPGEYSLKNATGLGLIVTSTGILILL HYYVFSTAIGLTSFVIAILVIQVIAYILAVVGLSLCIAACIPMHGPLLISGLSILALAQLLGLVYMKFV |
| 7 | Mature human CD47 isoform OA3-305 (UniProt: Q08722-3, positions 19-305) | QLLFNKTKSVEFTFCNDTVVIPCFVTNMEAQNTTEVYVKWKFKGRDIYTFDGALNKSTVPTDFSSA KIEVSQLLKGDASLKMDKSDAVSHTGNYTCEVTELTREGETIIELKYRVVSWFSPNENILIVIFPIFAI LLFWGQFGIKTLKYRSGGMDEKTIALLVAGLVITVIVIVGAILFVPGEYSLKNATGLGLIVTSTGILILL HYYVFSTAIGLTSFVIAILVIQVIAYILAVVGLSLCIAACIPMHGPLLISGLSILALAQLLGLVYMKFVAS NQKTIQPPRNN |
| 8 | Mature human CD47 isoform OA3-312 (UniProt: Q08722-4 positions 19-311) | QLLFNKTKSVEFTFCNDTVVIPCFVTNMEAQNTTEVYVKWKFKGRDIYTFDGALNKSTVPTDFSSA KIEVSQLLKGDASLKMDKSDAVSHTGNYTCEVTELTREGETIIELKYRVVSWFSPNENILIVIFPIFAI LLFWGQFGIKTLKYRSGGMDEKTIALLVAGLVITVIVIVGAILFVPGEYSLKNATGLGLIVTSTGILILL HYYVFSTAIGLTSFVIAILVIQVIAYILAVVGLSLCIAACIPMHGPLLISGLSILALAQLLGLVYMKFVAS NQKTIQPPRKAVEEPLN |
| 9 | V-type Ig-like domain (UniProt: Q08722-1 positions 19-127) | QLLFNKTKSVEFTFCNDTVVIPCFVTNMEAQNTTEVYVKWKFKGRDIYTFDGALNKSTVPTDFSSA KIEVSQLLKGDASLKMDKSDAVSHTGNYTCEVTELTREGETII |
| 10 | Human CD47 extracellular region 1 (UniProt: Q08722-1 positions 19-141) | QLLFNKTKSVEFTFCNDTVVIPCFVTNMEAQNTTEVYVKWKFKGRDIYTFDGALNKSTVPTDFSSA KIEVSQLLKGDASLKMDKSDAVSHTGNYTCEVTELTREGETIIELKYRVVSWFSPNE |
| 11 | Human CD47 transmembrane region 1 (UniProt: Q08722-1 positions 142-162) | NILIVIFPIFAILLFWGQFGI |
| 12 | Human CD47 cytoplasmic region 1 (UniProt: Q08722-1 positions 163-176) | KTLKYRSGGMDEKT |
| 13 | Human CD47 transmembrane region 2 (UniProt: Q08722-1 positions 177-197) | IALLVAGLVITVIVIVGAILF |

-continued

| SEQ ID NO: | DESCRIPTION | SEQUENCE |
|---|---|---|
| 14 | Human CD47 extracellular region 2 (UniProt: Q08722-1 positions 198-207) | VPGEYSLKNA |
| 15 | Human CD47 transmembrane region 3 (UniProt: Q08722-1 positions 208-228) | TGLGLIVTSTGILILLHYYVF |
| 16 | Human CD47 cytoplasmic region 2 (UniProt: Q08722-1 positions 229-235) | STAIGLT |
| 17 | Human CD47 transmembrane region 4 (UniProt: Q08722-1 positions 236-256) | SFVIAILVIQVIAYILAVVGL |
| 18 | Human CD47 extracellular region 3 (UniProt: Q08722-1 positions 257-268) | SLCIAACIPMHG |
| 19 | Human CD47 transmembrane region 5 (UniProt: Q08722-1 positions 269-289) | PLLISGLSILALAQLLGLVYM |
| 20 | Human CD47 cytoplasmic region 3 (UniProt: Q08722-1 positions 290-323) | KFVASNQKTIQPPRKAVEEPLNAFKESKGMMNDE |
| 21 | Region of human CD47 targeted by 1-1-A1 and 1-1-A1_BM (UniProt: Q08722-1 positions 56-65) | VKWKFKGRDI |
| 22 | Region of human CD47 targeted by 5-48-A6 and 5-48-D2 (UniProt: Q08722-1 positions 24-34) | KTKSVEFTFCN |
| 23 | 1-1-A1_BM heavy chain variable region | QVQLQQSGPDLKKPGASVKVSCKVSGYTFTNYVIHWVRQKPGQGLEWMGYINPYNDGTKSNEK FKGKATLTSDKSSTSAYMELSSLTSEDTAVYYCASGGYYTMDYWGQGTSVTVSS |
| 24 | 1-1-A1_BM, 1-1-A1, 11A1H1, 11A1H2, 11A1H3, 11A1H4, 11A1H6, 11A1H8 heavy chain CDR1 | GYTFTNYV |
| 25 | 1-1-A1_BM, 1-1-A1, 11A1H1, 11A1H2, 11A1H3, 11A1H4, 11A1H6, 11A1H8 heavy chain CDR2 | INPYNDGT |

-continued

| SEQ ID NO: | DESCRIPTION | SEQUENCE |
|---|---|---|
| 26 | 1-1-A1_BM, 1-1-A1, 11A1H1, 11A1H2, 11A1H3, 11A1H4, 11A1H6, 11A1H8, 11A1H5, 11A1H7, 11A1H9, 11A1H10, 11A1H11 heavy chain CDR3 | ASGGYYTMDY |
| 27 | 1-1-A1_BM heavy chain FR1 | QVQLQQSGPDLKKPGASVKVSCKVS |
| 28 | 1-1-A1_BM heavy chain FR2 | IHWVRQKPGQGLEWMGY |
| 29 | 1-1-A1_BM heavy chain FR3 | KSNEKFKGKATLTSDKSSTSAYMELSSLTSEDTAVYYC |
| 30 | 1-1-A1_BM heavy chain FR4 | WGQGTSVTVSS |
| 31 | 1-1-A1_BM light chain variable region | DVVMTQTPLSLPVTLGDQASISCRSSQHLEYSNGYSYLHWYQQRPGQSPQLLIYKISNRFSGVPD RFSGSGSGTDFTLKISRVEAEDLGVYYCSQSTHVPYTFGGGTKLEIK |
| 32 | 1-1-A1_BM, 1-1-A1, 11A1H1, 11A1H2, 11A1H3, 11A1H4, 11A1H5, 11A1H10, 11A1H11 light chain CDR1 | QHLEYSNGYSY |
| 33 | 1-1-A1_BM, 1-1-A1, 11A1H1, 11A1H2, 11A1H3, 11A1H4, 11A1H5, 11A1H11 light chain CDR2 | KIS |
| 34 | 1-1-A1_BM, 1-1-A1, 11A1H1, 11A1H2, 11A1H3, 11A1H4, 11A1H5, 11A1H6, 11A1H7 11A1H8, 11A1H9 11A1H10 light chain CDR3 | SQSTHVPYT |
| 35 | 1-1-A1_BM light chain FR1 | DVVMTQTPLSLPVTLGDQASISCRSS |
| 36 | 1-1-A1_BM light chain FR2 | LHWYQQRPGQSPQLLIY |
| 37 | 1-1-A1_BM light chain FR3 | NRFSGVPDRFSGSGSGTDFTLKISRVEAEDLGVYYC |
| 38 | 1-1-A1_BM light chain FR4 | FGGGTKLEIK |
| 39 | 1-1-A1 heavy chain variable region | EVQLQQSGPDLVKPGASVKMSCKASGYTFTNYVIHWVKQKPGQGLEWIGYINPYNDGTKSNEKF KGKATLTSDKSSTSAYMELSSLTSEDSAVYYCASGGYYTMDYWGQGTSVTVSS |
| 40 | 1-1-A1 heavy chain FR1 | EVQLQQSGPDLVKPGASVKMSCKAS |
| 41 | 1-1-A1 heavy chain FR2 | IHWVKQKPGQGLEWIGY |

| SEQ ID NO: | DESCRIPTION | SEQUENCE |
|---|---|---|
| 42 | 1-1-A1 heavy chain FR3 | KSNEKFKGKATLTSDKSSTSAYMELSSLTSEDSAVYYC |
| 43 | 1-1-A1 heavy chain FR4 | WGQGTSVTVSS |
| 44 | 1-1-A1 light chain variable region | DVVMTQTPLSLPVSLGDQASISCRSSQHLEYSNGYSYLHWYLQKPGQSPQLLIYKISNRFSGVPD RFSGSGSGTDFTLKISRVEAEDLGVYFCSQSTHVPYTFGGGTKLEIK |
| 45 | 1-1-A1 light chain FR1 | DVVMTQTPLSLPVSLGDQASISCRSS |
| 46 | 1-1-A1 light chain FR2 | LHWYLQKPGQSPQLLIY |
| 47 | 1-1-A1 light chain FR3 | NRFSGVPDRFSGSGSGTDFTLKISRVEAEDLGVYFC |
| 48 | 1-1-A1 light chain FR4 | FGGGTKLEIK |
| 49 | 5-48-A6 heavy chain variable region | QVQLKESGPGLVAPSQSLSITCTVSGFSLTSYGVHWVRQPPGKGLEWLGVIWAGGSTNYNSALM SRLSISKDNSKSQVFLKMNSLQTDDTAMYYCARVPTGRIKSYFYAMDYWGQGTSVTVSS |
| 50 | 5-48-A6 heavy chain CDR1 | GFSLTSYG |
| 51 | 5-48-A6 heavy chain CDR2 | IWAGGST |
| 52 | 5-48-A6 heavy chain CDR3 | ARVPTGRIKSYFYAMDY |
| 53 | 5-48-A6 heavy chain FR1 | QVQLKESGPGLVAPSQSLSITCTVS |
| 54 | 5-48-A6 heavy chain FR2 | VHWVRQPPGKGLEWLGV |
| 55 | 5-48-A6 heavy chain FR3 | NYNSALMSRLSISKDNSKSQVFLKMNSLQTDDTAMYYC |
| 56 | 5-48-A6 heavy chain FR4 | WGQGTSVTVSS |
| 57 | 5-48-A6 light chain variable region | DIKMTQSPSSMYSSLGERVTITCKASQDISSYLSWFQQKPGKSPKTLIYRANRLVDGVPSRFSGS GSGQDYSLTISSLEYEDMGIYYCLQYDEFPYTFGGGTKLEIK |
| 58 | 5-48-A6 light chain CDR1 | QDISSY |
| 59 | 5-48-A6 light chain CDR2 | RAN |
| 60 | 5-48-A6 light chain CDR3 | LQYDEFPYT |
| 61 | 5-48-A6 light chain FR1 | DIKMTQSPSSMYSSLGERVTITCKAS |
| 62 | 5-48-A6 light chain FR2 | LSWFQQKPGKSPKTLIY |
| 63 | 5-48-A6 light chain FR3 | RLVDGVPSRFSGSGSGQDYSLTISSLEYEDMGIYYC |
| 64 | 5-48-A6 light chain FR4 | FGGGTKLEIK |
| 65 | 5-48-D2 heavy chain variable region | EVKLLESGGGLVQPGGSLKLSCAASGFDFSRYWMSWVRQAPGKGLEWIGEINPDSSTINYTPSL KDKFIISRDNAKNTLYLQMSKVRSEDTALYYCATGTGFAYWGQGTLVTVSA |

| SEQ ID NO: | DESCRIPTION | SEQUENCE |
|---|---|---|
| 66 | 5-48-D2 heavy chain CDR1 | GFDFSRYW |
| 67 | 5-48-D2 heavy chain CDR2 | INPDSSTI |
| 68 | 5-48-D2 heavy chain CDR3 | ATGTGFAY |
| 69 | 5-48-D2 heavy chain FR1 | EVKLLESGGGLVQPGGSLKLSCAAS |
| 70 | 5-48-D2 heavy chain FR2 | MSWVRQAPGKGLEWIGE |
| 71 | 5-48-D2 heavy chain FR3 | NYTPSLKDKFHSRDNAKNTLYLQMSKVRSEDTALYYC |
| 72 | 5-48-D2 heavy chain FR4 | WGQGTLVTVSA |
| 73 | 5-48-D2 light chain variable region | DIQMTQSPASLSASVGETVTITCRASENIYSYLAWYQQKGKSPQLLVYNAKTLAEGVPSRFSGSGSGTQFSLKINSLQPEDFGSYYCQHHYVTPWTFGGVTKLEIK |
| 74 | 5-48-D2 light chain CDR1 | ENIYSY |
| 75 | 5-48-D2 light chain CDR2 | NAK |
| 76 | 5-48-D2 light chain CDR3 | QHHYVTPWT |
| 77 | 5-48-D2 light chain FR1 | DIQMTQSPASLSASVGETVTITCRAS |
| 78 | 5-48-D2 light chain FR2 | LAWYQQKGKSPQLLVY |
| 79 | 5-48-D2 light chain FR3 | TLAEGVPSRFSGSGSGTQFSLKINSLQPEDFGSYYC |
| 80 | 5-48-D2 light chain FR4 | FGGVTKLEIK |
| 81 | 1-1-A1 heavy chain SignalP | MEWSWIFLFLLSGTAGVHS |
| 82 | 1-1-A1 light chain SignalP | MKLPVRLLVLMFWIPASSS |
| 83 | 5-48-A6 heavy chain SignalP | MAVLVLFLCLVAFPSCVLS |
| 84 | 5-48-A6 light chain SignalP | MRTPAQFLGILLLWFPGIKC |
| 85 | 5-48-D2 heavy chain SignalP | MDFGLIFFIVALLKGVQC |
| 86 | 5-48-D2 light chain SignalP | MSVPTQVLGLLLLWLTGARC |
| 87 | 1-1-A1_BM heavy chain DNA | CAGGTGCAGCTGCAGCAGTCTGGACCAGACCTGAAGAAGCCTGGAGCCAGCGTGAAGGTGT<br>CCTGTAAGGTGTCCGGCTACACCTTCACAAACTATGTGATCCACTGGGTGAGGCAGAAGCCA<br>GGACAGGGCCTGGAGTGGATGGGCTACATCAACCCCTATAATGACGGCACCAAGTCTAATGA<br>AGAGTTTAAGGGCAAGGCCACCCTGACATCTGATAAGAGCAGCACCAGCGCCTACATGGAGC<br>TGTCTAGCCTGACCAGCGAGGACACAGCCGTGTACTATTGCGCTTCCGGCGGCTACTATACA<br>ATGGATTATTGGGGCCAGGGCACCAGCGTGACAGTGTCCTCT |

-continued

| SEQ ID NO: | DESCRIPTION | SEQUENCE |
|---|---|---|
| 88 | 1-1-A1_BM light chain DNA | GACGTGGTCATGACCCAGACACCACTGTCCCTGCCTGTGACCCTGGGCGATCAGGCCTCTAT<br>CAGCTGTAGAAGCTCCCAGCACCTGGAGTACAGCAACGGCTACTCCTATCTGCACTGGTATC<br>AGCAGCGCCCAGGACAGTCTCCACAGCTGCTGATCTACAAGATCTCTAATCGGTTCAGCGGC<br>GTGCCTGACAGGTTTTCCGGCTCTGGCAGCGGCACCGATTTCACACTGAAGATCAGCAGAGT<br>GGAGGCTGAGGACCTGGGCGTGTACTATTGCTCCCAGTCTACCCACGTGCCCTATACATTTG<br>GCGGCGGCACCAAGCTGGAGATCAAG |
| 89 | 1-1-A1 heavy chain DNA | GAGGTCCAGCTGCAGCAGTCTGGACCTGACCTAGTAAAGCCTGGGGCTTCAGTGAAGATGTC<br>CTGCAAGGCTTCTGGATACACATTCACTAATTATGTTATACACTGGGTGAAGCAGAAGCCTGG<br>GCAGGGCCTTGAGTGGATTGGATATATTAATCCTTACAATGATGGTACTAAGTCCAATGAGAA<br>GTTCAAAGGCAAGGCCACACTGACTTCAGACAAATCCTCCACCTCAGCCTACATGGAGCTCA<br>GCAGCCTGACCTCTGAGGACTCTGCGGTCTATTACTGTGCAAGCGGAGGGTACTATACTATG<br>GACTATTGGGGTCAAGGAACCTCAGTCACCGTCTCCTCG |
| 90 | 1-1-A1 light chain DNA | GATGTTGTGATGACCCAAACTCCACTCTCCCTGCCTGTCAGTCTTGGAGATCAAGCCTCCATC<br>TCTTGCAGATCTAGTCAACACCTTGAATACAGTAATGGATACTCCTATTTGCATTGGTACCTGC<br>AGAAGCCAGGCCAGTCTCCACAGCTCCTGATCTACAAATTTTCCAACCGATTTTCTGGGGTCC<br>CAGACAGGTTCAGTGGCAGTGGATCAGGGACAGATTTCACACTCAAGATCAGCAGAGTGGAG<br>GCTGAGGATCTGGGGGTTTATTTCTGCTCTCAAAGTACACATGTTCCGTACACATTCGGAGGG<br>GGGACCAAGCTGGAAATAAAA |
| 91 | 5-48-A6 heavy chain DNA | CAGGTGCAGCTGAAGGAGTCAGGACCTGGCCTGGTGGCGCCCTCACAGAGCCTGTCCATCA<br>CTTGCACTGTCTCTGGGTTTTCATTAACCAGTTATGGTGTACACTGGGTTCGCCAGCCTCCAG<br>GAAAGGGTCTGGAGTGGCTGGGAGTAATATGGGCTGGTGGAAGCACAAATTATAATTCGGCT<br>CTCATGTCCAGACTGAGCATCAGCAAAGACAACTCCAAGAGCCAAGTTTTCTTAAAAATGAAC<br>AGTCTGCAAACTGATGACACAGCCATGTACTACTGTGCCAGAGTTCCGACAGGTCGGATTAA<br>ATCTTATTTCTATGCTATGGACTACTGGGGTCAAGGAACCTCAGTCACCGTCTCCTCG |
| 92 | 5-48-A6 light chain DNA | GACATCAAGATGACCCAGTCTCCATCTTCCATGTATTCATCTCTTGGAGAGAGAGTCACTATC<br>ACTTGCAAGGCGAGTCAGGACATTAGTAGCTATTTAAGCTGGTTCCAGCAGAAACCAGGGAA<br>GTCTCCTAAGACCCTGATCTATCGTGCAAACAGATTGGTGGATGGGGTCCCATCAAGGTTCA<br>GTGGCAGTGGATCTGGGCAAGATTATTCTCTCACCATCAGCAGCCTGGAGTATGAAGATATG<br>GGAATTTATTATTGTCTACAGTATGATGAGTTTCCGTACACGTTCGGAGGGGGGACCAAGCTG<br>GAAATAAAA |
| 93 | 5-48-D2 heavy chain DNA | GAGGTGAAGCTTCTCGAGTCTGGAGGTGGCCTGGTGCAGCCTGGAGGATCCCTGAAACTCT<br>CCTGTGCAGCCTCAGGATTCGAIIIIAGTAGATACTGGATGAGTTGGGTCCGGCAGGCTCCA<br>GGGAAAGGGCTAGAATGGATTGGAGAAATTAATCCAGATAGCAGTACGATAAACTATACGCC<br>ATCTCTAAAGGATAAATTCATCATCTCCAGAGACAACGCCAAAAATACGCTGTACCTGCAAAT<br>GAGCAAAGTGAGATCTGAGGACACAGCCCTTTATTACTGTGCAACTGGGACGGGGTTTGCTT<br>ACTGGGGCCAAGGGACTCTGGTCACTGTCTCTGCG |
| 94 | 5-48-D2 light chain DNA | GACATCCAGATGACTCAGTCTCCAGCTTCCCTATCTGCATCTGTGGGAGAAACTGTCACCATC<br>ACATGTCGAGCAAGTGAGAATATTTACAGTTATTTAGCATGGTATCAGCAGAAACAGGGAAAA<br>TCTCCTCAGCTCCTGGTCTATAATGCAAAAACCTTAGCAGAAGGTGTGCCCTCAAGGTTCAGT<br>GGCAGTGGATCAGGCACACAGTTTTCTCTGAAGATCAACAGCCTGCAGCCTGAAGATTTTGG<br>GAGTTATTACTGTCAACATCATTATGTTACTCCGTGGACGTTCGGTGGAGTCACCAAGCTGGA<br>AATCAAA |
| 95 | Human SIRPA isoform 1 (UniProt: P78324-1, v2) | MEPAGPAPGRLGPLLCLLLAASCAWSGVAGEEELQVIQPDKSVLVAAGETATLRCTATSLIPVGPI<br>QWFRGAGPGRELIYNQKEGHFPRVTTVSDLTKRNNMDFSIRIGNITPADAGTYYCVKFRKGSPDD<br>VEFKSGAGTELSVRAKPSAPVVSGPAARATPQHTVSFTCESHGFSPRDITLKWFKNGNELSDFQT<br>NVDPVGESVSYSIHSTAKVVLTREDVHSQVICEVAHVTLQGDPLRGTANLSETIRVPPTLEVTQQP<br>VRAENQVNVTCQVRKFYPQRLQLTWLENGNVSRTETASTVTENKDGTYNWMSWLLVNVSAHRD<br>DVKLTCQVEHDGQPAVSKSHDLKVSAHPKEQGSNTAAENTGSNERNIYIVVGVVCTLLVALLMAA<br>LYLVRIRQKKAQGSTSSTRLHEPEKNAREITQDTNDITYADLNLPKGKKPAPQAAEPNNHTEYASI<br>QTSPQPASEDTLTYADLDMVHLNRTPKQPAPKPEPSFSEYASVQVPRK |
| 96 | Human SIRPA isoform 2 (UniProt: P78324-2) | MEPAGPAPGRLGPLLCLLLAASCAWSGVAGEEELQVIQPDKSVLVAAGETATLRCTATSLIPVGPI<br>QWFRGAGPGRELIYNQKEGHFPRVTTVSDLTKRNNMDFSIRIGNITPADAGTYYCVKFRKGSPDD<br>VEFKSGAGTELSVRAKPSAPVVSGPAARATPQHTVSFTCESHGFSPRDITLKWFKNGNELSDFQT<br>NVDPVGESVSYSIHSTAKVVLTREDVHSQVICEVAHVTLQGDPLRGTANLSETIRVPPTLEVTQQP<br>VRAENQVNVTCQVRKFYPQRLQLTWLENGNVSRTETASTVTENKDGTYNWMSWLLVNVSAHRD<br>DVKLTCQVEHDGQPAVSKSHDLKVSAHPKEQGSNTAAENTGSNERNIYIVVGVVCTLLVALLMAA<br>LYLVRIRQKKAQGSTSSTRLHEPEKNAREITQVQSLDTNDITYADLNLPKGKKPAPQAAEPNNHTE<br>YASIQTSPQPASEDTLTYADLDMVHLNRTPKQPAPKPEPSFSEYASVQVPRK |

| SEQ ID NO: | DESCRIPTION | SEQUENCE |
|---|---|---|
| 97 | Human SIRPA isoform 4 (UniProt: P78324-4) | MEPAGPAPGRLGPLLCLLLAASCAWSGVAGEEELQVIQPDKSVLVAAGETATLRCTATSLIPVGPI QWFRGAGPGRELIYNQKEGHFPRVTTVSDLTKRNNMDFSIRIGNITPADAGTYYCVKFRKGSPDV EFKSGAGTELSVRAKPSAPVVSGPAARATPQHTVSFTCESHGFSPRDITLKWFKNGNELSDFQTN VDPVGESVSYSIHSTAKVVLTREDVHSQVICEVAHVTLQGDPLRGTANLSETIRVPPTLEVTQQPV RAENQVNVTCQVRKFYPQRLQLTWLENGNVSRTETASTVTENKDGTYNWMSWLLVNVSAHRDD VKLTCQVEHDGQPAVSKSHDLKVSAHPKEQGSNTAAENTGSNERNIYIVVGVVCTLLVALLMAAL YLVRIRQKKAQGSTSSRLHEPEKNAREITQDTNDITYADLNLPKGKKPAPQAAEPNNHTEYASIQ TSPQPASEDTLTYADLDMVHLNRTPKQPAPKPEPSFSEYASVQVPRK |
| 98 | Mature human SIRPA isoform 1 (UniProt: P20138-1 positions 31-504) | EEELQVIQPDKSVLVAAGETATLRCTATSLIPVGPIQWFRGAGPGRELIYNQKEGHFPRVTTVSDL TKRNNMDFSIRIGNITPADAGTYYCVKFRKGSPDDVEFKSGAGTELSVRAKPSAPVVSGPAARAT PQHTVSFTCESHGFSPRDITLKWFKNGNELSDFQTNVDPVGESVSYSIHSTAKVVLTREDVHSQVI CEVAHVTLQGDPLRGTANLSETIRVPPTLEVTQQPVRAENQVNVTCQVRKFYPQRLQLTWLENG NVSRTETASTVTENKDGTYNWMSWLLVNVSAHRDDVKLTCQVEHDGQPAVSKSHDLKVSAHPK EQGSNTAAENTGSNERNIYIVVGVVCTLLVALLMAALYLVRIRQKKAQGSTSSRLHEPEKNAREIT QDTNDITYADLNLPKGKKPAPQAAEPNNHTEYASIQTSPQPASEDTLTYADLDMVHLNRTPKQPA PKPEPSFSEYASVQVPRK |
| 99 | Mature human SIRPA isoform 2 (UniProt: P78324-2 positions 31-478) | EEELQVIQPDKSVLVAAGETATLRCTATSLIPVGPIQWFRGAGPGRELIYNQKEGHFPRVTTVSDL TKRNNMDFSIRIGNITPADAGTYYCVKFRKGSPDDVEFKSGAGTELSVRAKPSAPVVSGPAARAT PQHTVSFTCESHGFSPRDITLKWFKNGNELSDFQTNVDPVGESVSYSIHSTAKVVLTREDVHSQVI CEVAHVTLQGDPLRGTANLSETIRVPPTLEVTQQPVRAENQVNVTCQVRKFYPQRLQLTWLENG NVSRTETASTVTENKDGTYNWMSWLLVNVSAHRDDVKLTCQVEHDGQPAVSKSHDLKVSAHPK EQGSNTAAENTGSNERNIYIVVGVVCTLLVALLMAALYLVRIRQKKAQGSTSSRLHEPEKNAREIT QVQSLDTNDITYADLNLPKGKKPAPQAAEPNNHTEYASIQTSPQPASEDTLTYADLDMVHLNRTP KQPAPKPEPSFSEYASVQVPRK |
| 100 | Mature human SIRPA isoform 4 (UniProt: P78324-4 positions 31-473) | EEELQVIQPDKSVLVAAGETATLRCTATSLIPVGPIQWFRGAGPGRELIYNQKEGHFPRVTTVSDL TKRNNMDFSIRIGNITPADAGTYYCVKFRKGSPDDVEFKSGAGTELSVRAKPSAPVVSGPAARATP QHTVSFTCESHGFSPRDITLKWFKNGNELSDFQTNVDPVGESVSYSIHSTAKVVLTREDVHSQVI CEVAHVTLQGDPLRGTANLSETIRVPPTLEVTQQPVRAENQVNVTCQVRKFYPQRLQLTWLENG NVSRTETASTVTENKDGTYNWMSWLLVNVSAHRDDVKLTCQVEHDGQPAVSKSHDLKVSAHPK EQGSNTAAENTGSNERNIYIVVGVVCTLLVALLMAALYLVRIRQKKAQGSTSSRLHEPEKNAREIT QDTNDITYADLNLPKGKKPAPQAAEPNNHTEYASIQTSPQPASEDTLTYADLDMVHLNRTPKQPA PKPEPSFSEYASVQVPRK |
| 101 | Human SIRPA extracellular domain (UniProt: P78324-1 positions 31-373) | EEELQVIQPDKSVLVAAGETATLRCTATSLIPVGPIQWFRGAGPGRELIYNQKEGHFPRVTTVSDL TKRNNMDFSIRIGNITPADAGTYYCVKFRKGSPDDVEFKSGAGTELSVRAKPSAPVVSGPAARAT PQHTVSFTCESHGFSPRDITLKWFKNGNELSDFQTNVDPVGESVSYSIHSTAKVVLTREDVHSQVI CEVAHVTLQGDPLRGTANLSETIRVPPTLEVTQQPVRAENQVNVTCQVRKFYPQRLQLTWLENG NVSRTETASTVTENKDGTYNWMSWLLVNVSAHRDDVKLTCQVEHDGQPAVSKSHDLKVSAHPK EQGSNTAAENTGSNERNIY |
| 102 | Human SIRPA transmembrane domain (UniProt: P78324-1 positions 374-394) | IVVGVVCTLLVALLMAALYLV |
| 103 | Human SIRPA cytoplasmic domain (UniProt: P78324-1 positions 395-504) | RIRQKKAQGSTSSRLHEPEKNAREITQDTNDITYADLNLPKGKKPAPQAAEPNNHTEYASIQTSP QPASEDTLTYADLDMVHLNRTPKQPAPKPEPSFSEYASVQVPRK |
| 104 | Human SIRPA V-type Ig-like domain (UniProt: P78324-1 positions 32-137) | EELQVIQPDKSVLVAAGETATLRCTATSLIPVGPIQWFRGAGPGRELIYNQKEGHFPRVTTVSDLT KRNNMDFSIRIGNITPADAGTYYCVKFRKGSPDDVEFKSG |
| 105 | Human SIRPA C1-type Ig-like domain 1 (UniProt: P78324-1 positions 148-247) | PSAPVVSGPAARATPQHTVSFTCESHGFSPRDITLKWFKNGNELSDFQTNVDPVGESVSYSIHST AKVVLTREDVHSQVICEVAHVTLQGDPLRGTANLS |
| 106 | Human SIRPA C1-type Ig-like domain 2 (UniProt: P78324-1 positions 254-348) | PTLEVTQQPVRAENQVNVTCQVRKFYPQRLQLTWLENGNVSRTETASTVTENKDGTYNWMSWL LVNVSAHRDDVKLTCQVEHDGQPAVSKSHDLK |

| SEQ ID NO: | DESCRIPTION | SEQUENCE |
|---|---|---|
| 107 | 1-1-A1_BM VH-CH1-CH2-CH3 | QVQLQQSGPDLKKPGASVKVSCKVSGYTFTNYVIHWVRQKPGQGLEWMGYINPYNDGTKSNEK FKGKATLTSDKSSTSAYMELSSLTSEDTAVYYCASGGYYTMDYWGQGTSVTVSSASTKGPSVFP LAPSSKSTSGGTAALGCLVKDYFPEPVTVSWNSGALTSGVHTFPAVLQSSGLYSLSSVVTVPSSS LGTQTYICNVNHKPSNTKVDKKVEPKSCDKTHTCPPCPAPELLGGPSVFLFPPKPKDTLMISRTPE VTCVVVDVSHEDPEVKFNWYVDGVEVHNAKTKPREEQYNSTYRVVSVLTVLHQDWLNGKEYKC KVSNKALPAPIEKTISKAKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHNHYTQKSLSLSPGK |
| 108 | 1-1-A1_BM VL-C$_K$ | DVVMTQTPLSLPVTLGDQASISCRSSQHLEYSNGYSYLHWYQQRPGQSPQLLIYKISNRFSGVPD RFSGSGSGTDFTLKISRVEAEDLGVYYCSQSTHVPYTFGGGTKLEIKRTVAAPSVFIFPPSDEQLK SGTASVVCLLNNFYPREAKVQWKVDNALQSGNSQESVTEQDSKDSTYSLSSTLTLSKADYEKHK VYACEVTHQGLSSPVTKSFNRGEC |
| 109 | 1-1-A1 VH-CH1-CH2-CH3 | EVQLQQSGPDLVKPGASVKMSCKASGYTFTNYVIHWVKQKPGQGLEWIGYINPYNDGTKSNEKF KGKATLTSDKSSTSAYMELSSLTSEDSAVYYCASGGYYTMDYWGQGTSVTVSSASTKGPSVFPL APSSKSTSGGTAALGCLVKDYFPEPVTVSWNSGALTSGVHTFPAVLQSSGLYSLSSVVTVPSSSL GTQTYICNVNHKPSNTKVDKKVEPKSCDKTHTCPPCPAPELLGGPSVFLFPPKPKDTLMISRTPEV TCVVVDVSHEDPEVKFNWYVDGVEVHNAKTKPREEQYNSTYRVVSVLTVLHQDWLNGKEYKCK VSNKALPAPIEKTISKAKGQPREPQVYTLPPSREEMTKNQVSLTCLVKGFYPSDIAVEWESNGQP ENNYKTTPPVLDSDGSFFLYSKLTVDKSRWQQGNVFSCSVMHEALHNHYTQKSLSLSPGK |
| 110 | 1-1-A1 VL-C$_K$ | DVVMTQTPLSLPVSLGDQASISCRSSQHLEYSNGYSYLHWYLQKPGQSPQLLIYKISNRFSGVPD RFSGSGSGTDFTLKISRVEAEDLGVYFCSQSTHVPYTFGGGTKLEIKRTVAAPSVFIFPPSDEQLK SGTASVVCLLNNFYPREAKVQWKVDNALQSGNSQESVTEQDSKDSTYSLSSTLTLSKADYEKHK VYACEVTHQGLSSPVTKSFNRGEC |
| 111 | 5-48-A6 VH-CH1-CH2-CH3 | QVQLKESGPGLVAPSQSLSITCTVSGFSLTSYGVHWVRQPPGKGLEWLGVIWAGGSTNYNSALM SRLSISKDNSKSQVFLKMNSLQTDDTAMYYCARVPTGRIKSYFYAMDYWGQGTSVTVSSASTKG PSVFPLAPSSKSTSGGTAALGCLVKDYFPEPVTVSWNSGALTSGVHTFPAVLQSSGLYSLSSVVT VPSSSLGTQTYICNVNHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRVVSVLTVLHQDWLNG KEYKCKVSNKALPAPIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEALHNHYTQKSLSLSPG K |
| 112 | 5-48-A6 VL-C$_K$ | DIKMTQSPSSMYSSLGERVTITCKASQDISSYLSWFQQKPGKSPKTLIYRANRLVDGVPSRFSGS GSGQDYSLTISSLEYEDMGIYYCLQYDEFPYTFGGGTKLEIKRTVAAPSVFIFPPSDEQLKSGTASV VCLLNNFYPREAKVQWKVDNALQSGNSQESVTEQDSKDSTYSLSSTLTLSKADYEKHKVYACEV THQGLSSPVTKSFNRGEC |
| 113 | 5-48-D2 VH-CH1-CH2-CH3 | EVKLLESGGGLVQPGGSLKLSCAASGFDFSRYWMSWVRQAPGKGLEWIGEINPDSSTINYTPSL KDKFIISRDNAKNTLYLQMSKVRSEDTALYYCATGTGFAYWGQGTLVTSAASTKGPSVFPLAPS SKSTSGGTAALGCLVKDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTVLHQDWLNGKEYKCKVSN KALPAPIEKTISKAKGQPREPQVYTLPPSREEMTKNQVSLTCLVKGFYPSDIAVEWESNGQPENN YKTTPPVLDSDGSFFLYSKLTVDKSRWQQGNVFSCSVMHEALHNHYTQKSLSLSPGK |
| 114 | 5-48-D2 VL-C$_K$ | DIQMTQSPASLSASVGETVTITCRASENIYSYLAWYQQKQGKSPQLLVYNAKTLAEGVPSRFSGS GSGTQFSLKINSLQPEDFGSYYCQHHYVTPWTFGGVTKLEIKRTVAAPSVFIFPPSDEQLKSGTAS VVCLLNNFYPREAKVQWKVDNALQSGNSQESVTEQDSKDSTYSLSSTLTLSKADYEKHKVYACE VTHQGLSSPVTKSFNRGEC |
| 115 | anti-CD33 VH-CH1-CH2-CH3 | QVQLVQSGAEVKKPGSSVKVSCKASGYTFTDYNMHWVRQAPGQGLEWIGYIYPYNGGTYNQK FKSKATITADESTNTAYMELSSLRSEDTAVYYCARGRPAMDYWGQGTLVTVSSASTKGPSVFPLA PSSKSTSGGTAALGCLVKDYFPEPVTVSWNSGALTSGVHTFPAVLQSSGLYSLSSVVTVPSSSLG TQTYICNVNHKPSNTKVDKKVEPKSCDKTHTCPPCPAPELLGGPSVFLFPPKPKDTLMISRTPEVT CVVVDVSHEDPEVKFNWYVDGVEVHNAKTKPREEQYNSTYRVVSVLTVLHQDWLNGKEYKCKV SNKALPAPIEKTISKAKGQPREPQVYTLPPSREEMTKNQVSLTCLVKGFYPSDIAVEWESNGQPE NNYKTTPPVLDSDGSFFLYSKLTVDKSRWQQGNVFSCSVMHEALHNHYTQKSLSLSPGK |
| 116 | anti-CD33 VL-C$_K$ | DIQMTQSPSSLSASVGDRVTITCRASESVDNYGISFMNWFQQKPGKAPKLLIYAASNQGSGVPSR FSGSGSGTDFTLTISSLQPDDFATYYCQQSKEVPWTFGQGTKVEIKRTVAAPSVFIFPPSDEQLKS GTASVVCLLNNFYPREAKVQWKVDNALQSGNSQESVTEQDSKDSTYSLSSTLTLSKADYEKHKV YACEVTHQGLSSPVTKSFNRGEC |
| 117 | Rhesus macaque CD47 (UniProt: F7F5Y9-1, v2) | MWPLVAALLLGSACCGSAQLLFNKTKSVEFTFCNDTVVIPCFVTNMEAQNTTEVYVKWKFKGRDI YTFDGALNKSTAPANFSSAKIEVSQLLKGDASLKMDKSDAVSHTGNYTCEVTELTREGETIIELKYR VVSWFSPNENILIVIFPIFAILLFWGQFGIKTLKYRSGGMDEKTIALLVAGLMITVIVGAILFVPGEYS LKNATGLGLIVTSTGILILLHYYVFSTAIGLTSFVIAILVIQVIAYILAVVGLSLCIAACIPMHGPLLISGLSI LALAQLLGLVYMKFVASNQKTIQPPRNDNFRLKNEEKFILN |

| SEQ ID NO: | DESCRIPTION | SEQUENCE |
|---|---|---|
| 118 | Human IgG1 constant region (IGHG1; UniProt: P01857-1, v1) | ASTKGPSVFPLAPSSKSTSGGTAALGCLVKDYFPEPVTVSWNSGALTSGVHTFPAVLQSSGLYSL SSVVTVPSSSLGTQTYICNVNHKPSNTKVDKKVEPKSCDKTHTCPPCPAPELLGGPSVFLFPPKP KDTLMISRTPEVTCVVVDVSHEDPEVKFNWYVDGVEVHNAKTKPREEQYNSTYRVVSVLTVLHQ DWLNGKEYKCKVSNKALPAPIEKTISKAKGQPREPQVYTLPPSRDELTKNQVSLTCLVKGFYPSDI AVEWESNGQPENNYKTTPPVLDSDGSFFLYSKLTVDKSRWQQGNVFSCSVMHEALHNHYTQKS LSLSPGK |
| 119 | CH1 IgG1 (positions 1-98 of P01857-1, v1) | ASTKGPSVFPLAPSSKSTSGGTAALGCLVKDYFPEPVTVSWNSGALTSGVHTFPAVLQSSGLYSL SSVVTVPSSSLGTQTYICNVNHKPSNTKVDKKV |
| 120 | Hinge IgG1 (positions 99-110 of P01857-1, v1) | EPKSCDKTHTCP |
| 121 | CH2 IgG1 (positions 111-223 of P01857-1, v1) | PCPAPELLGGPSVFLFPPKPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAK |
| 122 | CH3 IgG1 (positions 224-330 of P01857-1, v1) | GQPREPQVYTLPPSRDELTKNQVSLTCLVKGFYPSDIAVEWESNGQPENNYKTTPPVLDSDGSF FLYSKLTVDKSRWQQGNVFSCSVMHEALHNHYTQKSLSLSPGK |
| 123 | CH3 (D356E, L358M; positions numbered according to EU numbering) | GQPREPQVYTLPPSREEMTKNQVSLTCLVKGFYPSDIAVEWESNGQPENNYKTTPPVLDSDGSF FLYSKLTVDKSRWQQGNVFSCSVMHEALHNHYTQKSLSLSPGK |
| 124 | $C_K$ CL (IGCK; UniProt: P01834-1, v2) | RTVAAPSVFIFPPSDEQLKSGTASVVCLLNNFYPREAKVQWKVDNALQSGNSQESVTEQDSKDS TYSLSSTLTLSKADYEKHKVYACEVTHQGLSSPVTKSFNRGEC |
| 125 | J6M0 VH-CH1-CH2-CH3 | QVQLVQSGAEVKKPGSSVKVSCKASGGTFSNYWMHWVRQAPGQGLEWMGATYRGHSDTYYN QKFKGRVTITADKSTSTAYMELSSLRSEDTAVYYCARGAIYDGYDVLDNWGQGTLVTVSSASTKG PSVFPLAPSSKSTSGGTAALGCLVKDYFPEPVTVSWNSGALTSGVHTFPAVLQSSGLYSLSSVVT VPSSSLGTQTYICNVNHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRVVSVLTVLHQDWLNG KEYKCKVSNKALPAPIEKTISKAKGQPREPQVYTLPPSRDELTKNQVSLTCLVKGFYPSDIAVEWE SNGQPENNYKTTPPVLDSDGSFFLYSKLTVDKSRWQQGNVFSCSVMHEALHNHYTQKSLSLSPG K |
| 126 | J6M0 VL-$C_K$ | DIQMTQSPSSLSASVGDRVTITCSASQDISNYLNWYQQKPGKAPKLLIYYTSNLHSGVPSRFSGS GSGTDFTLTISSLQPEDFATYYCQQYRKLPWTFGQGTKLEIKRTVAAPSVFIFPPSDEQLKSGTAS VVCLLNNFYPREAKVQWKVDNALQSGNSQESVTEQDSKDSTYSLSSTLTLSKADYEKHKVYACE VTHQGLSSPVTKSFNRGEC |
| 127 | 11A1H1 VH | QVQLVQSGAEVKKPGASVKVSCKASGYTFTNYVIHWVRQAPGKGLEWMGYINPYNDGTKSNEK FKGRVTLTSDKSSTSAYMELSSLRSEDTAVYYCASGGYYTMDYWGQGTLVTVSS |
| 128 | 11A1H1, 11A1H2, 11A1H3, 11A1H4, 11A1H5 VL | DVVMTQSPLSLPVTLGQPASISCRSSQHLEYSNGYSYLHWYQQRPGQSPRLLIYKISNRFSGVPD RFSGSGSGTDFTLKISRVEAEDVGVYYCSQSTHVPYTFGGGTKVEIK |
| 129 | 11A1H2 VH | QVQLVQSGAEVKKPGASVKVSCKASGYTFTNYVIHWVRQAPGKGLEWMGYINPYNDGTKSNEK FKGRVTLTSDTSTTAYMELSSLRSEDTAVYYCASGGYYTMDYWGQGTLVTVSS |
| 130 | 11A1H3 VH | QVQLVQSGAEVKKPGASVKVSCKASGYTFTNYVMHWVRQAPGQGLEWMGYINPYNDGTKSNE KFQGRVTLTSDTSTSTAYMELSSLRSEDTAVYYCASGGYYTMDYWGQGTLV |
| 131 | 11A1H4, 11A1H6, 11A1H8 VH | QVQLVQSGAEVKKPGASVKVSCKASGYTFTNYVIHWVRQAPGKGLEWMGYINPYNDGTKYNQK FKGRVTLTSDTSTTAYMELSRLRSDDTAVYYCASGGYYTMDYWGQGTLV |
| 132 | 11A1H5, 11A1H7, 11A1H9, 11A1H10, 11A1H11 VH | QVQLVQSGAEVKKPGASVKVSCKASGYTFTGYVIHWVRQAPGQGLEWMGYINPYNGGTNYAQK FKGRVTLTSDTSTTAYMELSRLRSEDTAVYYCASGGYYTMDYWGQGTLVTVSS |
| 133 | 11A1H6, 11A1H7 VL | DVVMTQSPLSLPVTLGQPASISCRSSQHLEYSQGYSYLHWYQQRPGQSPRLLIYKVSNRDSGVP DRFSGSGSGTDFTLKISRVEAEDVGVYYCSQSTHVPYTFGGGTKVEIK |
| 134 | 11A1H8, 11A1H9 VL | DVVMTQSPLSLPVTLGQPASISCRSSQHLEYSTGYSYLHWYQQRPGQSPRLLIYKVSNRDSGVP DRFSGSGSGTDFTLKISRVEAEDVGVYYCSQSTHVPYTFGGGTKVEIK |

-continued

| SEQ ID NO: | DESCRIPTION | SEQUENCE |
|---|---|---|
| 135 | 11A1H10 VL | DVVMTQSPLSLPVTLGQPASISCRSSQHLEYSNGYSYLHWYQQRPGQSPRLLIYKVSNRDSGVPDRFSGSGSGTDFTLKISRVEAEDVGVYYCSQSTHVPYTFGGGTKVEIK |
| 136 | 11A1H11 VL | DVVMTQSPLSLPVTLGQPASISCRSSQHLEYSNGYSYLHWYQQRPGQSPRLLIYKISNRFSGVPDRFSGSGSGTDFTLKISRVEAEDVGVYYCSQGTHVPYTFGGGTKVEIK |
| 137 | 11A1H5, 11A1H7, 11A1H9, 11A1H10, 11A1H11 HC-CDR1 | GYTFTGYV |
| 138 | 11A1H5, 11A1H7, 11A1H9, 11A1H10, 11A1H11 HC-CDR2 | INPYNGGT |
| 139 | 11A1H6, 11A1H7 LC-CDR1 | QHLEYSQGYSY |
| 140 | 11A1H8, 11A1H9 LC-CDR1 | QHLEYSTGYSY |
| 141 | 11A1H6, 11A1H7, 11A1H8, 11A1H9, 11A1H10 LC-CDR2 | KVS |
| 142 | 11A1H11 LC-CDR3 | SQGTHVPYT |
| 143 | 11A1H1, 11A1H2, 11A1H3, 11A1H4, 11A1H5, 11A1H6, 11A1H7, 11A1H8, 11A1H9, 11A1H10, 11A1H11 HC-FR1 | QVQLVQSGAEVKKPGASVKVSCKAS |
| 144 | 11A1H1, 11A1H2, HC-FR2 | IHWVRQAPGKGLEWMGY |
| 145 | 11A1H3 HC-FR2 | MHWVRQAPGQGLEWMGY |
| 146 | 11A1H4, 11A1H5, 11A1H6, 11A1H7, 11A1H8, 11A1H9, 11A1H10, 11A1H11 HC-FR2 | IHWVRQAPGQGLEWMGY |
| 147 | 11A1H1 HC-FR3 | KSNEKFKGRVTLTSDKSSTSAYMELSSLRSEDTAVYYC |
| 148 | 11A1H2 HC-FR3 | KSNEKFKGRVTLTSDTSTTAYMELSSLRSEDTAVYYC |
| 149 | 11A1H3 HC-FR3 | KSNEKFQGRVTLTSDTSTSAYMELSSLRSEDTAVYYC |
| 150 | 11A1H4, 11A1H6, 11A1H8 HC-FR3 | KYNQKFKGRVTLTSDTSTTAYMELSRLRSDDTAVYYC |
| 151 | 11A1H5, 11A1H7, 11A1H9, 11A1H10, 11A1H11 HC-FR3 | NYAQKFKGRVTLTSDTSTTAYMELSRLRSEDTAVYYC |
| 152 | 11A1H1, 11A1H2, 11A1H5, 11A1H7, 11A1H9, 11A1H10, 11A1H11 HC-FR4 | WGQGTLVTVSS |
| 153 | 11A1H3, 11A1H4, 11A1H6, 11A1H8 HC-FR4 | WGQGTLV |

| SEQ ID NO: | DESCRIPTION | SEQUENCE |
|---|---|---|
| 154 | 11A1H1, 11A1H2, 11A1H3, 11A1H4, 11A1H5, 11A1H6, 11A1H7, 11A1H8, 11A1H9, 11A1H10, 11A1H11 LC-FR1 | DVVMTQSPLSLPVTLGQPASISCRSS |
| 155 | 11A1H1, 11A1H2, 11A1H3, 11A1H4, 11A1H5, 11A1H6, 11A1H7, 11A1H8, 11A1H9, 11A1H10, 11A1H11 LC-FR2 | LHWYQQRPGQSPRLLIY |
| 156 | 11A1H1, 11A1H2, 11A1H3, 11A1H4, 11A1H5, 11A1H11 LC-FR3 | NRFSGVPDRFSGSGSGTDFTLKISRVEAEDVGVYYC |
| 157 | 11A1H6, 11A1H7, 11A1H8, 11A1H9, 11A1H10 LC-FR3 | NRDSGVPDRFSGSGSGTDFTLKISRVEAEDVGVYYC |
| 158 | 11A1H1, 11A1H2, 11A1H3, 11A1H4, 11A1H5, 11A1H6, 11A1H7, 11A1H8, 11A1H9, 11A1H10, 11A1H11 LC-FR4 | FGGGTKVEIK |
| 159 | 11A1H1 VH-CH1-CH2-CH3 | QVQLVQSGAEVKKPGASVKVSCKASGYTFTNYVIHWVRQAPGKGLEWMGYINPYNDGTKSNEKFKGRVTLTSDKSSTSAYMELSSLRSEDTAVYYCASGGYYTMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 160 | 11A1H1, 11A1H2, 11A1H3, 11A1H4, 11A1H5 VL-CK | DVVMTQSPLSLPVTLGQPASISCRSSQHLEYSNGYSYLHWYQQRPGQSPRLLIYKISNRFSGVPDRFSGSGSGTDFTLKISRVEAEDVGVYYCSQSTHVPYTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 161 | 11A1H2 VH-CH1-CH2-CH3 | QVQLVQSGAEVKKPGASVKVSCKASGYTFTNYVIHWVRQAPGKGLEWMGYINPYNDGTKSNEKFKGRVTLTSDTSTTAYMELSSLRSEDTAVYYCASGGYYTMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 162 | 11A1H3 VH-CH1-CH2-CH3 | QVQLVQSGAEVKKPGASVKVSCKASGYTFTNYVMHWVRQAPGQGLEWMGYINPYNDGTKSNEKFQGRVTLTSDTSTSAYMELSSLRSEDTAVYYCASGGYYTMDYWGQGTLVASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 163 | 11A1H4, 11A1H6, 11A1H8 VH-CH1-CH2-CH3 | QVQLVQSGAEVKKPGASVKVSCKASGYTFTNYVIHWVRQAPGQGLEWMGYINPYNDGTKYNQKFKGRVTLTSDTSTTAYMELSRLRSDDTAVYYCASGGYYTMDYWGQGTLVASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVWDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 164 | 11A1H5, 11A1H7, 11A1H9, 11A1H10, | QVQLVQSGAEVKKPGASVKVSCKASGYTFTGYVIHWVRQAPGQGLEWMGYINPYNGGTNYAQKFKGRVTLTSDTSTTAYMELSRLRSEDTAVYYCASGGYYTMDYWGQGTLVTVSSASTKGPSVFPLAPSSKSTSGGTAALGCLVKDYFPEPVTVSWNSGALTSGVHTFPAVLQSSGLYSLSSVVTVPSSS |

| SEQ ID NO: | DESCRIPTION | SEQUENCE |
|---|---|---|
|  | 11A1H11 VH-CH1-CH2-CH3 | LGTQTYICNVNHKPSNTKVDKKVEPKSCDKTHTCPPCPAPELLGGPSVFLFPPKPKDTLMISRTPE VTCVVVDVSHEDPEVKFNWYVDGVEVHNAKTKPREEQYNSTYRVVSVLTVLHQDWLNGKEYKC KVSNKALPAPIEKTISKAKGQPREPQVYTLPPSRDELTKNQVSLTCLVKGFYPSDIAVEWESNGQP ENNYKTTPPVLDSDGSFFLYSKLTVDKSRWQQGNVFSCSVMHEALHNHYTQKSLSLSPGK |
| 165 | 11A1H6, 11A1H7 VL-CK | DVVMTQSPLSLPVTLGQPASISCRSSQHLEYSQGYSYLHWYQQRPGQSPRLLIYKVSNRDSGVP DRFSGSGSGTDFTLKISRVEAEDVGVYYCSQSTHVPYTFGGGTKVEIKRTVAAPSVFIFPPSDEQL KSGTASVVCLLNNFYPREAKVQWKVDNALQSGNSQESVTEQDSKDSTYSLSSTLTLSKADYEKH KVYACEVTHQGLSSPVTKSFNRGEC |
| 166 | 11A1H8, 11A1H9 VL-CK | DVVMTQSPLSLPVTLGQPASISCRSSQHLEYSTGYSYLHWYQQRPGQSPRLLIYKVSNRDSGVP DRFSGSGSGTDFTLKISRVEAEDVGVYYCSQSTHVPYTFGGGTKVEIKRTVAAPSVFIFPPSDEQL KSGTASVVCLLNNFYPREAKVQWKVDNALQSGNSQESVTEQDSKDSTYSLSSTLTLSKADYEKH KVYACEVTHQGLSSPVTKSFNRGEC |
| 167 | 11A1H10 VL-CK | DVVMTQSPLSLPVTLGQPASISCRSSQHLEYSNGYSYLHWYQQRPGQSPRLLIYKVSNRDSGVP DRFSGSGSGTDFTLKISRVEAEDVGVYYCSQSTHVPYTFGGGTKVEIKRTVAAPSVFIFPPSDEQL KSGTASVVCLLNNFYPREAKVQWKVDNALQSGNSQESVTEQDSKDSTYSLSSTLTLSKADYEKH KVYACEVTHQGLSSPVTKSFNRGEC |
| 168 | 11A1H11 VL-CK | DVVMTQSPLSLPVTLGQPASISCRSSQHLEYSNGYSYLHWYQQRPGQSPRLLIYKISNRFSGVPD RFSGSGSGTDFTLKISRVEAEDVGVYYCSQGTHVPYTFGGGTKVEIKRTVAAPSVFIFPPSDEQLK SGTASVVCLLNNFYPREAKVQWKVDNALQSGNSQESVTEQDSKDSTYSLSSTLTLSKADYEKHK VYACEVTHQGLSSPVTKSFNRGEC |
| 169 | 11A1H_C HC-CDR1 | GYTFTX$_1$YV<br>X$_1$ = N or G |
| 170 | 11A1H_C HC-CDR2 | INPYNX$_2$GT<br>X$_2$ = D or G |
| 171 | 11A1H_C LC-CDR1 | QHLEYSX$_3$GYSY<br>X$_3$ = N, Q or T |
| 172 | 11A1H_C LC-CDR2 | KX$_4$S<br>X$_4$ = I or V |
| 173 | 11A1H_C LC-CDR3 | SQX5THVPYT<br>X5 = S or G |
| 174 | 11A1H_C HC-FR2 | X$_6$HWVRQAPGX$_7$GLEWMGY<br>X$_6$ = I or M<br>X$_7$ = Q or K |
| 175 | 11A1H_C HC-FR3 | X$_8$X$_9$X$_{10}$X$_{11}$KFX$_{12}$GRVTLTSDX$_{13}$SX$_{14}$SX$_{15}$AYMELSX$_{16}$LRSX$_{17}$DTAVYYC<br>X$_8$ = K or N<br>X$_9$ = S or Y<br>X$_{10}$ = N or A<br>X$_{11}$ = E or Q<br>X$_{12}$ = K or Q<br>X$_{13}$ = T or K<br>X$_{14}$ = T or S<br>X$_{15}$ = T or S<br>X$_{16}$ = S or R<br>X$_{17}$ = E or D |
| 176 | 11A1H_C HC-FR4 | WGQGTLVX$_{18}$X$_{19}$X$_{20}$X$_{21}$<br>X$_{18}$ = T or absent<br>X$_{19}$ = V or absent<br>X$_{20}$ = S or absent<br>X$_{21}$ = S or absent |
| 177 | 11A1H_C LC-FR3 | NRX$_{22}$SGVPDRFSGSGSGTDFTLKISRVEAEDVGVYYC<br>X$_{22}$ = D or F |
| 178 | 11A1H_C VH | QVQLVQSGAEVKKPGASVKVSCKASGYTFTX$_{22}$YVX$_{23}$HWVRQAPGX$_{24}$GLEWMGYINPYNX$_{25}$GT X$_{26}$X$_{27}$X$_{28}$X$_{29}$KFX$_{30}$GRVTLTSDX$_{31}$SX$_{32}$SX$_{33}$AYMELSX$_{34}$LRSX$_{35}$DTAVYYCASGGYYTMDYWGQG TLVX$_{36}$X$_{37}$X$_{38}$X$_{39}$<br>X$_{22}$ = N or G<br>X$_{23}$ = I or M<br>X$_{24}$ = Q or K<br>X$_{25}$ = D or G<br>X$_{26}$ = K or N<br>X$_{27}$ = S or Y |

| SEQ ID NO: | DESCRIPTION | SEQUENCE |
|---|---|---|
| | | $X_{28}$ = N or A
$X_{29}$ = E or Q
$X_{30}$ = K or Q
$X_{31}$ = T or K
$X_{32}$ = T or S
$X_{33}$ = T or S
$X_{34}$ = S or R
$X_{35}$ = E or D
$X_{36}$ = T or absent
$X_{37}$ = V or absent
$X_{38}$ = S or absent
$X_{39}$ = S or absent |
| 179 | 11A1H_C VL | DVVMTQSPLSLPVTLGQPASISCRSSQHLEYSX$_{40}$GYSYLHWYQQRPGQSPRLLIYKX$_{41}$SNRX$_{42}$S
GVPDRFSGSGSGTDFTLKISRVEAEDVGVYYCSQX$_{43}$THVPYTFGGGTKVEIK
$X_{40}$ = N, Q or T
$X_{41}$ = I or V
$X_{42}$ = D or F
$X_{43}$ = S or G |

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Where a nucleic acid sequence is disclosed herein, the reverse complement thereof is also expressly contemplated.

Methods described herein may preferably performed in vitro. The term "in vitro" is intended to encompass procedures performed with cells in culture whereas the term "in vivo" is intended to encompass procedures with/on intact multi-cellular organisms.

BRIEF DESCRIPTION OF THE FIGURES

Embodiments and experiments illustrating the principles of the invention will now be discussed with reference to the accompanying figures.

EXAMPLES

In the following Examples, the inventors describe the generation of novel CD47-specific antibody clones targeted to specific regions of interest in the CD47 molecule, the biophysical and functional characterisation and the therapeutic evaluation of these antigen-binding molecules.

Example 1: CD47 Target Design and Anti-CD47 Antibody Hybridoma Production

Figure 1:
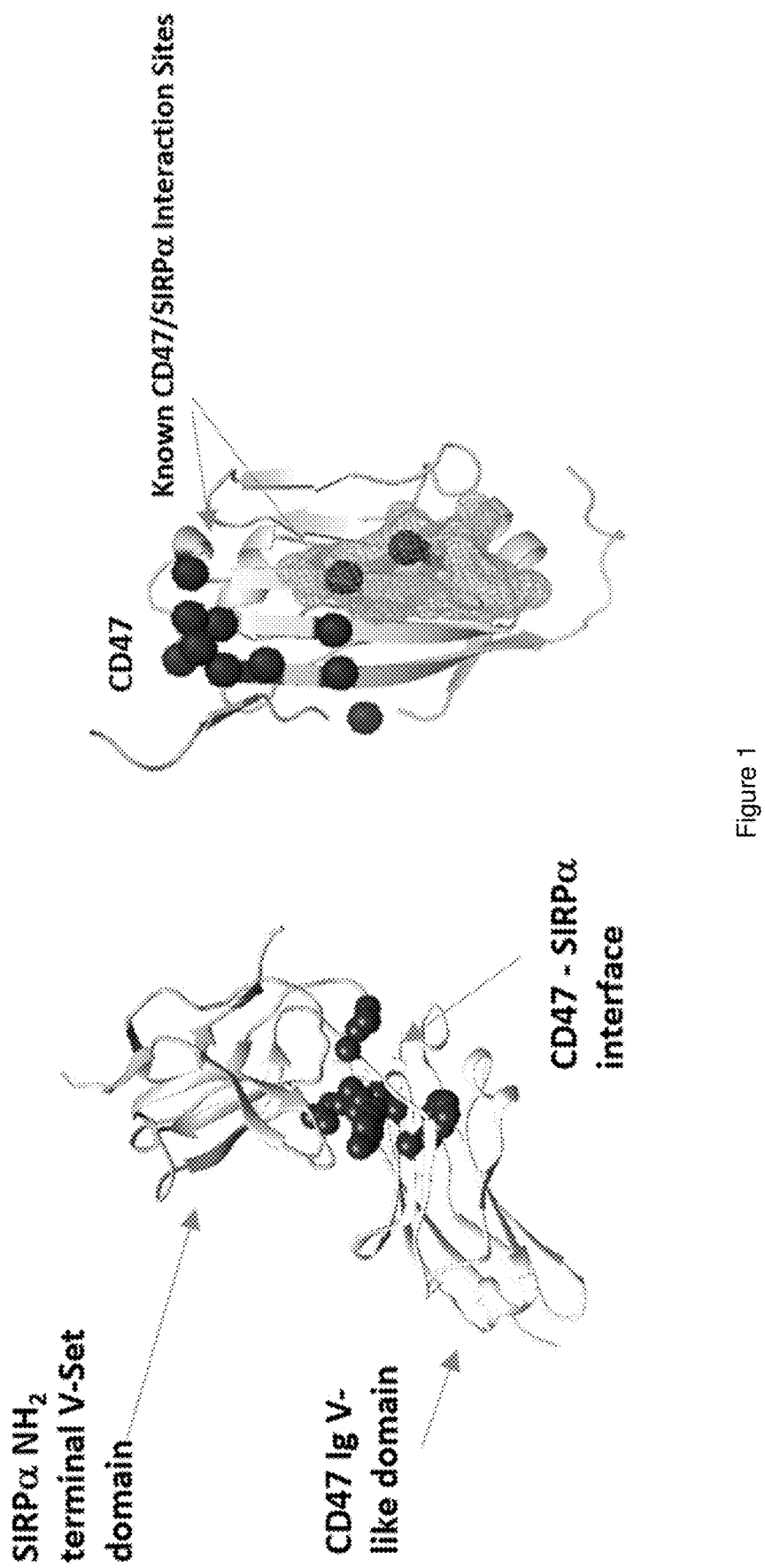
FIG. 1. Ribbon diagram showing the 3D structure of interacting SIPRPα and CD47 domains, with regions used as immunogens for raising anti-CD47 antibodies overlain with spheres.

The inventors selected two regions in the Ig-like V region (SEQ ID NO:9) of the extracellular region 1 of human CD47 (SEQ ID NO:10) for raising CD47-binding monoclonal antibodies. The inventors focussed on regions of CD47 known to be involved in the interaction between CD47 and SIRPα (FIG. 1).

1.1 Hybridoma Production

Approximately 6 week old female BALB/c mice were obtained from InVivos (Singapore). Animals were housed under specific pathogen-free conditions and were treated in compliance with the Institutional Animal Care and Use Committee (IACUC) guidelines.

For hybridoma production, mice were immunized with proprietary mixtures of antigenic peptide for a total of 4 intraperitoneal injections with a 2 week interval between each injection. Antigen for immunizations included one of the following:

i) Up to 50 pg of synthetic peptide conjugated with KLH (China Peptides Co. Ltd, China)
  ii) Up to 50 pg of commercially available recombinant Fc-tagged human CD47 (Sinobiological Inc, China)
  iii) Up to $20 \times 10^6$ isogenic cells overexpressing human CD47.

Prior to harvesting the spleen for fusion, mice were boosted with antigen mixture for three consecutive days. 24 h after the final boost total splenocytes were isolated and fused with the myeloma cell line P3X63.Ag8.653 (ATCC, USA), with PEG using ClonaCell-HY Hybridoma Cloning Kit, in accordance with the manufacturer's instructions (Stemcell Technologies, Canada).

Fused cells were cultured in ClonaCell-HY Medium C (Stemcell Technologies, Canada) overnight at 37° C. in a 5% $CO_2$ incubator. The next day, fused cells were centrifuged and resuspended in 10 ml of ClonaCell-HY Medium C and then gently mixed with 90 ml of semisolid methylcellulose-based ClonaCell-HY Medium D (StemCell Technologies, Canada) containing HAT components, which combines the hybridoma selection and cloning into one step.

The fused cells were then plated into 96 well plates and allowed to grow at 37° C. in a 5% $CO_2$ incubator. After 7-10 days, single hybridoma clones were isolated and antibody producing hybridomas were selected by screening the supernatants by Enzyme-linked immunosorbent assay (ELISA) and Fluorescence-activated cell sorting (FACs).

1.2 Antibody Variable Region Amplification and Sequencing

Total RNA was extracted from hybridoma cells using TRIzol reagent (Life Technologies, Inc., USA) using manufacturer's protocol. Double-stranded cDNA was synthesized using SMARTer RACE 5'/3' Kit (Clontech™, USA) in accordance with the manufacturer's instructions. Briefly, 1 μg total RNA was used to generate full-length cDNA using 5'-RACE CDS primer (provided in the kit), and the 5' adaptor (SMARTer II A primer) was then incorporated into each cDNA according to manufacturer's instructions. cDNA synthesis reactions contained: 5× First-Strand Buffer, DTT (20 mM), dNTP Mix (10 mM), RNase Inhibitor (40 U/μl) and SMARTScribe Reverse Transcriptase (100 U/μl).

The race-ready cDNAs were amplified using SeqAmp DNA Polymerase (Clontech™, USA). Amplification reactions contained SeqAmp DNA Polymerase, 2× Seq AMP buffer, 5' universal primer provided in the 5' SMARTer Race kit, that is complement to the adaptor sequence, and 3' primers that anneal to respective heavy chain or light chain constant region primer. The 5' constant region were designed based on previously reported primer mix either by Krebber et al. J. Immunol. Methods 1997; 201: 35-55, Wang et al. Journal of Immunological Methods 2000, 233; 167-177 or Tiller et al. Journal of Immunological Methods 2009; 350:183-193. The following thermal protocol was used: pre-denature cycle at 94° C. for 1 min; 35 cycles of 94° C., 30 s, 55° C., 30 s and 72° C., 45 s; final extension at 72° C. for 3 min.

The resulting VH and VL PCR products, approximately 550 bp, were cloned into pJET1.2/blunt vector using Clone-JET PCR Cloning Kit (Thermo Scientific, USA) and used to transform highly competent E. coli DH5α. From the resulting transformants, plasmid DNA was prepared using Miniprep Kit (Qiagene, Germany) and sequenced. DNA sequencing was carried out by AITbiotech. These sequencing data were analyzed using the international IMGT (ImMunoGeneTics) information system (LeFranc et al., Nucleic Acids Res. (2015) 43 (Database issue):D413-22) to characterize the individual CDRs and framework sequences. The signal peptide at 5' end of the VH and VL was identified by SignalP (v 4.1; Nielsen, in Kihara, D (ed): Protein Function Prediction (Methods in Molecular Biology vol. 1611) 59-73, Springer 2017).

Three monoclonal anti-CD47 antibody clones were selected for further development: 1-1-A1, 5-48-A6 and 5-48-D2.

A humanised version of antibody clone 1-1-A1 was also prepared according to standard methods by cloning the CDRs of antibody clone 1-1-A1 into VH and VL comprising human antibody framework regions. This antibody clone was designated antibody clone 1-1-A1_BM.

| Antibody clone | VH/VL sequence | Peptide immunogen used to raise the antibody |
|---|---|---|
| 1-1-A1_BM | VH = SEQ ID NO: 23<br>VL = SEQ ID NO: 31 | SEQ ID NO: 21 |
| 1-1-A1 | VH = SEQ ID NO: 39<br>VL = SEQ ID NO: 44 | |
| 5-48-A6 | VH = SEQ ID NO: 49<br>VL = SEQ ID NO: 57 | SEQ ID NO: 22 |
| 5-48-D2 | VH = SEQ ID NO: 65<br>VL = SEQ ID NO: 73 | |

Example 2: Antibody Production and Purification 2.1 Cloning VH and VL into Expression Vectors:

DNA sequence encoding the heavy and light chain variable regions of the anti-CD47 antibody clones were subcloned into the pFUSE-CHIg-hG1 and pFUSE2ss-CLIg-hk (InvivoGen, USA) eukaryotic expression vectors for construction of human-mouse chimeric antibodies. Human IgG1 constant region encoded by pFUSE-CHIg-hG1 comprises the substitutions D356E, L358M (positions numbered according to EU numbering) in the CH3 region relative to Human IgG1 constant region (IGHG1; UniProt:P01857-1, v1). pFUSE2ss-CLIg-hk encodes human IgG1 light chain kappa constant region (IGCK; UniProt: P01834-1, v2).

Variable regions along with the signal peptides were amplified from the cloning vector using SeqAmp enzyme (Clontech™, USA) following the manufacturer's protocol. Forward and reverse primers having 15-20 bp overlap with the appropriate regions within VH or VL plus 6 bp at 5' end as restriction sites were used. The DNA insert and the pFuse vector were digested with restriction enzyme recommended by the manufacturer to ensure no frameshift was introduced (e.g., EcoRI and NheI for VH, AgeI and BsiWI for VL) and ligated into its respective plasmid using T4 ligase enzyme (Thermo Scientific, USA). The molar ratio of 3:1 of DNA insert to vector was used for ligation.

2.2 Expression of Antibodies in Mammalian Cells

Antibodies were expressed using either 1) Expi293 Transient Expression System Kit (Life Technologies, USA), or 2) HEK293-6E Transient Expression System (CNRC-NRC, Canada) following the manufacturer's instructions.

1) Expi293 Transient Expression System:
Cell Line Maintenance:

HEK293F cells (Expi293F) were obtained from Life Technologies, Inc (USA). Cells were cultured in serum-free, protein-free, chemically defined medium (Expi293 Expression Medium, Thermo Fisher, USA), supplemented with 50 IU/ml penicillin and 50 µg/ml streptomycine (Gibco, USA) at 37° C., in 8% $CO_2$ and 80% humidified incubators with shaking platform.

Transfection:

Expi293F cells were transfected with expression plasmids using ExpiFectamine 293 Reagent kit (Gibco, USA) according to its manufacturer's protocol. Briefly, cells at maintenance were subjected to a media exchange to remove antibiotics by spinning down the culture, cell pellets were re-suspended in fresh media without antibiotics at 1 day before transfection. On the day of transfection, $2.5 \times 10^6$/ml of viable cells were seeded in shaker flasks for each transfection. DNA-ExpiFectamine complexes were formed in serum-reduced medium, Opti-MEM (Gibco, USA), for 25 min at room temperature before being added to the cells. Enhancers were added to the transfected cells at 16-18 h post transfection. An equal amount of media was topped up to the transfectants at day 4 post-transfection to prevent cell aggregation. Transfectants were harvested at day 7 by centrifugation at 4000×g for 15 min, and filtered through 0.22 µm sterile filter units.

2) HEK293-6E Transient Expression System
Cell Line Maintenance:

HEK293-6E cells were obtained from National Research Council Canada. Cells were cultured in serum-free, protein-free, chemically defined Freestyle F17 Medium (Invitrogen, USA), supplemented with 0.1% Kolliphor-P188 and 4 mM L-Glutamine (Gibco, USA) and 25 µg/ml G-418 at 37° C., in 5% $CO_2$ and 80% humidified incubators with shaking platform.

Transfection:

HEK293-6E cells were transfected with expression plasmids using PEIpro™ (Polyplus, USA) according to its manufacturer's protocol. Briefly, cells at maintenance were subjected to a media exchange to remove antibiotics by centrifugation, cell pellets were re-suspended with fresh media without antibiotics at 1 day before transfection. On the day of transfection, $1.5-2 \times 10^6$ cells/ml of viable cells were seeded in shaker flasks for each transfection. DNA and PEIpro™ were mixed to a ratio of 1:1 and the complexes were allowed to form in F17 medium for 5 min at RT before adding to the cells. 0.5% (w/v) of Tryptone N1 was fed to transfectants at 24-48 h post transfection. Transfectants were harvested at day 6-7 by centrifugation at 4000×g for 15 min and the supernatant was filtered through 0.22 µm sterile filter units.

Cells were transfected with vectors encoding the following combinations of polypeptides:

| Antigen-binding molecule | Polypeptides | Antibody |
|---|---|---|
| [1] | 1-1-A1_BM VH-CH1-CH2-CH3 (SEQ ID NO: 107) +<br>1-1-A1_BM VL-Cκ (SEQ ID NO: 108) | anti-CD47 clone 1-1-A1_BM IgG1 |
| [2] | 1-1-A1 VH-CH1-CH2-CH3 (SEQ ID NO: 109) +<br>1-1-A1 VL-Cκ (SEQ ID NO: 110) | anti-CD47 clone 1-1-A1 IgG1 |
| [3] | 5-48-A6 VH-CH1-CH2-CH3 (SEQ ID NO: 111) +<br>5-48-A6 VL-Cκ (SEQ ID NO: 112) | anti-CD47 clone 5-48-A6 IgG1 |
| [4] | 5-48-D2 VH-CH1-CH2-CH3 (SEQ ID NO: 113) +<br>5-48-D2 VL-Cκ (SEQ ID NO: 114) | anti-CD47 clone 5-48-D2 IgG1 |
| [5] | anti-CD33 VH-CH1-CH2-CH3 (SEQ ID NO: 115) +<br>anti-CD33 VL-Cκ (SEQ ID NO: 116) | anti-CD33 IgG1 |

2.3 Antibody Purification

Affinity Purification, Buffer Exchange and Storage:

Antibodies secreted by the transfected cells into the culture supernatant were purified using liquid chromatography system AKTA Start (GE Healthcare, UK). Specifically, supernatants were loaded onto HiTrap Protein G column (GE Healthcare, UK) at a binding rate of 5 ml/min, followed by washing the column with 10 column volumes of washing buffer (20 mM sodium phosphate, pH 7.0). Bound mAbs were eluted with elution buffer (0.1 M glycine, pH 2.7) and the eluents were fractionated to collection tubes which contain appropriate amount of neutralization buffer (1 M Tris, pH 9). Neutralised elution buffer containing purified mAb were exchanged into PBS using 30K MWCO protein concentrators (Thermo Fisher, USA) or 3.5K MWCO dialysis cassettes (Thermo Fisher, USA). Monoclonal antibodies were sterilized by passing through 0.22 µm filter, aliquoted and snap-frozen in −80° C. for storage.

2.4 Antibody-Purity Analysis

Size Exclusion Chromatography (SEC):

Antibody purity was analyzed by size exclusion chromatography (SEC) using HiLoad 16/600 Superdex 200 pg column (GE Healthcare, UK) on a AKTA Explorer liquid chromatography system (GE Healthcare, UK). Protein samples are injected to SEC column at concentrations ranging between 0.2-1.5 mg/ml and 1×PBS was pumped to the column at a flow rate of 1 ml/min. Proteins were eluted according to their molecular weights.

Sodium-Dodecyl Sulfate Polyacrylamide Gel Electrophoresis (SDS-PAGE):

Antibody purity was also analysed by SDS-PAGE under reducing and non-reducing conditions according to standard methods. Briefly, 4%-20% TGX protein gels (Bio-Rad, USA) were used to resolve proteins using a Mini-Protean Electrophoresis System (Bio-Rad, USA). For non-reducing condition, protein samples were denatured by mixing with 2× Laemmli sample buffer (Bio-Rad, USA) and boiled at 95° C. for 5-10 min before loading to the gel. For reducing conditions, 2× sample buffer containing 5% of β-mercaptoethanol (βME), or 40 mM DTT (dithiothreitol) was used. Electrophoresis was carried out at a constant voltage of 150V for 1 h in SDS running buffer (25 mM Tris, 192 mM glycine, 1% SDS, pH 8.3).

Example 3: Biophysical Characterisation 3.1 Global Affinity Study Using BLITz System Bio-Layer Interferometry (BLI) experiments were performed using a single channel BLItz system (ForteBio, Menlo Park, Calif.) using Anti-human immunoglobulin G (IgG) Fc (AHC) coated biosensor tips (Pall ForteBio, Menlo Park, Calif.) for capturing human IgGs. Biosensors were first hydrated for at least 10 m in assay buffer (phosphate buffered saline) followed by buffer baseline for 30 s and loading of the human IgGs onto the biosensor tips at concentrations ranging from 25-50 nM for 120 s. The tips were then washed briefly for 30 s with the assay buffer to remove nonspecifically bound proteins or unbound IgGs for obtaining a second buffer baseline. The association phase of the IgGs with antigens (500 nM-0 nM) was set up at 120 s which was followed by a dissociation phase (assay buffer alone) for 120 s. All the BLITz runs were measured at room temperature at a stirring speed of 1000 rpm and AHC biosensors were regenerated using 10 mM of glycine (pH 2.7) after the assay. Binding affinity between the immobilized antibodies on the AHC sensors and human CD47 were determined by analyzing the binding kinetic curves using the software BLItz Pro. All the sensorgrams were reference subtracted and globally fitted into a 1:1 model which analysed the binding curves at different concentrations of antigens and generated kinetic constants (KD/Ka/Kd) for the globally fitted data. All the binding curves were subjected to step correction which corrects the misalignment between association and dissociation steps and only the curves with $R^2$ values greater than 0.9 were used for analysis.

The anti-CD47 antibody clones in IgG1 format were analyzed for binding affinity to human CD47.

Figure 2A:
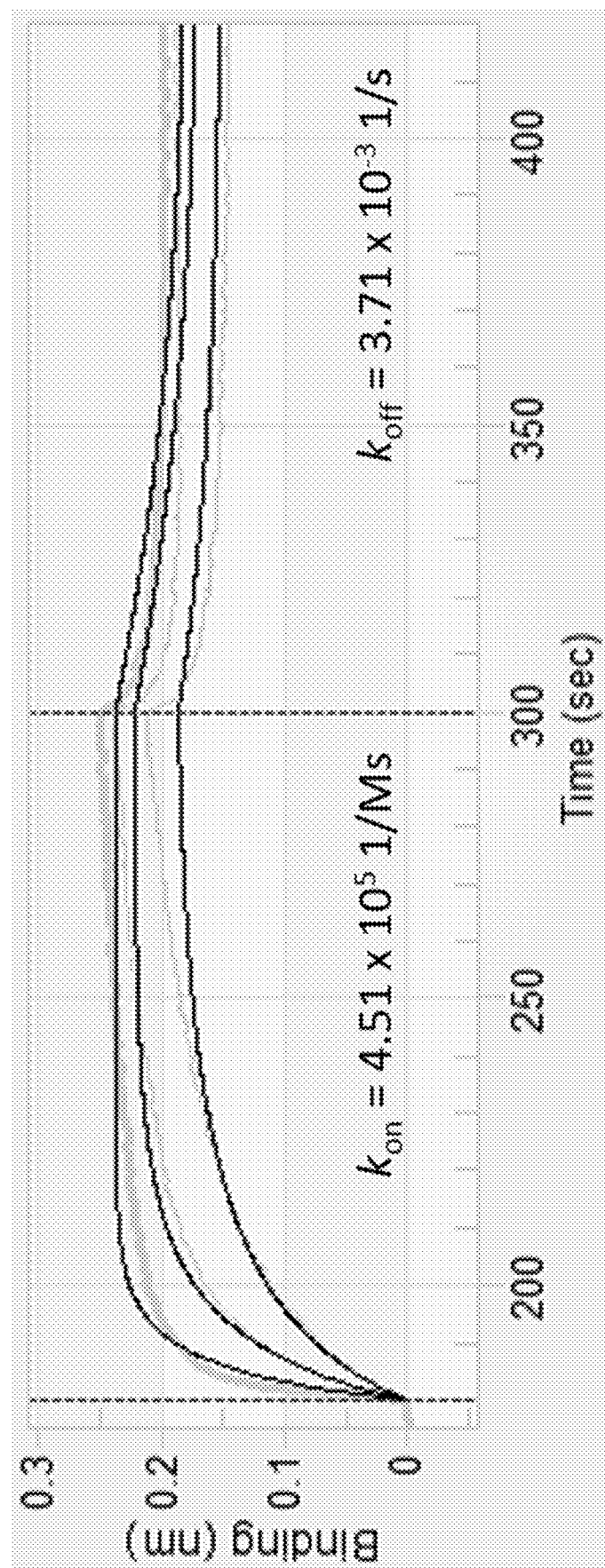
FIGS. 2A and 2B. Sensorgrams showing affinity of binding of anti-CD47 antibodies to human CD47. (2A) Sensorgram for 1-1-A1. (2B) Sensorgram for 1-1-A1 BM.
Figure 2B:
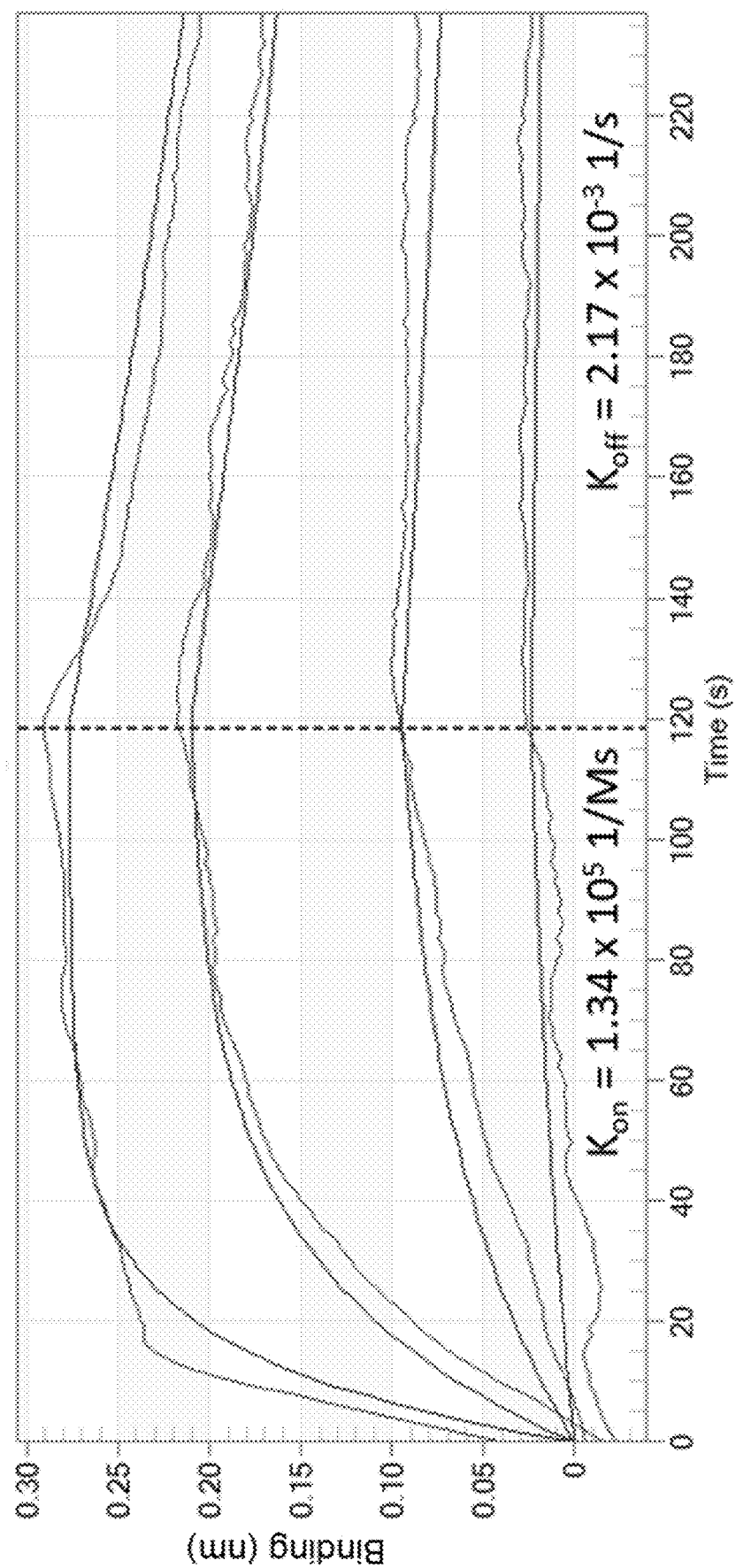

Representative sensorgrams for the analysis are shown in FIGS. 2A and 2B. Clone 1-1-A1 was found to have a $K_D$ of 9 nM, and 1-1-A1 BM was found to have a $K_D$ of 16.1 nM.

In a separate experiment, the affinity of 1-1-A1_BM ([1] of Example 2.2) for human CD47 was analysed by BLI using an anti-Penta-HIS (HIS1K) Octet sensors. Buffer baseline was obtained for 30 s, and then sensors were loaded with his-tagged human CD47 (1.2 µM) for 120 s. A second buffer baseline was obtained for 60 s, followed by an association phase with 1-1-A1_BM at concentrations ranging from 15.6 M to 500 nM for 120 s, and a dissociation phase in buffer for 120 s.

Figure 8:
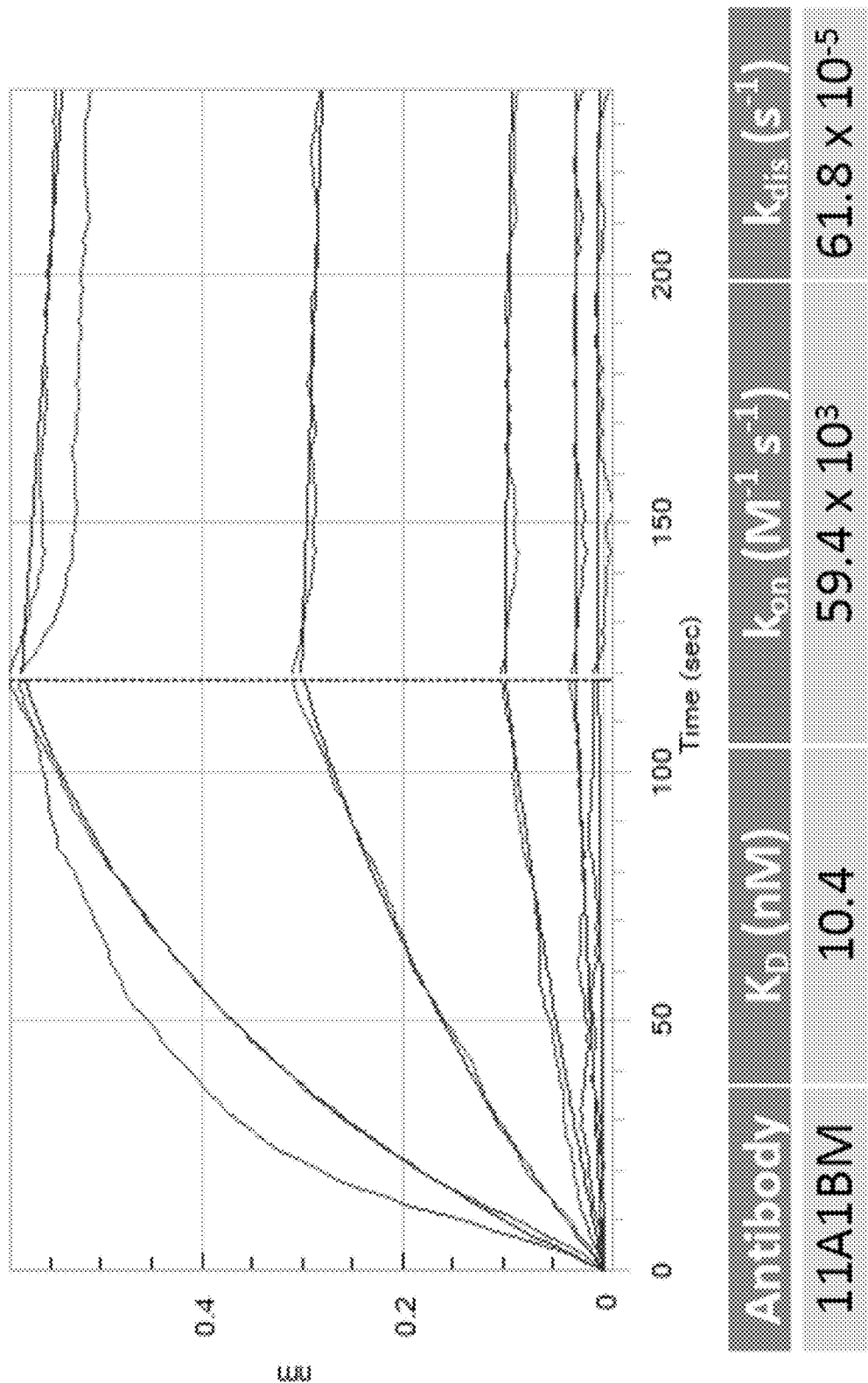
FIG. 8. Sensorgram showing affinity of binding of anti-CD47 antibody 1-1-A1 BM to human CD47.

The results are shown in FIG. 8. 1-1-A1_BM was found to bind to human CD47 in this assay with a $K_D$=10.4 nM.

3.2 Analysis of Cell Surface Antigen-Binding by Flow Cytometry

HEK293T cells (which express high levels of CD47) and cells of a HEK293T cell-derived CD47 knockout cell line were incubated with 20 µg/ml of anti-CD47 antibody or isotype control antibody at 4° C. for 1 hr. The anti-CD47 antibody clone B6H12 (Santa Cruz Biotechnology, cat no. sc-12730) was included in the analysis as a positive control.

The cells were washed thrice with FACS buffer (PBS with 5 mM EDTA and 0.5% BSA) and resuspended in FITC-conjugated anti-FC antibody (Invitrogen, USA) for 40 min at 2-8° C. Cells were washed again and resuspended in 200 µL of FACS flow buffer (PBS with 5 mM EDTA) for flow cytometric analysis using MACSQuant 10 (Miltenyi Biotec, Germany). After acquisition, all raw data were analyzed using Flowlogic software. Cells were gated using forward and side scatter profile and Median of Fluorescence Intensity (MFI) value was determined for native and overexpressing cell populations.

Figure 3A:
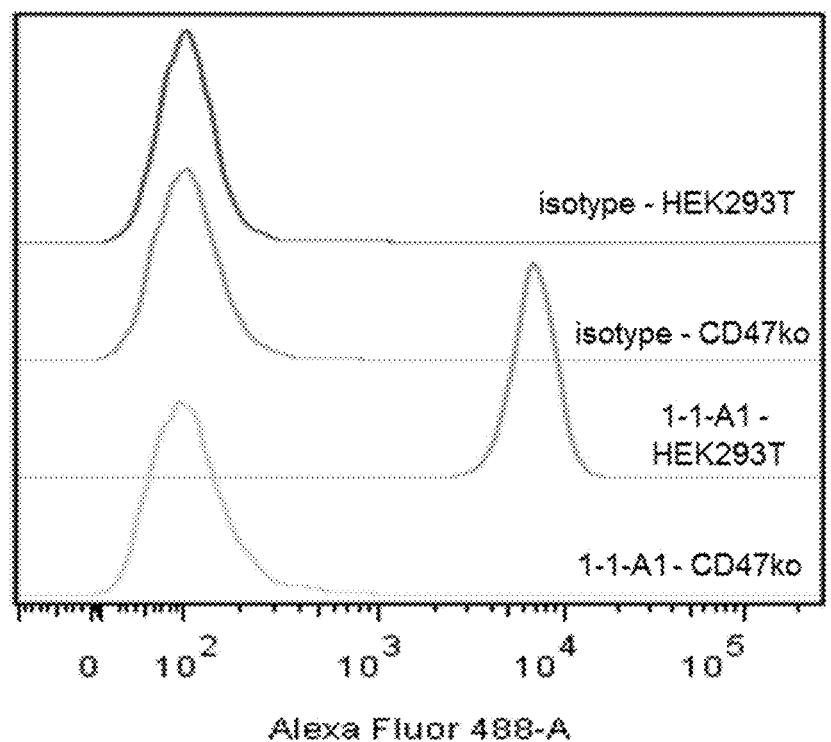
FIGS. 3A to 3D. Histograms showing staining of CD47-expressing cells by anti-CD47 antibodies as determined by flow cytometry. (3A) Histogram showing staining of HEK293T cells (which express CD47), or HEK293T-derived CD47 knockout cells, by anti-CD47 antibody clone 1-1-A1 or isotype control antibody. (3B) Histogram showing staining of HEK293T cells, or HEK293T-derived CD47 knockout cells, by anti-CD47 antibody clone 1-1-A1 BM or isotype control antibody. (3C) Histogram showing staining of HEK293T cells, or HEK293T-derived CD47 knockout cells, by anti-CD47 antibody clone B6H12 or isotype control antibody. (3D) Histogram showing staining of MM.1S cells, H929 cells, U226 cells, 8226 cells and RAJI cells by anti-CD47 antibody clone B6H12.
Figure 3B:
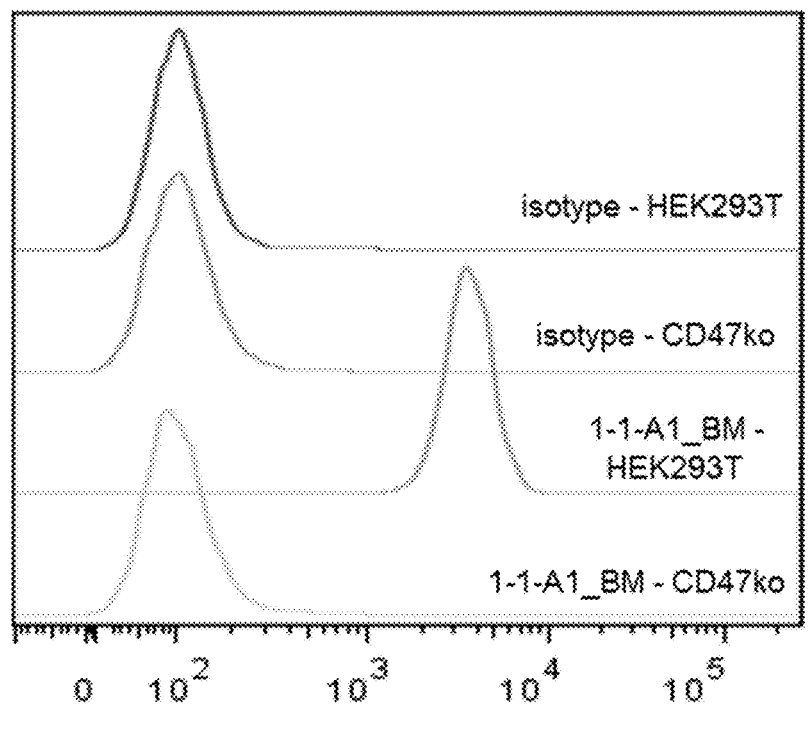
Figure 3C:
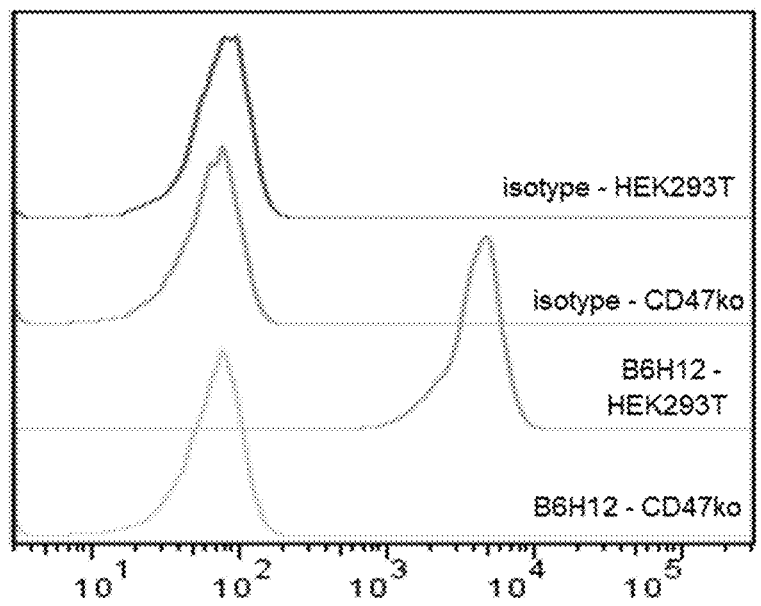

The anti-CD47 antibodies were shown to bind to human CD47 with high specificity. FIGS. 3A and 3B show the results obtained using clones 1-1-A1 and 1-1-A1 BM, and FIG. 3C shows results obtained using the commercially-available anti-CD47 antibody clone B6H12 (positive control).

Figure 3D:
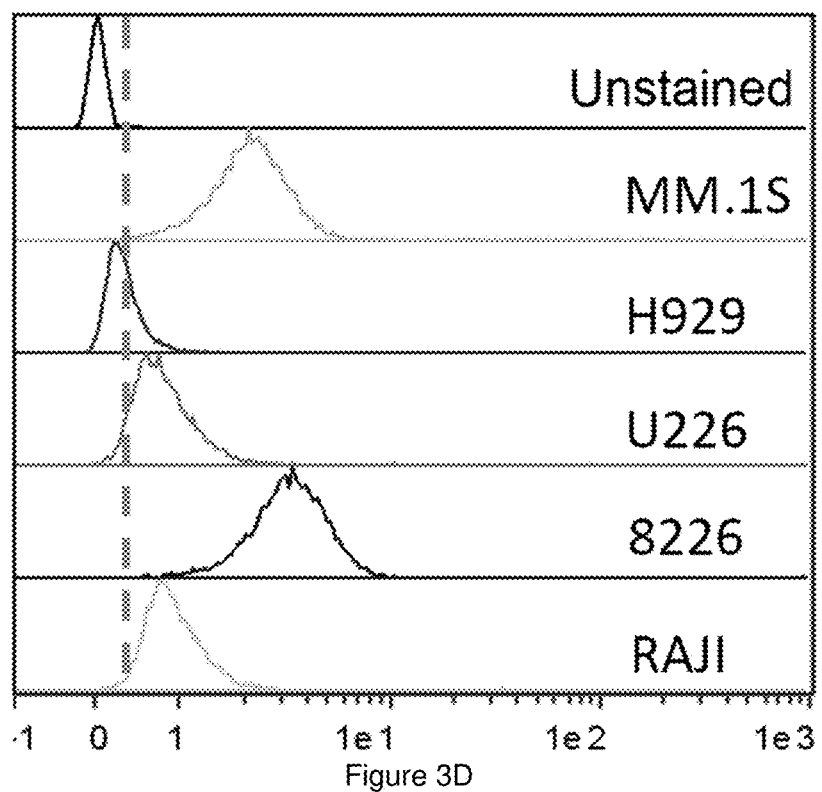

Multiple myeloma and Burkitt's lymphoma cell lines were analysed for CD47 expression by flow cytometry using anti-CD47 antibody clone B6H12. Briefly, $0.5 \times 10^6$ cells were fixed by treatment with 4% paraformaldehyde for 10 min at room temperature, and subsequently stained with APC-conjugated anti-CD47 antibody at a 1:11 dilution, for 30 min at 4° C. The results of the analysis are shown in FIG. 3D and in the table below:

| Cell Line | % cells positive for CD47 |
| --- | --- |
| MM.1S | 99.9 |
| H929 | 2.23 |
| U226 | 93.3 |

3.3 ELISAs for Determining Antibody Specificity

ELISAs were used to determine the binding specificity of the antibodies. The antibodies were tested against target peptide and protein as well as respective mouse, rat and monkey homologues (Sino Biological Inc., China).

ELISAs were carried out according to standard protocols. Briefly, 96-well plates (Nunc, Denmark) were coated with 1 μg/ml of Fc-tagged human CD47 in phosphate-buffered saline (PBS) for 16 h at 4° C. After blocking for 1 h with 1% BSA in Tris buffer saline (TBS) at room temperature, the candidate antigen-binding molecule was serially diluted with the highest conc. being 10 μg/ml and added to the plate. Post 1 h incubation at RT, plates were washed three times with TBS containing 0.05% Tween 20 (TBS-T) and were then incubated with a HRP-conjugated anti-His antibody (Life Technologies, Inc., USA) for 1 h at room temperature. After washing, plates were developed with colorimetric detection substrate 3,3',5,5'-tetramethylbenzidine (Turbo-TMB; Pierce, USA). The reaction was stopped with 2M $H_2SO_4$, and OD was measured at 450 nM.

Binding of anti-CD47 clone 1-1-A1 BM IgG1 ([1] of Example 2.2) to rhesus macaque CD47 (RhCD47) was compared to binding to human CD47 (hCD47).

Figure 5:
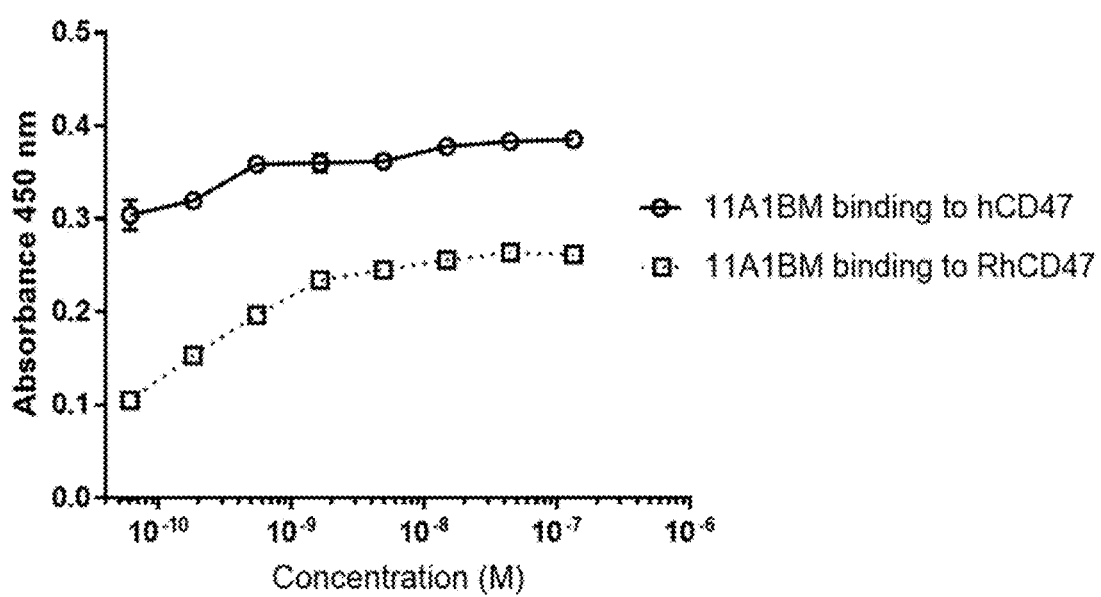
FIG. 5. Graph showing binding to human CD47 (hCD47) and rhesus macaque CD47 (RhCD47) by the indicated antigen-binding molecules, as determined by ELISA.

The results are shown in FIG. 5.

Example 4: Functional Characterisation 4.1 Analysis of Ability to Block CD47-SIRPα Interaction 96-well plates (Nunc, Denmark) were coated with 1 μg/ml of untagged human CD47 protein (Sinobiological Inc, China) in 1×PBS for 16 h at 4° C. After blocking for 1 h with 1% BSA in TBS at room temperature, 1 μg/ml of SIRPα/human His tagged fusion protein (Sinobiological Inc, China) was added either in the absence of antibody, or in the presence of increasing concentrations of anti-CD47 antibody at room temperature for 1 hr. Plates were subsequently washed three times with TBS-T and incubated with an HRP-conjugated anti-his secondary antibody (Thermo Scientific, USA) for 1 h at room temperature. After washing, plates were developed with colorimetric detection substrate Turbo-TMB (Pierce, USA). The reaction was stopped with 2M $H_2SO_4$, and OD was measured at 450 nM.

Percent inhibition of CD47-SIRPα interaction calculated relative to the signal in the absence of SIRPα (100%).

In a first experiment, inhibition of interaction between CD47 and SIRPα was evaluated for the following antigen-binding molecules:

anti-CD47 clone 1-1-A1 IgG1 ([2] of Example 2.2)
anti-CD47 clone 5-48-A6 IgG1 ([3] of Example 2.2)
anti-CD47 clone 5-48-D2 IgG1 ([4] of Example 2.2)

Figure 4:
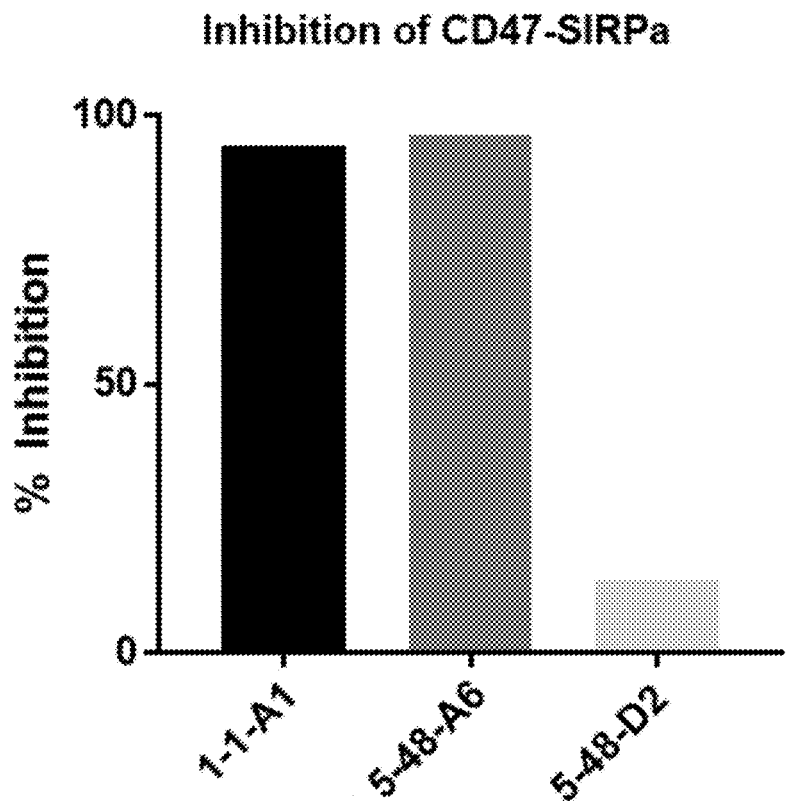
FIG. 4. Bar chart showing inhibition of interaction between human CD47 and human SIRPα by antigen-binding molecules as determined by ELISA.

The results are shown in FIG. 4. Several of the anti-CD47 binding antibodies were found to be potent inhibitors of CD47-SIRPα interaction.

4.2 In Vitro Phagocytosis Assay

In vitro phagocytosis assays were performed according to standard protocols. Briefly, Raji or HL60 cells were cultured in RPMI-1640 supplemented with 10% fetal bovine serum (FBS) and 1% Pen/Strep at 37° C. in a 5% $CO_2$ incubator. HL-60 or Raji cells were then harvested and CFSE-labelled using CellTrace CFSE Cell Proliferation Kit (Thermo Scientific, USA), in accordance with the manufacturer's protocol. The labelled cells were then incubated with human peripheral blood-derived macrophages (Stemcell Technologies, Canada) in the presence of 20 μg/ml of anti-CD47 antibody, or an isotype control antibody for 2 h at 37° C. Cells were washed thrice with 1×PBS to remove all the non-phagocytosed labelled cells and resuspended in 200 μL of FACS flow buffer (PBS with 5 mM EDTA) for flow cytometric analysis using MACSQuant 10 (Miltenyi Biotec, Germany). After acquisition, all raw data were analyzed using Flowlogic software. Cells were gated using forward and side scatter profile and percentage of the engulfed effector cells were calculated.

In a first experiment, antigen-binding molecules were analysed for their ability to promote phagocytosis of CSFE-labelled Raji cells by macrophages, compared to a negative control condition in which PBS was added instead of antibodies.

The following antigen-binding molecules were analysed in the experiment:

anti-CD47 clone 1-1-A1_BM IgG1 ([1] of Example 2.2)

Anti-CD47 antibody clone B6H12 (Santa Cruz Biotechnology, cat no. sc-12730) was included as a positive control condition.

Figure 6:
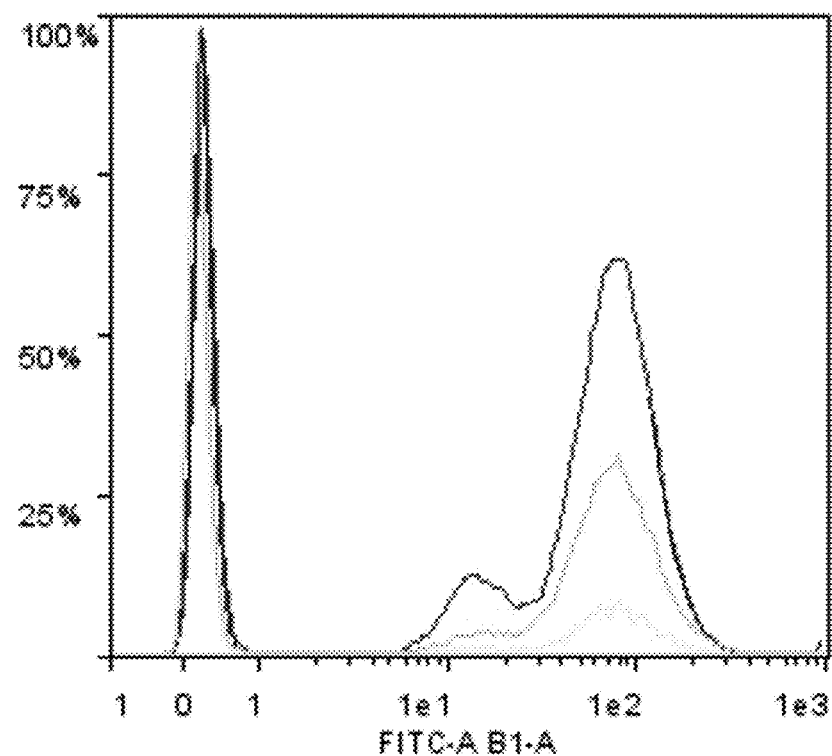
FIG. 6. Histogram showing phagocytosis of CFSE-labelled Raji cells by macrophages in the presence of the indicated antigen-binding molecules or PBS, as determined by flow cytometry.

The results are shown in FIG. 6. Anti-CD47 clone 1-1-A1_BM IgG1 was found to be extremely potent at promoting phagocytosis of Raji cells by macrophages.

In a separate experiment, antigen-binding molecules were analysed for their ability to promote phagocytosis of CSFE-labelled HL-60 cells by macrophages, as determined by fluorescence microscopy. Phagocytic index was calculated as the number of engulfed CFSE-labelled HL-60 cells per phagocyte, for 200 cells using the fluorescence microscope.

The anti-CD47 clone 1-1-A1_BM IgG1 ([1] of Example 2.2) was analysed in the experiment, and an isotype control condition was included as a negative control.

Figure 7A:
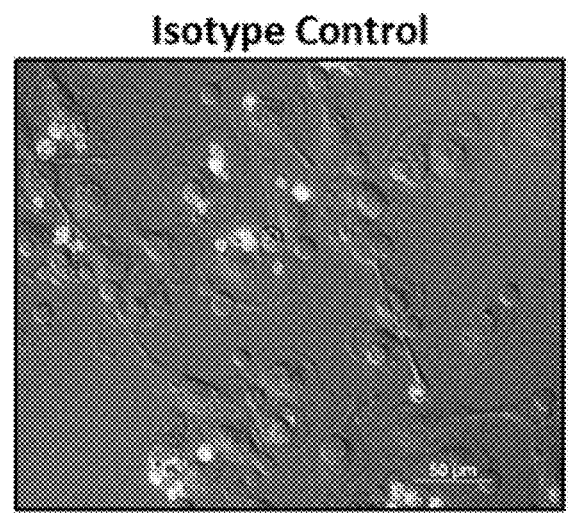
FIGS. 7A to 7C. Fluorescence microscopy images and bar chart showing phagocytosis of CFSE-labelled HL-60 cells by macrophages in the presence of the indicated antigen-binding molecules. (7A and 7B) Images showing binding phagocytosis in the presence of (7A) isotype control antibody (negative control), (7B) anti-CD47 clone 1-1-A1 BM IgG1, (7C) Bar chart summarising phagocytic indices for CFSE-labelled HL-60 cells by macrophages in the presence of the indicated antigen-binding molecules.
Figure 7B:
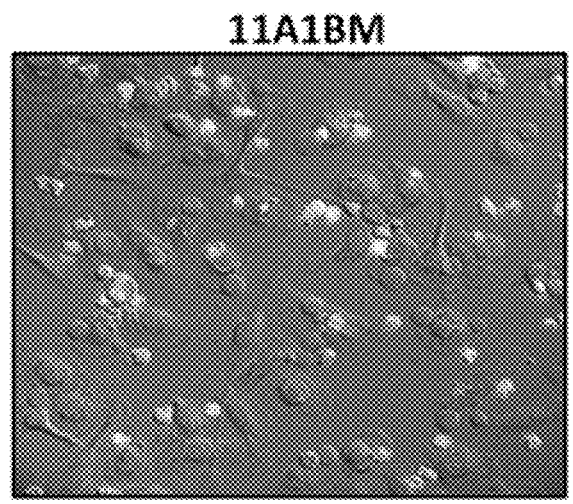
Figure 7C:
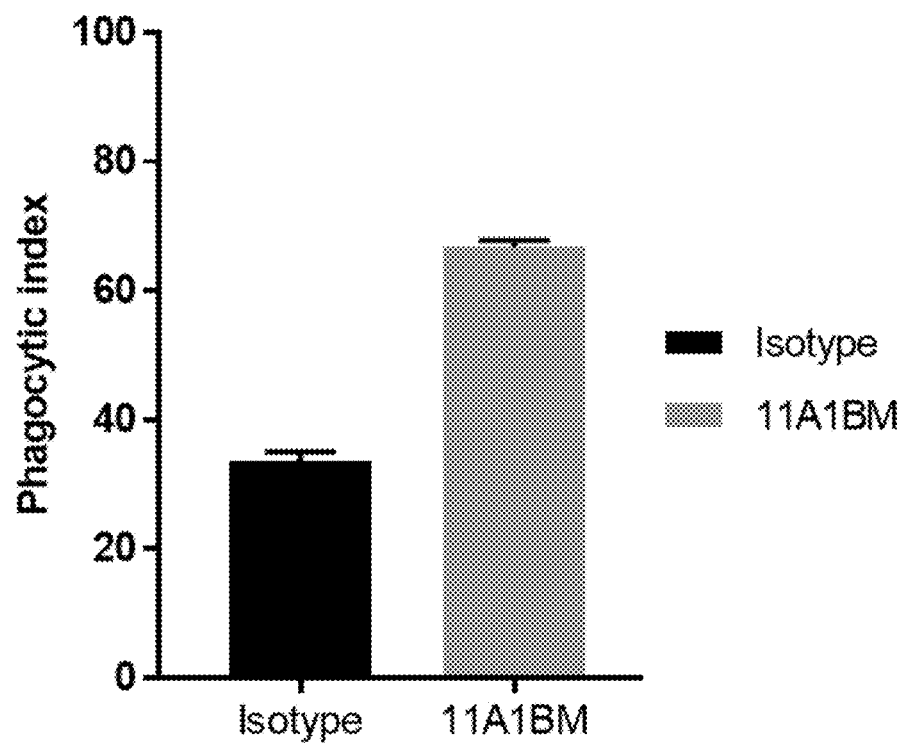

The results are shown in FIGS. 7A to 7C. Anti-CD47 clone 1-1-A1_BM IgG1 was shown to be potent at inducing phagocytosis of HL-60 cells by macrophages.

Example 5: Production of Humanised Versions of Anti-CD47 Clone 1-1-A1

Humanised versions of anti-CD47 antibody clone 1-1-A1 were produced and purified as described in Example 2.

| Antigen-binding molecule | Polypeptides | Antibody |
| --- | --- | --- |
| [6] | SEQ ID NO: 159 + SEQ ID NO: 160 | 11A1H1-IgG1 |
| [7] | SEQ ID NO: 161 + SEQ ID NO: 160 | 11A1H2-IgG1 |
| [8] | SEQ ID NO: 162 + SEQ ID NO: 160 | 11A1H3-IgG1 |
| [9] | SEQ ID NO: 163 + SEQ ID NO: 160 | 11A1H4-IgG1 |
| [10] | SEQ ID NO: 164 + SEQ ID NO: 160 | 11A1H5-IgG1 |
| [11] | SEQ ID NO: 163 + SEQ ID NO: 165 | 11A1H6-IgG1 |
| [12] | SEQ ID NO: 164 + SEQ ID NO: 165 | 11A1H7-IgG1 |
| [13] | SEQ ID NO: 163 + SEQ ID NO: 166 | 11A1H8-IgG1 |
| [14] | SEQ ID NO: 164 + SEQ ID NO: 166 | 11A1H9-IgG1 |
| [15] | SEQ ID NO: 164 + SEQ ID NO: 167 | 11A1H10-IgG1 |
| [16] | SEQ ID NO: 164 + SEQ ID NO: 168 | 11A1H11-IgG1 |

The CDRs of the humanised versions of anti-CD47 antibody clone 1-1-A1 are shown below:

-continued

| Cell Line | % cells positive for CD47 |
| --- | --- |
| 8226 | 99.4 |
| RAJI | 97.9 |

| Clone | HC-CDR1 | HC-CDR2 | HC-CDR3 | LC-CDR1 | LC-CDR2 | LC-CDR3 |
|---|---|---|---|---|---|---|
| 1A11H1 1A11H2 1A11H3 1A11H4 | GYTFTNYV (SEQ ID NO: 24) | INPYNDGT (SEQ ID NO: 25) | ASGGYYTMDY (SEQ ID NO: 26) | QHLEYSNGYSY (SEQ ID NO: 32) | KIS (SEQ ID NO: 33) | SQSTHVPYT (SEQ ID NO: 34) |
| 1A11H5 | GYTFTGYV (SEQ ID NO: 137) | INPYNGGT (SEQ ID NO: 138) | | | | |
| 1A11H6 | GYTFTNYV (SEQ ID NO: 24) | INPYNDGT (SEQ ID NO: 25) | | QHLEYSQGYSY (SEQ ID NO: 139) | KVS (SEQ ID NO: 141) | |
| 1A11H7 | GYTFTGYV (SEQ ID NO: 137) | INPYNGGT (SEQ ID NO: 138) | | | | |
| 1A11H8 | GYTFTNYV (SEQ ID NO: 24) | INPYNDGT (SEQ ID NO: 25) | | QHLEYSTGYSY (SEQ ID NO: 140) | | |
| 1A11H9 1A11H10 1A11H11 | GYTFTGYV (SEQ ID NO: 137) | INPYNGGT (SEQ ID NO: 138) | | QHLEYSNGYSY (SEQ ID NO: 32) | KIS (SEQ ID NO: 33) | SQGTHVPYT (SEQ ID NO: 142) |
| Consensus | GYTFTX$_1$YV X$_1$ = N or G (SEQ ID NO: 169) | INPYNX$_2$GT X$_2$ = D or G (SEQ ID NO: 170) | ASGGYYTMDY (SEQ ID NO: 26) | QHLEYSX$_3$GYSY X$_3$ = N, Q or T (SEQ ID NO: 171) | KX$_4$S X$_4$ = I or V (SEQ ID NO: 172) | SQX$_5$THVPYT X$_5$ = S or G (SEQ ID NO: 173) |

The FRs of the humanised versions of anti-CD47 antibody clone 1-1-A1 are shown below:

| Clone | HC-FR1 | HC-FR2 | HC-FR3 | HC-FR4 |
|---|---|---|---|---|
| 1A11H1 | QVQLVQSGAEVKKP GASVKVSCKAS (SEQ ID NO: 143) | IHWVRQAPGKGLEW MGY (SEQ ID NO: 144) | KSNEKFKGRVTLTS DKSSTSAYMELSSL RSEDTAVYYC (SEQ ID NO: 147) | WGQGTLVTVSS (SEQ ID NO: 152) |
| 1A11H2 | | | KSNEKFKGRVTLTS DTSTTTAYMELSSL RSEDTAVYYC (SEQ ID NO: 148) | |
| 1A11H3 | | MHWVRQAPGQGLEW MGY (SEQ ID NO: 145) | KSNEKFQGRVTLTS DTSTSTAYMELSSL RSEDTAVYYC (SEQ ID NO: 149) | WGQGTLV (SEQ ID NO: 153) |
| 1A11H4 | | IHWVRQAPGQGLEW MGY (SEQ ID NO: 146) | KYNQKFKGRVTLTS DTSTTTAYMELSRL RSDDTAVYYC (SEQ ID NO: 150) | |
| 1A11H5 | | | NYAQKFKGRVTLTS DTSTTTAYMELSRL RSEDTAVYYC (SEQ ID NO: 151) | WGQGTLVTVSS (SEQ ID NO: 152) |
| 1A11H6 | | | KYNQKFKGRVTLTS DTSTTTAYMELSRL RSDDTAVYYC (SEQ ID NO: 150) | WGQGTLV (SEQ ID NO: 153) |
| 1A11H7 | | | NYAQKFKGRVTLTS DTSTTTAYMELSRL RSEDTAVYYC (SEQ ID NO: 151) | WGQGTLVTVSS (SEQ ID NO: 152) |
| 1A11H8 | | | KYNQKFKGRVTLTS DTSTTTAYMELSRL RSDDTAVYYC (SEQ ID NO: 150) | WGQGTLV (SEQ ID NO: 153) |
| 1A11H9 1A11H10 1A11H11 | | | NYAQKFKGRVTLTS DTSTTTAYMELSRL RSEDTAVYYC (SEQ ID NO: 151) | WGQGTLVTVSS (SEQ ID NO: 152) |

-continued

| Clone | HC-FR1 | HC-FR2 | HC-FR3 | HC-FR4 |
|---|---|---|---|---|
| Consensus | QVQLVQSGAEVKKP GASVKVSCKAS (SEQ ID NO: 143) | $X_6$HWVRQAPGX$_7$GLE WMGY $X_6$ = I or M $X_7$ = Q or K (SEQ ID NO: 174) | $X_8X_9X_{10}X_{11}$KFX$_{12}$GRV TLTSDX$_{13}$SX$_{14}$SX$_{15}$A YMELSX$_{16}$LRSX$_{17}$DT AVYYC $X_8$ = K or N $X_9$ = S or Y $X_{10}$ = N or A $X_{11}$ = E or Q $X_{12}$ = K or Q $X_{13}$ = T or K $X_{14}$ = T or S $X_{15}$ = T or S $X_{16}$ = S or R $X_{17}$ = E or D (SEQ ID NO: 175) | WGQGTLVX$_{18}$X$_{19}$X$_{20}$ X$_{21}$ $X_{18}$ = T or absent $X_{19}$ = V or absent $X_{20}$ = S or absent $X_{21}$ = S or absent (SEQ ID NO: 176) |

| Clone | LC-FR1 | LC-FR2 | LC-FR3 | LC-FR4 |
|---|---|---|---|---|
| 1A11H1 1A11H2 1A11H3 1A11H4 1A11H5 | DVVMTQSPLSLPVT LGQPASISCRSS (SEQ ID NO: 154) | LHWYQQRPGQSPRLL IY (SEQ ID NO: 155) | NRFSGVPDRFSGSG SGTDFTLKISRVEAE DVGVYYC (SEQ ID NO: 156) | FGGGTKVEIK (SEQ ID NO: 158) |
| 1A11H6 1A11H7 1A11H8 1A11H9 1A11H10 | | | NRDSGVPDRFSGS GSGTDFTLKISRVEA EDVGVYYC (SEQ ID NO: 157) | |
| 1A11H11 | | | NRFSGVPDRFSGSG SGTDFTLKISRVEAE DVGVYYC (SEQ ID NO: 156) | |
| Consensus | DVVMTQSPLSLPVT LGQPASISCRSS (SEQ ID NO: 154) | LHWYQQRPGQSPRLL IY (SEQ ID NO: 155) | NRX$_{22}$SGVPDRFSGS GSGTDFTLKISRVEA EDVGVYYC $X_{22}$ = D or F (SEQ ID NO: 177) | FGGGTKVEIK (SEQ ID NO: 158) |

Example 6: Biophysical Characterisation of Humanised Versions of Anti-CD47 Antibody Clone 1-1-A1

6.1 ELISAs for Determining Antibody Specificity

The binding specificity of the humanised versions of anti-CD47 clone 1-1-A1 was analysed be ELISA.

96-well plates (Nunc, Denmark) were coated with 1 µg/ml of human CD47 or VISTA protein in PBS, for 1 h at room temperature. Plates were blocked for 1 h at room temperature with 1% BSA in Tris buffer saline containing 0.05% Tween 20 (TBS-T). The test antigen-binding molecules were added at concentrations ranging from to 0.002 µg/ml to 200 µg/ml, and the plates were incubated at room temperature for 1 h. Plates were then washed three times with TBS-T, and were then incubated with a HRP-conjugated secondary antibody for 1 h at room temperature. After washing, plates were developed with colorimetric detection substrate 3,3',5,5'-tetramethylbenzidine (Turbo-TMB; Pierce, USA). The reaction was stopped after 3.5 min with 2M $H_2SO_4$, and OD was measured at 450 nM.

Figure 9:
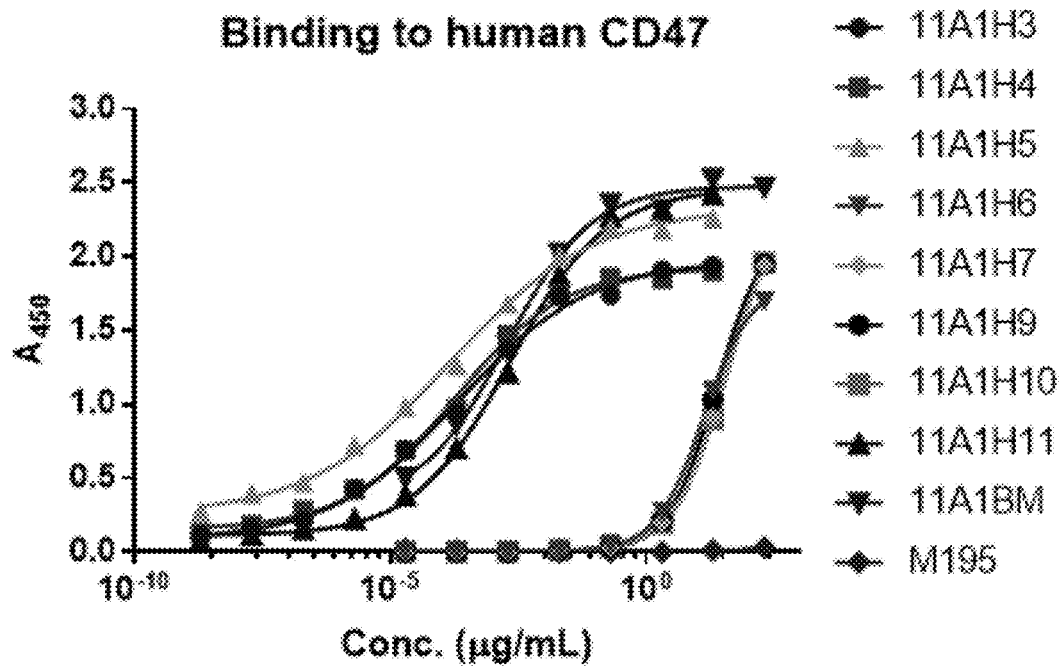
FIG. 9. Graph showing binding to human CD47 by the indicated antigen-binding molecules, as determined by ELISA.

The following antigen-binding molecules were analysed in the experiment:

11A1H3-IgG1 ([8] of Example 5).
11A1H4-IgG1 ([9] of Example 5).
11A1H5-IgG1 ([10] of Example 5).
11A1H6-IgG1 ([11] of Example 5).
11A1H7-IgG1 ([12] of Example 5).
11A1H9-IgG1 ([14] of Example 5).
11A1H10-IgG1 ([15] of Example 5).
11A1H11-IgG1 ([16] of Example 5).
anti-CD47 clone 1-1-A1_BM IgG1 ([1] of Example 2.2).
anti-CD33 IgG1 ([5] of Example 2.2) (negative control)—referred to as 'M195' in FIG. 9.

The results are shown in FIG. 9. The humanised antibodies displayed binding to human CD47. EC50 values were calculated, and the fold increase in EC50 value relative to EC50 for 1-1-A1_BM are shown below.

| Antibody | $EC_{50}$ (µg/mL) | Fold increase in $EC_{50}$ relative to 1-1-A1_BM |
|---|---|---|
| 11A1H3 | 0.00022 | 0.12 |
| 11A1H4 | 0.00018 | 0.10 |
| 11A1H5 | 0.00015 | 0.08 |
| 11A1H6 | 13.4 | 7444 |
| 11A1H7 | 36.8 | 20444 |
| 11A1H9 | 23.5 | 13056 |
| 11A1H10 | 38.1 | 21167 |
| 11A1H11 | 0.0021 | 1.17 |
| 11A1BM | 0.0018 | 1.0 |

In a separate ELISA, the antigen-binding molecules were evaluated for binding to human VISTA. Anti-human VISTA antibody VSTB112 (described e.g. in WO 2015/097536) was included as a positive control.

Figure 10:
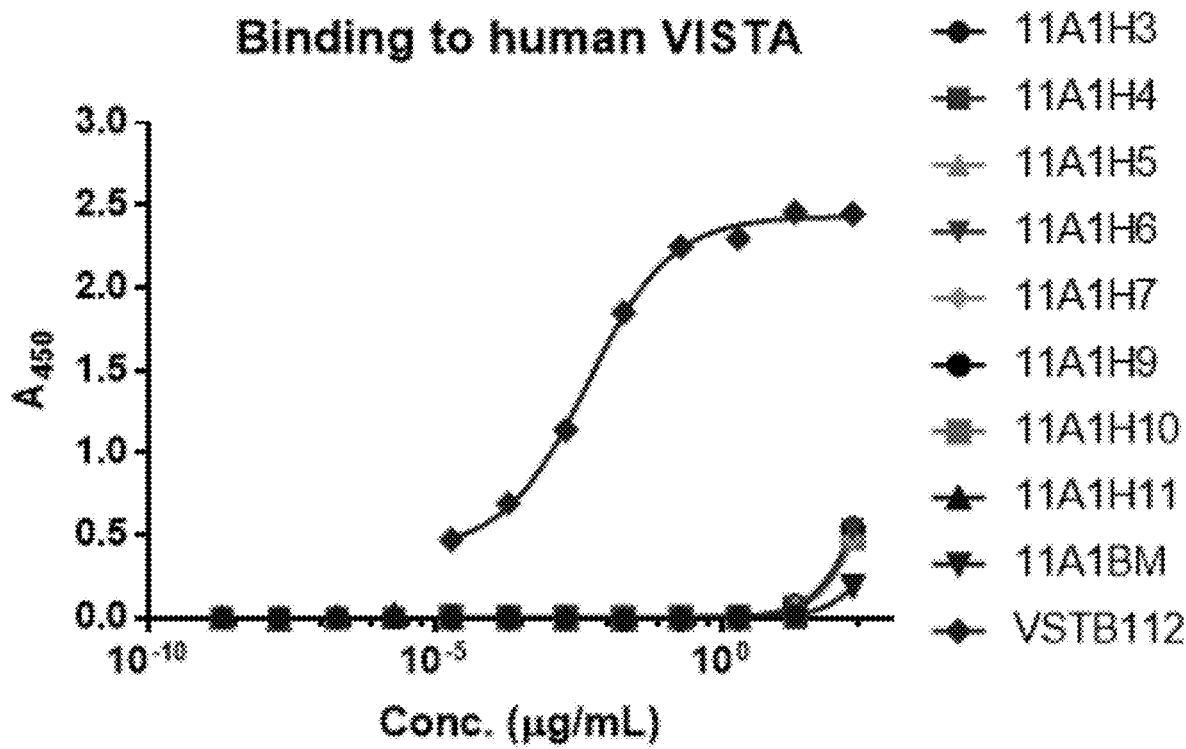
FIG. 10. Graph showing binding to human VISTA by the indicated antigen-binding molecules, as determined by ELISA.
Figure 11A:
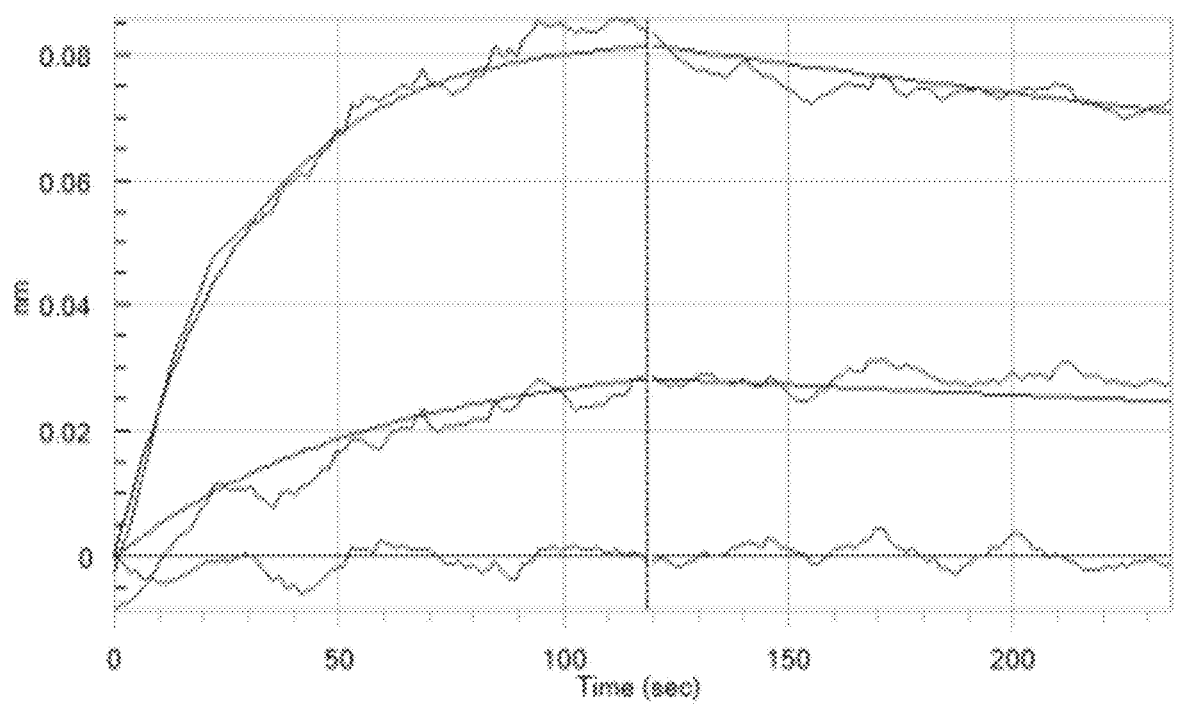
FIGS. 11A to 11H. Sensorgrams showing affinity of binding of anti-CD47 antibodies to human CD47. (11A) Sensorgram for 11A1 BM. (11B) Sensorgram for 11A1H3. (11C) Sensorgram for 11A1H5. (11D) Sensorgram for 11A1H6. (11E) Sensorgram for 11A1H7. (11F) Sensorgram for 11A1H9. (11G) Sensorgram for 11A1H10. (11H) Sensorgram for 11A1H11.
Figure 11B:
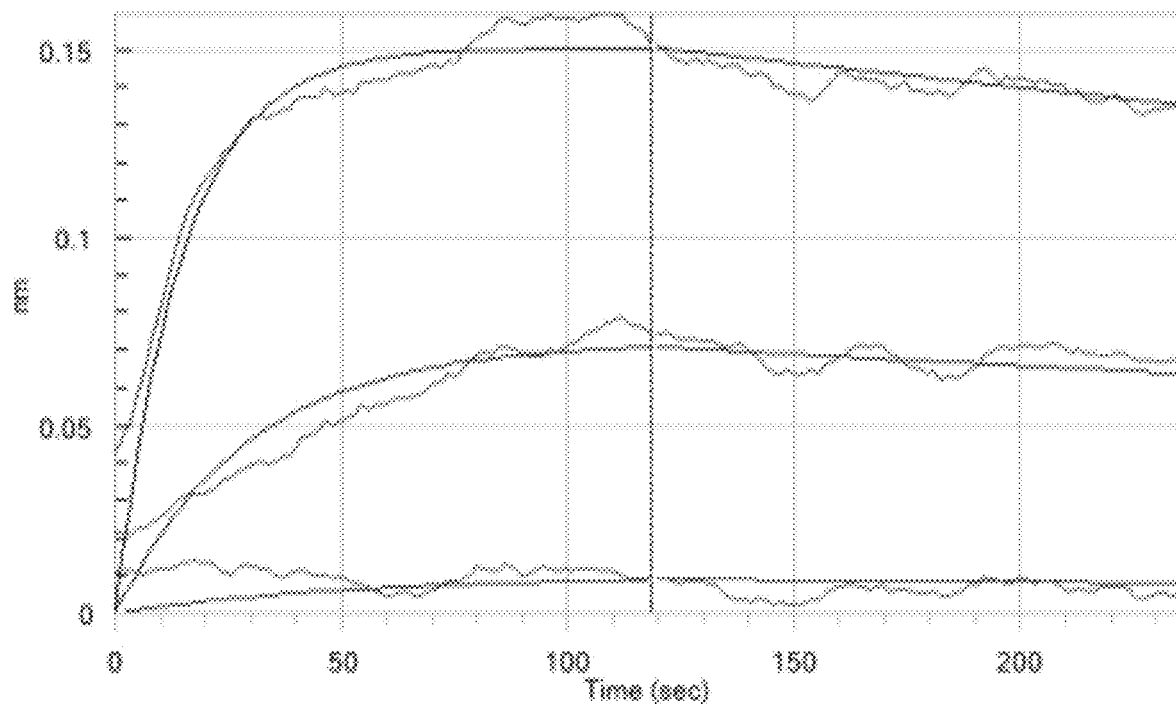
Figure 11C:
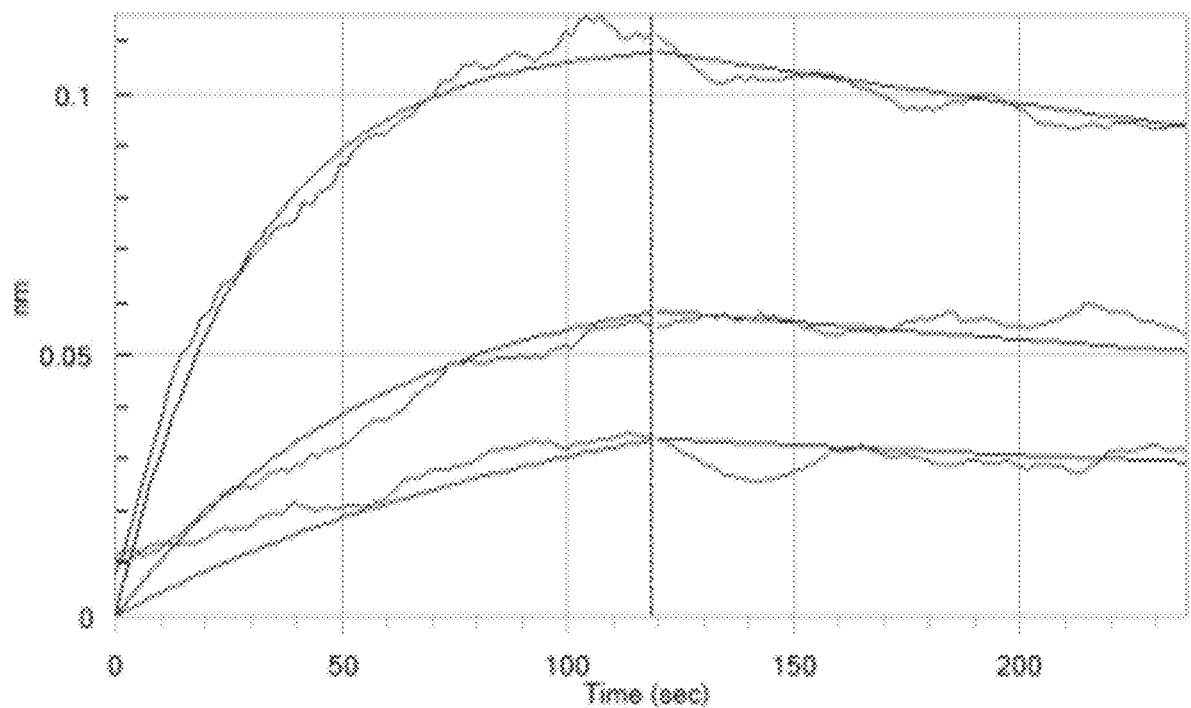
Figure 11D:
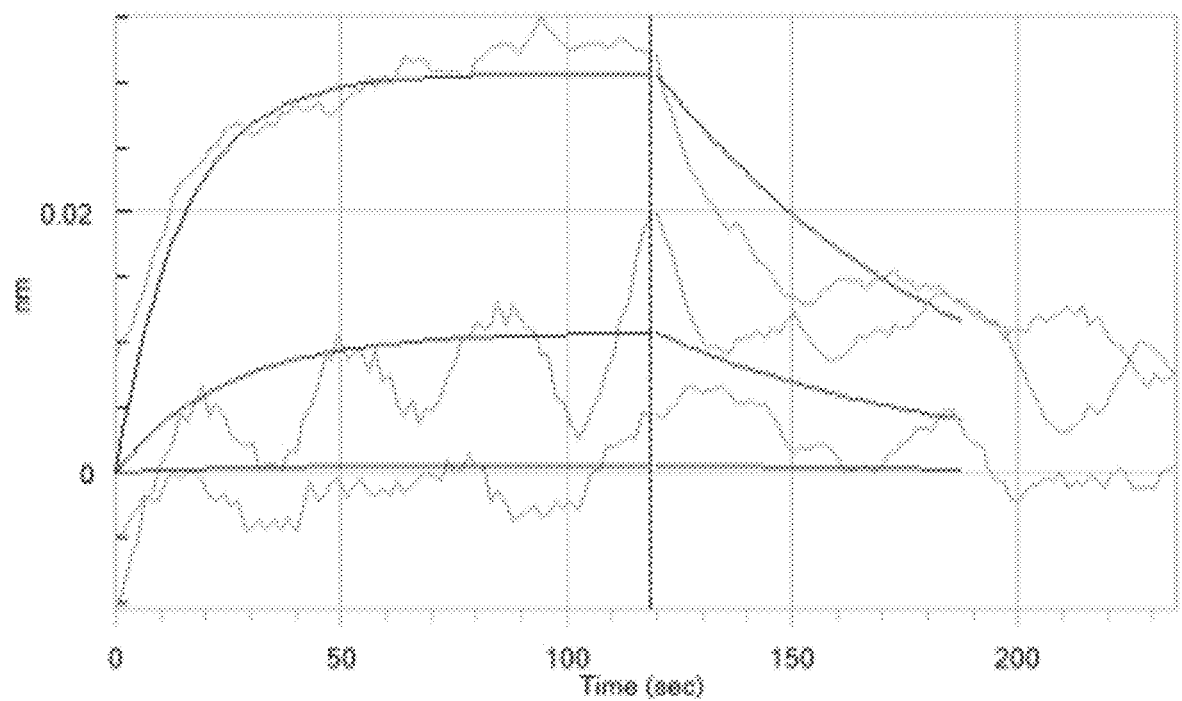
Figure 11E:
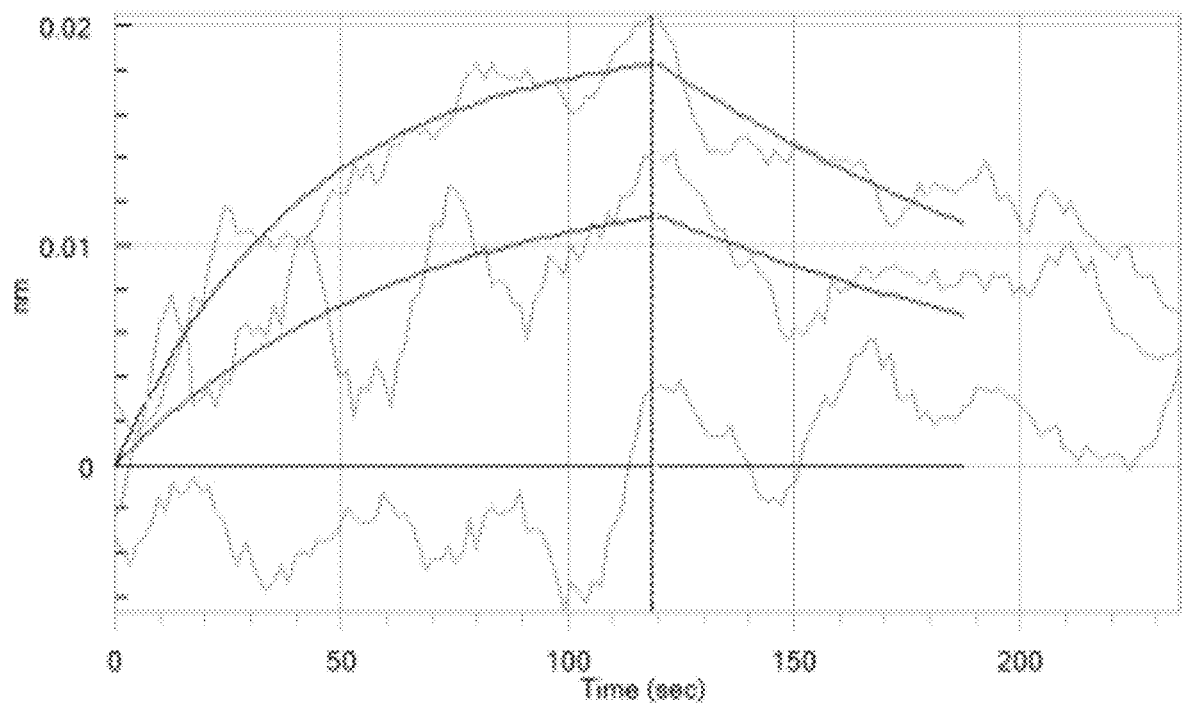
Figure 11F:
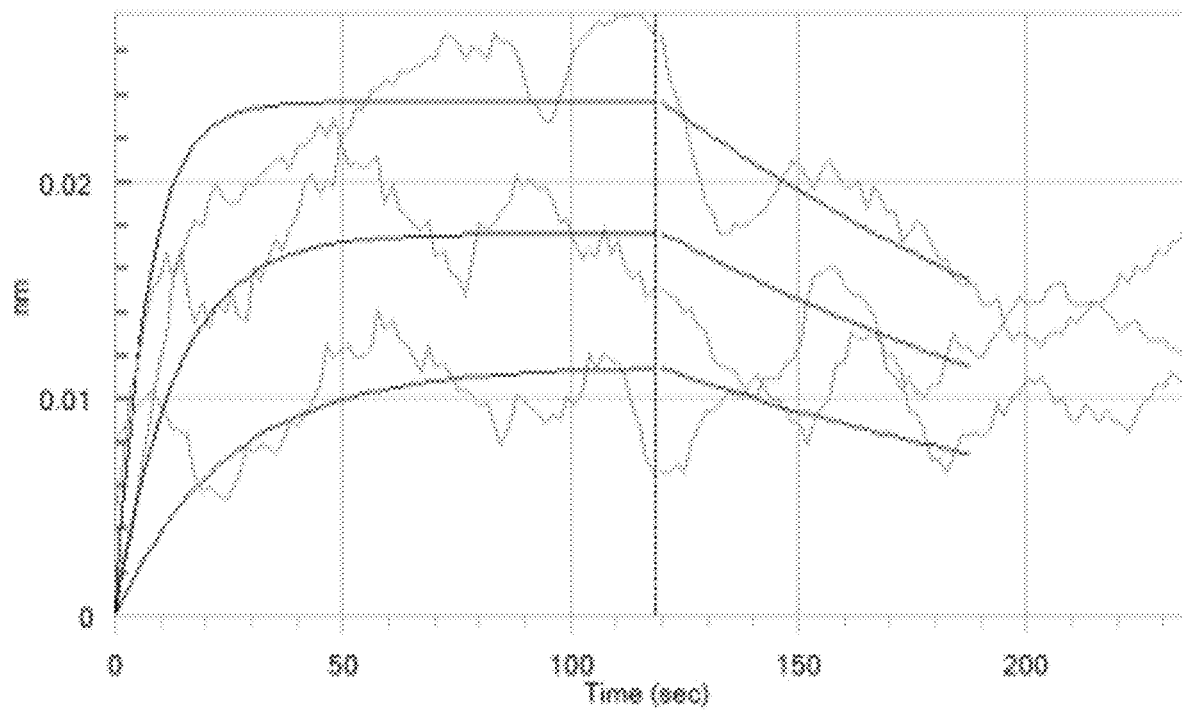
Figure 11G:
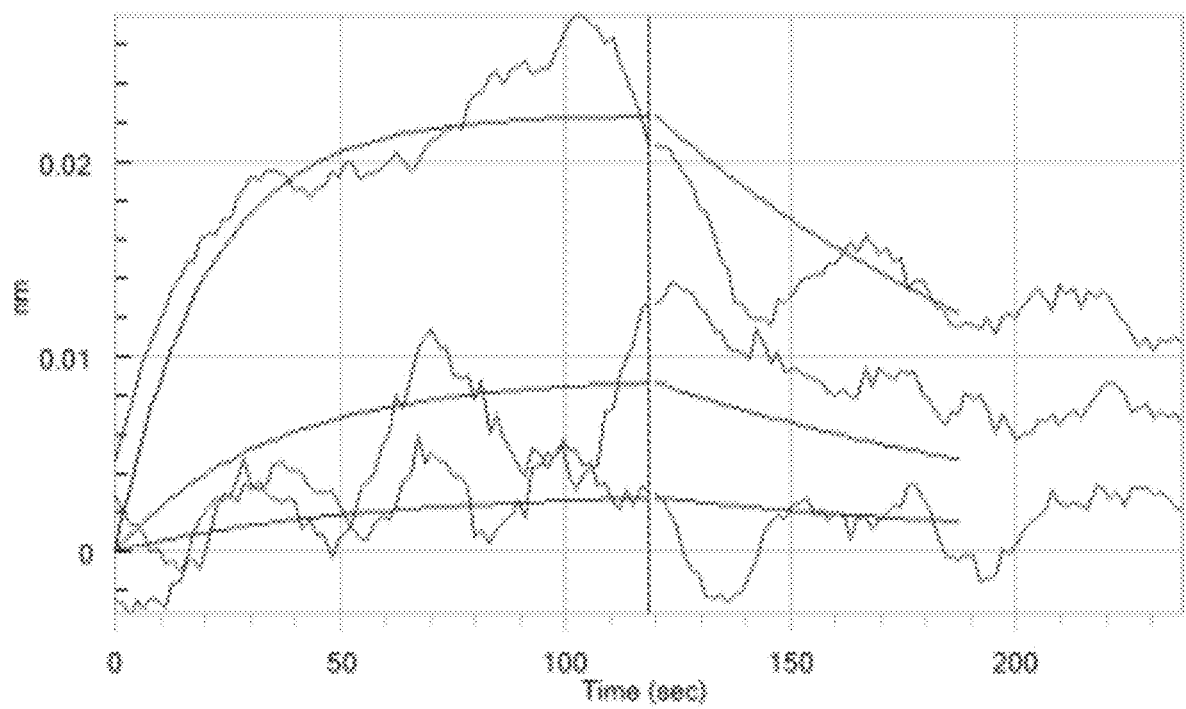
Figure 11H:
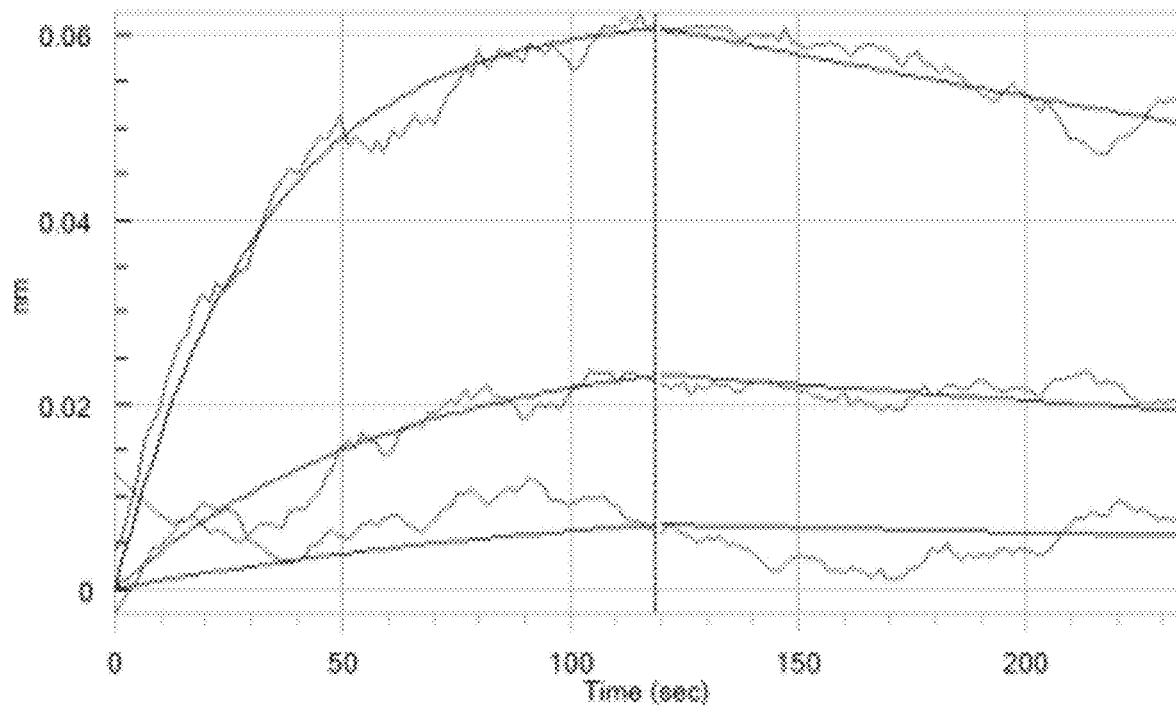

The results are shown in FIG. 10. The humanised antibodies were found not to cross-react with human VISTA.

6.2 Global Affinity Study Using BLITz System

The affinity of binding of humanised versions of anti-CD47 clone 1-1-A1 to human CD47 was in BLI experiments performed using a single channel BLItz system (ForteBio, Menlo Park, Calif.) using Anti-human immunoglobulin G (IgG) Fc (AHC) coated biosensor tips (Pall ForteBio, Menlo Park, Calif.) for capturing human IgGs. Biosensors were first hydrated for at least 10 m in assay buffer (phosphate buffered saline) followed by buffer baseline for 60 s and loading of the human IgGs onto the biosensor tips at 25 nM for 120 s. The tips were then washed briefly for 60 s with the assay buffer to remove nonspecifically bound proteins or unbound IgGs for obtaining a second buffer baseline. The association phase of the IgGs with antigens (250 nM to 62.5 nM) was set up at 120 s which was followed by a dissociation phase (assay buffer alone) for 120 s. All the BLITz runs were measured at room temperature at a stirring speed of 1000 rpm and AHC biosensors were regenerated using 10 mM of glycine (pH 2.7) after the assay. Binding affinity between the immobilized antibodies on the AHC sensors and human CD47 were determined by analyzing the binding kinetic curves using the software BLItz Pro. All the sensorgrams were reference subtracted and globally fitted into a 1:1 model which analysed the binding curves at different concentrations of antigens and generated kinetic constants (KD/Ka/Kd) for the globally fitted data. All the binding curves were subjected to step correction which corrects the misalignment between association and dissociation steps and only the curves with $R^2$ values greater than 0.9 were used for analysis.

Representative sensorgrams are shown in FIGS. 11A to 11H, and the calculated kinetic and thermodynamic constants are shown below.

| Antibody | $K_D$ (nM) | $K_{on}$ (M$^{-1}$s$^{-1}$) | $K_{dis}$ (s$^{-1}$) |
|---|---|---|---|
| 11A1BM | 9.31 | $1.30 \times 10^5$ | $1.21 \times 10^{-3}$ |
| 11A1H3 | 3.39 | $2.66 \times 10^5$ | $9.04 \times 10^{-4}$ |
| 11A1H5 | 9.28 | $1.29 \times 10^5$ | $1.20 \times 10^{-3}$ |
| 11A1H6 | 134 | $1.08 \times 10^5$ | $1.44 \times 10^{-2}$ |
| 11A1H7 | 232 | $3.24 \times 10^5$ | $7.50 \times 10^{-3}$ |
| 11A1H9 | 23.3 | $2.73 \times 10^5$ | $6.35 \times 10^{-3}$ |
| 11A1H10 | 111 | $8.09 \times 10^4$ | $8.98 \times 10^{-3}$ |
| 11A1H11 | 13.8 | $1.18 \times 10^5$ | $4.28 \times 10^{-3}$ |

Example 7: Functional Characterisation of Humanised Versions of Anti-CD47 Antibody Clone 1-1-A1

7.1 Analysis of Ability to Block CD47-SIRPα Interaction

The ability of humanised versions of anti-CD47 antibody clone 1-1-A1 to inhibit interaction between human CD47 and SIRPα was investigated by ELISA, as described in Example 4.1.

Figure 12:
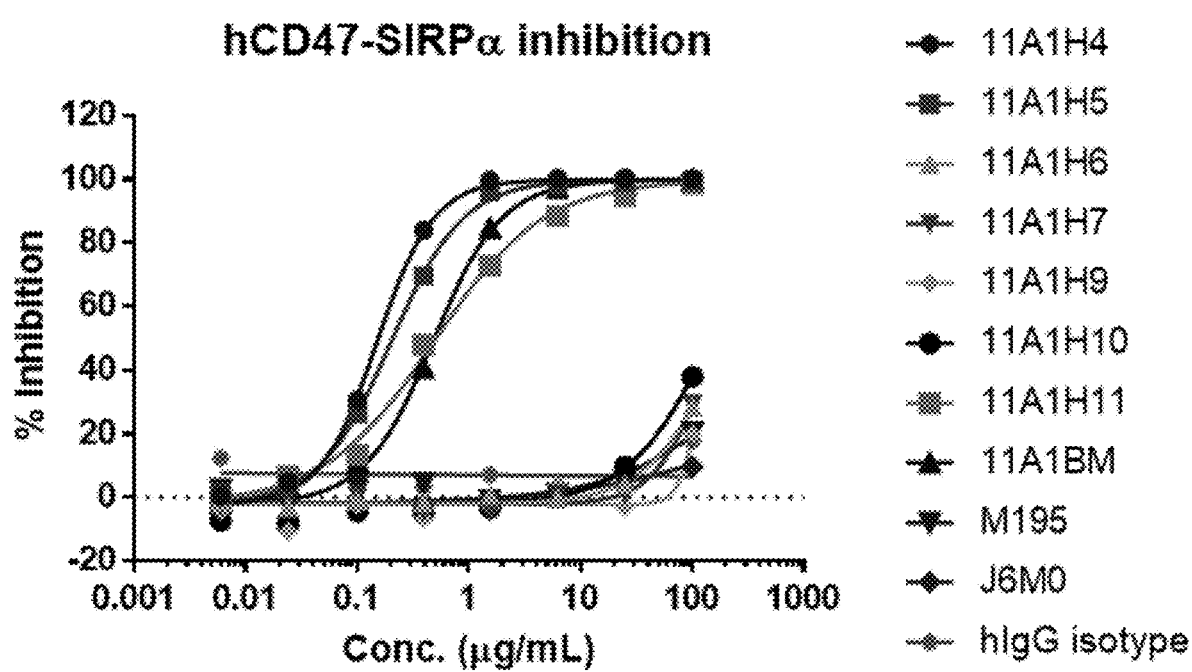
FIG. 12. Graph showing inhibition of interaction between human CD47 and SIRPα by the indicated antigen-binding molecules, as determined by ELISA.

The following antigen-binding molecules were analysed in the experiment:
11A1H4-IgG1 ([9] of Example 5).
11A1H5-IgG1 ([10] of Example 5).
11A1H6-IgG1 ([11] of Example 5).
11A1H7-IgG1 ([12] of Example 5).
11A1H9-IgG1 ([14] of Example 5).
11A1H10-IgG1 ([15] of Example 5).
11A1H11-IgG1 ([16] of Example 5).
anti-CD47 clone 1-1-A1_BM IgG1 ([1] of Example 2.2).
anti-CD33 IgG1 ([5] of Example 2.2) (negative control)—referred to as 'M195' in FIG. 12.
J6M0-IgG1 ([17] below) (negative control).
Isotype control hIgG (negative control).

| Antigen-binding molecule | Polypeptides | Antibody |
|---|---|---|
| [17] | J6M0 VH-CH1-CH2-CH3 (SEQ ID NO: 125) + J6M0 VL-Cκ (SEQ ID NO: 126), | J6M0-IgG1 |

The results are shown in FIG. 12. $IC_{50}$ values were calculated, and the fold increase in 1050 value for the inhibition of interaction between CD47 and SIRPα relative to 1050 for 1-1-A1_BM are shown below.

| Antibody | $IC_{50}$ (μg/mL) | Fold increase in $IC_{50}$ relative to 1-1-A1_BM |
|---|---|---|
| 11A1H4 | 0.150 | 0.32 |
| 11A1H5 | 0.201 | 0.42 |
| 11A1H6 | >100 | >200 |
| 11A1H7 | >100 | >200 |
| 11A1H9 | >100 | >200 |
| 11A1H10 | >100 | >200 |
| 11A1H11 | 0.483 | 1.02 |
| 11A1BM | 0.474 | 1.00 |

7.2 In Vitro Hemagglutination Assay

The hemagglutinating capacity of the humanised versions of anti-CD47 antibody clone 1-1-A1 was investigated using an in vitro hemagglutination assay.

To evaluate the hemagglutinating capacity of the test antigen-binding molecules, human RBCs were prepared by extensively washing blood with 1×PBS and centrifuging at 1500 rpm for 5 min, until a clear supernatant was observed. For the assay, 1% human RBCs were incubated for 1 hr at RT in presence or absence of increasing concentrations of the test antigen-binding molecules in a round bottom 96 well plate. Presence of hemagglutination was accessed by the presence of non-settled RBCs, appearing as a haze compared to a punctuated red dot of non-hemagglutinated RBCs.

An anti-red blood cells antibody (AbCam, cat. no. ab34858) condition was included as a positive control for hemagglutination, and an isotype control antibody condition was included as a negative control.

Figure 13:
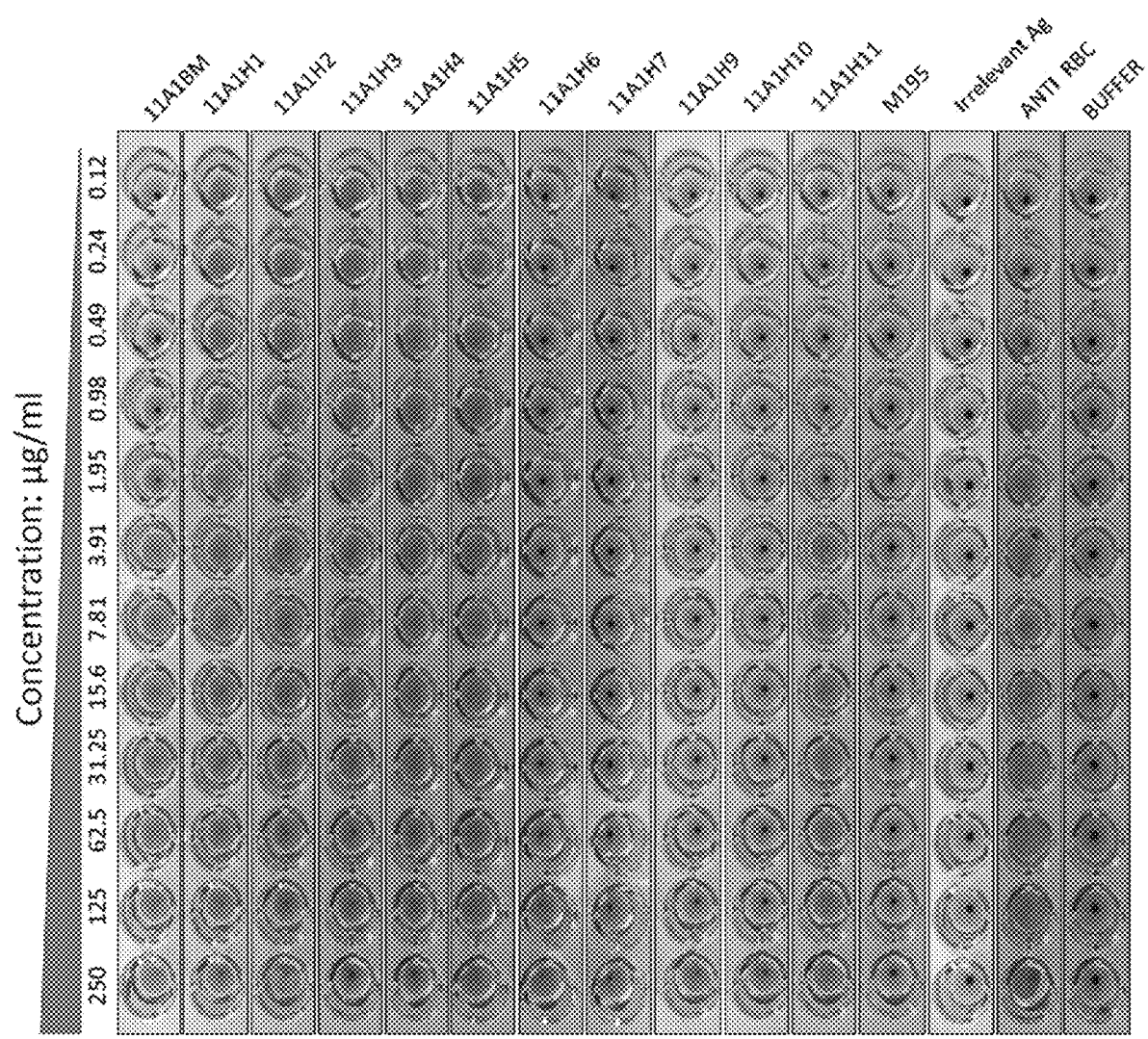
FIG. 13. Images showing the results of analysis of hemagglutination by the indicated antigen-binding molecules. Positive control=anti-red blood cells antibody (ANTI RBC), negative control=isotype matched antibody specific for an irrelevant target antigen (Irrelevant Ag), and buffer only (BUFFER).

The following antigen-binding molecules were analysed in the experiment:
11A1H1-IgG1 ([6] of Example 5).
11A1H2-IgG1 ([7] of Example 5).
11A1H3-IgG1 ([7] of Example 5).
11A1H4-IgG1 ([8] of Example 5).
11A1H5-IgG1 ([10] of Example 5).
11A1H6-IgG1 ([11] of Example 5).
11A1H7-IgG1 ([12] of Example 5).
11A1H9-IgG1 ([14] of Example 5).
11A1H10-IgG1 ([15] of Example 5).
11A1H11-IgG1 ([16] of Example 5).
anti-CD47 clone 1-1-A1_BM IgG1 ([1] of Example 2.2).
anti-CD33 IgG1 ([5] of Example 2.2) (negative control)—referred to as 'M195' in FIG. 13.
J6M0-IgG1 ([17] of Example 7.1) (negative control)—referred to as 'Irrelevant Ag' in FIG. 13.
An anti-red blood cells antibody (AbCam, cat. no. ab34858)— referred to as 'ANTI RBC' in FIG. 13.
The results are shown in FIG. 13.

The invention claimed is:

1. An antigen-binding molecule which binds to CD47, comprising:

(a)
- (i) a heavy chain variable (VH) region incorporating the following CDRs:
  - HC-CDR1 having the amino acid sequence of SEQ ID NO:137
  - HC-CDR2 having the amino acid sequence of SEQ ID NO:138
  - HC-CDR3 having the amino acid sequence of SEQ ID NO:26; and
- (ii) a light chain variable (VL) region incorporating the following CDRs:
  - LC-CDR1 having the amino acid sequence of SEQ ID NO:32
  - LC-CDR2 having the amino acid sequence of SEQ ID NO:33
  - LC-CDR3 having the amino acid sequence of SEQ ID NO:34 or (b)
- (i) a heavy chain variable (VH) region incorporating the following CDRs:
  - HC-CDR1 having the amino acid sequence of SEQ ID NO:24
  - HC-CDR2 having the amino acid sequence of SEQ ID NO:25
  - HC-CDR3 having the amino acid sequence of SEQ ID NO:26 and
- (ii) a light chain variable (VL) region incorporating the following CDRs:
  - LC-CDR1 having the amino acid sequence of SEQ ID NO:32
  - LC-CDR2 having the amino acid sequence of SEQ ID NO:33
  - LC-CDR3 having the amino acid sequence of SEQ ID NO:34;

or (c)
- (i) a heavy chain variable (VH) region incorporating the following CDRs:
  - HC-CDR1 having the amino acid sequence of SEQ ID NO:24
  - HC-CDR2 having the amino acid sequence of SEQ ID NO:25
  - HC-CDR3 having the amino acid sequence of SEQ ID NO:26; and
- (ii) a light chain variable (VL) region incorporating the following CDRs:
  - LC-CDR1 having the amino acid sequence of SEQ ID NO:139
  - LC-CDR2 having the amino acid sequence of SEQ ID NO:141
  - LC-CDR3 having the amino acid sequence of SEQ ID NO:34;

or (d)
- (i) a heavy chain variable (VH) region incorporating the following CDRs:
  - HC-CDR1 having the amino acid sequence of SEQ ID NO:137
  - HC-CDR2 having the amino acid sequence of SEQ ID NO:138
  - HC-CDR3 having the amino acid sequence of SEQ ID NO:26; and
- (ii) a light chain variable (VL) region incorporating the following CDRs:
  - LC-CDR1 having the amino acid sequence of SEQ ID NO:139
  - LC-CDR2 having the amino acid sequence of SEQ ID NO:141

LC-CDR3 having the amino acid sequence of SEQ ID NO:34;

or (e)
(i) a heavy chain variable (VH) region incorporating the following CDRs:
HC-CDR1 having the amino acid sequence of SEQ ID NO:24
HC-CDR2 having the amino acid sequence of SEQ ID NO:25
HC-CDR3 having the amino acid sequence of SEQ ID NO:26; and
(ii) a light chain variable (VL) region incorporating the following CDRs:
LC-CDR1 having the amino acid sequence of SEQ ID NO:140
LC-CDR2 having the amino acid sequence of SEQ ID NO:141
LC-CDR3 having the amino acid sequence of SEQ ID NO:34;

or (f)
(i) a heavy chain variable (VH) region incorporating the following CDRs:
HC-CDR1 having the amino acid sequence of SEQ ID NO:137
HC-CDR2 having the amino acid sequence of SEQ ID NO:138
HC-CDR3 having the amino acid sequence of SEQ ID NO:26; and
(ii) a light chain variable (VL) region incorporating the following CDRs:
LC-CDR1 having the amino acid sequence of SEQ ID NO:140
LC-CDR2 having the amino acid sequence of SEQ ID NO:141
LC-CDR3 having the amino acid sequence of SEQ ID NO:34;

or (g)
(i) a heavy chain variable (VH) region incorporating the following CDRs:
HC-CDR1 having the amino acid sequence of SEQ ID NO:137
HC-CDR2 having the amino acid sequence of SEQ ID NO:138
HC-CDR3 having the amino acid sequence of SEQ ID NO:26; and
(ii) a light chain variable (VL) region incorporating the following CDRs:
LC-CDR1 having the amino acid sequence of SEQ ID NO:32
LC-CDR2 having the amino acid sequence of SEQ ID NO:141
LC-CDR3 having the amino acid sequence of SEQ ID NO:34;

or (h)
(i) a heavy chain variable (VH) region incorporating the following CDRs:
HC-CDR1 having the amino acid sequence of SEQ ID NO:137
HC-CDR2 having the amino acid sequence of SEQ ID NO:138
HC-CDR3 having the amino acid sequence of SEQ ID NO:26; and
(ii) a light chain variable (VL) region incorporating the following CDRs:
LC-CDR1 having the amino acid sequence of SEQ ID NO:32
LC-CDR2 having the amino acid sequence of SEQ ID NO:33
LC-CDR3 having the amino acid sequence of SEQ ID NO:142.

2. The antigen-binding molecule according to claim 1, wherein the antigen-binding molecule comprises:
a VH region comprising an amino acid sequence having at least 70% sequence identity to the amino acid sequence of SEQ ID NO:132, 23, 39, 127, 129, 130 or 131; and
a VL region comprising an amino acid sequence having at least 70% sequence identity to the amino acid sequence of SEQ ID NO:128, 31, 44, 133, 134, 135 or 136.

3. The antigen-binding molecule according to claim 1, wherein the antigen-binding molecule comprises:
(i) a VH region comprising an amino acid sequence having at least 70% sequence identity to the amino acid sequence of SEQ ID NO:132; and
a VL region comprising an amino acid sequence having at least 70% sequence identity to the amino acid sequence of SEQ ID NO:128;

or (ii) a VH region comprising an amino acid sequence having at least 70% sequence identity to the amino acid sequence of SEQ ID NO:23; and
a VL region comprising an amino acid sequence having at least 70% sequence identity to the amino acid sequence of SEQ ID NO:31;

or (iii) a VH region comprising an amino acid sequence having at least 70% sequence identity to the amino acid sequence of SEQ ID NO:39; and
a VL region comprising an amino acid sequence having at least 70% sequence identity to the amino acid sequence of SEQ ID NO:44;
a VH region comprising an amino acid sequence having at least 70% sequence identity to the amino acid sequence of SEQ ID NO:127; and
(iv) a VL region comprising an amino acid sequence having at least 70% sequence identity to the amino acid sequence of SEQ ID NO:128;

or (v) a VH region comprising an amino acid sequence having at least 70% sequence identity to the amino acid sequence of SEQ ID NO:129; and
a VL region comprising an amino acid sequence having at least 70% sequence identity to the amino acid sequence of SEQ ID NO:128;

or (vi) a VH region comprising an amino acid sequence having at least 70% sequence identity to the amino acid sequence of SEQ ID NO:130; and
a VL region comprising an amino acid sequence having at least 70% sequence identity to the amino acid sequence of SEQ ID NO:128;

or (vii) a VH region comprising an amino acid sequence having at least 70% sequence identity to the amino acid sequence of SEQ ID NO:131; and
a VL region comprising an amino acid sequence having at least 70% sequence identity to the amino acid sequence of SEQ ID NO:128;

or
(viii) a VH region comprising an amino acid sequence having at least 70% sequence identity to the amino acid sequence of SEQ ID NO:131; and
a VL region comprising an amino acid sequence having at least 70% sequence identity to the amino acid sequence of SEQ ID NO:133;
or
(ix) a VH region comprising an amino acid sequence having at least 70% sequence identity to the amino acid sequence of SEQ ID NO:132; and
a VL region comprising an amino acid sequence having at least 70% sequence identity to the amino acid sequence of SEQ ID NO:133;
or
(x) a VH region comprising an amino acid sequence having at least 70% sequence identity to the amino acid sequence of SEQ ID NO:131; and
a VL region comprising an amino acid sequence having at least 70% sequence identity to the amino acid sequence of SEQ ID NO:134;
or
(xi) a VH region comprising an amino acid sequence having at least 70% sequence identity to the amino acid sequence of SEQ ID NO:132; and
a VL region comprising an amino acid sequence having at least 70% sequence identity to the amino acid sequence of SEQ ID NO:134;
or
(xii) a VH region comprising an amino acid sequence having at least 70% sequence identity to the amino acid sequence of SEQ ID NO:132; and
a VL region comprising an amino acid sequence having at least 70% sequence identity to the amino acid sequence of SEQ ID NO:135;
or
(xiii) a VH region comprising an amino acid sequence having at least 70% sequence identity to the amino acid sequence of SEQ ID NO:132; and
a VL region comprising an amino acid sequence having at least 70% sequence identity to the amino acid sequence of SEQ ID NO:136.

4. The antigen-binding molecule according to claim 1, wherein the antigen-binding molecule inhibits interaction between CD47 and SIRPα.

5. The antigen-binding molecule according to claim 1, wherein the antigen-binding molecule is a multispecific antigen-binding molecule, and further comprises an antigen-binding domain specific for a target antigen other than CD47.

6. A method of treating a cancer in a subject, comprising administering to the subject a therapeutically effective amount of an antigen-binding molecule which binds to CD47 and comprises:
(a)
(i) a heavy chain variable (VH) region incorporating the following CDRs:
HC-CDR1 having the amino acid sequence of SEQ ID NO:137
HC-CDR2 having the amino acid sequence of SEQ ID NO:138
HC-CDR3 having the amino acid sequence of SEQ ID NO:26; and
(ii) a light chain variable (VL) region incorporating the following CDRs:
LC-CDR1 having the amino acid sequence of SEQ ID NO:32
LC-CDR2 having the amino acid sequence of SEQ ID NO:33
LC-CDR3 having the amino acid sequence of SEQ ID NO:34;
or
(b)
(i) a heavy chain variable (VH) region incorporating the following CDRs:
HC-CDR1 having the amino acid sequence of SEQ ID NO:24
HC-CDR2 having the amino acid sequence of SEQ ID NO:25
HC-CDR3 having the amino acid sequence of SEQ ID NO:26; and
(ii) a light chain variable (VL) region incorporating the following CDRs:
LC-CDR1 having the amino acid sequence of SEQ ID NO:32
LC-CDR2 having the amino acid sequence of SEQ ID NO:33
LC-CDR3 having the amino acid sequence of SEQ ID NO:34;
or
(c)
(i) a heavy chain variable (VH) region incorporating the following CDRs:
HC-CDR1 having the amino acid sequence of SEQ ID NO:24
HC-CDR2 having the amino acid sequence of SEQ ID NO:25
HC-CDR3 having the amino acid sequence of SEQ ID NO:26; and
(ii) a light chain variable (VL) region incorporating the following CDRs:
LC-CDR1 having the amino acid sequence of SEQ ID NO:139
LC-CDR2 having the amino acid sequence of SEQ ID NO:141
LC-CDR3 having the amino acid sequence of SEQ ID NO:34;
or
(d)
(i) a heavy chain variable (VH) region incorporating the following CDRs:
HC-CDR1 having the amino acid sequence of SEQ ID NO:137
HC-CDR2 having the amino acid sequence of SEQ ID NO:138
HC-CDR3 having the amino acid sequence of SEQ ID NO:26; and
(ii) a light chain variable (VL) region incorporating the following CDRs:
LC-CDR1 having the amino acid sequence of SEQ ID NO:139
LC-CDR2 having the amino acid sequence of SEQ ID NO:141
LC-CDR3 having the amino acid sequence of SEQ ID NO:34;
or
(e)
(i) a heavy chain variable (VH) region incorporating the following CDRs:
HC-CDR1 having the amino acid sequence of SEQ ID NO:24
HC-CDR2 having the amino acid sequence of SEQ ID NO:25

HC-CDR3 having the amino acid sequence of SEQ ID NO:26; and
(ii) a light chain variable (VL) region incorporating the following CDRs:
LC-CDR1 having the amino acid sequence of SEQ ID NO:140
LC-CDR2 having the amino acid sequence of SEQ ID NO:141
LC-CDR3 having the amino acid sequence of SEQ ID NO:34;
or
(f)
(i) a heavy chain variable (VH) region incorporating the following CDRs:
HC-CDR1 having the amino acid sequence of SEQ ID NO:137
HC-CDR2 having the amino acid sequence of SEQ ID NO:138
HC-CDR3 having the amino acid sequence of SEQ ID NO:26; and
(ii) a light chain variable (VL) region incorporating the following CDRs:
LC-CDR1 having the amino acid sequence of SEQ ID NO:140
LC-CDR2 having the amino acid sequence of SEQ ID NO:141
LC-CDR3 having the amino acid sequence of SEQ ID NO:34;
or
(g)
(i) a heavy chain variable (VH) region incorporating the following CDRs:
HC-CDR1 having the amino acid sequence of SEQ ID NO:137
HC-CDR2 having the amino acid sequence of SEQ ID NO:138
HC-CDR3 having the amino acid sequence of SEQ ID NO:26; and
(ii) a light chain variable (VL) region incorporating the following CDRs:
LC-CDR1 having the amino acid sequence of SEQ ID NO:32
LC-CDR2 having the amino acid sequence of SEQ ID NO:141
LC-CDR3 having the amino acid sequence of SEQ ID NO:34;
or
(h)
(i) a heavy chain variable (VH) region incorporating the following CDRs:
HC-CDR1 having the amino acid sequence of SEQ ID NO:137
HC-CDR2 having the amino acid sequence of SEQ ID NO:138
HC-CDR3 having the amino acid sequence of SEQ ID NO:26; and
(ii) a light chain variable (VL) region incorporating the following CDRs:
LC-CDR1 having the amino acid sequence of SEQ ID NO:32
LC-CDR2 having the amino acid sequence of SEQ ID NO:33
LC-CDR3 having the amino acid sequence of SEQ ID NO:142.

7. The method according to claim 6, wherein the antigen-binding molecule comprises:

a VH region comprising an amino acid sequence having at least 70% sequence identity to the amino acid sequence of SEQ ID NO:132, 23, 39, 127, 129, 130 or 131; and
a VL region comprising an amino acid sequence having at least 70% sequence identity to the amino acid sequence of SEQ ID NO:128, 31, 44, 133, 134, 135 or 136.

8. The method according to claim 6, wherein the antigen-binding molecule comprises:
(i) a VH region comprising an amino acid sequence having at least 70% sequence identity to the amino acid sequence of SEQ ID NO:132; and
a VL region comprising an amino acid sequence having at least 70% sequence identity to the amino acid sequence of SEQ ID NO:128;
or
(ii) a VH region comprising an amino acid sequence having at least 70% sequence identity to the amino acid sequence of SEQ ID NO:23; and
a VL region comprising an amino acid sequence having at least 70% sequence identity to the amino acid sequence of SEQ ID NO:31;
or
(iii) a VH region comprising an amino acid sequence having at least 70% sequence identity to the amino acid sequence of SEQ ID NO:39; and
a VL region comprising an amino acid sequence having at least 70% sequence identity to the amino acid sequence of SEQ ID NO:44;
or
(iv)
a VH region comprising an amino acid sequence having at least 70% sequence identity to the amino acid sequence of SEQ ID NO:127; and
a VL region comprising an amino acid sequence having at least 70% sequence identity to the amino acid sequence of SEQ ID NO:128;
or
(v) a VH region comprising an amino acid sequence having at least 70% sequence identity to the amino acid sequence of SEQ ID NO:129; and
a VL region comprising an amino acid sequence having at least 70% sequence identity to the amino acid sequence of SEQ ID NO:128;
or
(vi) a VH region comprising an amino acid sequence having at least 70% sequence identity to the amino acid sequence of SEQ ID NO:130; and
a VL region comprising an amino acid sequence having at least 70% sequence identity to the amino acid sequence of SEQ ID NO:128;
or
(vii) a VH region comprising an amino acid sequence having at least 70% sequence identity to the amino acid sequence of SEQ ID NO:131; and
a VL region comprising an amino acid sequence having at least 70% sequence identity to the amino acid sequence of SEQ ID NO:128;
or
(viii) a VH region comprising an amino acid sequence having at least 70% sequence identity to the amino acid sequence of SEQ ID NO:131; and a VL region comprising an amino acid sequence having at least 70% sequence identity to the amino acid sequence of SEQ ID NO:133;
or
(ix) a VH region comprising an amino acid sequence having at least 70% sequence identity to the amino acid sequence of SEQ ID NO:132; and
a VL region comprising an amino acid sequence having at least 70% sequence identity to the amino acid sequence of SEQ ID NO:133;
or
(x) a VH region comprising an amino acid sequence having at least 70% sequence identity to the amino acid sequence of SEQ ID NO:131; and
a VL region comprising an amino acid sequence having at least 70% sequence identity to the amino acid sequence of SEQ ID NO:134;
or
(xi) a VH region comprising an amino acid sequence having at least 70% sequence identity to the amino acid sequence of SEQ ID NO:132; and
a VL region comprising an amino acid sequence having at least 70% sequence identity to the amino acid sequence of SEQ ID NO:134;
or
(xii) a VH region comprising an amino acid sequence having at least 70% sequence identity to the amino acid sequence of SEQ ID NO:132; and
a VL region comprising an amino acid sequence having at least 70% sequence identity to the amino acid sequence of SEQ ID NO:135;
or
(xiii) a VH region comprising an amino acid sequence having at least 70% sequence identity to the amino acid sequence of SEQ ID NO:132; and
a VL region comprising an amino acid sequence having at least 70% sequence identity to the amino acid sequence of SEQ ID NO:136.

9. The method according to claim 6, wherein the antigen-binding molecule inhibits interaction between CD47 and SIRPα.

10. The method according to claim 6, wherein the antigen-binding molecule is a multispecific antigen-binding molecule, and further comprises an antigen-binding domain specific for a target antigen other than CD47.

11. The method according to claim 6, wherein the cancer is selected from: a hematologic malignancy, a myeloid hematologic malignancy, a lymphoblastic hematologic malignancy, myelodysplastic syndrome (MDS), acute myeloid leukemia (AML), chronic myeloid leukemia (CML), acute lymphoblastic leukemia (ALL), non-Hodgkin's lymphoma (NHL), multiple myeloma (MM), bladder cancer, brain cancer, glioblastoma, ovarian cancer, breast cancer, colon cancer, liver cancer, hepatocellular carcinoma, prostate cancer, lung cancer, Non-small Cell Lung Cancer (NSCLC), skin cancer and melanoma.

* * * * *